US012624035B2

(12) United States Patent
Mcgarry et al.

(10) Patent No.: US 12,624,035 B2
(45) Date of Patent: May 12, 2026

(54) COMPOUNDS FOR TARGETED PROTEIN DEGRADATION

(71) Applicant: Amphista Therapeutics Limited, Cambridge (GB)

(72) Inventors: David Mcgarry, Cambridge (GB); Giles Albert Brown, Cambridge (GB); Pauline Drouhin, Cambridge (GB)

(73) Assignee: AMPHISTA THERAPEUTICS LIMITED, Cambridge (GB)

( * ) Notice: Subject to any disclaimer, the term of this patent is extended or adjusted under 35 U.S.C. 154(b) by 0 days.

(21) Appl. No.: 19/320,604

(22) Filed: Sep. 5, 2025

(65) Prior Publication Data

US 2026/0070904 A1 Mar. 12, 2026

(30) Foreign Application Priority Data

| | | | |
|---|---|---|---|
| Sep. 6, 2024 | (GB) | ...................................... | 2413095 |
| Mar. 21, 2025 | (GB) | ...................................... | 2504199 |
| Jun. 18, 2025 | (GB) | ...................................... | 2509688 |

(51) Int. Cl.

| | |
|---|---|
| ***C07D 471/04*** | (2006.01) |
| ***A61K 31/499*** | (2006.01) |
| ***A61P 35/00*** | (2006.01) |
| ***C07B 59/00*** | (2006.01) |
| ***C07D 401/14*** | (2006.01) |

(52) U.S. Cl.

CPC .......... *C07D 471/04* (2013.01); *A61K 31/499* (2013.01); *A61P 35/00* (2018.01); *C07B 59/002* (2013.01); *C07D 401/14* (2013.01)

(58) Field of Classification Search

CPC .. C07D 471/04; C07D 401/14; A61K 31/499; A61P 35/00; C07B 59/002

See application file for complete search history.

(56) References Cited

U.S. PATENT DOCUMENTS

| | | | |
|---|---|---|---|
| 5,530,118 | A | 6/1996 | Oinuma et al. |
| 2018/0015087 | A1 | 1/2018 | Liu et al. |
| 2019/0247509 | A1 | 8/2019 | Buckley et al. |
| 2023/0142883 | A1 | 5/2023 | Ruppel et al. |
| 2024/0115711 | A1 | 4/2024 | Testa et al. |

FOREIGN PATENT DOCUMENTS

| | | | |
|---|---|---|---|
| CN | 115261469 | A | 11/2022 |
| EP | 0468054 | B1 | 5/1997 |
| WO | WO-2005094816 | A1 | 10/2005 |
| WO | WO-2006131552 | A1 | 12/2006 |
| WO | WO-2007009250 | A1 | 1/2007 |
| WO | WO-2009121872 | A2 | 10/2009 |
| WO | WO-2013191965 | A1 | 12/2013 |
| WO | WO-2014114721 | A1 | 7/2014 |
| WO | WO-2015023355 | A1 | 2/2015 |
| WO | WO-2015179299 | A1 | 11/2015 |
| WO | WO-2015195950 | A1 | 12/2015 |
| WO | WO-2016001485 | A1 | 1/2016 |
| WO | WO-2016036804 | A1 | 3/2016 |
| WO | WO-2016077375 | A1 | 5/2016 |
| WO | WO-2016077378 | A1 | 5/2016 |
| WO | WO-2016138300 | A1 | 9/2016 |
| WO | WO-2016139361 | A1 | 9/2016 |
| WO | WO-2016151432 | A1 | 9/2016 |
| WO | WO-2016173682 | A1 | 11/2016 |
| WO | WO-2016210165 | A1 | 12/2016 |
| WO | WO-2017166104 | A1 | 10/2017 |
| WO | WO-2017223452 | A1 | 12/2017 |
| WO | WO-2018004306 | A1 | 1/2018 |
| WO | WO-2018071606 | A1 | 4/2018 |
| WO | WO-2018102725 | A1 | 6/2018 |
| WO | WO-2019099582 | A1 | 5/2019 |
| WO | WO-2019152440 | A1 | 8/2019 |
| WO | WO-2019238816 | A1 | 12/2019 |

(Continued)

OTHER PUBLICATIONS

Byun, W.S., et al., "Discovery of BRD9 Molecular Glue Degraders That Spare Cardiomyocytes," Journal of the American Chemical Society doi: 10.1021/jacs.5c09857, American Chemical Society, United States (Sep. 2025), 12 pages.

Byun, W.S., et al., "Discovery of BRD9 Molecular Glue Degraders That Spare Cardiomyocytes," Journal of the American Chemical Society, Supporting Information for doi: 10.1021/jacs.5c09857, American Chemical Society, United States (Sep. 2025), 54 pages.

Bolden, J.E., et al., "Inducible in Vivo Silencing of BRD4 Identifies Potential Toxicities of Sustained BET Protein Inhibition," Cell Reports 8(6):1919-1929, Cell Press, United States (Sep. 2014).

(Continued)

*Primary Examiner* — Rayna Rodriguez

(74) *Attorney, Agent, or Firm* — Sterne, Kessler, Goldstein & Fox P.L.L.C.

(57) ABSTRACT

This disclosure provides a compound of formula (III):

(III)

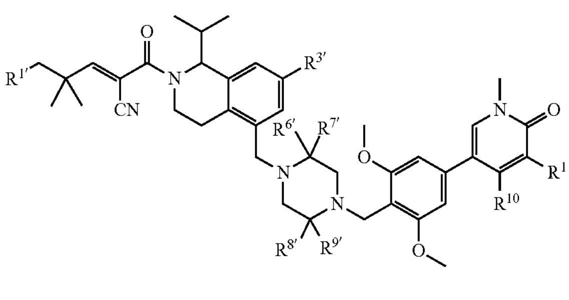

or a pharmaceutically acceptable salt, solvate or derivative thereof, wherein the substituents are as defined herein. The disclosure also provides pharmaceutical compositions comprising said compounds and the use of said compounds in the treatment of diseases, e.g. cancer.

2 Claims, 17 Drawing Sheets

Specification includes a Sequence Listing.

(56) References Cited

FOREIGN PATENT DOCUMENTS

| | | | | |
|---|---|---|---|---|
| WO | WO-2019238886 A1 | | 12/2019 | |
| WO | WO-2019246423 A1 | | 12/2019 | |
| WO | WO-2019246430 A1 | | 12/2019 | |
| WO | WO-2020051235 A1 | | 3/2020 | |
| WO | WO-2020077278 A1 | | 4/2020 | |
| WO | WO-2020106915 A1 | | 5/2020 | |
| WO | WO-2020160192 A1 | | 8/2020 | |
| WO | WO-2020160193 A2 | | 8/2020 | |
| WO | WO-2020160196 A1 | | 8/2020 | |
| WO | WO-2020160198 A1 | | 8/2020 | |
| WO | WO-2020252397 A1 | | 12/2020 | |
| WO | WO-2021022163 A2 | | 2/2021 | |
| WO | WO-2021026349 A1 | | 2/2021 | |
| WO | WO-2021051034 A1 | | 3/2021 | |
| WO | WO-2021155100 A1 | | 8/2021 | |
| WO | WO-2021155225 A1 | | 8/2021 | |
| WO | WO-2021178920 A1 | | 9/2021 | |
| WO | WO-2021207172 A1 | | 10/2021 | |
| WO | WO-2022025880 A1 | | 2/2022 | |
| WO | WO-2022129925 A1 | | 6/2022 | |
| WO | WO-2022270994 A1 | | 12/2022 | |
| WO | WO-2023283263 A1 | | 1/2023 | |
| WO | WO-2023009701 A2 | | 2/2023 | |
| WO | WO-2023009719 A2 | | 2/2023 | |
| WO | WO-2023039208 A1 | | 3/2023 | |
| WO | WO-2023109892 A1 | | 6/2023 | |
| WO | WO-2023143370 A1 | | 8/2023 | |
| WO | WO-2023200800 A1 | | 10/2023 | |
| WO | WO-2023242597 A1 | | 12/2023 | |
| WO | WO-2023242598 A1 | | 12/2023 | |
| WO | WO-2023244806 A1 | | 12/2023 | |
| WO | WO-2024057021 A1 | * | 3/2024 | ........... C07D 487/10 |
| WO | WO-2024163609 A1 | | 8/2024 | |
| WO | WO-2024259336 A2 | | 12/2024 | |
| WO | WO-2024259341 A2 | | 12/2024 | |
| WO | WO-2024259345 A2 | | 12/2024 | |
| WO | WO-2025015152 A1 | | 1/2025 | |
| WO | WO-2025101944 A1 | | 5/2025 | |
| WO | WO-2025125688 A2 | | 6/2025 | |
| WO | WO-2025191109 A1 | | 9/2025 | |

OTHER PUBLICATIONS

Clark, P.G.K., et al., "LP99: Discovery and Synthesis of the First Selective BRD7/9 Bromodomain Inhibitor," Angewandte Chemie 127(21):6315-6319, Wiley-VCH Verlag GmbH & Co, Germany (May 2015).
Hay, D.A., et al., "Design and Synthesis of Potent and Selective Inhibitors of BRD7 and BRD9 Bromodomains," MedChemComm 6:1381-1386, Royal Society of Chemistry, United Kingdom (Jun. 2015).
Hohmann, A.F., et al., "Sensitivity and Engineered Resistance of Myeloid Leukemia Cells to BRD9 Inhibition," Nature Chemical Biology 12(9):672-679, Nature Publishing Group, United Kingdom (Sep. 2016).
Loo, C.-S., et al., "A Genome-wide CRISPR Screen Reveals a Role for the Non-Canonical Nucleosome-Remodeling BAF Complex in Foxp3 Expression and Regulatory T Cell Function," Immunity 53(1):143-157, Cell Press, United States (Jul. 2020).
Martin, L.J., et al., "Structure-Based Design of an in Vivo Active Selective BRD9 Inhibitor," Journal of Medicinal Chemistry 59(10):4462-4475, American Chemical Society, United States (May 2016).
Mita, M.M., and Mita, A.C., "Bromodomain Inhibitors a Decade Later: A Promise Unfulfilled?" British Journal of Cancer 123(12):1713-1714, Nature Publishing Group, United Kingdom (Dec. 2020).
Theodoulou, N.H., et al., "Discovery of I-BRD9, a Selective Cell Active Chemical Probe for Bromodomain Containing Protein 9 Inhibition," Journal of Medicinal Chemistry 59(4):1425-1439, American Chemical Society, United States (Feb. 2016).
Wang, X., et al., "BRD9 defines a SWI/SNF Sub-complex and Constitutes a Specific Vulnerability in Malignant Rhabdoid Tumors," Nature Communications 10(1):1881, Nature Publishing Group, United Kingdom (Apr. 2019), 11 pages.
Zhu, X., et al., "Targeting BRD9 for Cancer Treatment: A New Strategy," Oncotargets and Therapy 13:13191-13200, Dove Medical Press, New Zealand (Dec. 2020).
Zoppi, V., et al., "Iterative Design and Optimization of Initially Inactive Proteolysis Targeting Chimeras (PROTACs) Identify VZ185 as a Potent, Fast, and Selective von Hippel-Lindau (VHL) Based Dual Degrader Probe of BRD9 and BRD7," Journal of Medicinal Chemistry 62(2):699-726, American Chemical Society, United States (Jan. 2019).
Anonymous, "Corporate Presentation," C4 Therapeutics, May 2021, 42 pages.
Anonymous, "Protein Degraded. Disease Targeted. Lives Transformed," C4 Therapeutics (Aug. 2023), 26 pages.
Biotech Webinar, BRD9: Drugging the Undruggable With a Heterobifunctional Degrader, C4 Therapeutics, 2022, 22 pages.
Brown, G., "Rational design of novel DCAF16-recruiting BRD9 Targeted Glue™," ACS Fall 2025, MEDI: General Orals, Amphista Therapeutics, presented Aug. 19, 2025, 24 pages.
Carrara, M., "Rational Design of a Novel DCAF16-recruiting BRD9 Targeted Glue®," 2nd SMR Molecular Glues Meeting, Amphista Therapeutics, presented Mar. 21, 2025, 17 pages.
Carrara, M., "Rational Design of a Novel DCAF16-recruiting BRD9 Targeted Glue®," 5th TPD & Induced Proximity Summit Europe, Amphista Therapeutics, presented Mar. 26, 2025, 17 pages.
Carrara, M., "Rational design of novel DCAF16-recruiting BRD9 Targeted Glue™ Degraders," Pharmaron Drug Discovery Webinar, Discovery and Optimisation of Molecular Glues: Concepts and Case Studies, Amphista Therapeutics, presented Jun. 18, 2025, 14 pages.
Collins, M., "Pharmacodynamics and Mechanistic Impacts of FHD-609, a BRD9 Degrader, in a Phase 1 Study in Patients With Advanced Synovial Sarcoma or SMARCB1-Loss Tumors," Poster Presentation, Foghorn Therapeutics, 1 page.
Dominici, C., et al., "Investigation of FHD-609, a potent degrader of BRD9, in preclinical models of acute myeloid leukemia (AML)," Poster Presentation, Foghorn Therapeutics, 1 page.
Fisher, S., "Undruggable Leaders Forum Europe," C4 Therapeutics, presented Apr. 13, 2021, 23 pages.
Fritzen, E.L., et al., "The Solid Phase Synthesis of Tetrahydroisoquinolines Having cdc25B Inhibitory Activity," Bioorganic Medicinal Chemistry Letters 10(7):649-652, Elsevier, Netherlands (Apr. 2000).
Gabizon, R., et al., "Efficient Targeted Degradation via Reversible and Irreversible Covalent PROTACs," Journal of the American Chemical Society 142(27):11734-11742, American Chemical Society, United States (May 2020).
Hughes, S., "Degradation of BRD9 by a Novel Targeted Glue," 5th TPD & Induced Proximity Symposium, Amphista Therapeutics, presented Jul. 10, 2024, 13 pages.
Hughes, S.J., et al., "Selective Degradation of BRD9 by a DCAF16-recruiting Targeted Glue: Mode of Action Elucidation and in Vivo Proof of Concept," BioRxiv doi:10.1101/2024.12.31.630899, openRxiv, United States (Jan. 2025), 27 pages.
Jackson, K., "Discovery of a Potent and Selective BRD9 BiDAC Degrader with Activity in a Preclinical Model of Synovial Sarcoma," 4th Targeted Protein Degradation Summit, C4 Therapeutics, Oct. 26-28, 2021, 29 pages.
Jackson, K.L., et al., "The Discovery and Characterisation of CFT8634: a Potent and Selective Degrader of BRD9 for the Treatment of SMARCB1 Perturbed Cancers," AACR Annual Meeting 2022—New Orleans, LA (Apr. 8-13, 2022), Presentation Deck, American Association for Cancer Research, United States (Apr. 2022), 18 pages.
Krishnan, S., et al., "Design of Reversible, Cysteine-Targeted Michael Acceptors Guided by Kinetic and Computational Analysis," Journal of The American Chemical Society 136(36):12624-12630, American Chemical Society, United States (Sep. 2014).
Kulkarni, M.R., et al., "Synthesis, in Vitro Cytotoxicity, and Molecular Docking Study of Novel 3,4-dihydroisoquinolin-1(2H)-one Based

(56) References Cited

OTHER PUBLICATIONS

Piperlongumine Analogues," Journal of Heterocyclic Chemistry 58(6):1359-1370, Wiley-Blackwell, United States (Jun. 2021), 12 Pages.
Lahr, D.L., "Discovery of IRF8 as a Potential Selection Biomarker for FHD-609, a Degrader of BRD9, in Preclinical Models of Acute Myeloid Leukemia (AML)," Epicypher 2023, Foghorn Therapeutics (2023), 16 pages.
Lee, S.Y., et al., "Depletion of BRD9-mediated R-loop accumulation inhibits leukemia cell growth via transcription-replication conflict," Nucleic Acids Res 53(12):gkaf613, Oxford University Press, United Kingdom (Jun. 2025).
Lin, M.Y., et al., "Long Acting Injectable FHD-609 Microsuspension: A Potent BRD9 Degrader with Comparable Efficacy, Reduced Frequency of Docing in Preclinical Models," Poster Presentation, Foghorn Therapeutics, 1 page.
Livingston, J.A., et al., "A Phase I Study of FHD-609, a Heterobifunctional Degrader of Bromodomain-Containing Protein 9, in Patients with Advanced Synovial Sarcoma or SMARCB1-Deficient Tumors," Clinical Cancer Research 31(4):628-638, American Association for Cancer Research, United States (Feb. 2025).
Netherton, M.R., "Discovery of FHD-609, a Potent and Selective Heterobifunctional Degrader of BRD9," Cambridge Health Institute 18th Annual Drug Discovery Chemistry Meeting, Foghorn Therapeutics, presented Apr. 13, 2023, 24 pages.
Nie, W., et al., "Design, Synthesis, and Biological Evaluation of Quinazoline Derivatives With Covalent Reversible Warheads as Potential FGFR4 Inhibitors," Bioorganic Chemistry 121:105673, Elsevier, United States (Apr. 2022).
Owens, T.D., et al., "Discovery of Reversible Covalent Bruton's Tyrosine Kinase Inhibitors PRN473 and PRN1008 (Rilzabrutinib)," J Med Chem 65(7):5300-5316, American Chemical Society, United States (Apr. 2022).
Pels, K., et al., "DNA-Compatible Solid-Phase Combinatorial Synthesis of—Cyanoacrylamides and Related Electrophiles," ACS Combinatorial Science 20(2):61-69, American Chemical Society, United States (Feb. 2018).
Pierri, M., "Unveiling New Triazoloquinoxaline-Based PROTACs Designed for the Selective Degradation of the ncBAF Chromatin Remodeling Subunit BRD9," Chemistry. 31(34):e202404218, Wiley-VCH GmbH, Germany (Jun. 2025).
Poling, L.L., et al., "CFT8634, a BRD9 BiDAC™ Degrader, is Active in a Subset of Multiple Myeloma Cell Line Models and Synergistic When Combined With Pomalidomide or Dexamethasone," AACR Annual Meeting, Poster 6046, American Association for Cancer Research, United States (Apr. 2024), 1 page.
Poling, L.L., et al., "CFT8634, a Clinical Stage BRD9 BiDAC™ Degrader, is Active in a Subset of Multiple Myeloma Cell Line Models and Synergistic When Combined With Pomalidomide," Blood 142(Suppl 1):6594-6595, American Society of Hematology, United States (Nov. 2023).
Remillard, D., et al., "Degradation of the BAF Complex Factor BRD9 by Heterobifunctional Ligands," Angewandte Chemie 56(21):5738-5743, Wiley-VCH, Germany (May 2017).
Sarott, R.C., et al., "Chemical Specification of E3 Ubiquitin Ligase Engagement by Cysteine-Reactive Chemistry," J Am Chem Soc 145(40):21937-21944, American Chemical Society, United States (Oct. 2023).
Topal, S., et al., "Investigating the Molecular Role of BRD9 in Synovial Sarcoma," Poster Presentation, Foghorn Therapeutics, 1 page.
Weisberg, E., et al., "BRD9 Degraders as Chemosensitizers in Acute Leukemia and Multiple Myeloma," Blood Cancer Journal 12(7):110, Nature Publishing Group, United Kingdom (Jul. 2022), 10 pages.
Zeid, R., "Pioneering Transformative Protein Degradation Therapies," Targeted Protein Degradation Summit, C4 Therapeutics, presented Oct. 14, 2020, 25 pages.
Zhang, J., et al., "Structural Feature Analyzation Strategies toward Discovery of Orally Bioavailable PROTACs of Bruton's Tyrosine Kinase for the Treatment of Lymphoma," Journal of Medicinal Chemistry 65(13):9096-9125, American Chemical Society, United States (Jul. 2022).
Zhang, X., et al., "Electrophilic PROTACs That Degrade Nuclear Proteins by Engaging DCAF16," Nature Chemical Biology 15(7):737-746, Nature Publishing Group, United Kingdom (Jul. 2019).
Borthakur, G., et al., "A phase 1 study of the pan-bromodomain and extraterminal inhibitor mivebresib (ABBV-075) alone or in combination with venetoclax in patients with relapsed/refractory acute myeloid leukemia," *Cancer* 127(16): 2943-2953, Wiley, United States (Aug. 2021).
Duplaquet, L., et al., "Mammalian SWI/SNF complex activity regulates POU2F3 and constitutes a targetable dependency in small cell lung cancer," *Cancer Cell* 42(8):1352-1369, Elsevier, Netherlands (Aug. 2024).
International Search Report and Written Opinion for International Application No. PCT/EP2025/075384, European Patent Office, Netherlands, mailed on Jan. 20, 2026, 13 pages.
Sosič, I., et al., "E3 ligase ligand chemistries: from building blocks to protein degraders," *Chem. Soc. Rev.* 51(9):3487-3534, RSC Publishing, United Kingdom (Apr. 2022).

* cited by examiner

SEQUENCE LISTING

```
Sequence total quantity: 1
SEQ ID NO: 1          moltype = AA  length = 216
FEATURE               Location/Qualifiers
source                1..216
                      mol_type = protein
                      organism = Homo sapiens
SEQUENCE: 1
MGPRNPSPDH LSESESEEEE NISYLNESSG EEWDSSEEED SMVPNLSPLE SLAWQVKCLL  60
KYSTTWKPLN PNSWLYHAKL LDPSTPVHIL REIGLRLSHC SHCVPKLEPI PEWPPLASCG  120
VPPFQKPLTS PSRLSRDHAT LNGALQFATK QLSRTLSRAT PIPEYLKQIP NSCVSGCCCG  180
WLTKTVKETT RTEPINTTYS YTDFQKAVNK LLTASL                           216
```

COMPOUNDS FOR TARGETED PROTEIN DEGRADATION

REFERENCE TO SEQUENCE LISTING SUBMITTED ELECTRONICALLY

The content of the electronically submitted sequence listing (Name: 5700_0130003_SequenceListing_ST26.xml; Size: 2,170 bytes; Date of Creation: Sep. 4, 2025) submitted in this application is incorporated herein by reference in its entirety.

FIELD

The present disclosure relates to degradation of the Bromodomain-containing protein 9 (BRD9) protein. BRD9 has been linked to the proliferation of cancers, and the present disclosure relates to treatment of cancers, for example by BRD9 degradation. Specifically, the present disclosure relates to novel compounds that are useful in a targeted or selective degradation of BRD9, together with methods of preparing such molecules and therapeutic uses thereof. The present disclosure further relates to methods of treating cancer comprising the selective and/or targeted degradation of BRD9.

BACKGROUND

BRD9 is a protein encoded by the BRD9 gene on chromosome 5. BRD9 is a component of the BAF (BRG1- or BRM-associated factors) complex, a SWI/SNF ATPase chromatin remodeling complex, and belongs to family IV of the bromodomain-containing proteins (D. Hay et al., Med. Chem. Commun., 2015, 6, 1381-1386). SWI/SNF uses the energy of ATP hydrolysis to remodel chromatin and mobilize nucleosomes. SWI/SNF is implicated in activating transcription by remodelling nucleosomes, thereby permitting increased access of transcription factors for their binding sites. It is also required for transcriptional repression of some genes, and so controls transcription in various ways.

Recurrent inactivating mutations in certain subunits of SWI/SNF complex have been identified in different cancers. Despite its known roles in tumour suppression, the mammalian SWI/SNF complex has recently received attention as a potential target for therapeutic inhibition (L. J. Martin et al., J. Med. Chem., 2016, 59, 4462-4475).

Studies have shown that BRD9 is preferentially used by cancers that harbour SMARCB1 abnormalities such as malignant rhabdoid tumors and several specific types of sarcoma (X. Zhu, Y. Liao and L. Tang, Onco Targets Ther., 2020, 13, 13191-13200). BRD9-containing complexes bind to both active promoters and enhancers, where they contribute to gene expression. Loss of BRD9 results in gene expression changes related to apoptosis regulation, translation, and development regulation. BRD9 is essential for the proliferation of SMARCB1-deficient cancer cell lines, suggesting it is a therapeutic target for these lethal cancers. (Xiaofeng Wang et. al., Nature Communications, 2019, 10 (1881)). Recent studies highlight a role of BRD9 in leukemia growth: BRD9 was shown to be required for the proliferation of acute myeloid leukemia (AML) cells (Nature Chemical Biology, 2016, 101038/nchembio.2115). In addition to the role of BRD9 as a functional dependency in certain cancers, BRD9 also plays a pivotal role in immune cells as a regulator of regulatory T cells (Tregs) via transcriptional control of Foxp3 target genes, "BioRxiv, 10.1101/2020.02.26.964981.

Because of BRD9's role in cancer proliferation there has been interest in the development of BRD9 inhibitors for the treatment of cancers including those described in: WO 2014/114721, WO 2016/077375, WO 2016/077378, WO 2016/139361, WO 2019/152440, a paper by Martin L. J. et. al., (Journal of Medicinal Chemistry 2016, 59, 4462-4475) titled "Structure-Based Design of an in Vivo Active Selective BRD9 Inhibitor"; a paper by Theodoulou N. H. et. al., (Journal of Medicinal Chemistry 2015, 59, 1425-1439) titled "Discovery of I-BRD9, a selective Cell Active Chemical Probe for Bromodomain Containing Protein 9 Inhibition"; and a paper by Clack P. et. al., (Angewandte Chemie, 2015, 127, 6315-6319).

There is interest in the development of inhibitors or degraders that target BRD9 and not BRD4. Targeting BRD4 through genetic depletion, degradation or inhibition has significant effects on a diverse range of physiological functions including normal haematopoiesis, T cell viability and function, epidermal hyperplasia and homeostasis of different normal tissues in BRD4 genetically knocked out animals (Bolden et al Cell Rep. 2014; 8 (6): 1919-1929). In clinical trials, BRD4 inhibition has several dose limiting toxicities including fatigue, gastrointestinal symptoms, and thrombocytopenia, all of which have limited the efficacy of BRD4 inhibitors due to a small therapeutic window. (Mita et al. 2020. British Journal of Cancer 123, 1713-1714).

Targeted Protein Degradation (TPD) is a therapeutic modality, which relies on the use of synthetic molecules to repurpose cellular degradation machinery to induce degradation of specific disease-causing proteins. TPD approaches offer a number of advantages over other drug modalities (e.g. small molecule inhibitors, antibodies & protein-based agents, antisense oligonucleotides & related knockdown approaches) including: potentiated pharmacology due to catalytic protein removal from within cells; ability to inhibit multiple functions of a specific drug target including e.g. scaffolding function through target knockdown; opportunity for systemic dosing with good biodistribution; potent in vivo efficacy due to catalytic potency and long duration of action limited only by de novo protein resynthesis; and facile chemical synthesis and formulation using application of small molecule processes.

Protein degrading compounds that have an E3 ligase binding portion and a BRD9 binding portion wherein the BRD9 binding ligand binds to BRD9 and brings it to the ligase for ultimate degradation by the proteasome are described in Ciulli et al, (J. Med. Chem. 2019, 62, 2, 699 to 726), WO 2017/223452, WO 2019/152440, WO 2019/246423, WO 2019/246430, WO 2020/051235, WO 2020/106915, WO 2020/160192, WO 2020/160193, WO 2020/160196, WO 2021/022163, WO 2021/178920, WO 2020/160198, WO 2020/160196, and WO2024/057021.

Most of the known BRD9 inhibitors exhibit poor efficacy. Due to the important role BRD9 plays in cancer, there remains a need to identify compounds which show efficient BRD9 degradation across a range of cellular systems and/or with improved profiles suitable for drug development.

BRIEF SUMMARY

The present disclosure is based on the identification of novel compounds that are useful in a targeted and/or selective degradation of BRD9. In particular, the present disclosure provides compounds which facilitate proteasomal degradation of BRD9. The compounds of the present disclosure facilitate proteasomal degradation of BRD9 selectively compared to proteasomal degradation of BRD4.

Furthermore, the compounds of the present disclosure have advantageous low rates of hepatic clearance.

In one aspect, the present disclosure provides a compound of formula (III)

(III)

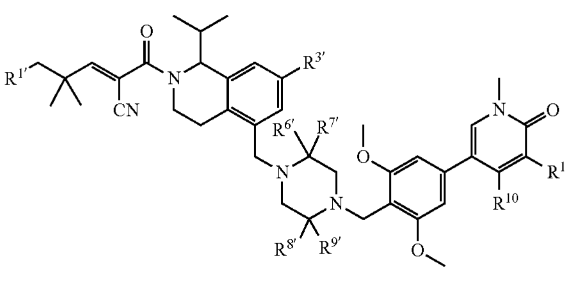

or a pharmaceutically acceptable salt, solvate or derivative thereof, wherein $R^{1'}$ is selected from H, F, $C_1$-$C_4$ alkyl, and methoxy;

$R^{3'}$ is selected from halogen, OH, $C_1$-$C_4$ alkyl, $C_1$-$C_2$ haloalkyl, $C_1$-$C_2$ alkoxy, and $C_1$-$C_2$ haloalkoxy;

$R^{6'}$, $R^{7'}$, $R^{8'}$ and $R^{9'}$ are each H, or $R^{6'}$ and $R^{7'}$ together with the carbon atom to which they are attached form a $C_3$ cycloalkyl, and/or $R^{8'}$ and $R^{9'}$ together with the carbon atom to which they are attached form a $C_3$ cycloalkyl;

$R^{10}$ and $R^{11}$ are independently selected from H and methyl, or $R^{10}$ and $R^{11}$ together with the atoms to which they are attached form a 5- or 6-membered heteroaryl group comprising one or more heteroatoms selected from the group consisting of N, S and O, optionally substituted by a 4- or 5-membered heteroalkyl group comprising one or more heteroatoms selected from the group consisting of N, S and O;

wherein the compound of formula (III) is not 2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or 2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

In another aspect, the present disclosure provides a compound of formula (IV)

(IV)

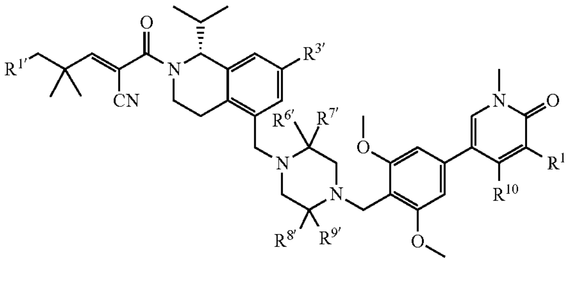

or a pharmaceutically acceptable salt, solvate or derivative thereof, wherein $R^{1'}$, $R^{3'}$, $R^{6'}$, $R^{7'}$, $R^{8'}$, $R^{9'}$, $R^{10}$ and $R^{11}$ are as defined for a compound of formula (III);

wherein the compound of formula (IV) is not (R)-2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or (R)-2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

In another aspect, the present disclosure provides a compound of formula (V)

(V)

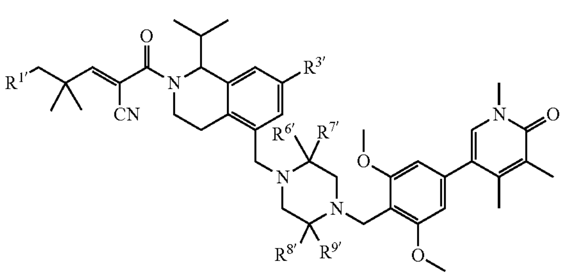

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined for a compound of formula (III);

wherein the compound of formula (V) is not 2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or 2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

In another aspect, the present disclosure provides a compound of formula (VI)

(VI)

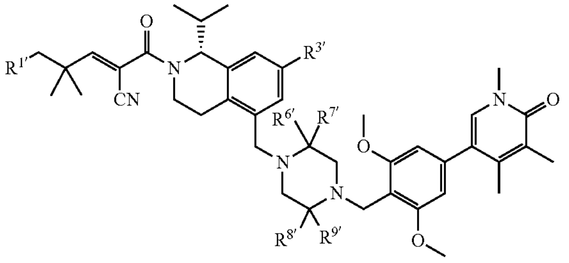

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined for a compound of formula (III);

wherein the compound of formula (VI) is not (R)-2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or (R)-2-(5-((4-(2,6-dimethoxy-4-(1,4,5-trimethyl-6-oxo-1,6-dihydropyridin-3-yl)benzyl)-4,7- diazaspiro[2.5]octan-7-yl)methyl)-7-fluoro-1-isopropyl-1,2,3,4-tetrahydroisoquinoline-2-carbonyl)-4,4-dimethylpent-2-enenitrile.

In another aspect, the present disclosure provides a compound of formula (VII)

(VII)

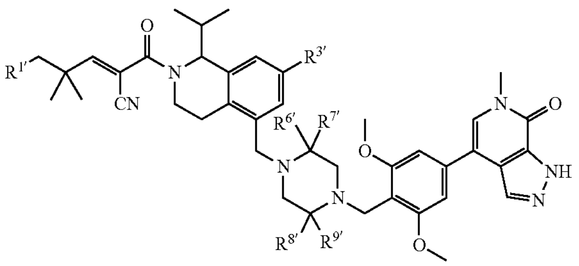

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined for a compound of formula (III).

In another aspect, the present disclosure provides a compound of formula (VIII)

(VIII)

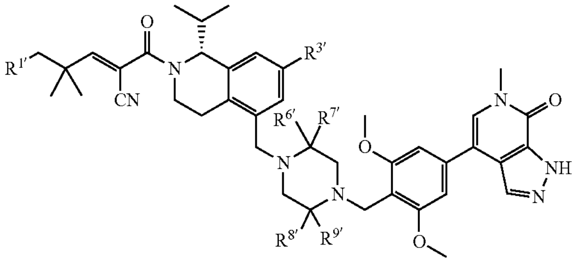

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined for a compound of formula (III).

In another aspect, the present disclosure provides a compound of formula (IX)

(IX)

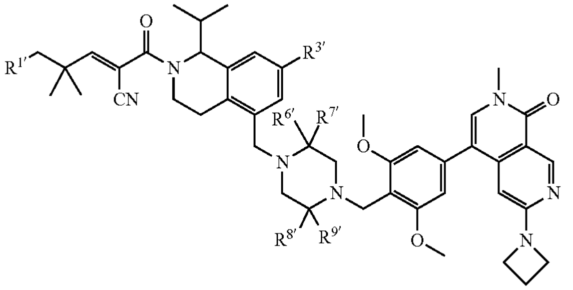

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined for a compound of formula (III).

In another aspect, the present disclosure provides a compound of formula (X)

(X)

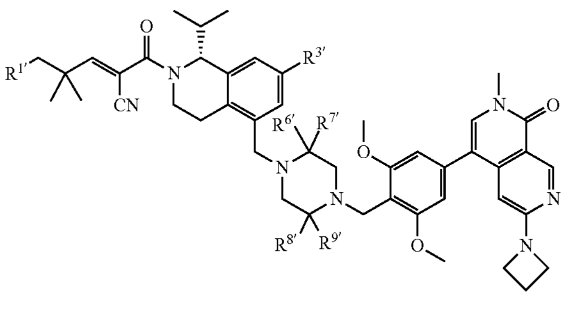

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined for a compound of formula (III).

In another aspect, the disclosure provides a DCAF16 conjugate that comprises a DCAF16 protein covalently bound to a compound of formula (III), (IV), (V), (VI), (VII), (Vill), (IX) or (X) as described herein at a cysteine residue.

In another aspect, the present disclosure provides a pharmaceutical composition comprising a compound of formula (III), (IV), (V), (VI), (VII), (VIII), (IX) or (X) as defined herein, together with a pharmaceutically acceptable carrier, optionally wherein the compound of formula (I), (II), (III), (IV), (V), (VI), (VII), (VIII), (IX) or (X) is present in the composition as a pharmaceutically acceptable salt, solvate or derivative.

In another aspect, the present disclosure provides a compound of formula (III), (IV), (V), (VI), (VII), (VIII), (IX) or (X) as defined herein, or a pharmaceutical composition comprising a compound of formula (III), (IV), (V), (VI), (VII), (VIII), (IX) or (X) as defined herein, for use in medicine.

In another aspect, the present disclosure provides a method of selectively degrading and/or increasing proteolysis of BRD9 in a cell or a subject in need thereof, the method comprising contacting and/or treating the cell with a compound of formula (III), (IV), (V), (VI), (VII), (VIII), (IX) or (X) as defined herein or a pharmaceutical composition comprising a compound of formula (III), (IV), (V), (VI), (VII), (VIII), (IX) or (X) as defined herein.

In another aspect, the present disclosure provides a method of making a compound of formula (III), (IV), (V), (VI), (VII), (VIII), (IX) or (X) as defined herein.

In another aspect, the present disclosure provides a compound library comprising a plurality of compounds of formula (III), (IV), (V), (VI), (VII), (VIII), (IX) or (X).

DETAILED DESCRIPTION

Figure 1:
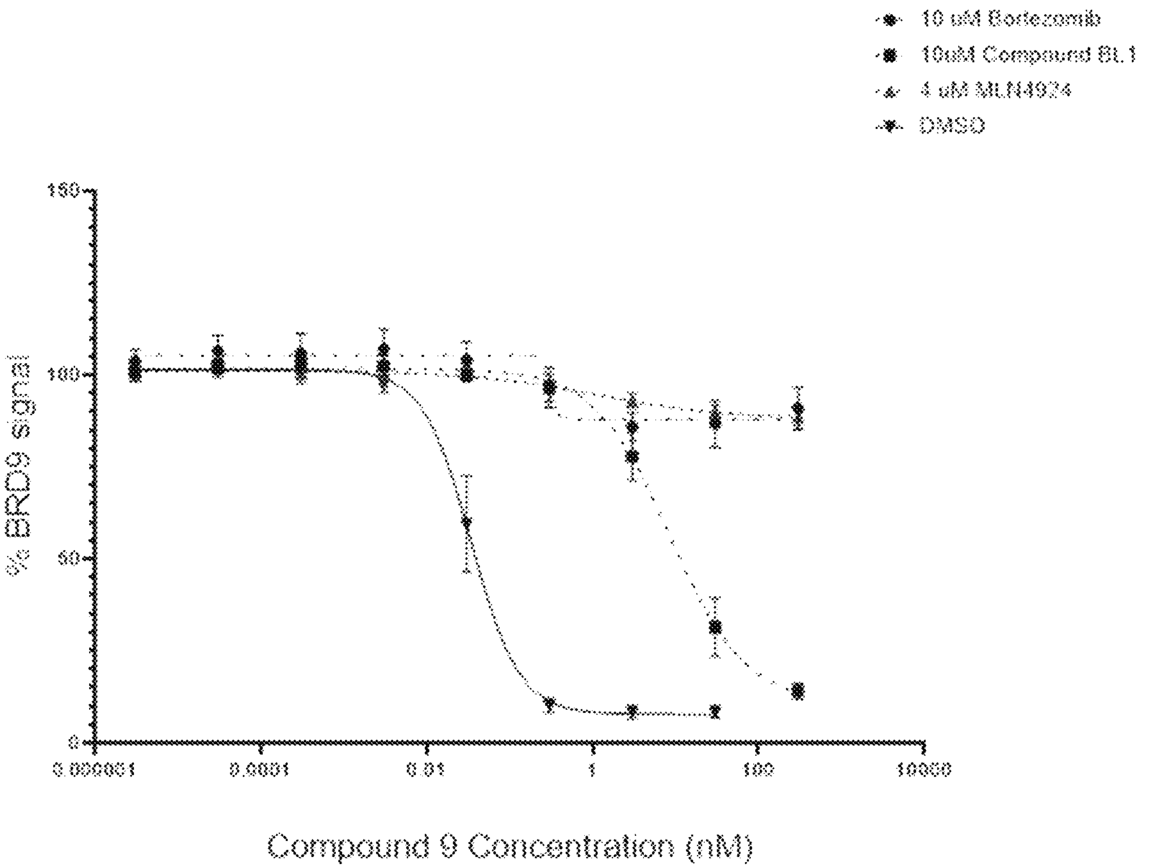
FIG. 1 is a line graph showing that dose dependent degradation of BRD9 at 4 hrs in MV4-11 cells induced by compound 9 can be out-competed using the BRD9 binding ligand BL1 (5-(3,5-dimethoxy-4-((4-methyl-4,7-diazaspiro[2.5]octan-7-yl)methyl)phenyl)-1,3,4-trimethylpyridin-2(1H)-one) and prevented by pre-treating with the Neddylation inhibitor MLN4924 or Bortezomib.

Disclosed herein is a compound of formula (I)

(I)

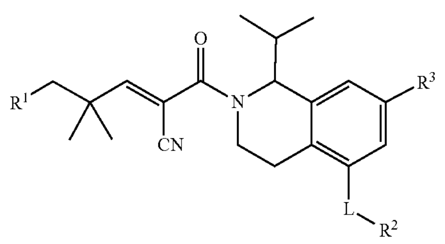

or a pharmaceutically acceptable salt, solvate or derivative thereof, wherein

L is a covalent bond or linker;

$R^1$ is selected from H, F, $C_1$-$C_4$ alkyl and $C_1$-$C_4$ alkoxy;

$R^2$ is a BRD9 binder;

$R^3$ is selected from halogen, $OR^4$, $C_1$-$C_6$ alkyl, and $N(R^5)_2$ wherein each alkyl is optionally substituted with one or more groups independently selected from halogen, $OR^4$, and $N(R^5)_2$;

each $R^4$ is independently selected from H, $C_1$-$C_6$ alkyl and $C_1$-$C_6$ haloalkyl; and each $R^5$ is independently selected from H, $C_1$-$C_6$ alkyl and $C_1$-$C_6$ haloalkyl;

wherein the compound of formula (I) is not 2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or 2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

In embodiments of the compounds of formula (I), L is a linker.

In embodiments of the compounds of formula (I), L is a moiety of formula (Ia)

(Ia)

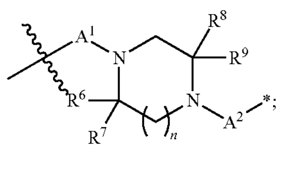

wherein $A^1$ and $A^2$ are each independently absent, or selected from $CH_2$, O and N;

n is selected from 0 and 1; and $R^6$, $R^7$, $R^8$ and $R^9$ are each independently selected from H, halogen, $C_1$-$C_6$ alkyl, and $C_1$-$C_6$ haloalkyl, or $R^6$ and $R^7$ together with the carbon atom to which they are attached form a $C_3$-$C_5$ cycloalkyl, or $R^8$ and $R^9$ together with the carbon atom to which they are attached form a $C_3$-$C_5$ cycloalkyl;

wherein * indicates the position that is attached to $R^2$ and the wavy line intersects the bond between L and the rest of the compound.

In embodiments of the compounds of formula (I), L is a moiety selected from:

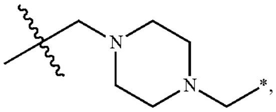,
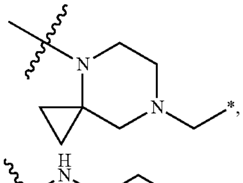,
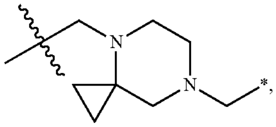,
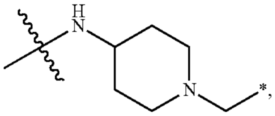,
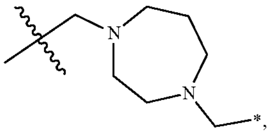,
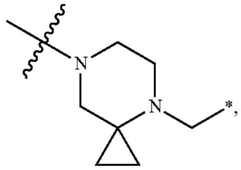,
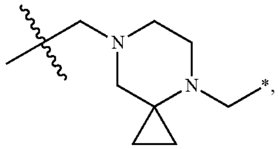,
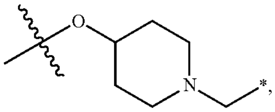,
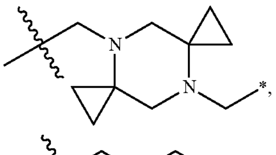, and
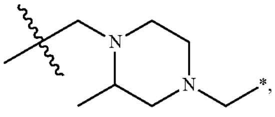, wherein * indicates the position that is attached to $R^2$ and the wavy line intersects the bond between L and the rest of the compound.

In embodiments of the compounds of formula (I), the -L-$R^2$ moiety is a group of formula (Ib)

(Ib)

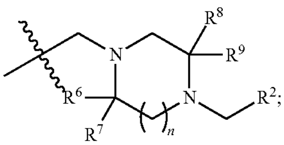;

wherein n is selected from 0 and 1; and $R^6$, $R^7$, $R^8$ and $R^9$ are each independently selected from H, halogen, $C_1$-$C_6$ alkyl, and $C_1$-$C_6$ haloalkyl, or $R^6$ and $R^7$ together with the carbon atom to which they are attached form a $C_3$-$C_5$ cycloalkyl, or $R^8$ and $R^9$ together with the carbon atom to which they are attached form a $C_3$-$C_5$ cycloalkyl;

wherein the wavy line intersects the bond between the -L-$R^2$ moiety and the rest of the compound.

In embodiments of the compounds of formula (I), the -L-$R^2$ moiety is a group selected from:

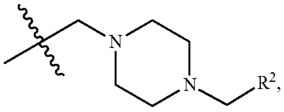,
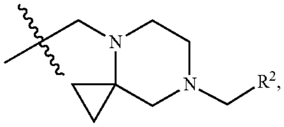,
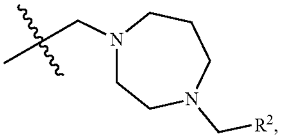,
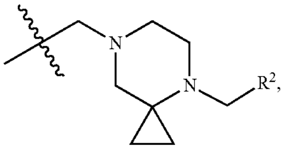,
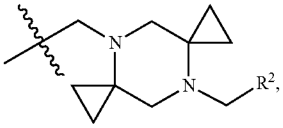, and
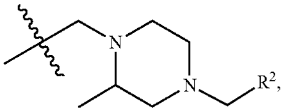, wherein the wavy line intersects the bond between -L-$R^2$ moiety and the rest of the compound.

In embodiments of the compounds of formula (I), the -L-$R^2$ moiety is a group of formula (Ic)

(Ic)

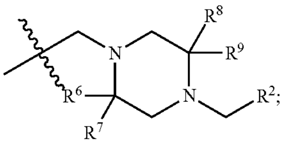;

wherein $R^6$, $R^7$, $R^8$ and $R^9$ are each independently selected from H, halogen, $C_1$-$C_6$ alkyl, and $C_1$-$C_6$ haloalkyl, or $R^6$ and $R^7$ together with the carbon atom to which they are attached form a $C_3$-$C_5$ cycloalkyl, and/or $R^8$ and $R^9$ together with the carbon atom to which they are attached form a $C_3$-$C_5$ cycloalkyl;

wherein the wavy line intersects the bond between the -L-$R^2$ moiety and the rest of the compound.

In embodiments of the compounds of formula (I), $R^6$, $R^7$, $R^8$ and $R^9$ are each H, or $R^6$ and $R^7$ together with the carbon atom to which they are attached form a $C_3$-$C_5$ cycloalkyl, and/or $R^8$ and $R^9$ together with the carbon atom to which they are attached form a $C_3$-$C_5$ cycloalkyl.

In embodiments of the compounds of formula (I), $R^6$, $R^7$, $R^8$ and $R^9$ are each H, or $R^6$ and $R^7$ together with the carbon atom to which they are attached form a cyclopropyl, and/or $R^8$ and $R^9$ together with the carbon atom to which they are attached form a cyclopropyl.

In embodiments of the compounds of formula (I):

$R^6$ and $R^7$ are each H, and $R^8$ and $R^9$ together with the carbon atom to which they are attached form a cyclopropyl; or $R^6$ and $R^7$ together with the carbon atom to which they are attached form a cyclopropyl, and $R^8$ and $R^9$ are each H; or $R^6$ and $R^7$ together with the carbon atom to which they are attached form a cyclopropyl, and $R^8$ and $R^9$ together with the carbon atom to which they are attached form a cyclopropyl.

In embodiments of the compounds of formula (I):

$R^6$ and $R^7$ are each H, and $R^8$ and $R^9$ together with the carbon atom to which they are attached form a cyclopropyl; or $R^6$ and $R^7$ together with the carbon atom to which they are attached form a cyclopropyl, and $R^8$ and $R^9$ are each H.

In embodiments of the compounds of formula (I), $R^6$ and $R^7$ together with the carbon atom to which they are attached form a cyclopropyl, and $R^8$ and $R^9$ are each H.

In embodiments of the compounds of formula (I), the -L-$R^2$ moiety is a group selected from:

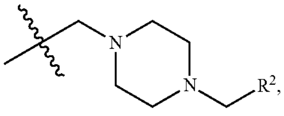

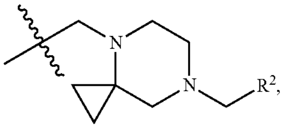

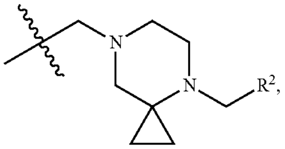

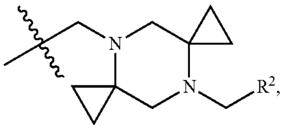

and

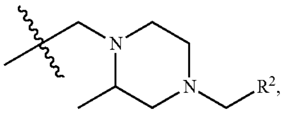

wherein the wavy line intersects the bond between -L-$R^2$ moiety and the rest of the compound.

In embodiments of the compounds of formula (I), the -L-$R^2$ moiety is a group selected from:

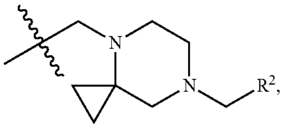

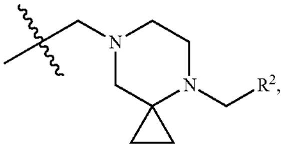

and

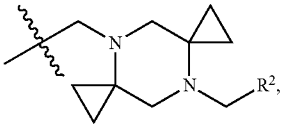

wherein the wavy line intersects the bond between -L-$R^2$ moiety and the rest of the compound.

In embodiments of the compounds of formula (I), the -L-$R^2$ moiety is a group selected from:

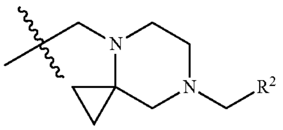

and

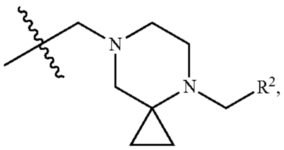

wherein the wavy line intersects the bond between -L-$R^2$ moiety and the rest of the compound.

In embodiments of the compounds of formula (I), the -L-$R^2$ moiety is:

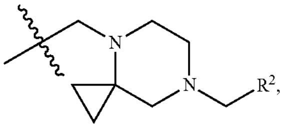

wherein the wavy line intersects the bond between -L-$R^2$ moiety and the rest of the compound.

In embodiments of the compounds of formula (I), $R^1$ is selected from H, F, $C_1$-$C_4$ alkyl and methoxy.

In embodiments of the compounds of formula (I), $R^1$ is selected from H, F, methyl and methoxy.

In embodiments of the compounds of formula (I), $R^1$ is selected from H, F and methyl.

In embodiments of the compounds of formula (I), $R^1$ is selected from H and F.

In embodiments of the compounds of formula (I), $R^1$ is F.

In embodiments of the compounds of formula (I), $R^2$ is a moiety of formula (1a), (1b) or (1c)

(1a)

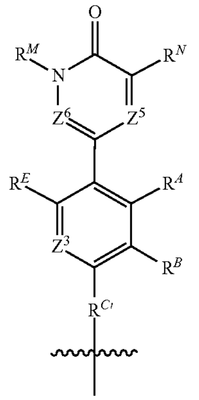

(1b)

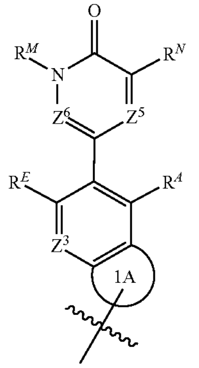

(1c)

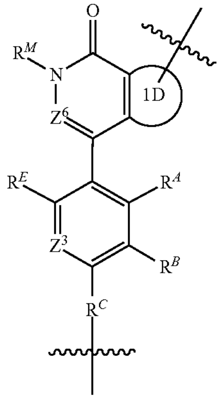

wherein the wavy line intersects the bond between $R^2$ and L;

$R^A$ and $R^E$ are each independently selected from the group consisting of H, $C_1$-$C_3$ alkoxy and $C_1$-$C_3$alkyl;

$R^B$ and $R^D$ are each independently selected from the group consisting of $C_1$-$C_3$ alkoxy, H, OH, halogen, $NH_2$, $C_1$-$C_3$alkyl, $C_1$-$C_3$ haloalkoxy, $C_1$-$C_3$alkyl-O—$C_1$-$C_3$alkyl, 4-7 membered heterocycloalkyl, $C_1$-$C_3$alkyl-$SO_2$—$C_1$-$C_3$alkyl, $C_1$-$C_3$alkyl-$NH_2$, $C_1$-$C_3$alkyl-N(—$C_1$-$C_3$alkyl)$_2$, N($C_1$-$C_3$alkyl)$_2$, NH—$R^F$, wherein the heterocycloalkyl comprises one or more heteroatoms selected from the group consisting of N, S and O;

alternatively, $R^A$ and $R^B$ taken together form a benzene ring;

$R^C$ is selected from the group consisting of H, —Y—$R^{G3}$, $NH_2$, $C_1$-$C_3$ alkyl and 4-7 membered heterocycloalkyl comprising one or more heteroatoms selected from the group consisting of N, S and O;

alternatively, $R^C$ and $Z^2$ or $R^C$ and $Z^3$ taken together form a 5-7 membered heterocycloalkyl comprising one or more heteroatoms selected from the group consisting of N, S and O, optionally substituted with $C_1$-$C_3$ alkyl;

wherein when $R^C$ is Y—$R^{G3}$, $R^B$ and $R^D$ are each independently selected from H, OH, halogen, $NH_2$, CN, $C_1$-$C_3$ alkyl, $C_1$-$C_3$ haloalkyl, $C_1$-$C_3$ alkoxy, $C_1$-$C_3$ haloalkoxy and $C_1$-$C_3$alkoxy-$C_1$-$C_3$alkyl; wherein at least one of the substituents $R^A$ to $R^E$ is not hydrogen;

$R^{C'}$ is absent, or is as defined for $R^C$ $R^F$ is selected from $SO_2$—$C_1$-$C_3$alkyl and $C_1$-$C_3$ alkyl, wherein the $C_1$-$C_3$ alkyl is optionally substituted with a 5 to 6 membered heteroaryl comprising one or more heteroatoms selected from the group consisting of N, S and O;

$R^{G3}$ is selected from the group consisting of $NH_2$, OH, $C_1$-$C_3$ alkyl, N($R^JR^K$), $OR^L$, aryl, 5-6 membered heteroaryl, wherein the aryl and heteroaryl are optionally and independently substituted with one or more halogen, optionally substituted 4- to 7-membered monocyclic heterocycloalkyl, and optionally substituted 7- to 12-membered bicyclic heterocycloalkyl, which monocyclic or bicyclic heterocycloalkyl comprise one or more heteroatoms selected from the group consisting of N, S and O, and are optionally substituted with one or more groups independently selected from halogen, OH, $NH_2$, $C_1$-$C_3$ alkyl, $NHC_1$-$C_3$alkyl, N($C_1$-$C_3$alkyl)$_2$, $C_1$-$C_3$ alkoxy and $CH_2$—$R^{M1}$;

$R^H$ and $R^I$ are each independently selected from H or $C_1$-$C_3$ alkyl; or $R^H$ and $R^I$ taken together form a $C_3$-$C_4$cycloalkyl;

$R^J$ is H or $C_1$-$C_3$alkyl;

$R^K$ is selected from the group consisting of $C_1$-$C_3$ alkyl, $C_2$-$C_3$alkyl-N($C_1$-$C_3$alkyl)$_2$, $C_2$-$C_3$alkyl-$NHC_1$-$C_3$alkyl, 4- to 7-membered monocyclic heterocycloalkyl, and 7- to 12-membered bicyclic heterocycloalkyl, wherein each monocyclic and bicyclic heterocycloalkyl comprises one or more heteroatoms selected from the group consisting of N, S and O, and is optionally substituted with $C_1$-$C_3$alkyl;

$R^L$ is $C_1$-$C_3$ alkyl or a 4-7 membered heterocycloalkyl, wherein the heterocycloalkyl comprises one or more heteroatoms selected from the group consisting of N, S and O, and is optionally substituted with $C_1$-$C_3$ alkyl;

$R^M$ is selected from the group consisting of $C_1$-$C_6$ alkyl, $C_2$-$C_6$ alkenyl, $C_1$-$C_6$ heteroalkyl comprising one or more heteroatoms selected from the group consisting of N, S and O, $C_3$-$C_{10}$ cycloalkyl, $C_2$-$C_6$ alkynyl and H, wherein the alkyl, alkenyl, heteroalkyl and cycloalkyl are each optionally substituted with $C_1$-$C_3$ alkyl;

$R^{M1}$ is selected from 5-10 membered mono- or bicyclic aryl or heteroaryl comprising one or more heteroatoms selected from the group consisting of N, S and O, which is optionally substituted with $NH_2$, OH, halogen, CN, $C_1$-$C_3$ alkyl, $C_1$-$C_3$ alkoxy;

$R^N$ is selected from the group consisting of H, halogen, $C_1$-$C_6$alkyl, C(O)$C_1$-$C_5$alkyl, $NH_2$, optionally substituted amino, OH, cyano, $C_1$-$C_6$heteroalkyl, $C_3$-$C_{10}$ cycloalkyl, $C_2$-$C_9$heterocycloalkyl, $C_6$-$C_{10}$aryl, $C_2$-$C_9$heteroaryl, $C_2$-$C_6$alkenyl, $C_2$-$C_6$heteroalkenyl and thiol, wherein each heteroalkyl and heteroalkenyl comprises one or more heteroatoms selected from the group consisting of N, S and O, each heterocycloalkyl and heteroaryl comprises one or more heteroatoms selected from the group consisting of N, S and O, and the alkyl, heteroalkyl, cycloalkyl, heterocycloalkyl, aryl, heteroaryl, alkenyl and heteroalkenyl are each optionally substituted with $C_1$-$C_3$ alkyl;

$R^O$ is H, halogen, cyano, $C_1$-$C_6$alkyl, $C_1$-$C_6$heteroalkyl, $C_3$-$C_{10}$cycloalkyl, $C_2$-$C_9$heterocycloalkyl, $C_6$-$C_{10}$aryl, $C_2$-$C_9$heteroaryl, $C_2$-$C_6$alkenyl, $C_2$-$C_6$heteroalkenyl, hydroxy, and thiol, wherein each heteroalkyl and heteroalkenyl comprises one or more heteroatoms selected from the group consisting of N, S and O, each heterocycloalkyl and heteroaryl comprises one or more heteroatoms selected from the group consisting of N, S and O, and the alkyl, heteroalkyl, cycloalkyl, heterocycloalkyl, aryl, heteroaryl, alkenyl and heteroalkenyl are each optionally substituted with $C_1$-$C_3$ alkyl;

alternatively, $R^N$ and $Z^5$ taken together, combine to form a $C_6$-$C_{10}$arene or $C_2$-$C_9$heteroarene, wherein the heteroarene comprises one or more heteroatoms selected from the group consisting of N, S and O, and the arene or heteroarene are each optionally substituted with $C_1$-$C_3$ alkyl; optionally wherein $R^N$ and $R^O$ taken together with the carbon atoms to which they are joined, combine to form a $C_6$-$C_{10}$arene or $C_2$-$C_9$heteroarene, wherein the heteroarene comprises one or more heteroatoms selected from the group consisting of N, S and O, and the arene or heteroarene are each optionally substituted with $C_1$-$C_3$ alkyl;

$R^P$ is selected from the group consisting of H, halogen, $C_1$-$C_6$ alkyl, $C_1$-$C_6$ heteroalkyl comprising one or more heteroatoms selected from the group consisting of N, S and O, $C_3$-$C_{10}$ cycloalkyl and $C_6$-$C_{10}$ aryl, wherein the alkyl, heteroalkyl, cycloalkyl, and aryl are each optionally substituted with $C_1$-$C_3$ alkyl;

$Z^3$ is N or $CR^D$;

$Z^5$ is N or $CR^O$;

$Z^6$ is N or $CR^P$;

Y is absent or is selected from the group consisting of —$CR^HR^I$—, —$SO_2$— and —CO—;

ring 1A is a 5-7 membered heterocycloalkane comprising one or two heteroatoms selected from the list consisting of N, S and O, optionally substituted with $C_1$-$C_3$alkyl; and ring 1D is a $C_6$-$C_{10}$aryl or $C_2$-$C_9$heteroaryl comprising one or more heteroatoms selected from the group consisting of N, S and O, each of which are optionally substituted with $C_1$-$C_3$ alkyl.

In embodiments of the compounds of formula (I), $R^2$ is a moiety selected from formulae (1d) to (1w)

(1d)

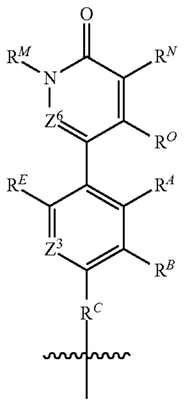

-continued (1e)

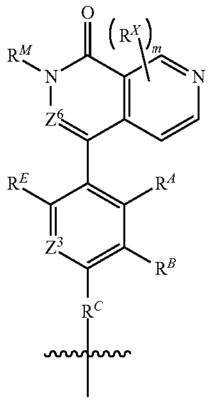

(1f)

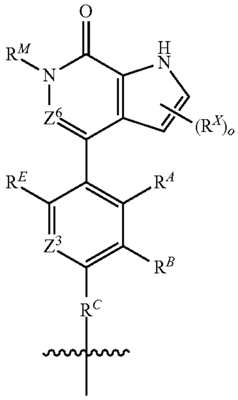

(1g)

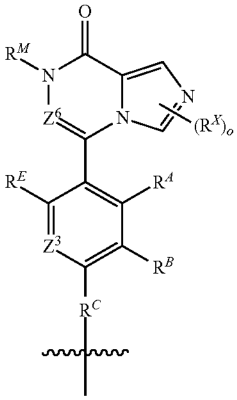

(1h)

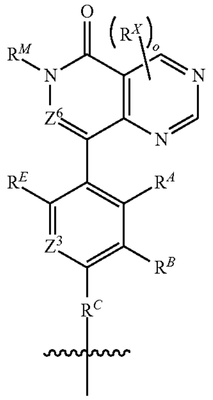

-continued
(1j)
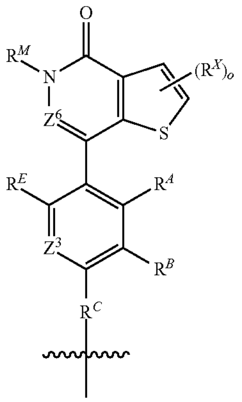
(1k)
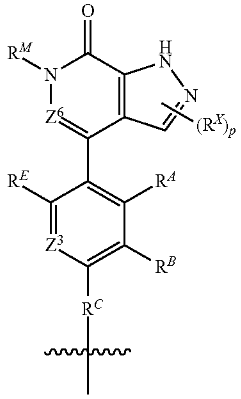
(1m)
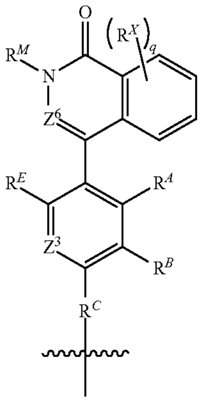
(1n)
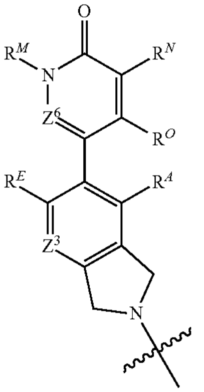
-continued
(1p)
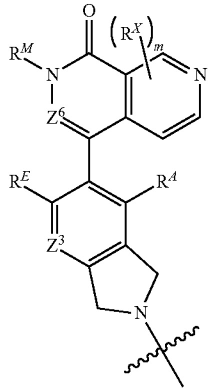
(1q)
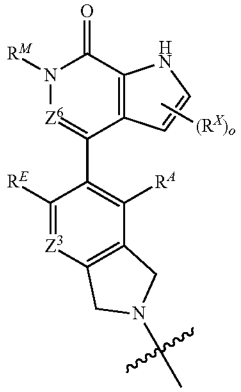
(1r)
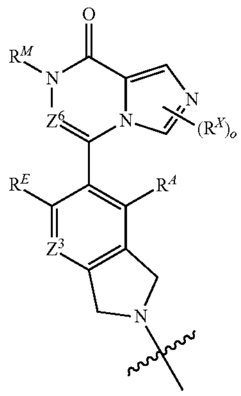
(1s)
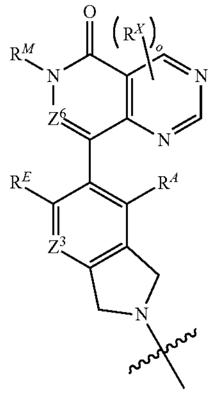

-continued (1t)

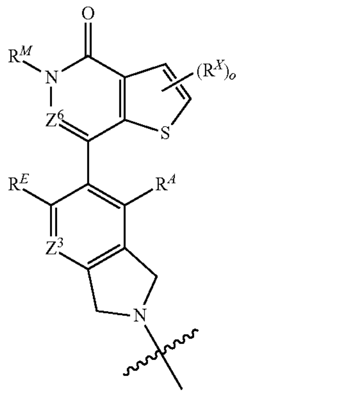

(1u)

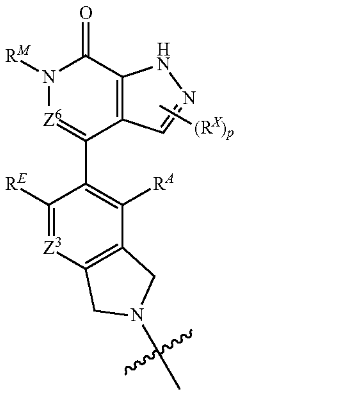

(1v)

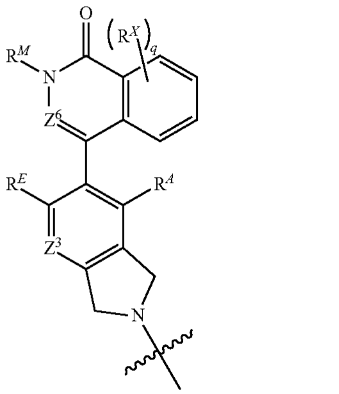

(1w)

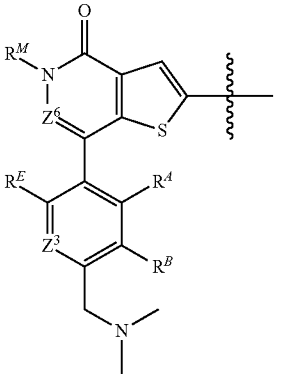

wherein the wavy line intersects the bond between $R^2$ and L;

$R^A$, $R^B$, $R^E$, $R^M$, $Z^3$ and $Z^6$ are as defined herein;

$R^C$ is absent or as defined herein;

$R^N$ is selected from the group consisting of halogen, $C_1$-$C_5$ alkyl, $C_1$-$C_3$ haloalkyl, H, $C(O)C_1$-$C_5$alkyl, $NH_2$, $NHC_1$-$C_3$alkyl and OH;

$R^O$ is H or $C_1$-$C_3$ alkyl;

each $R^X$ is independently selected from the group consisting of halogen, OH, $NH_2$, NH—$C_1$-$C_3$alkyl, $C_1$-$C_5$ alkyl, $C_1$-$C_5$ haloalkyl, $C_1$-$C_5$ alkoxy and $C_1$-$C_4$ haloalkoxy;

m is 0 to 3;

o is 0 to 2;

p is 0 or 1; and q is 0 to 4.

In embodiments of the compounds of formula (I), $R^2$ is a moiety according to formula (1x)

(1x)

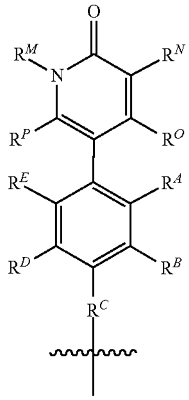

wherein the wavy line intersects the bond between $R^2$ and L;

$R^A$ and $R^E$ are each independently selected from H and $C_1$-$C_3$ alkoxy;

$R^B$ and $R^D$ are each independently selected from $C_1$-$C_3$ alkoxy, H, halogen, $C_1$-$C_3$ alkyl, and $C_1$-$C_3$ haloalkoxy;

$R^C$ is absent, or is Y—$R^{G3}$;

Y is selected from the group consisting of —$CR^HR^I$—, and —CO—;

$R^H$ and $R^I$ are each independently selected from H or $C_1$-$C_3$ alkyl; or $R^H$ and $R^I$ taken together form a $C_3$-$C_4$ cycloalkyl;

$R^{G3}$ is selected from the group consisting of $N(R^JR^K)$, $N(C_1$-$C_3$alkyl)(4- to 7-membered monocyclic heterocycloalkylene), or —$N(C_1$-$C_3$alkyl)(7- to 12-membered bicyclic heterocycloalkylene)); —O—; 4- to 7-membered monocyclic heterocycloalkylene; and 7- to 12-membered heterocycloalkylene, wherein each heterocycloalkene comprises one or more heteroatoms selected from the group consisting of N, S and O, and is optionally substituted with $C_1$-$C_3$ alkyl;

$R^J$ is H or $C_{1-3}$alkyl;

$R^K$ is selected from the group consisting of $C_1$-$C_3$ alkyl, $C_2$-$C_3$alkyl-$N(C_1$-$C_3$alkyl$)_2$, $C_2$-$C_3$alkyl-$NHC_1$-$C_3$alkyl, 4- to 7-membered monocyclic heterocycloalkyl, and 7- to 12-membered bicyclic heterocycloalkyl, wherein each monocyclic or bicyclic heterocycloalkyl comprises one or more heteroatoms selected from the group consisting of N, S and O, and is optionally substituted with $C_1$-$C_3$ alkyl;

$R^M$ is $C_1$-$C_3$ alkyl; and $R^N$, $R^O$ and $R^P$ are each independently selected from the group consisting of halogen, $C_1$-$C_3$ alkyl, and $C_1$-$C_3$ haloalkyl.
In embodiments of the compounds of formula (I), $R^2$ is a moiety of formulae (1y), (1z), (1a') to (1z'), or (1aa)
(1y)
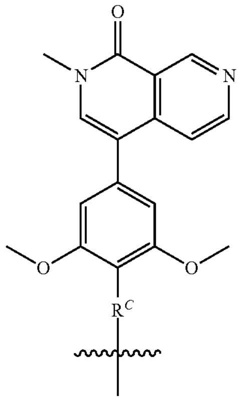
(1z)
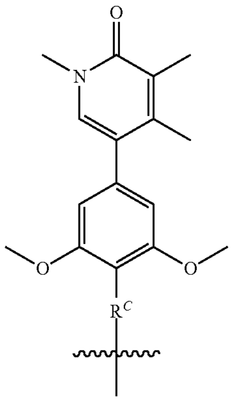
(1a')
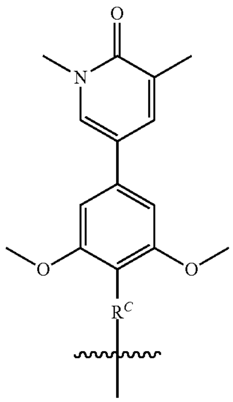
-continued
(1b')
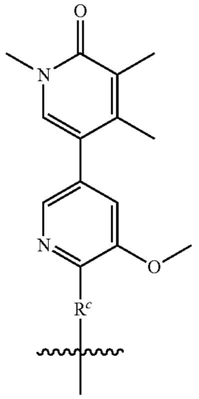
(1c')
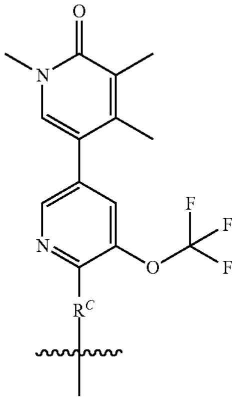
(1d')
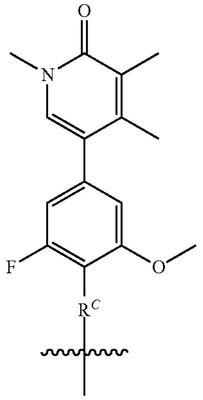
(1e')
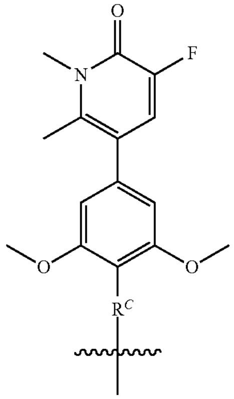

-continued
(1f')
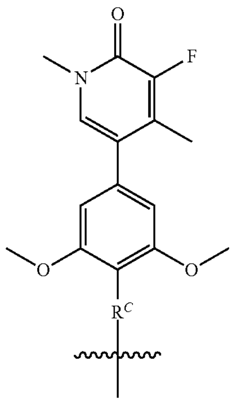
(1g')
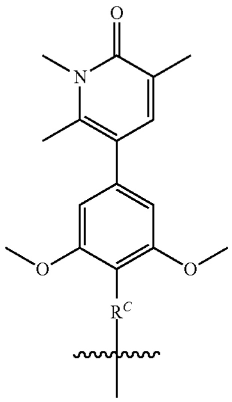
(1h')
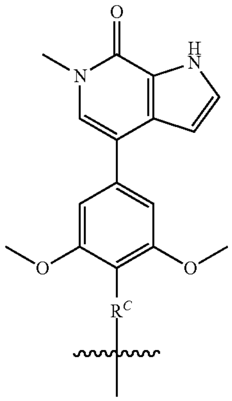
(1j')
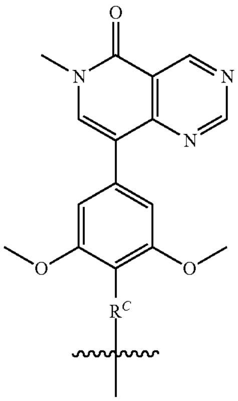
-continued
(1k')
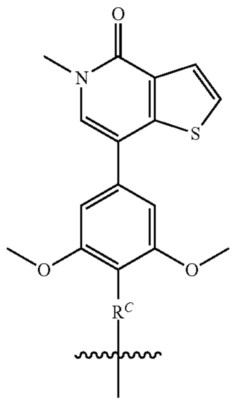
(1m')
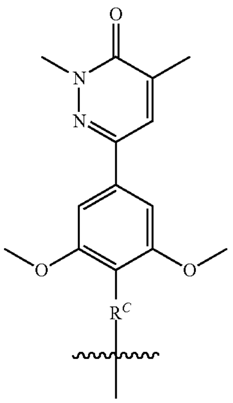
(1n')
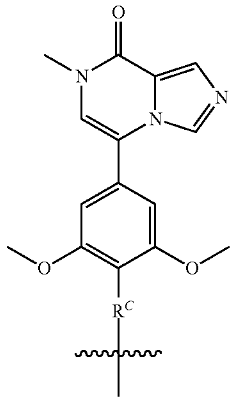
(1p')
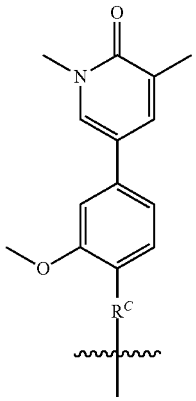

-continued
(1q′)
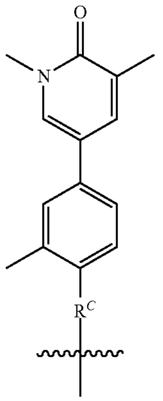
(1r′)
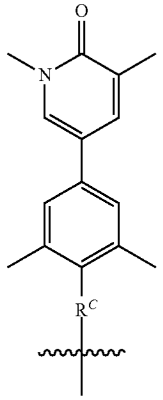
(1s′)
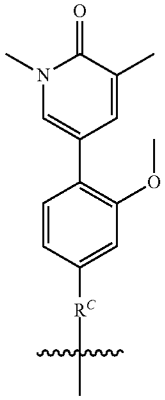
(1t′)
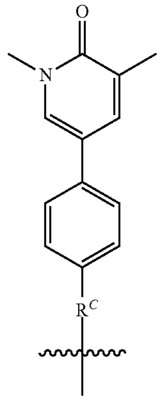
-continued
(1u′)
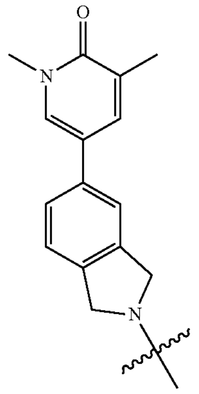
(1v′)
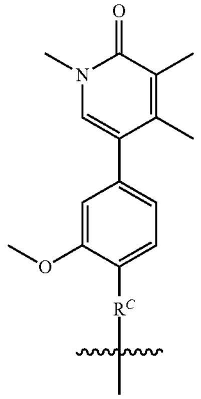
(1w′)
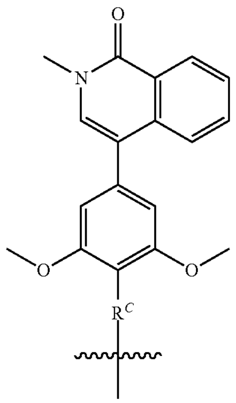
(1x′)
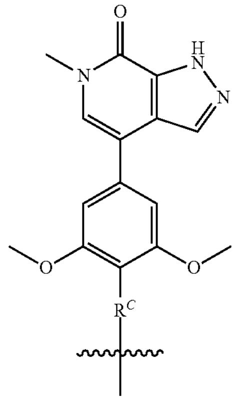

-continued (1y')

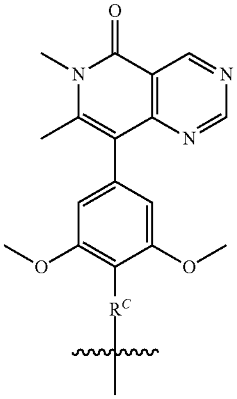

(1z')

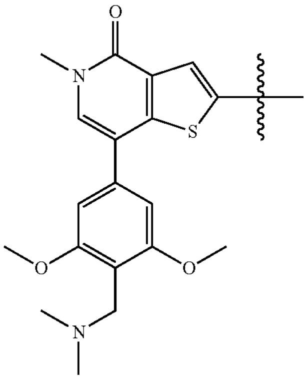

(1aa)

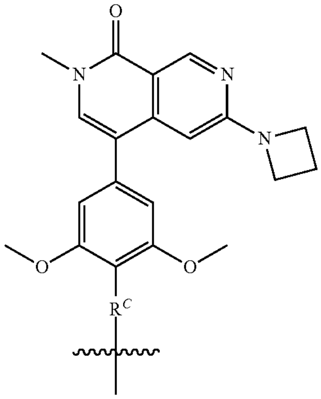

wherein the wavy line intersects the bond between $R^2$ and L;

$R^C$ is absent, or is —Y—$R^{G3}$

Y is selected from the group consisting of —$CR^HR^I$—, and —CO—;

$R^H$ and $R^I$ are each H; or $R^H$ and $R^I$ taken together form a $C_3$-$C_4$cycloalkyl;

$R^{G3}$ is selected from the group consisting of $N(R^JR^K)$, $N(C_1$-$C_3$alkyl)(4- to 7-membered monocyclic heterocycloalkylene), or $N(C_1$-$C_3$alkyl)(7- to 12-membered bicyclic heterocycloalkylene)); —O—; 4- to 7-membered monocyclic heterocycloalkylene; and 7- to 12-membered bicyclic heterocycloalkylene, wherein each monocyclic or bicyclic heterocycloalkyl comprises one or more heteroatoms selected from the group consisting of N, S and O, and is optionally substituted with $C_1$-$C_3$ alkyl;

$R^J$ is H or $C_1$-$C_3$alkyl;

$R^K$ is selected from the group consisting of $C_1$-$C_3$ alkyl, $C_2$-$C_3$alkyl-$N(C_1$-$C_3$alkyl$)_2$, $C_2$-$C_3$alkyl-$NHC_1$-$C_3$alkyl, 4- to 7-membered monocyclic heterocycloalkyl, and 7- to 12-membered bicyclic heterocycloalkyl, wherein each monocyclic or bicyclic heterocycloalkyl comprises one or more heteroatoms selected from the group consisting of N, S and O, and is optionally substituted with $C_1$-$C_3$alkyl.

In embodiments of the compounds of formula (I), $R^2$ is a moiety of formulae (1ab) to (1 bb):

(1ab)

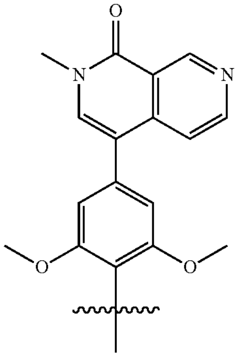

(1ac)

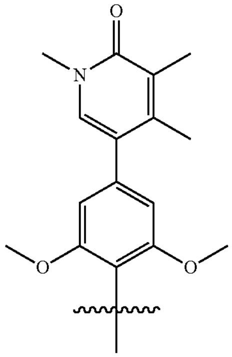

(1ad)

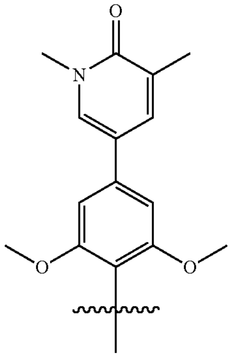

-continued
(1ae)
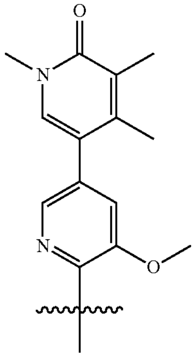
(1af)
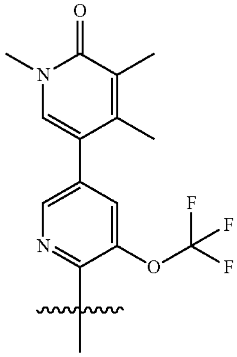
(1ag)
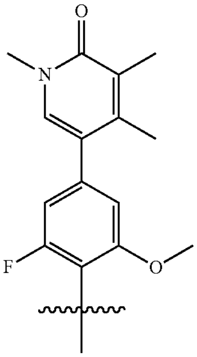
(1ah)
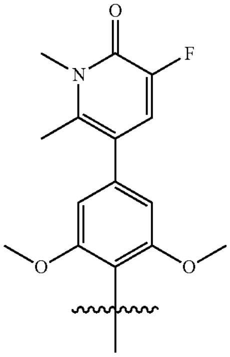
-continued
(1aj)
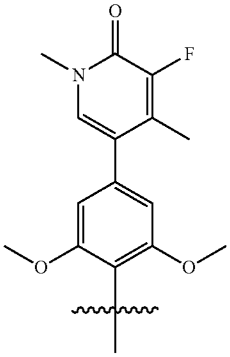
(1ak)
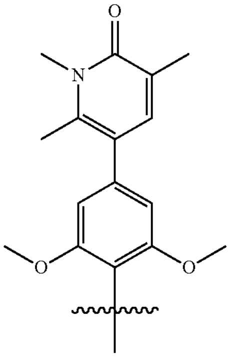
(1am)
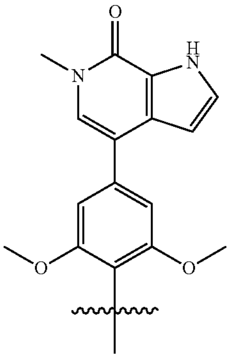
(1an)
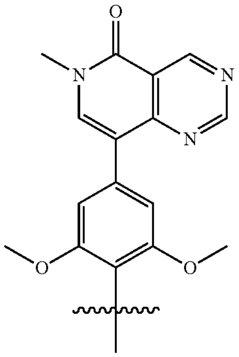

-continued
(1ap)
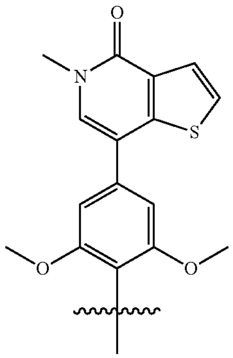
(1aq)
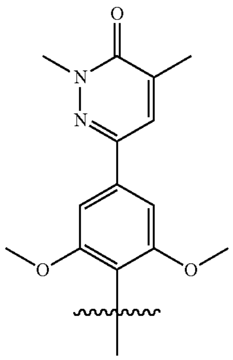
(1ar)
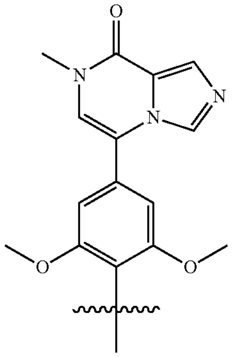
(1as)
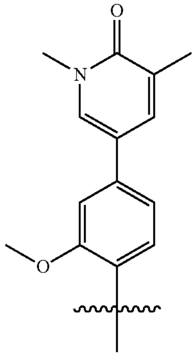
-continued
(1at)
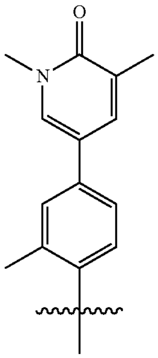
(1au)
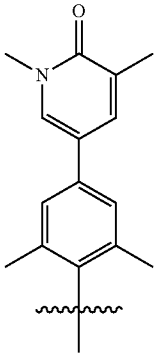
(1av)
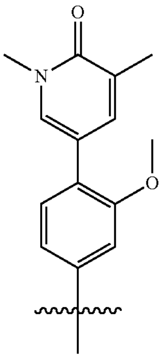
(1aw)
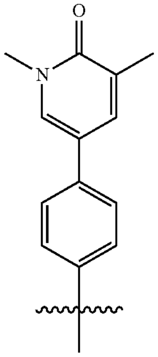

-continued
(1ax)
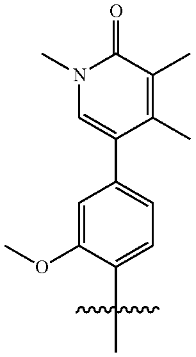
(1ay)
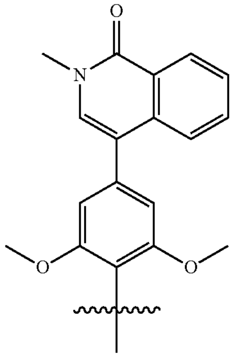
(1az)
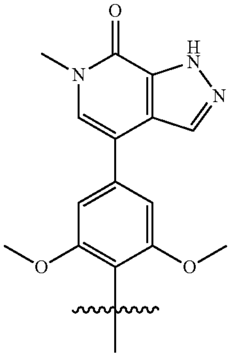
(1ba)
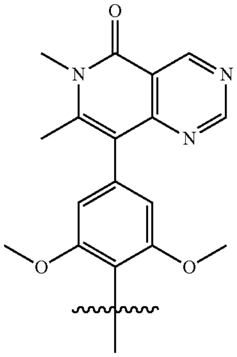
-continued
(1bb)
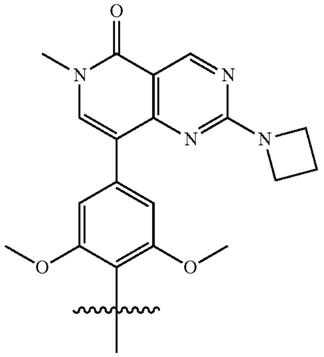
wherein the wavy line intersects the bond between $R^2$ and L.
In embodiments of the compounds of formula (I), $R^2$ is a moiety of formula (1ac), (1az) or (1bb)
(1ac)
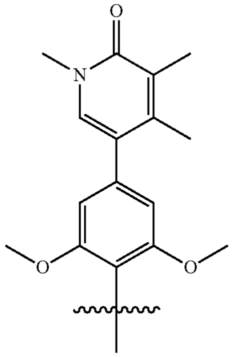
(1az)
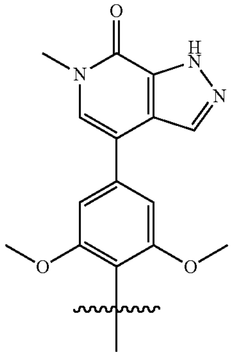
(1bb)
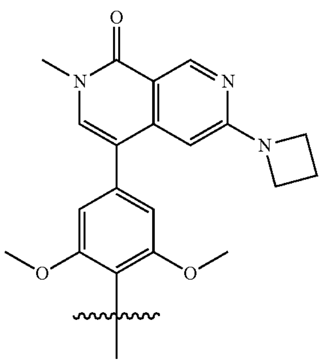

wherein the wavy line intersects the bond between $R^2$ and L.

In embodiments of the compounds of formula (I), $R^2$ is a moiety of formula (1ac)

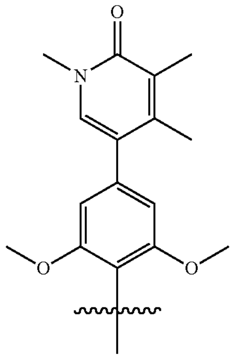

(1ac)

wherein the wavy line intersects the bond between $R^2$ and L.

In embodiments of the compounds of formula (I), $R^3$ is selected from halogen, OH, $C_1$-$C_4$ alkyl, $C_1$-$C_4$ haloalkyl, $C_1$-$C_4$ alkoxy, and $C_1$-$C_4$ haloalkoxy.

In embodiments of the compounds of formula (I), $R^3$ is selected from halogen, OH, $C_1$-$C_2$ alkyl, $C_1$-$C_2$ haloalkyl, $C_1$-$C_2$ alkoxy, and $C_1$-$C_2$ haloalkoxy In embodiments of the compounds of formula (I), $R^3$ is selected from F, OH, methyl, halomethyl, methoxy, and halomethoxy.

In embodiments of the compounds of formula (I), $R^3$ is selected from F, OH, $C_1$-$C_4$ alkyl, $C_1$-$C_4$ fluoroalkyl, $C_1$-$C_4$ difluoroalkyl, $C_1$-$C_4$ trifluoroalkyl, $C_1$-$C_4$ alkoxy, $C_1$-$C_4$ fluoroalkoxy, $C_1$-$C_4$ difluoroalkoxy, and $C_1$-$C_4$ trifluoroalkoxy.

In embodiments of the compounds of formula (I), $R^3$ is selected from F, OH, $C_1$-$C_2$ alkyl, $C_1$-$C_2$ fluoroalkyl, $C_1$-$C_2$ difluoroalkyl, $C_1$-$C_2$ trifluoroalkyl, $C_1$-$C_2$ alkoxy, $C_1$-$C_2$ fluoroalkoxy, $C_1$-$C_2$ difluoroalkoxy, and $C_1$-$C_2$ trifluoroalkoxy.

In embodiments of the compounds of formula (I), $R^3$ is selected from F, OH, methyl, fluoromethyl, difluoromethyl, trifluoromethyl, methoxy, fluoromethoxy, difluoromethoxy, and trifluoromethoxy.

In embodiments of the compounds of formula (I), $R^3$ is selected from F, OH, and methoxy.

In embodiments of the compounds of formula (I), $R^3$ is methoxy.

Also disclosed herein is a compound of formula (II)

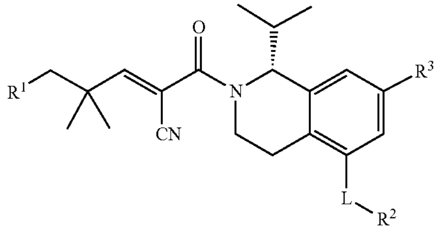

(II)

or a pharmaceutically acceptable salt, solvate or derivative thereof, wherein L, $R^1$, $R^2$, and $R^3$ are as defined for a compound of formula (I);

wherein the compound of formula (II) is not (R)-2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or (R)-2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

In one aspect, the present disclosure provides a compound of formula (III)

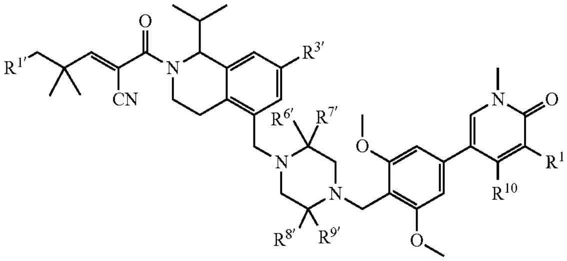

(III)

or a pharmaceutically acceptable salt, solvate or derivative thereof, wherein $R^{1'}$ is selected from H, F, $C_1$-$C_4$ alkyl, and methoxy;

$R^{3'}$ is selected from halogen, OH, $C_1$-$C_4$ alkyl, $C_1$-$C_2$ haloalkyl, $C_1$-$C_2$ alkoxy, and $C_1$-$C_2$ haloalkoxy;

$R^{6'}$, $R^{7'}$, $R^{8'}$ and $R^{9'}$ are each H, or $R^{6'}$ and $R^{7'}$ together with the carbon atom to which they are attached form a $C_3$ cycloalkyl, and/or $R^{8'}$ and $R^{9'}$ together with the carbon atom to which they are attached form a $C_3$ cycloalkyl;

$R^{10}$ and $R^{11}$ are independently selected from H and methyl, or $R^{10}$ and $R^{11}$ together with the atoms to which they are attached form a 5- or 6-membered heteroaryl group comprising one or more heteroatoms selected from the group consisting of N, S and O, optionally substituted by a 4- or 5-membered heteroalkyl group comprising one or more heteroatoms selected from the group consisting of N, S and O;

wherein the compound of formula (III) is not 2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or 2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

In embodiments of the compounds of formula (III), $R^{1'}$ is selected from H and F.

In embodiments of the compounds of formula (III), $R^{1'}$ is F.

In embodiments of the compounds of formula (III), $R^{3'}$ is selected from F, OH, methyl, halomethyl, methoxy, and halomethoxy.

In embodiments of the compounds of formula (III), $R^{3'}$ is selected from F, OH, $C_1$-$C_2$ alkyl, $C_1$-$C_2$ fluoroalkyl, $C_1$-$C_2$ difluoroalkyl, $C_1$-$C_2$ trifluoroalkyl, $C_1$-$C_2$ alkoxy, $C_1$-$C_2$ fluoroalkoxy, $C_1$-$C_2$ difluoroalkoxy, and $C_1$-$C_2$ trifluoroalkoxy.

In embodiments of the compounds of formula (III), $R^{3'}$ is selected from OH, $C_1$-$C_2$ alkoxy, and $C_1$-$C_2$ haloalkoxy.

In embodiments of the compounds of formula (III), $R^{3'}$ is selected from OH, methoxy, and halomethoxy.

In embodiments of the compounds of formula (III), $R^{3'}$ is selected from OH, $C_1$-$C_2$ alkoxy, $C_1$-$C_2$ fluoroalkoxy, $C_1$-$C_2$ difluoroalkoxy, and $C_1$-$C_2$ trifluoroalkoxy.

In embodiments of the compounds of formula (III), $R^{3'}$ is selected from F, OH, methyl, fluoromethyl, difluoromethyl, trifluoromethyl, methoxy, fluoromethoxy, difluoromethoxy, and trifluoromethoxy.

In embodiments of the compounds of formula (III), $R^{3'}$ is selected from OH, methoxy, fluoromethoxy, difluoromethoxy, and trifluoromethoxy.

In embodiments of the compounds of formula (III), $R^{3'}$ is selected from F, OH, and methoxy.

In embodiments of the compounds of formula (III), $R^{3'}$ is selected from OH and methoxy.

In embodiments of the compounds of formula (III), $R^{3'}$ is methoxy.

In embodiments of the compounds of formula (III):

$R^{6'}$ and RT are each H, and $R^{8'}$ and $R^{9'}$ together with the carbon atom to which they are attached form a cyclopropyl; or $R^{6'}$ and $R^{7'}$ together with the carbon atom to which they are attached form a cyclopropyl, and $R^{8'}$ and $R^{9'}$ are each H; or $R^{6'}$ and $R^{7}$ together with the carbon atom to which they are attached form a cyclopropyl, and $R^{8'}$ and $R^{9'}$ together with the carbon atom to which they are attached form a cyclopropyl.

In embodiments of the compounds of formula (III):

$R^{6'}$ and $R^{7'}$ are each H, and $R^{8'}$ and $R^{9'}$ together with the carbon atom to which they are attached form a cyclopropyl; or $R^{6'}$ and $R^{7'}$ together with the carbon atom to which they are attached form a cyclopropyl, and $R^{8'}$ and $R^{9'}$ are each H.

In embodiments of the compounds of formula (III), $R^{6'}$ and $R^{7'}$ together with the carbon atom to which they are attached form a cyclopropyl, and $R^{8'}$ and $R^{9'}$ are each H.

In embodiments of the compounds of formula (III), $R^{10}$ and $R^{11}$ are independently selected from H and methyl, or $R^{10}$ and $R^{11}$ together with the atoms to which they are attached form a 5- or 6-membered heteroaryl group comprising one or more N atoms, optionally substituted by a 4- or 5-membered heteroalkyl group comprising one or more N atoms.

In embodiments of the compounds of formula (III), $R^{10}$ and $R^{11}$ are each methyl, or $R^{10}$ and $R^{11}$ together with the atoms to which they are attached form a 5- or 6-membered heteroaryl group comprising one or two N atoms, optionally substituted by a 4- or 5-membered heteroalkyl group comprising one N atom.

In embodiments of the compounds of formula (III), $R^{10}$ and $R^{11}$ are each methyl, or $R^{10}$ and $R^{11}$ together with the atoms to which they are attached form a 5- or 6-membered heteroaryl group comprising one or two N atoms, optionally substituted by a 4-membered heteroalkyl group comprising one N atom.

In embodiments of the compounds of formula (III), $R^{10}$ and $R^{11}$ are each methyl.

In another aspect, the present disclosure provides a compound of formula (IV)

(IV)

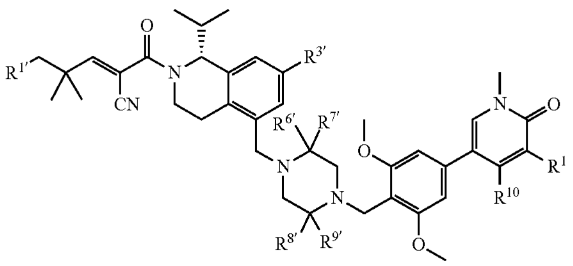

or a pharmaceutically acceptable salt, solvate or derivative thereof, wherein $R^{1'}$, $R^{3'}$, $R^{6'}$, $R^{7'}$, $R^{8'}$, $R^{9'}$, $R^{10}$ and $R^{11}$ are as defined for a compound of formula (III), wherein the compound of formula (IV) is not (R)-2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or (R)-2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

In another aspect, the present disclosure provides a compound of formula (V)

(V)

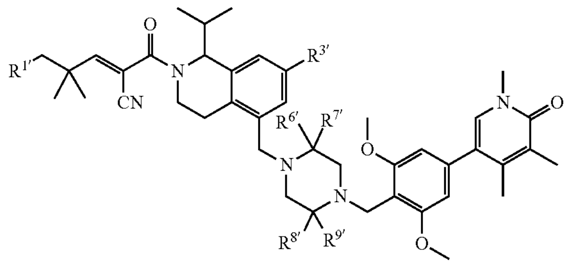

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined for a compound of formula (III);

wherein the compound of formula (V) is not 2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or 2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

In another aspect, the present disclosure provides a compound of formula (VI)

(VI)

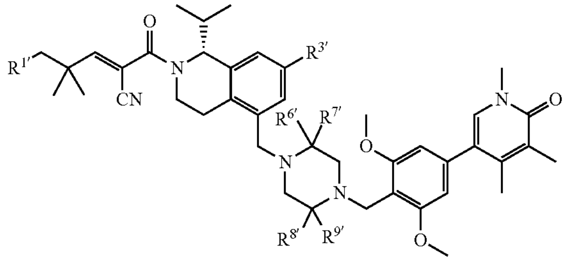

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined for a compound of formula (III);

wherein the compound of formula (VI) is not (R)-2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or (R)-2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

In another aspect, the present disclosure provides a compound of formula (VII)

(VII)

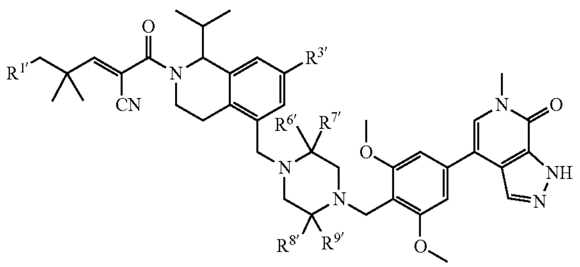

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined for a compound of formula (III).

In another aspect, the present disclosure provides a compound of formula (VIII)

(VIII)

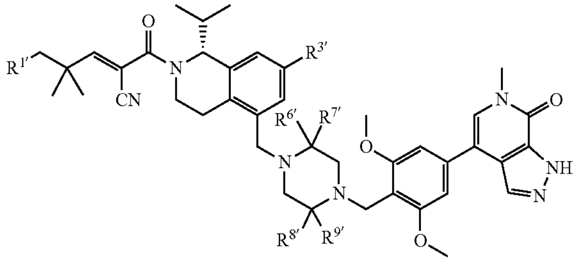

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined for a compound of formula (III).

In another aspect, the present disclosure provides a compound of formula (IX)

(IX)

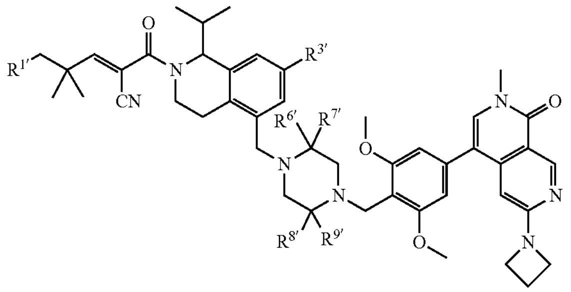

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined for a compound of formula (III).

In another aspect, the present disclosure provides a compound of formula (X)

(X)

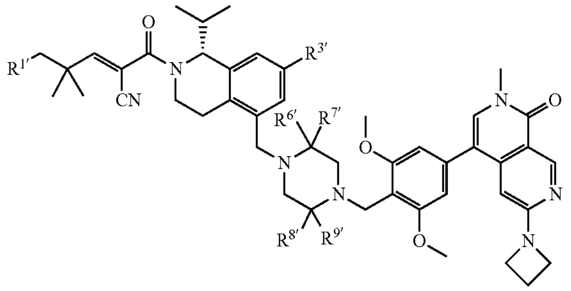

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined for a compound of formula (III).

In embodiments, the compound of formula (III), (IV), (V), (VI), (VII), (VIII), (IX) or (X) is a compound which has the structure as shown in Table 1, Table 3 or Table 5, i.e. the compound is one of compounds 1 to 14 (e.g. one of compounds 1 to 13).

In another aspect, the disclosure provides a DCAF16 conjugate that comprises a DCAF16 protein covalently bound (e.g. reversibly covalently bound) to a compound of formula (III), (IV), (V), (VI), (VII), (VIII), (IX) or (X) as described herein. In embodiments, the disclosure provides a DCAF16 conjugate that comprises a DCAF16 protein covalently bound (e.g. reversibly covalently bound) to a compound of formula (III), (IV), (V), (VI), (VII), (VIII), (IX) or (X) as described herein at a cysteine residue. In embodiments, the cysteine residue is at a position corresponding to residue 58, 100, 103, 119, 173, 177, 178, or 179 of SEQ ID NO: 1. In embodiments, the cysteine residue is at a position corresponding to residue 58, 173, 177, 178, or 179 of SEQ ID NO: 1. In embodiments, the cysteine residue is at a position corresponding to residue 173, 177, 178, or 179 of SEQ ID NO: 1. In embodiments, the cysteine residue is at a position corresponding to residue 177 or 179 of SEQ ID NO: 1. In embodiments, the cysteine residue is at a position corresponding to residue 58 of SEQ ID NO: 1. In embodiments, the cysteine residue is at a position corresponding to residue 58, 100, 103, or 119 of SEQ ID NO: 1. In embodiments, the cysteine residue is at a position corresponding to residue 100, 103, or 119 of SEQ ID NO: 1. In embodiments, the cysteine residue is at a position corresponding to residue 173 or 178 of SEQ ID NO: 1. In some embodiments, the compound of formula (III), (IV), (V), (VI), (VII), (VIII), (IX) or (X) as described herein is covalently bound (e.g. reversibly covalently bound) to DCAF16 residue C58, C100, C103, C119, C173, C177, C178, or C179 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C58, C173, C177, C178, or C179 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C173, C177, C178, or C179 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C177 or C179 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C58, C100, C103, or C119 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C100, C103, or C119 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C173 or C178 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C58 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C100 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C103 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C119 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C173 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C177 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C178 of SEQ ID NO: 1.

In embodiments, the DCAF16 protein comprises a sequence identity that is about 80%, 85%, 90%, 95%, or 99% to SEQ ID NO: 1. In such cases, the compound of formula (III), (IV), (V), (VI), (VII), (VIII), (IX) or (X) as described herein is covalently bound (e.g. reversibly covalently bound) to the DCAF16 protein comprising about 80%, 85%, 90%, 95%, or 99% sequence identity to SEQ ID NO: 1.

In embodiments, the cyanoacrylamide moiety of the compound of formula (III), (IV), (V), (VI), (VII), (VIII), (IX) or (X) as described herein forms a covalent bond (e.g. a reversible covalent bond) with the cysteine residue at a position corresponding to residue 58, 173, 177, 178, or 179 of SEQ ID NO: 1. In embodiments, the cyanoacrylamide moiety of the compound of formula (III), (IV), (V), (VI), (VII), (VIII), (IX) or (X) as described herein forms a covalent bond (e.g. a reversible covalent bond) with the cysteine residue at a position corresponding to residue 173, 177, 178, or 179 of SEQ ID NO: 1. In embodiments, the cyanoacrylamide moiety of the compound of formula (III), (IV), (V), (VI), (VII), (VIII), (IX) or (X) as described herein forms a covalent bond (e.g. a reversible covalent bond) with the cysteine residue at a position corresponding to residue 177 or 179 of SEQ ID NO: 1. In embodiments, the cyanoacrylamide moiety of the compound of formula (III), (IV), (V), (VI), (VII), (VIII), (IX) or (X) as described herein forms a covalent bond (e.g. a reversible covalent bond) with the cysteine residue at a position corresponding to residue 58, 100, 103, or 119 of SEQ ID NO: 1. In embodiments, the cyanoacrylamide moiety of the compound of formula (III), (IV), (V), (VI), (VII), (VIII), (IX) or (X) as described herein forms a covalent bond (e.g. a reversible covalent bond) with the cysteine residue at a position corresponding to residue 100, 103, or 119 of SEQ ID NO: 1. In embodiments, the cyanoacrylamide moiety of the compound of formula (III), (IV), (V), (VI), (VII), (VIII), (IX) or (X) as described herein forms a covalent bond (e.g. a reversible covalent bond) with the cysteine residue at a position corresponding to residue 173 or 178 of SEQ ID NO: 1. In embodiments, the cyanoacrylamide moiety of the compound of formula (III), (IV), (V), (VI), (VII), (VIII), (IX) or (X) as described herein forms a covalent bond (e.g. a reversible covalent bond) with the cysteine residue at a position corresponding to residue 58 of SEQ ID NO: 1.

In embodiments, the cyanoacrylamide moiety of the compound of formula (III), (IV), (V), (VI), (VII), (VIII), (IX) or (X) as described herein forms a covalent bond (e.g. a reversible covalent bond) with a cysteine residue (e.g. as described above) of DCAF16 comprising about 80%, 85%, 90%, 95%, or 99% sequence identity to SEQ ID NO: 1.

In embodiments, the compound of formula (III), (IV), (V), (VI), (VII), (VIII), (IX) or (X) is covalently bound (e.g. reversibly covalently bound) to DCAF16 via Michael addition. In embodiments, the compound of formula (III), (IV), (V), (VI), (VII), (VIII), (IX) or (X) is covalently bound (e.g. reversibly covalently bound) to the cysteine residue at a position corresponding to residue 58, 173, 177, 178, or 179 of SEQ ID NO: 1 via Michael addition. In embodiments, the compound of formula (III), (IV), (V), (VI), (VII), (VIII), (IX) or (X) is covalently bound (e.g. reversibly covalently bound) to the cysteine residue at a position corresponding to residue 173, 177, 178, or 179 of SEQ ID NO: 1 via Michael addition. In embodiments, the compound of formula (III), (IV), (V), (VI), (VII), (VIII), (IX) or (X) is covalently bound (e.g. reversibly covalently bound) to the cysteine residue at a position corresponding to residue 177 or 179 of SEQ ID NO: 1 via Michael addition. In embodiments, the compound of formula (III), (IV), (V), (VI), (VII), (VIII), (IX) or (X) is covalently bound (e.g. reversibly covalently bound) to the cysteine residue at a position corresponding to residue 58, 100, 103, or 119 of SEQ ID NO: 1 via Michael addition. In embodiments, the compound of formula (III), (IV), (V), (VI), (VII), (VIII), (IX) or (X) is covalently bound (e.g. reversibly covalently bound) to the cysteine residue at a position corresponding to residue 100, 103, or 119 of SEQ ID NO: 1 via Michael addition. In embodiments, the compound of formula (III), (IV), (V), (VI), (VII), (VIII), (IX) or (X) is covalently bound (e.g. reversibly covalently bound) to the cysteine residue at a position corresponding to residue 173 or 178 of SEQ ID NO: 1 via Michael addition. In embodiments, the compound of formula (III), (IV), (V), (VI), (VII), (VIII), (IX) or (X) is covalently bound (e.g. reversibly covalently bound) to the cysteine residue at a position corresponding to residue 58 of SEQ ID NO: 1 via Michael addition.

In embodiments, the compound of formula (III), (IV), (V), (VI), (VII), (VIII), (IX) or (X) is covalently bound (e.g. reversibly covalently bound) to the cysteine residue of DCAF16 comprising about 80%, 85%, 90%, 95%, or 99% sequence identity to SEQ ID NO: 1 via Michael addition.

In another aspect, the disclosure provides a method of treating and/or preventing a disease or condition comprising administering a compound of formula (III), (IV), (V), (VI), (VII), (VIII), (IX) or (X) to a human patient, wherein the compound of formula (III), (IV), (V), (VI), (VII), (Vill), (IX) or (X) forms in vivo a DCAF16 conjugate comprising a DCAF16 protein covalently bound (e.g. reversibly covalently bound) to the compound of formula (III), (IV), (V), (VI), (VII), (VIII), (IX) or (X).

In embodiments, the DCAF16 conjugate formed in vivo comprises a DCAF16 protein covalently bound (e.g. reversibly covalently bound) to a compound of formula (III), (IV), (V), (VI), (VII), (VIII), (IX) or (X) as described herein at a cysteine residue. In embodiments, the cysteine residue is at a position corresponding to residue 58, 100, 103, 119, 173, 177, 178, or 179 of SEQ ID NO: 1. In embodiments, the cysteine residue is at a position corresponding to residue 58, 173, 177, 178, or 179 of SEQ ID NO: 1. In embodiments, the cysteine residue is at a position corresponding to residue 173, 177, 178, or 179 of SEQ ID NO: 1. In embodiments, the cysteine residue is at a position corresponding to residue 177 or 179 of SEQ ID NO: 1. In embodiments, the cysteine residue is at a position corresponding to residue 58 of SEQ ID NO: 1. In embodiments, the cysteine residue is at a position corresponding to residue 58, 100, 103, or 119 of SEQ ID NO: 1. In embodiments, the cysteine residue is at a position corresponding to residue 100, 103, or 119 of SEQ ID NO: 1. In embodiments, the cysteine residue is at a position corresponding to residue 173 or 178 of SEQ ID NO: 1. In some embodiments, the compound of formula (III), (IV), (V), (VI), (VII), (VIII), (IX) or (X) as described herein is covalently bound (e.g. reversibly covalently bound) to DCAF16 residue C58, C100, C103, C119, C173, C177, C178, or C179 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C58, C173, C177, C178, or C179 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C173, C177, C178, or C179 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C177 or C179 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C58, C100, C103, or C119 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C100, C103, or C119 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C173 or C178 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C58 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C100 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C103 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C119 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C173 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C177 of SEQ ID NO: 1. In embodiments, the compound of formula (III), (IV), (V), (VI), (VII), (VIII), (IX) or (X) as described herein is covalently bound (e.g. reversibly covalently bound) to DCAF16 residue C178 of SEQ ID NO: 1.

In embodiments, the DCAF16 protein comprises a sequence identity that is about 80%, 85%, 90%, 95%, or 99% to SEQ ID NO: 1. In such cases, the compound of formula (III), (IV), (V), (VI), (VII), (VIII), (IX) or (X) as described herein is covalently bound (e.g. reversibly covalently bound) to the DCAF16 protein comprising about 80%, 85%, 90%, 95%, or 99% sequence identity to SEQ ID NO: 1.

In embodiments, the cyanoacrylamide moiety of the compound of formula (III), (IV), (V), (VI), (VII), (VIII), (IX) or (X) as described herein forms a covalent bond (e.g. a reversible covalent bond) with the cysteine residue at a position corresponding to residue 58, 173, 177, 178, or 179 of SEQ ID NO: 1. In embodiments, the cyanoacrylamide moiety of the compound of formula (III), (IV), (V), (VI), (VII), (VIII), (IX) or (X) as described herein forms a covalent bond (e.g. a reversible covalent bond) with the cysteine residue at a position corresponding to residue 173, 177, 178, or 179 of SEQ ID NO: 1. In embodiments, the cyanoacrylamide moiety of the compound of formula (III), (IV), (V), (VI), (VII), (VIII), (IX) or (X) as described herein forms a covalent bond (e.g. a reversible covalent bond) with the cysteine residue at a position corresponding to residue 177 or 179 of SEQ ID NO: 1. In embodiments, the cyanoacrylamide moiety of the compound of formula (III), (IV), (V), (VI), (VII), (VIII), (IX) or (X) as described herein forms a covalent bond (e.g. a reversible covalent bond) with the cysteine residue at a position corresponding to residue 58, 100, 103, or 119 of SEQ ID NO: 1. In embodiments, the cyanoacrylamide moiety of the compound of formula (III), (IV), (V), (VI), (VII), (VIII), (IX) or (X) as described herein forms a covalent bond (e.g. a reversible covalent bond) with the cysteine residue at a position corresponding to residue 100, 103, or 119 of SEQ ID NO: 1. In embodiments, the cyanoacrylamide moiety of the compound of formula (III), (IV), (V), (VI), (VII), (VIII), (IX) or (X) as described herein forms a covalent bond (e.g. a reversible covalent bond) with the cysteine residue at a position corresponding to residue 173 or 178 of SEQ ID NO: 1. In embodiments, the cyanoacrylamide moiety of the compound of formula (III), (IV), (V), (VI), (VII), (VIII), (IX) or (X) as described herein forms a covalent bond (e.g. a reversible covalent bond) with the cysteine residue at a position corresponding to residue 58 of SEQ ID NO: 1.

In embodiments, the cyanoacrylamide moiety of the compound of formula (III), (IV), (V), (VI), (VII), (VIII), (IX) or (X) as described herein forms a covalent bond (e.g. a reversible covalent bond) with a cysteine residue (e.g. as described above) of DCAF16 comprising about 80%, 85%, 90%, 95%, or 99% sequence identity to SEQ ID NO: 1.

In embodiments, this method of treating and/or preventing a disease or condition can be used to treat and/or prevent the diseases and conditions mentioned herein with respect to the compounds of formula (III), (IV), (V), (VI), (VII), (VIII), (IX) or (X), and the compounds of formula (III), (IV), (V), (VI), (VII), (VIII), (IX) or (X) are administered in the same way as mentioned elsewhere herein.

Also disclosed herein is a pharmaceutical composition comprising a compound of formula (I), (II), (III), (IV), (V), (VI), (VII), (VIII), (IX) or (X) as defined herein, together with a pharmaceutically acceptable carrier, optionally wherein the compound of formula (I), (II), (III), (IV), (V), (VI), (VII), (VIII), (IX) or (X) is present in the composition as a pharmaceutically acceptable salt, solvate or derivative.

In another aspect, the present disclosure provides a pharmaceutical composition comprising a compound of formula (III), (IV), (V), (VI), (VII), (VIII), (IX) or (X) as defined herein, together with a pharmaceutically acceptable carrier, optionally wherein the compound of formula (I), (II), (III), (IV), (V), (VI), (VII), (VIII), (IX) or (X) is present in the composition as a pharmaceutically acceptable salt, solvate or derivative.

Also disclosed herein is a compound of formula (I), (II), (III), (IV), (V), (VI), (VII), (VIII), (IX) or (X) as defined herein, or a pharmaceutical composition comprising a compound of formula (III), (IV), (V), (VI), (VII), (VIII), (IX) or (X) as defined herein, for use in medicine.

Also disclosed herein is a compound of formula (I), (II), (III), (IV), (V), (VI), (VII), (VIII), (IX) or (X) as defined herein, or a pharmaceutical composition comprising a compound of formula (III), (IV), (V), (VI), (VII), (VIII), (IX) or (X) as defined herein, for use in medicine, wherein the use comprises the treatment and/or prevention of any disease or condition which is associated with and/or is caused by an abnormal level of BRD9 activity.

Also disclosed herein is a compound of formula (I), (II), (III), (IV), (V), (VI), (VII), (VIII), (IX) or (X) as defined herein, or a pharmaceutical composition comprising a compound of formula (III), (IV), (V), (VI), (VII), (VIII), (IX) or (X) as defined herein, for use in the treatment and/or prevention of cancer.

In another aspect, the present disclosure provides a compound of formula (III), (IV), (V), (VI), (VII), (VIII), (IX) or (X) as defined herein, or a pharmaceutical composition comprising a compound of formula (III), (IV), (V), (VI), (VII), (VIII), (IX) or (X) as defined herein, for use in medicine.

In embodiments, the present disclosure provides a compound of formula (III), (IV), (V), (VI), (VII), (VIII), (IX) or (X) as defined herein, or a pharmaceutical composition comprising a compound of formula (III), (IV), (V), (VI), (VII), (VIII), (IX) or (X) as defined herein, for use in medicine, wherein the use comprises the treatment and/or prevention of any disease or condition which is associated with and/or is caused by an abnormal level of BRD9 activity.

In embodiments, the present disclosure provides a compound of formula (III), (IV), (V), (VI), (VII), (VIII), (IX) or (X) as defined herein, or a pharmaceutical composition comprising a compound of formula (III), (IV), (V), (VI), (VII), (VIII), (IX) or (X) as defined herein, for use in the treatment and/or prevention of cancer.

Also disclosed herein is a method of selectively degrading and/or increasing proteolysis of BRD9 in a cell or a subject in need thereof, the method comprising contacting and/or treating the cell with a compound of formula (I), (II), (III), (IV), (V), (VI), (VII), (VIII), (IX) or (X) as defined herein or a pharmaceutical composition comprising a compound of formula (III), (IV), (V), (VI), (VII), (VIII), (IX) or (X) as defined herein.

In another aspect, the present disclosure provides a method of selectively degrading and/or increasing proteolysis of BRD9 in a cell or a subject in need thereof, the method comprising contacting and/or treating the cell with a compound of formula (III), (IV), (V), (VI), (VII), (VIII), (IX) or (X) as defined herein or a pharmaceutical composition comprising a compound of formula (III), (IV), (V), (VI), (VII), (VIII), (IX) or (X) as defined herein.

Also disclosed herein are methods of making a compound of formula (I), (II), (III), (IV), (V), (VI), (VII), (VIII), (IX) or (X) as defined herein.

In another aspect, the present disclosure provides a method of making a compound of formula (III), (IV), (V), (VI), (VII), (VIII), (IX) or (X) as defined herein.

Also disclosed herein is a compound library comprising a plurality of compounds of formula (I), (II), (III), (IV), (V), (VI), (VII), (VIII), (IX) or (X).

In another aspect, the present disclosure provides a compound library comprising a plurality of compounds of formula (III), (IV), (V), (VI), (VII), (VIII), (IX) or (X).

It will be appreciated that the compounds of the present disclosure may exist in different stereoisomeric forms. The present disclosure includes within its scope the use of all stereoisomeric forms, or the use of a mixture of stereoisomers of the compounds, By way of example, where the compound comprises one or more chiral centres, the present disclosure encompasses each individual enantiomer of the compound as well as mixtures of enantiomers including racemic mixtures of such enantiomers. By way of further example, where the compound comprises two or more chiral centres, the present disclosure encompasses each individual diastereomer of the compound, as well as mixtures of the various diastereomers.

Unless otherwise indicated, the various structures shown herein encompass all isomeric (e.g. enantiomeric, diastereomeric, and geometric (or conformational) forms of the structure). For example, the present disclosure embraces the R and S configurations for each asymmetric centre, and Z and E double bond isomers. A wavy bond from a double bond encompasses the Z or E double bond isomer, and any mixture thereof. For example, (I)

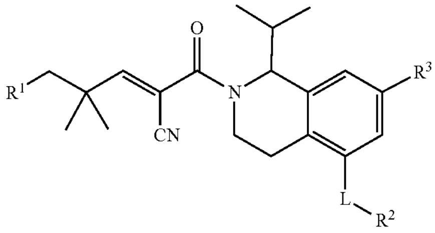

encompasses both of the following structures, or any mixture thereof:

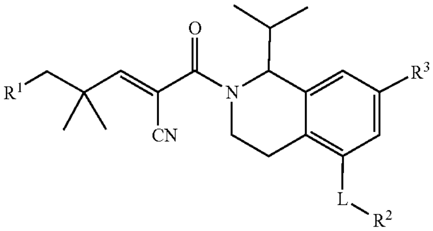

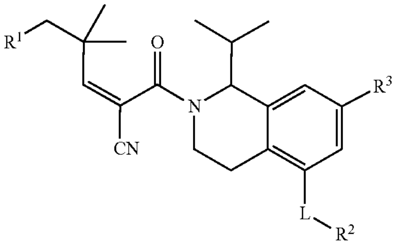

Therefore, single stereochemical isomers as well as enantiomeric, diastereomeric, and geometric (or conformational) mixtures of the present compounds are to be understood to be within the scope of the present disclosure. Additionally, unless otherwise stated, where present, all tautomeric forms of the compounds described herein are to be understood to be within the scope of the present disclosure.

It should be understood that throughout this specification, the terms "comprise", "comprising" and/or "comprises" is/are used to denote that aspects, embodiments and examples of this disclosure "comprise" a particular feature or features. It should be understood that this/these terms may also encompass aspects, embodiments and/or examples which "consist essentially of" or "consist of" the relevant feature or features.

The disclosure also includes various deuterated forms of the compounds disclosed herein, or of any of the formulae disclosed herein, including formulae (I), (II), (III), (IV), (V), (VI), (VII), (VIII), (IX) or (X) and corresponding subgeneric formulae defined herein (e.g. formulae (III), (IV), (V), (VI), (VII), (VIII), (IX) or (X) and corresponding subgeneric formulae defined herein), respectively, or a pharmaceutically acceptable salt, solvate or derivative thereof and/or a corresponding tautomer form thereof (including subgeneric formulas, as defined above) of the present disclosure. Each available hydrogen atom attached to a carbon atom may be independently replaced with a deuterium atom. A person of ordinary skill in the art will know how to synthesize deuterated forms of the compounds of any of the formulae disclosed herein, including formulae (I), (II), (III), (IV), (V), (VI), (VII), (VIII), (IX) or (X) and corresponding subgeneric formulae defined herein (e.g. formulae (III), (IV), (V), (VI), (VII), (VIII), (IX) or (X) and corresponding subgeneric formulae defined herein), respectively, or a pharmaceutically acceptable salt, solvate or derivative thereof and/or a corresponding tautomer form thereof (including subgeneric formulae, as defined above) of the present disclosure. For example, deuterated materials, such as alkyl groups may be prepared by conventional techniques (see for example: methyl-$d_3$-amine available from Aldrich Chemical Co., Milwaukee, WI, Cat. No. 489,689-2).

The disclosure also includes isotopically-labelled compounds which are identical to those recited in any of the formulae disclosed herein, including formulae (I), (II), (III), (IV), (V), (VI), (VII), (VIII), (IX) or (X) and corresponding subgeneric formulae defined herein (e.g. formulae (III), (IV), (V), (VI), (VII), (VIII), (IX) or (X) and corresponding subgeneric formulae defined herein), respectively, or a pharmaceutically acceptable salt, solvate or derivative thereof and/or a corresponding tautomer form thereof (including subgeneric formulae, as defined above) of the present disclosure but for the fact that one or more atoms are replaced by an atom having an atomic mass or mass number different from the atomic mass or mass number most commonly found in nature. Examples of isotopes that can be incorporated into compounds of the disclosure include isotopes of hydrogen, carbon, nitrogen, oxygen, fluorine, iodine and chlorine such as $^{3}H$, $^{11}C$, $^{14}C$, $^{18}F$, $^{123}I$ or $^{125}I$. Compounds of the present disclosure and pharmaceutically acceptable salts, solvates or derivatives of said compounds that contain the aforementioned isotopes and/or other isotopes of other atoms are within the scope of the present disclosure. Isotopically labelled compounds of the present disclosure, for example those into which radioactive isotopes such as $^{3}H$ or $^{14}C$ have been incorporated, are useful in drug and/or substrate tissue distribution assays. Tritiated, i.e. $^{3}H$, and carbon-14, i.e. $^{14}C$, isotopes are particularly preferred for their ease of preparation and detectability. $^{11}C$ and $^{18}F$ isotopes are particularly useful in PET (positron emission tomography).

Degradation may be determined by measuring the amount of a BRD9 target protein in the presence of a compound of formula (I), (II), (III), (IV), (V), (VI), (VII), (VIII), (IX) or (X) as described herein and/or comparing this to the amount of the BRD9 target protein observed in the absence of the compound of formula (I), (II), (III), (IV), (V), (VI), (VII), (VIII), (IX) or (X). For example, the amount of BRD9 target protein in a cell that has been contacted and/or treated with a compound of formula (I), (II), (III), (IV), (V), (VI), (VII), (VIII), (IX) or (X) as described herein may be determined. This amount may be compared to the amount of BRD9 target protein in a cell that has not been contacted and/or treated with the compound of formula (I), (II), (III), (IV), (V), (VI), (VII), (VIII), (IX) or (X) (e.g. as a control). If the amount of BRD9 target protein is decreased in the cell contacted and/or treated with the compound of formula (I), (II), (III), (IV), (V), (VI), (VII), (VIII), (IX) or (X), the compound of formula (I), (II), (III), (IV), (V), (VI), (VII), (VIII), (IX) or (X) may be considered as facilitating and/or promoting the degradation and/or proteolysis of the BRD9 target protein.

The amount of the BRD9 target protein can be determined using methods known in the art, for example, by performing immunoblotting assays, Western blot analysis and/or ELISA with cells that have been contacted and/or treated with a compound of formula (I), (II), (III), (IV), (V), (VI), (VII), (VIII), (IX) or (X).

Selective degradation and/or increased proteolysis may be considered to have occurred if at least a 10% decrease in the amount of a BRD9 target protein is observed compared to the control, for example, 20%, 30%, 40%, 50%, 60%, 70%, 80%, 90% or 100% following administration of the compound of formula (I), (II), (III), (IV), (V), (VI), (VII), (VIII), (IX) or (X) to the cell.

For example, selective degradation and/or increased proteolysis may be considered to have occurred if at least a 10% decrease in the amount of a BRD9 target protein is observed, (e.g. at least 20%, 30%, 40%, 50%, 60%, 70%, 80%, 90% or 100% decrease) within 4 hours or more (e.g. 4 hours, 8 hours, 12 hours, 24 hours, 30 hours, 36 hours, 42 hours, 48 hours, 54 hours, 60 hours, 66 hours and 72 hours) following administration of the compound of formula (I), (II), (III), (IV), (V), (VI), (VII), (VIII), (IX) or (X) to the cell. The compound of formula (I), (II), (III), (IV), (V), (VI), (VII), (VIII), (IX) or (X) may be administered at any concentration, e.g. a concentration between 0.01 nM to 10 μM, such as 0.01 nM, 0.1 nM, 1 nM, 10 nM, 100 nM, 1 μM, and 10 μM. In some instances, an increase of at least 30%, 40%, 50%, 60%, 70%, 80%, 90%, or approximately 100% in the degradation of the BRD9 target protein is observed following administration of the compound of formula (I), (II), (III), (IV), (V), (VI), (VII), (VIII), (IX) or (X) at a concentration of approximately 100 nM (e.g. following an incubation period of approximately 8 hours).

One measure of degrader activity of the compounds of formula (I), (II), (III), (IV), (V), (VI), (VII), (VIII), (IX) or (X) is the $DC_{50}$ value. As used herein, $DC_{50}$ is the concentration required to reach 50% of the maximal degradation of the BRD9 target protein. The compounds of formula (I), (II), (III), (IV), (V), (VI), (VII), (VIII), (IX) or (X) described herein may exhibit a $DC_{50}$ of less than or equal to 10000 nM, less than or equal to 1000 nM, less than or equal to 500 nM, less than or equal to 100 nM or less than or equal to 75 nM. In some cases, the compounds of formula (I), (II), (III), (IV), (V), (VI), (VII), (VIII), (IX) or (X) exhibit a $DC_{50}$ less than or equal to 50 nM, less than or equal to 25 nM, or less than or equal to 10 nM.

Another measure of the degrader activity of the compounds of formula (I), (II), (III), (IV), (V), (VI), (VII), (VIII), (IX) or (X) is the $D_{max}$ value. As used herein, $D_{max}$ represents the maximal percentage of BRD9 target protein degradation. The compounds of formula (I), (II), (III), (IV), (V), (VI), (VII), (VIII), (IX) or (X) described herein may exhibit a $D_{max}$ of at least 50%, at least 60%, at least 70%, at least 80%, at least 90%, at least 95% or about 100%.

Yet another measure of the efficacy of the described compounds of formula (I), (II), (III), (IV), (V), (VI), (VII), (VIII), (IX) or (X) may be their effect on cell viability and/or their $IC_{50}$ value. For example, an anti-proliferative effect of a compound of formula (I), (II), (III), (IV), (V), (VI), (VII), (VIII), (IX) or (X) as described herein may be assessed in a cell viability assay to provide an $IC_{50}$ value. As used herein, the $IC_{50}$ value represents the concentration at which 50% cell viability was observed in the cell viability assay (following administration of a compound of formula (I), (II), (III), (IV), (V), (VI), (VII), (VIII), (IX) or (X) as described herein). In terms of cell viability, the compounds of formula (I), (II), (III), (IV), (V), (VI), (VII), (VIII), (IX) or (X) described herein may exhibit an $IC_{50}$ of less than 1000 nM, less than 500 nM, less than 100 nM, less than 50 nM, less than 25 nM, less than 20 nM, or less than 10 nM. In some cases, the compounds of formula (I), (II), (III), (IV), (V), (VI), (VII), (VIII), (IX) or (X) described herein may exhibit an IC50 value of less than 5 nM.

Disclosed herein is a pharmaceutical composition comprising the compounds of formula (I), (II), (III), (IV), (V), (VI), (VII), (VIII), (IX) or (X) described herein. In such compositions, the compound of formula (I), (II), (III), (IV), (V), (VI), (VII), (VIII), (IX) or (X) may be suitably formulated such that it can be introduced into the environment of the cell by a means that allows for a sufficient portion of the molecule to enter the cell to induce degradation of the BRD9 target protein.

Accordingly, there is disclosed herein a pharmaceutical composition comprising a compound of formula (I), (II), (III), (IV), (V), (VI), (VII), (VIII), (IX) or (X) as described herein together with a pharmaceutically acceptable carrier. Optionally the compound of formula (I), (II), (III), (IV), (V), (VI), (VII), (VIII), (IX) or (X) is present in the pharmaceutical composition as a pharmaceutically acceptable salt, solvate or derivative.

Pharmaceutically acceptable carriers are well known to those skilled in the art and include, but are not limited to, phosphate buffer solutions and/or saline. Pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

In addition to the aforementioned carrier ingredients the pharmaceutical compositions described above may alternatively or additionally include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutical compositions may be present in any formulation typical for the administration of a pharmaceutical compound to a subject. Representative examples of typical formulations include, but are not limited to, capsules, granules, tablets, powders, lozenges, suppositories, pessaries, nasal sprays, gels, creams, ointments, sterile aqueous preparations, sterile solutions, aerosols, implants etc.

A pharmaceutical composition is formulated to be compatible with its intended route of administration. Examples of routes of administration include parenteral, e.g., intravenous, intradermal, subcutaneous, oral, transdermal, topical, transmucosal, vaginal and rectal administration. The pharmaceutical composition may formulated as a pre-loaded syringe. The pharmaceutical compositions may include those suitable for oral, parenteral (including subcutaneous, intradermal, intramuscular and intravenous), topical (including dermal, buccal and sublingual), rectal, nasal and pulmonary administration e.g., by inhalation. The composition may, where appropriate, be conveniently presented in discrete dosage units and may be prepared by any of the methods well known in the art of pharmacy. Methods typically include the step of bringing into association an active compound with liquid carriers or finely divided solid carriers or both and then, if necessary, shaping the product into the desired formulation.

Pharmaceutical compositions suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. The compounds of formula (I), (II), (III), (IV), (V), (VI), (VII), (VIII), (IX) or (X) may also be formulated as dispersible granules, which may for example be suspended in water before administration, or sprinkled on food. The granules may be packaged, e.g., in a sachet. Compositions suitable for oral administration wherein the carrier is a liquid may be presented as a solution or a suspension in an aqueous or non-aqueous liquid, or as an oil-in-water liquid emulsion. Compositions for oral administration include controlled release dosage forms, e.g., tablets wherein an active compound is formulated in an appropriate release-controlling matrix, or is coated with a suitable release-controlling film. Pharmaceutical compositions suitable for parenteral administration include sterile solutions or suspensions of an active compound in aqueous or oleaginous vehicles. Injectable preparations may be adapted for bolus injection or continuous infusion. Such preparations are conveniently presented in unit dose or multi-dose containers, which are sealed after introduction of the formulation until required for use. Alternatively, the compound of formula (I), (II), (III), (IV), (V), (VI), (VII), (VIII), (IX) or (X) may be in powder form, which is constituted with a suitable vehicle, such as sterile, pyrogen-free water, before use.

The pharmaceutical composition may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins.

Pharmaceutical compositions suitable for topical formulation may be provided for example as gels, creams or ointments.

The compound of formula (I), (II), (III), (IV), (V), (VI), (VII), (VIII), (IX) or (X) described herein may be present in the pharmaceutical compositions as a pharmaceutically and/or physiologically acceptable salt, solvate or derivative.

As used herein, the term "pharmaceutically acceptable salt" refers to those salts, which are generally considered suitable for use in medicine (including in a veterinary context). For example, pharmaceutically acceptable salts may be those which can be contacted with the tissues of a mammalian subject (e.g. humans) without undue toxicity, irritation, allergic response or the like. By way of further example of suitable pharmaceutically acceptable salts, S. M. Berge et al., describe pharmaceutically acceptable salts in detail in J. Pharmaceutical Sciences, 1977, 66, 1-19, the entire contents of which are incorporated herein by reference.

Representative examples of pharmaceutically and/or physiologically acceptable salts of the compounds of the disclosure may include, but are not limited to, acid addition salts formed with organic carboxylic acids such as acetic, lactic, tartaric, maleic, citric, pyruvic, oxalic, malonic, fumaric, oxaloacetic, isethionic, lactobionic and succinic acids; organic sulfonic acids such as methanesulfonic, ethanesulfonic, benzenesulfonic and p-toluenesulfonic acids and inorganic acids such as hydrochloric, hydrobromic, sulfuric, perchloric, phosphoric and sulfamic acids. Other pharmaceutically acceptable salts include (but are not limited to) adipate, alginate, ascorbate, aspartate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, 2-naphthalenesulfonate, nicotinate, nitrate, oleate, oxalate, palmitate, pamoate, pectinate, persulfate, 3-phenylpropionate, pivalate, propionate, stearate, thiocyanate, undecanoate, valerate salts, and the like.

In some examples, salts that may be derived from appropriate bases include alkali metal, alkaline earth metal, ammonium and $N^+(C_{1-4}alkyl)_4$ salts. Representative alkali or alkaline earth metal salts include, but are not limited to, sodium, lithium, potassium, calcium, magnesium, and the like. Further pharmaceutically acceptable salts may include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Pharmaceutically and/or physiologically functional derivatives of compounds of the present disclosure are derivatives, which may be converted in the body into the parent compound. Such pharmaceutically and/or physiologically functional derivatives may also be referred to as "pro-drugs" or "bioprecursors". Pharmaceutically and/or physiologically functional derivatives of compounds of the present disclosure may include hydrolysable esters or amides, particularly esters, in vivo.

It may be convenient or desirable to prepare, purify, and/or handle a corresponding pharmaceutically and/or physiologically acceptable solvate of the compounds described herein, which may be used in the any one of the uses/methods described. The term solvate is used herein to refer to a complex of solute, such as a compound or salt of the compound, and a solvent. If the solvent is water, the solvate may be termed a hydrate, for example a monohydrate, di-hydrate, tri-hydrate etc, depending on the number of water molecules present per molecule of substrate.

The compounds of formula (I), (II), (III), (IV), (V), (VI), (VII), (VIII), (IX) or (X) of the present disclosure may modulate, facilitate and/or promote proteasomal degradation of a BRD9 target protein. As such, there is provided a method of selectively degrading and/or increasing proteolysis of a BRD9 target protein in a cell, the method comprising contacting and/or treating the cell with a compound of formula (I), (II), (III), (IV), (V), (VI), (VII), (VIII), (IX) or (X) or a pharmaceutical composition comprising a compound of formula (I), (II), (III), (IV), (V), (VI), (VII), (VIII), (IX) or (X) as described herein. The method may be carried out in vivo or in vitro.

In particular, there is provided a method of selectively degrading and/or increasing proteolysis of a BRD9 target protein in a subject in need thereof, the method comprising administering to the subject a therapeutically effective amount of a compound of formula (I), (II), (III), (IV), (V), (VI), (VII), (VIII), (IX) or (X) or a pharmaceutical composition comprising a compound of formula (I), (II), (III), (IV), (V), (VI), (VII), (VIII), (IX) or (X) of the present disclosure.

As such, the compound of (I), (II), (III), (IV), (V), (VI), (VII), (VIII), (IX) or (X) (or a pharmaceutical composition comprising a compound of formula (I), (II), (III), (IV), (V), (VI), (VII), (VIII), (IX) or (X)) of the present disclosure may find application in medicine and/or therapy. Specifically, the compound of formula (I), (II), (III), (IV), (V), (VI), (VII), (VIII), (IX) or (X) (or a pharmaceutical composition comprising a compound of formula (I), (II), (III), (IV), (V), (VI), (VII), (VIII), (IX) or (X)) of the present disclosure may find use in the treatment and/or prevention of any disease or condition, which is modulated through the BRD9 target protein. For example, the compounds of formula (I), (II), (III), (IV), (V), (VI), (VII), (VIII), (IX) or (X) of the present disclosure may be useful in the treatment of any disease, which is modulated through the BRD9 target protein by lowering the level of that protein in the cell, e.g. cell of a subject. Reduction of BRD9 target protein levels in a cell following administration of a compound of formula (I), (II), (III), (IV), (V), (VI), (VII), (VIII), (IX) or (X) of the present disclosure wherein activity of the selected BRD9 protein is implicated in a disease state or a disorder, then it is to be understood that the compound of formula (I), (II), (III), (IV), (V), (VI), (VII), (VIII), (IX) or (X) is useful in the treatment of that disease.

There is further provided the use of the compounds of formula (I), (II), (III), (IV), (V), (VI), (VII), (VIII), (IX) or (X) (or a pharmaceutical composition comprising a compound of formula (I), (II), (III), (IV), (V), (VI), (VII), (VIII), (IX) or (X)) as described herein in the manufacture of a medicament for the treatment and/or prevention of any disease or condition, which is modulated through the BRD9 target protein.

Diseases and/or conditions that may be treated and/or prevented by the compounds of formula (I), (II), (III), (IV), (V), (VI), (VII), (VIII), (IX) or (X) (or a pharmaceutical composition comprising a compound of formula (I), (II), (III), (IV), (V), (VI), (VII), (VIII), (IX) or (X)) of the disclosure include any disease, which is associated with and/or is caused by an abnormal level of BRD9 protein activity.

Such diseases and conditions include those whose pathology is related at least in part to an abnormal (e.g. elevated) level of a BRD9 protein and/or the overexpression of a BRD9 protein. For example, the compounds of formula (I), (II), (III), (IV), (V), (VI), (VII), (VIII), (IX) or (X) may find use in the treatment and/or prevention of diseases where an elevated level of a BRD9 protein is observed in a subject suffering from the disease. In other examples, the diseases and/or conditions may be those whose pathology is related at least in part to inappropriate BRD9 protein expression (e.g., expression at the wrong time and/or in the wrong cell), or excessive BRD9 protein expression.

Accordingly, there is provided a method of treating and/or preventing a disease or condition, which is associated with and/or is caused by an abnormal level of BRD9 protein activity, which comprises administering a therapeutically effective amount of a compound of formula (I), (II), (III), (IV), (V), (VI), (VII), (VIII), (IX) or (X) as described herein.

Representative examples of the diseases and/or conditions that may be treated and/or prevented by the use of the described compounds of formula (I), (II), (III), (IV), (V), (VI), (VII), (VIII), (IX) or (X) (or a pharmaceutical composition comprising a compound of formula (I), (II), (III), (IV), (V), (VI), (VII), (VIII), (IX) or (X)) include (but are not limited to) cancer, and treatment to control the function of stem cells.

(i) Representative examples of cancers that may be treated and/or prevented using the described compounds of formula (I), (II), (III), (IV), (V), (VI), (VII), (VIII), (IX) or (X) include, but are not limited to haematological tumours, such as acute myeloid leukaemia (AML), multiple myeloma (MM), chronic lymphocytic leukaemia (CLL) and acute lymphocytic leukaemia (ALL); and solid tumours, including sarcomas, melanoma, and liver, lung, colorectal, gastric, pancreatic and prostate cancer.

In specific examples, the cancer is any one selected from the group consisting of hematopoietic malignancies or haematological tumours (including but not limited to AML, MM) and solid tumours including but not limited to sarcomas, lung, liver, colorectal, colon, gastric, brain, thyroid, pancreatic, breast, ovary and prostate cancer.

In one embodiment, the haematological tumour is myelodysplastic syndrome (MDS).

In one embodiment, the solid tumour is glioblastoma.

Other particular examples of cancers that may be treated by a targeted protein degradation of BRD9 may include cancers that harbour SMARCB1 abnormalities, for example SMARCB1-deficient cancers, such as malignant rhabdoid tumours and several specific types of sarcoma, as well as leukaemia such as acute myeloid leukaemia (AML). As used herein, the term "patient" or "subject" is used to describe an animal, such as a mammal (e.g. a human or a domesticated animal), to whom treatment, including prophylactic treatment, with the compositions according to the present disclosure is provided. For treatment of those infections, conditions or disease states which are specific to a specific animal such as a human patient, the term patient refers to that specific animal, including a domesticated animal such as a dog or cat or a farm animal such as a horse, cow, sheep, etc. In general, in the present disclosure, the term patient refers to a human patient unless stated or implied from the context of the use of the term.

Also disclosed herein is a method of making a compound of formula (III) (e.g. a compound of formula (IV), (V), (VI), (VII), (VIII), (IX) or (X)).

The method of making the compound of formula (I) may comprise the step of reacting a compound of formula (XI) (or a salt thereof) with a compound of formula (XII) to provide a compound of formula (I).

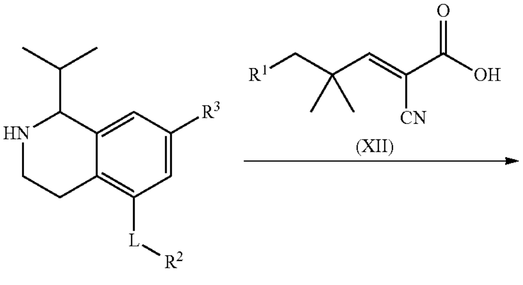

(XII)

(XI)

-continued

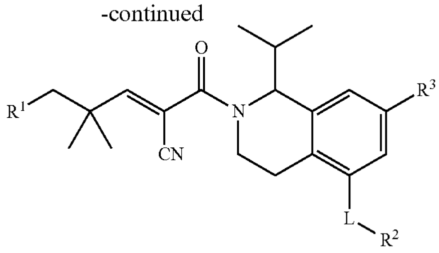

(I)

Alternatively, the method of making the compound of formula (I) may comprise the step of reacting a compound of formula (XIII) with a compound of formula (XIV) to provide a compound of formula (I).

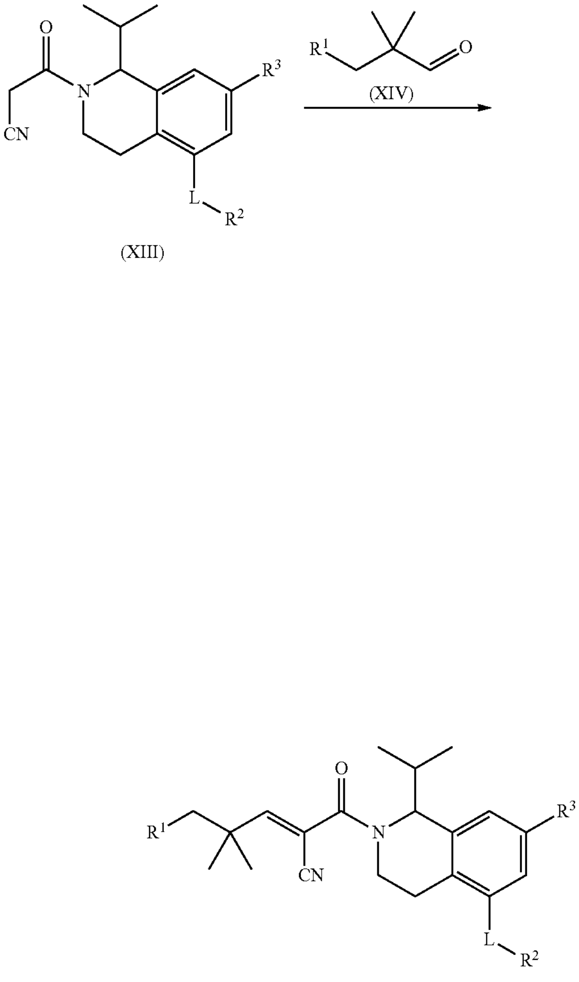

(XIII)

(XIV)

(I)

Alternatively, the method of making the compound of formula (I) may comprise the steps of:

a) reacting a compound of formula (XI) with 3-(3,5-dimethyl-1H-pyrazol-1-yl)-3-oxopropanenitrile to provide a compound of formula (XIII); and b) reacting a compound of formula (XIII) with a compound of formula (XIV) to provide a compound of formula (I).

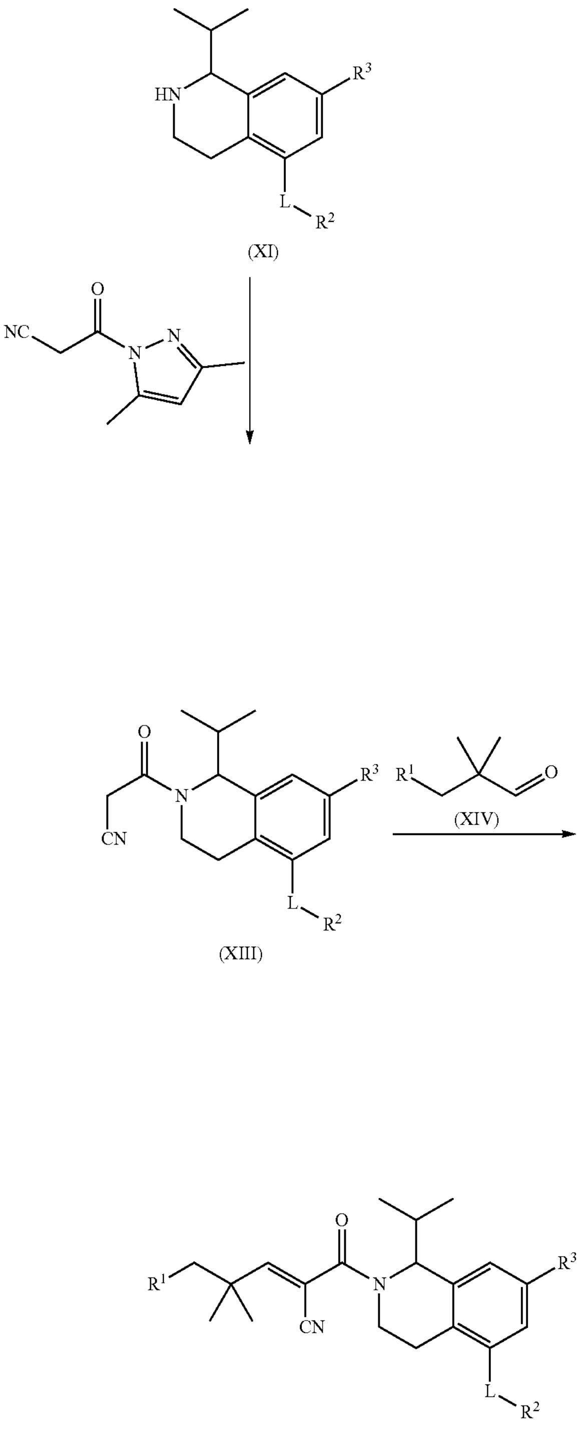

(XI)

(XIII)

(XIV)

(I)

In another aspect, the present disclosure provides a method of making a compound of formula (III) (e.g. a compound of formula (IV), (V), (VI), (VII), (VIII), (IX) or (X)).

The method of making the compound of formula (III) may comprise the step of reacting a compound of formula (XV) with a compound of formula (XVI) to provide a compound of formula (III).

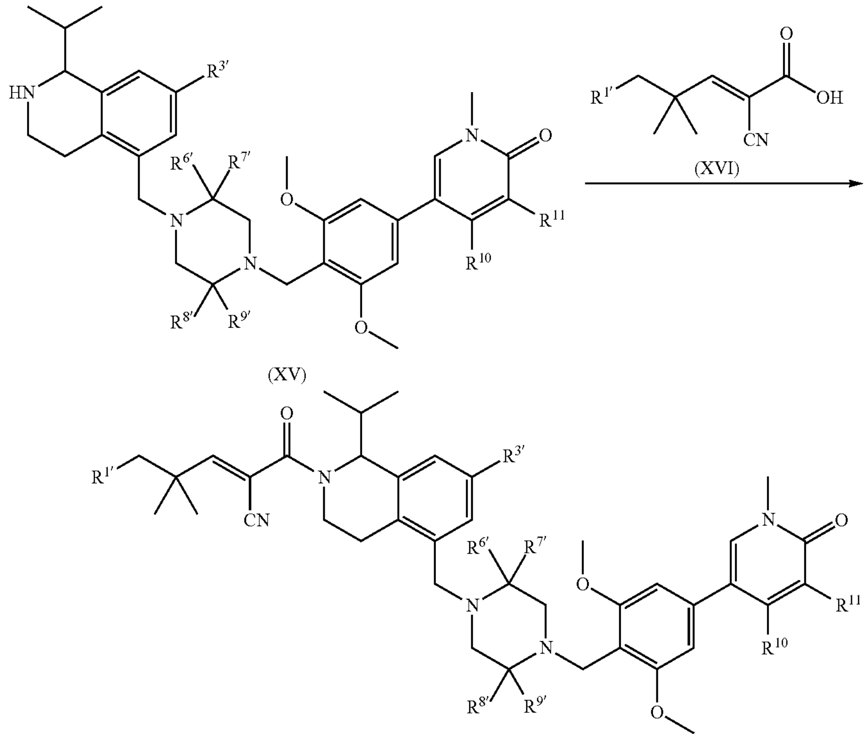
(XV)
(XVI)
(III)
Alternatively, the method of making the compound of formula (I) may comprise the step of reacting a compound of formula (XVII) with a compound of formula (XVIII) to provide a compound of formula (III).
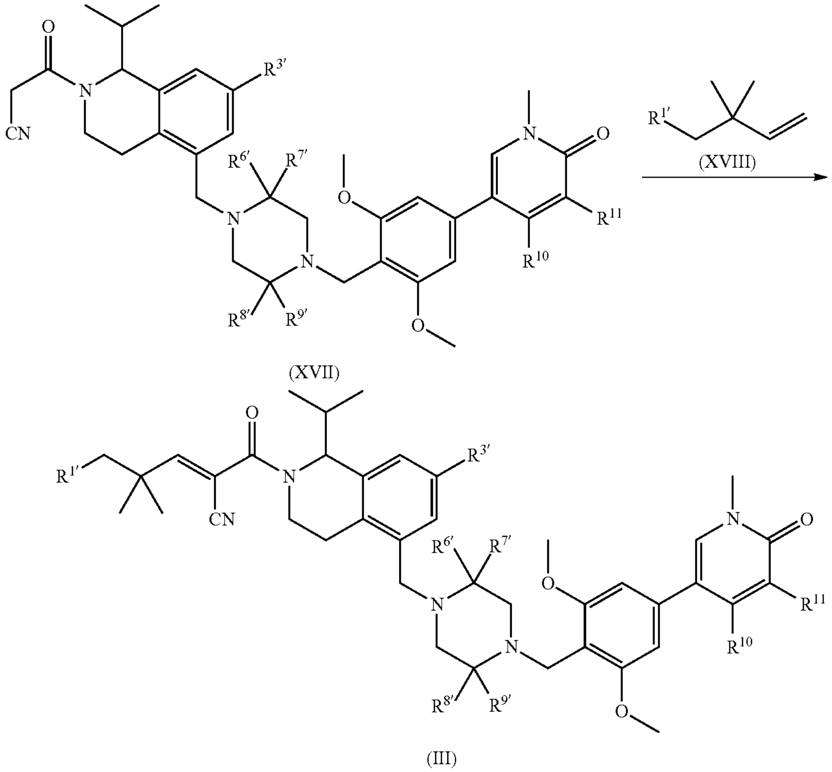
(XVII)
(XVIII)
(III)

Alternatively, the method of making the compound of formula (I) may comprise the steps of:

a) reacting a compound of formula (XV) with 3-(3,5-dimethyl-1H-pyrazol-1-yl)-3-oxopropanenitrile to provide a compound of formula (XVII); and b) reacting a compound of formula (XVII) with a compound of formula (XVIII) to provide a compound of formula (III).

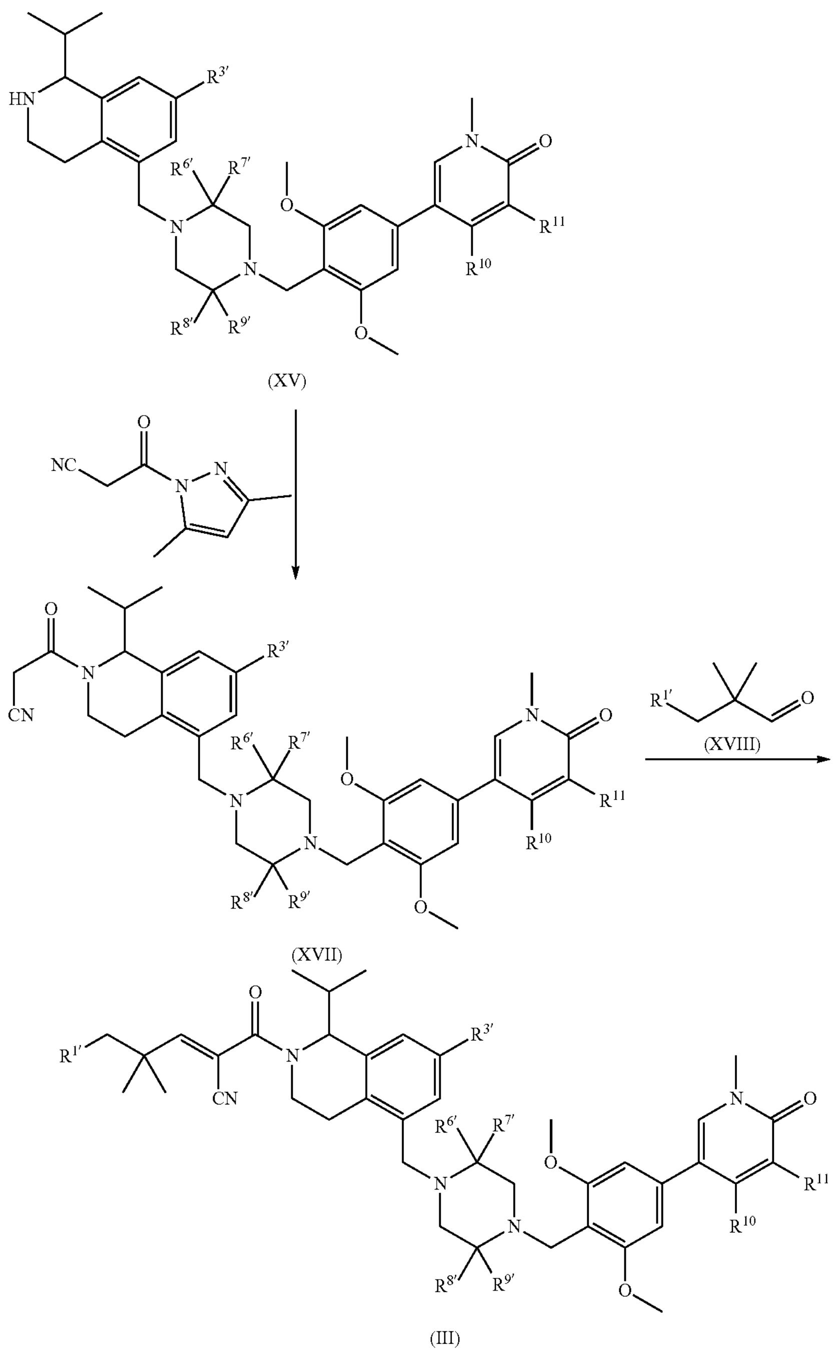

In the compounds of formula (XI), (XII), (XIII) and (XIV), L $R^1$, $R^2$, and $R^3$ are as defined herein for compounds of formula (I). In the compounds of formula (XV), (XVI), (XVII) and (XVIII), $R^{1'}$, $R^{2'}$, $R^{3'}$, $R^{6'}$, $R^{7'}$, $R^{8'}$, $R^{9'}$, $R^{10}$, and $R^{11}$ are as defined herein for compounds of formula (III).

The disclosure also provides a library of compounds of formula (I), (II), (III), (IV), (V), (VI), (VII), (VIII), (IX) and/or (X), the library comprising a plurality of compounds of formula (I), (II), (III), (IV), (V), (VI), (VII), (VIII), (IX) and/or (X).

The compounds of formula (I) (e.g. the compounds of formula (II)) may be used in a combination therapy with one or more additional chemotherapeutic agents. Combination therapy includes alternating between administration of the compounds of formula (III) (e.g. the compounds of formula (IV), (V), (VI), (VII), (VIII), (IX) or (X)) and the chemotherapeutic agent(s), as well as simultaneously administering the compounds of formula (III) (e.g. the compounds of formula (IV), (V), (VI), (VII), (VIII), (IX) or (X)) and the chemotherapeutic agents.

In the various combination therapies of the disclosure, it will be understood that administering the compounds of formula (III) (e.g. the compounds of formula (IV), (V), (VI), (VII), (VIII), (IX) or (X)) may occur prior to, concurrently with, or after, administration of the chemotherapeutic agent(s). Similarly, administering the chemotherapeutic agent(s) may occur prior to, concurrently with, or after, administration of the compounds of formula (III) (e.g. the compounds of formula (IV), (V), (VI), (VII), (VIII), (IX) or (X)).

Accordingly, the disclosure may provide a combination of a compound of formula (III) (e.g. a compound of formula (IV), (V), (VI), (VII), (VIII), (IX) or (X)) with at least one chemotherapeutic agent.

A chemotherapeutic agent is a therapeutic agent for treating cancer. A chemotherapeutic agent may also be referred to as an anti-cancer agent.

In embodiments, the at least one chemotherapeutic agent is a B-cell lymphoma 2 (Bcl-2) protein inhibitor or a DNA methyltransferase (DNMT) inhibitor. In embodiments, the at least one chemotherapeutic agent is Venetoclax or Azacitidine. In embodiments, the at least one chemotherapeutic agent is Venetoclax. In embodiments, the at least one chemotherapeutic agent is Azacitidine.

The disclosure also provides the compound of formula (III) (e.g. the compound of formula (IV), (V), (VI), (VII), (VIII), (IX) or (X)) for use in medicine wherein said compound is for administration as a part of a combination therapy with one or more chemotherapeutic agents.

In embodiments, the at least one chemotherapeutic agent is a B-cell lymphoma 2 (Bcl-2) protein inhibitor or a DNA methyltransferase (DNMT) inhibitor. In embodiments, the at least one chemotherapeutic agent is Venetoclax or Azacitidine. In embodiments, the at least one chemotherapeutic agent is Venetoclax. In embodiments, the at least one chemotherapeutic agent is Azacitidine.

In embodiments, the use in medicine wherein said compound of formula (III) (e.g. the compound of formula (IV), (V), (VI), (VII), (VIII), (IX) or (X)) is for administration as a part of a combination therapy with one or more chemotherapeutic agents comprises the treatment and/or prevention of any disease or condition which is associated with and/or is caused by an abnormal level of BRD9 activity. In embodiments, the disease or condition is cancer.

In embodiments, the pharmaceutical composition of the disclosure comprises one or more chemotherapeutic agent.

In embodiments, the pharmaceutical composition of the disclosure comprises a DNA methyltransferase (DNMT) inhibitor or a B-cell lymphoma 2 (Bcl-2) protein inhibitor. In embodiments, the pharmaceutical composition of the disclosure comprises azacitidine or venetoclax. In embodiments, the pharmaceutical composition of the disclosure comprises azacitidine.

In embodiments, the pharmaceutical composition of the disclosure comprises venetoclax. The compounds of formula (III) (e.g. the compounds of formula (IV), (V), (VI), (VII), (VIII), (IX) or (X)) may be used in a combination therapy with one or more additional chemotherapeutic agents. Combination therapy includes alternating between administration of the compounds of formula (III) (e.g. the compounds of formula (IV), (V), (VI), (VII), (VIII), (IX) or (X)) and the chemotherapeutic agent(s), as well as simultaneously administering the compounds of formula (III) (e.g. the compounds of formula (IV), (V), (VI), (VII), (VIII), (IX) or (X)) and the chemotherapeutic agents.

In the various combination therapies of the disclosure, it will be understood that administering the compounds of formula (III) (e.g. the compounds of formula (IV), (V), (VI), (VII), (VIII), (IX) or (X)) may occur prior to, concurrently with, or after, administration of the chemotherapeutic agent(s). Similarly, administering the chemotherapeutic agent(s) may occur prior to, concurrently with, or after, administration of the compounds of formula (III) (e.g. the compounds of formula (IV), (V), (VI), (VII), (VIII), (IX) or (X)).

Accordingly, the disclosure may provide a combination of a compound of formula (III) (e.g. a compound of formula (IV), (V), (VI), (VII), (VIII), (IX) or (X)) with at least one chemotherapeutic agent.

A chemotherapeutic agent is a therapeutic agent for treating cancer. A chemotherapeutic agent may also be referred to as an anti-cancer agent.

In embodiments, the at least one chemotherapeutic agent is a B-cell lymphoma 2 (Bcl-2) protein inhibitor or a DNA methyltransferase (DNMT) inhibitor. In embodiments, the at least one chemotherapeutic agent is Venetoclax or Azacitidine. In embodiments, the at least one chemotherapeutic agent is Venetoclax. In embodiments, the at least one chemotherapeutic agent is Azacitidine.

The disclosure also provides the compound of formula (III) (e.g. the compound of formula (IV), (V), (VI), (VII), (VIII), (IX) or (X)) for use in medicine wherein said compound is for administration as a part of a combination therapy with one or more chemotherapeutic agents.

In embodiments, the at least one chemotherapeutic agent is a B-cell lymphoma 2 (Bcl-2) protein inhibitor or a DNA methyltransferase (DNMT) inhibitor. In embodiments, the at least one chemotherapeutic agent is Venetoclax or Azacitidine. In embodiments, the at least one chemotherapeutic agent is Venetoclax. In embodiments, the at least one chemotherapeutic agent is Azacitidine.

In embodiments, the use in medicine wherein said compound of formula (III) (e.g. the compound of formula (IV), (V), (VI), (VII), (VIII), (IX) or (X)) is for administration as a part of a combination therapy with one or more chemotherapeutic agents comprises the treatment and/or prevention of any disease or condition which is associated with and/or is caused by an abnormal level of BRD9 activity. In embodiments, the disease or condition is cancer.

In embodiments, the pharmaceutical composition of the disclosure comprises one or more chemotherapeutic agent.

In embodiments, the pharmaceutical composition of the disclosure comprises a DNA methyltransferase (DNMT) inhibitor or a B-cell lymphoma 2 (Bcl-2) protein inhibitor. In embodiments, the pharmaceutical composition of the disclosure comprises azacitidine or venetoclax. In embodiments, the pharmaceutical composition of the disclosure comprises azacitidine.

In embodiments, the pharmaceutical composition of the disclosure comprises venetoclax. In the discussion above, reference is made to a number of terms, which are to be understood to have the meanings provided below, unless a context indicates to the contrary. The nomenclature used herein for defining compounds, in particular the compounds described herein, is intended to be in accordance with the rules of the International Union of Pure and Applied Chemistry (IUPAC) for chemical compounds, specifically the "IUPAC Compendium of Chemical Terminology (Gold Book)" (see A. D. Jenkins et al., Pure & Appl. Chem., 68, 2287-2311 (1996)). For the avoidance of doubt, if an IUPAC rule is contrary to a definition provided herein, the definition herein is to prevail. As used herein, the term "aryl" refers to a mono- or polycyclic aromatic hydrocarbon system having 6 to 14 carbon atoms, in some cases having 6 to 10 carbon atoms. Representative examples of suitable "aryl" groups include, but are not limited to, phenyl, biphenyl, naphthyl, 1-naphthyl, 2-naphthyl and anthracenyl. As used herein, "substituted aryl" refers to an aryl group as defined herein which comprises one or more substituents on the aromatic ring. When an aryl group is substituted, any hydrogen atom(s) may be replaced with the substituent(s), providing valencies are satisfied.

As used herein, "heteroaryl" may be a single or fused ring system having one or more aromatic rings containing 1 or more, in some cases 1 to 3, in some cases 1 to 2, in some cases a single O, N and/or S heteroatom(s). The term "heteroaryl" may refer to a mono- or polycyclic heteroaromatic system having 5 to 10 ring atoms. Representative examples of heteroaryl groups may include, but are not limited to, pyrrolyl, furanyl, thiophenyl, pyrazolyl, imidazolyl, oxazolyl, isoxazolyl, thiazolyl, pyridinyl, pyrimidinyl, pyridazinyl, pyrazinyl, indolyl, benzofuranyl, benzothiazolyl, benzimidazolyl, indazolyl, benzoxazolyl, benzisoxazolyl etc. As used herein, "substituted heteroaryl" refers to a heteroaryl group as defined herein which comprises one or more substituents on the heteroaromatic ring. As used herein, the term "alkyl" refers to a straight or branched chain hydrocarbyl group. The chain may be saturated or unsaturated, e.g. in some cases the chain may contain one or more double or triple bonds.

As used herein, "$C_1$-$C_4$ alkyl" refers to a straight or branched chain hydrocarbyl group containing from 1 to 4 carbon atoms. As used herein, a "$C_1$-$C_3$ alkyl" refers to a straight or branched chain hydrocarbyl group containing from 1 to 3 carbon atoms. Representative examples are methyl, ethyl, n-propyl, iso-propyl, n-butyl, sec-butyl, iso-butyl, tert-butyl etc. When an alkyl group is substituted, any hydrogen atom(s), $CH_3$, $CH_2$ or CH group(s) may be replaced with the substituent(s), providing valencies are satisfied.

As used herein, a "cycloalkyl" is a ring containing 3 to 10 carbon atoms, in some cases 3 to 8, or in some cases 5 to 6 carbon atoms. The ring may be saturated or unsaturated, e.g. in some cases the ring may contain one or more double or triple bonds. As used herein, a $C_3$-$C_6$ cycloalkyl is a cycloalkyl containing 3 to 6 carbon atoms in the ring. As used herein, a $C_3$-$C_5$ cycloalkyl is a cycloalkyl containing 3 to 5 carbon atoms in the ring. Representative examples of cycloalkyl groups include cyclopropyl, cyclobutyl, cyclopentyl, cyclohexyl, cycloheptyl, cyclooctyl, cyclobutenyl, cyclopentenyl, cyclohexenyl etc. When a cycloalkyl group is substituted, any hydrogen atom(s) may be replaced with the substituent(s), providing valencies are satisfied.

The term "alkenyl" defines monovalent groups derived from alkenes by removal of a hydrogen atom from any carbon atom, wherein the term "alkene" is intended to define acyclic branched or unbranched hydrocarbons having the general formula $CnH_{2n}$, wherein n is an integer ≥2. Examples of alkenyl groups include ethenyl, n-propylenyl, iso-propylenyl, n-butylenyl, sec-butylenyl, iso-butylenyl and tert-butylenyl. When an alkenyl group is substituted, any hydrogen atom(s) may be replaced with the substituent(s), providing valencies are satisfied. Where the alkenyl comprises a divalent hydrocarbon radical, this moiety may sometimes be referred to herein as an alkenylene.

The term "alkynyl" defines monovalent groups derived from alkynes by removal of a hydrogen atom from any carbon atom, wherein the term "alkyne" is intended to define acyclic branched or unbranched hydrocarbons having the general formula $CnH_{2n-2}$, wherein n is an integer 2. Examples of alkynyl groups include ethynyl, n-propylynyl, iso-propylynyl, n-butylynyl, sec-butylynyl, iso-butylynyl and tert-butylynyl. When an alkynyl group is substituted, any hydrogen atom(s) may be replaced with the substituent(s), providing valencies are satisfied. Where the alkynyl comprises a divalent hydrocarbon radical, this moiety may sometimes be referred to herein as an alkynylene.

"Benzyl" as used herein refers to a —$CH_2$Ph group. As used herein, a "substituted benzyl" refers to a benzyl group as defined herein which comprises one or more substituents on the aromatic ring. When a benzyl group is substituted, any hydrogen atom(s) may be replaced with the substituent(s), providing valencies are satisfied.

As used herein, "heterocycloalkyl" refers to a monocyclic or polycyclic ring having in one or more rings of the ring system at least one heteroatom selected from O, N and S (e.g. from one to five ring heteroatoms independently selected from the group consisting of O, N and S). The one or more rings may also contain one or more double bonds provided that the one or more rings are not fully aromaticized. The one or more rings of the heterocycloalkyl may comprise 3 to 10 atoms, in some cases 3 to 8 atoms. The one or more rings may be aliphatic. The one or more rings may be saturated or unsaturated, e.g. in some cases the one or more rings may contain one or more double or triple bonds. Any N heteroatom present in the heterocycloalkyl group may be $C_1$ to $C_6$ alkyl-substituted. In some cases, the heterocycloalkyl is a monocyclic or bicyclic ring, such as a monocyclic ring. Representative examples of heterocycloalkyl groups include, but are not limited to, pyrrolidinyl, tetrahydrofuranyl, dioxolanyl, dithiolanyl, thiazolidinyl, isothiazolidinyl, oxazolidinyl, isoxazolidinyl, pyrazolidinyl, imidazolidinyl, piperidinyl, piperazinyl, N-alkylpiperazinyl, morpholinyl, dioxanyl, oxazolidinyl, tetrahydropyranyl, diazaspiroundecane, diazaspiroheptane, azaspiroheptane, diazaspirodecane, octahydropyrrolopyrrole, etc. Where the heterocycloalkyl comprises a divalent radical, this moiety may sometimes be referred to herein as heterocycloalkylene.

As used herein, where a group comprising carbon atoms is defined as "saturated", only single bonds bind the carbon atoms to one another. Where a group comprising carbon atoms is defined as "unsaturated", at least two of the carbon atoms are connected by a double or triple bond.

The term "spiro" is used to refer to moieties comprising two or more ring systems, wherein at least two of the ring systems are connected by just one atom (typically a quaternary carbon atom).

"Monocyclic" is used herein to refer to moieties comprising one ring of atoms. "Bicyclic" is used herein to refer to moieties that feature two joined rings of atoms. "Tricyclic" is used herein to refer to moieties that feature three joined rings of atoms. "Polycyclic" is used herein to refer to moieties that comprise two or more joined rings. Unless the context indicates otherwise, bicyclic and polycyclic systems may comprise a fused ring system (in which at least two rings share a common bond). In other examples, the two or more rings may be joined by a bond between atoms on each of the two or more rings. In other examples, the bicyclic system may comprise a spiro centre (as defined above).

The term "fused" is used to refer to moieties comprising two or more ring systems, wherein at least two of the ring systems are connected by a [1,2] ring junction, i.e. a moiety comprising two or more ring systems wherein two, or more, of the rings present share a bond in each respective ring structure.

The term "aliphatic" refers to acyclic or cyclic, saturated or unsaturated compounds, excluding aromatic compounds, where "aromatic" defines a cyclically conjugated molecular entity with a stability (due to delocalisation) significantly greater than that of a hypothetical localised structure. The Hückel rule is often used in the art to assess aromatic character; monocyclic planar (or almost planar) systems of trigonally (or sometimes digonally) hybridised atoms that contain (4n+2) π-electrons (where n is a non-negative integer) will exhibit aromatic character. The rule is generally limited to n=0 to 5.

As used herein, an alkoxy refers to an alkyl group, as defined above, appended to the parent molecular moiety through an oxy group, —O—. As used herein, a $C_{1-4}$alkoxy refers to a $C_{1-4}$ alkyl group (as defined above), appended to the parent molecular moiety through a oxy group, —O—. Representative examples of alkoxy include, but are not limited to, methoxy, ethoxy, propoxy, 2-propoxy, butoxy, tert-butoxy etc.

As used herein, a "halo" or "halogen" group may be F, Cl, Br, or I. In some examples, halo or halogen may be F.

As used herein, "haloalkyl" may be an alkyl group in which one or more hydrogen atoms thereon have been replaced with a halogen atom, e.g. a $C_1$-$C_6$ haloalkyl may be a $C_1$ to $C_6$ alkyl in which one or more hydrogen atoms thereon have been replaced with a halogen atom. By way of a representative example, a $C_1$-$C_6$ haloalkyl may be a fluoroalkyl, such as fluoromethyl (—$CH_2F$), difluoromethyl (—$CHF_2$), trifluoromethyl (—$CF_3$) or 1,1-difluoroethyl (—$CH_2CHF_2$), and in particular fluoromethyl (—$CH_2F$), difluoromethyl (—$CHF_2$), or trifluoromethyl (—$CF_3$).

As used herein, a "haloalkoxy" (e.g. $C_{1-4}$ haloalkoxy) refers to an alkoxy (e.g. $C_1$-$C_4$ alkoxy) as defined above, in which one or more hydrogen atoms thereon have been replaced with a halogen atom.

As used herein, the terms "aryl", "heteroaryl", "cycloalkyl", "$C_1$ to $C_4$ alkyl", and "heterocycloalkyl" may refer to either a monovalent radical species or a divalent radical species.

It should be understood that throughout this specification, the terms "comprise", "comprising" and/or "comprises" is/are used to denote that aspects, embodiments and examples of this disclosure "comprise" a particular feature or features. It should be understood that this/these terms may also encompass aspects, embodiments and/or examples which "consist essentially of" or "consist of" the relevant feature or features.

The present disclosure may also be defined with reference to the following set of clauses:

Clause 1. A compound of formula (I)

(I)

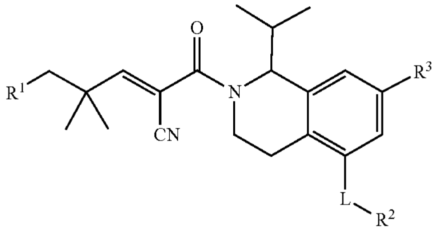

or a pharmaceutically acceptable salt, solvate or derivative thereof, wherein

L is a covalent bond or linker;

$R^1$ is selected from H, F, $C_1$-$C_4$ alkyl and $C_1$-$C_4$ alkoxy;

$R^2$ is a BRD9 binder;

$R^3$ is selected from halogen, $OR^4$, $C_1$-$C_6$ alkyl, and $N(R^5)_2$ wherein each alkyl is optionally substituted with one or more groups independently selected from halogen, $OR^4$, and $N(R^5)_2$;

each $R^4$ is independently selected from H, $C_1$-$C_6$ alkyl and $C_1$-$C_6$ haloalkyl; and each $R^5$ is independently selected from H, $C_1$-$C_6$ alkyl and $C_1$-$C_6$ haloalkyl;

wherein the compound of formula (I) is not 2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or 2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

Clause 2. The compound according to clause 1, wherein L is a linker.

Clause 3. The compound according to clause 1 or clause 2, wherein L is a moiety of formula (Ia)

(Ia)

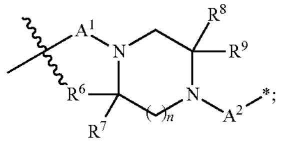

wherein $A^1$ and $A^2$ are each independently absent, or selected from $CH_2$, O and N;

n is selected from 0 and 1; and $R^6$, $R^7$, $R^8$ and $R^9$ are each independently selected from H, halogen, $C_1$-$C_6$ alkyl, and $C_1$-$C_6$ haloalkyl, or $R^6$ and $R^7$ together with the carbon atom to which they are attached form a $C_3$-$C_5$ cycloalkyl, or $R^8$ and $R^9$ together with the carbon atom to which they are attached form a $C_3$-$C_5$ cycloalkyl;

wherein * indicates the position that is attached to $R^2$ and the wavy line intersects the bond between L and the rest of the compound.

Clause 4. The compound according to any preceding clause, wherein L is a moiety selected from:

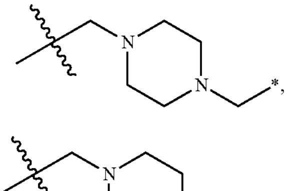

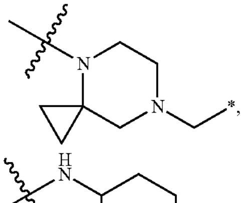

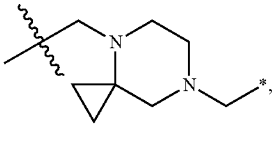

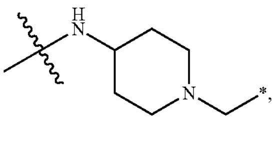

-continued

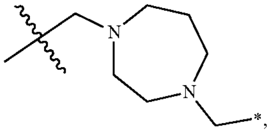

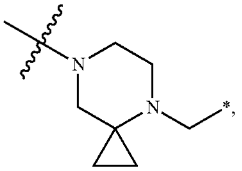

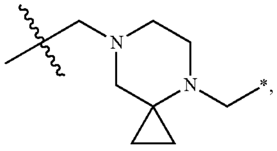

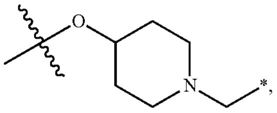

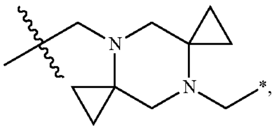

and

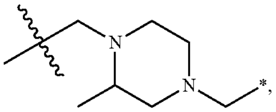

wherein * indicates the position that is attached to $R^2$ and the wavy line intersects the bond between L and the rest of the compound.

Clause 5. The compound according to clause 1 or clause 2, wherein the -L-$R^2$ moiety is a group of formula (Ib)

(Ib)

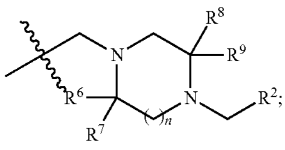

wherein n is selected from 0 and 1; and $R^6$, $R^7$, $R^8$ and $R^9$ are each independently selected from H, halogen, $C_1$-$C_6$ alkyl, and $C_1$-$C_6$ haloalkyl, or $R^6$ and $R^7$ together with the carbon atom to which they are attached form a $C_3$-$C_5$ cycloalkyl, or $R^8$ and $R^9$ together with the carbon atom to which they are attached form a $C_3$-$C_5$ cycloalkyl;

wherein the wavy line intersects the bond between the -L-$R^2$ moiety and the rest of the compound.

Clause 6. The compound according to clause 5, wherein the -L-$R^2$ moiety is a group selected from:

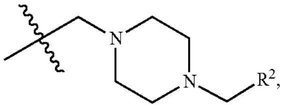

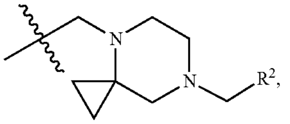

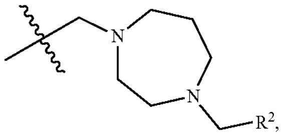

-continued

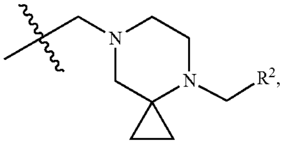

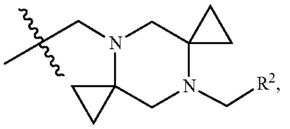

and

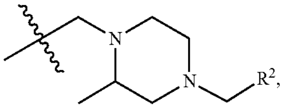

wherein the wavy line intersects the bond between -L-$R^2$ moiety and the rest of the compound.

Clause 7. The compound according to clause 5, wherein the -L-$R^2$ moiety is a group of formula (Ic)

(Ic)

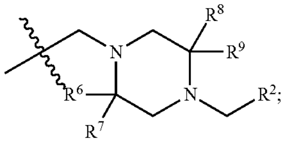

wherein $R^6$, $R^7$, $R^8$ and $R^9$ are each independently selected from H, halogen, $C_1$-$C_6$ alkyl, and $C_1$-$C_6$ haloalkyl, or $R^6$ and $R^7$ together with the carbon atom to which they are attached form a $C_3$-$C_5$ cycloalkyl, and/or $R^8$ and $R^9$ together with the carbon atom to which they are attached form a $C_3$-$C_5$ cycloalkyl;

wherein the wavy line intersects the bond between the -L-$R^2$ moiety and the rest of the compound.

Clause 8. The compound according to clause 7, wherein $R^6$, $R^7$, $R^8$ and $R^9$ are each H, or $R^6$ and $R^7$ together with the carbon atom to which they are attached form a $C_3$-$C_5$ cycloalkyl, and/or $R^8$ and $R^9$ together with the carbon atom to which they are attached form a $C_3$-$C_5$ cycloalkyl.

Clause 9. The compound according to clause 7 or clause 8, wherein $R^6$, $R^7$, $R^8$ and $R^9$ are each H, or $R^6$ and $R^7$ together with the carbon atom to which they are attached form a cyclopropyl, and/or $R^8$ and $R^9$ together with the carbon atom to which they are attached form a cyclopropyl.

Clause 10. A compound according to any one of clauses 7 to 9, wherein:

$R^6$ and $R^7$ are each H, and $R^8$ and $R^9$ together with the carbon atom to which they are attached form a cyclopropyl; or $R^6$ and $R^7$ together with the carbon atom to which they are attached form a cyclopropyl, and $R^8$ and $R^9$ are each H; or $R^6$ and $R^7$ together with the carbon atom to which they are attached form a cyclopropyl, and $R^8$ and $R^9$ together with the carbon atom to which they are attached form a cyclopropyl.

Clause 11. A compound according to any one of clauses 7 to 10, wherein:

$R^6$ and $R^7$ are each H, and $R^8$ and $R^9$ together with the carbon atom to which they are attached form a cyclopropyl; or $R^6$ and $R^7$ together with the carbon atom to which they are attached form a cyclopropyl, and $R^8$ and $R^9$ are each H.

Clause 12. A compound according to any one of clauses 7 to 11, wherein $R^6$ and $R^7$ together with the carbon atom to which they are attached form a cyclopropyl, and $R^8$ and $R^9$ are each H.

Clause 13. The compound according to clause 7, wherein the -L-$R^2$ moiety is a group selected from:

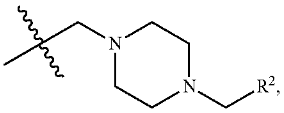

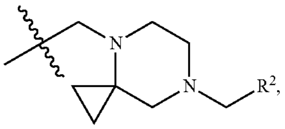

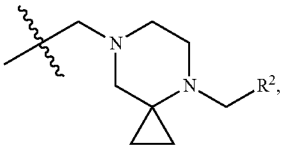

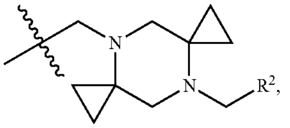

and

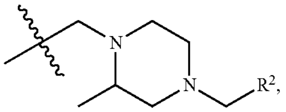

wherein the wavy line intersects the bond between -L-$R^2$ moiety and the rest of the compound.

Clause 14. The compound according to clause 7 or clause 13, wherein the -L-$R^2$ moiety is a group selected from:

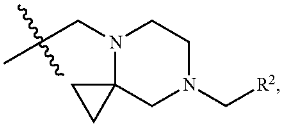

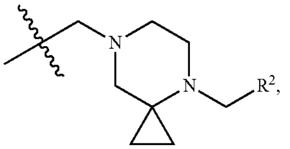

and

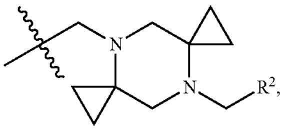

wherein the wavy line intersects the bond between -L-$R^2$ moiety and the rest of the compound.

Clause 15. The compound according to clause 7, clause 13 or clause 14, wherein the -L-$R^2$ moiety is a group selected from:

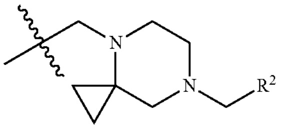

and

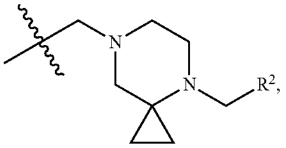

wherein the wavy line intersects the bond between -L-$R^2$ moiety and the rest of the compound.

Clause 16. The compound according to clause 7 or any one of clauses 13 to 15, wherein the -L-$R^2$ moiety is:

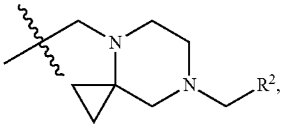

wherein the wavy line intersects the bond between -L-$R^2$ moiety and the rest of the compound.

Clause 17. The compound of any preceding clause, wherein $R^1$ is selected from H, F, $C_1$-$C_4$ alkyl and methoxy.

Clause 18. The compound of any preceding clause, wherein $R^1$ is selected from H, F, methyl and methoxy.

Clause 19. The compound of any preceding clause, wherein $R^1$ is selected from H, F and methyl.

Clause 20. The compound of any preceding clause, wherein $R^1$ is selected from H and F.

Clause 21. The compound of any preceding clause, wherein $R^1$ is F.

Clause 22. The compound of any preceding clause, wherein $R^2$ is a moiety of formula (1a), (1b) or (1c)

(1a)

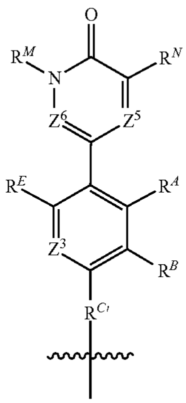

-continued (1b)

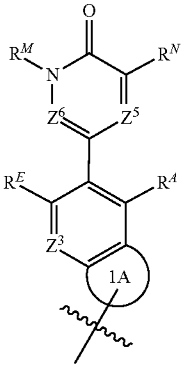

(1c)

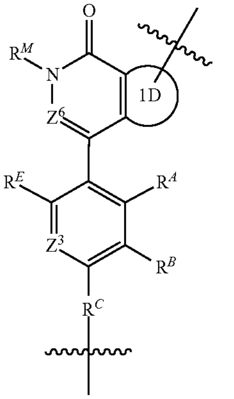

wherein the wavy line intersects the bond between $R^2$ and L;

$R^A$ and $R^E$ are each independently selected from the group consisting of H, $C_1$-$C_3$ alkoxy and $C_1$-$C_3$alkyl;

$R^B$ and $R^D$ are each independently selected from the group consisting of $C_1$-$C_3$ alkoxy, H, OH, halogen, $NH_2$, $C_1$-$C_3$alkyl, $C_1$-$C_3$ haloalkoxy, $C_1$-$C_3$alkyl-O—$C_1$-$C_3$alkyl, 4-7 membered heterocycloalkyl, $C_1$-$C_3$alkyl-$SO_2$—$C_1$-$C_3$alkyl, $C_1$-$C_3$alkyl-$NH_2$, $C_1$-$C_3$alkyl-N(—$C_1$-$C_3$alkyl)$_2$, N($C_1$-$C_3$alkyl)$_2$, NH—$R^F$, wherein the heterocycloalkyl comprises one or more heteroatoms selected from the group consisting of N, S and O;

alternatively, $R^A$ and $R^B$ taken together form a benzene ring;

$R^C$ is selected from the group consisting of H, —Y—$R^{G3}$, $NH_2$, $C_1$-$C_3$ alkyl and 4-7 membered heterocycloalkyl comprising one or more heteroatoms selected from the group consisting of N, S and O;

alternatively, $R^C$ and $Z^2$ or $R^C$ and $Z^3$ taken together form a 5-7 membered heterocycloalkyl comprising one or more heteroatoms selected from the group consisting of N, S and O, optionally substituted with $C_1$-$C_3$ alkyl;

wherein when $R^C$ is Y—$R^{G3}$, $R^B$ and $R^D$ are each independently selected from H, OH, halogen, $NH_2$, CN, $C_1$-$C_3$ alkyl, $C_1$-$C_3$ haloalkyl, $C_1$-$C_3$ alkoxy, $C_1$-$C_3$ haloalkoxy and $C_1$-$C_3$alkoxy-$C_1$-$C_3$alkyl; wherein at least one of the substituents $R^A$ to $R^E$ is not hydrogen;

$R^{C'}$ is absent, or is as defined for $R^C$ $R^F$ is selected from $SO_2$—$C_1$-$C_3$alkyl and $C_1$-$C_3$ alkyl, wherein the $C_1$-$C_3$ alkyl is optionally substituted with a 5 to 6 membered heteroaryl comprising one or more heteroatoms selected from the group consisting of N, S and O;

$R^{G3}$ is selected from the group consisting of $NH_2$, OH, $C_1$-$C_3$ alkyl, N($R^JR^K$), $OR^L$, aryl, 5-6 membered heteroaryl, wherein the aryl and heteroaryl are optionally and independently substituted with one or more halogen, optionally substituted 4- to 7-membered monocyclic heterocycloalkyl, and optionally substituted 7- to 12-membered bicyclic heterocycloalkyl, which monocyclic or bicyclic heterocycloalkyl comprise one or more heteroatoms selected from the group consisting of N, S and O, and are optionally substituted with one or more groups independently selected from halogen, OH, $NH_2$, $C_1$-$C_3$ alkyl, $NHC_1$-$C_3$alkyl, N($C_1$-$C_3$alkyl)$_2$, $C_1$-$C_3$ alkoxy and $CH_2$—$R^{M1}$;

$R^H$ and $R^I$ are each independently selected from H or $C_1$-$C_3$ alkyl; or $R^H$ and $R^I$ taken together form a $C_3$-$C_4$cycloalkyl;

$R^J$ is H or $C_1$-$C_3$alkyl;

$R^K$ is selected from the group consisting of $C_1$-$C_3$ alkyl, $C_2$-$C_3$alkyl-N($C_1$-$C_3$alkyl)$_2$, $C_2$-$C_3$alkyl-$NHC_1$-$C_3$alkyl, 4- to 7-membered monocyclic heterocycloalkyl, and 7- to 12-membered bicyclic heterocycloalkyl, wherein each monocyclic and bicyclic heterocycloalkyl comprises one or more heteroatoms selected from the group consisting of N, S and O, and is optionally substituted with $C_1$-$C_3$alkyl;

$R^L$ is $C_1$-$C_3$ alkyl or a 4-7 membered heterocycloalkyl, wherein the heterocycloalkyl comprises one or more heteroatoms selected from the group consisting of N, S and O, and is optionally substituted with $C_1$-$C_3$ alkyl;

$R^M$ is selected from the group consisting of $C_1$-$C_6$ alkyl, $C_2$-$C_6$ alkenyl, $C_1$-$C_6$ heteroalkyl comprising one or more heteroatoms selected from the group consisting of N, S and O, $C_3$-$C_{10}$ cycloalkyl, $C_2$-$C_6$ alkynyl and H, wherein the alkyl, alkenyl, heteroalkyl and cycloalkyl are each optionally substituted with $C_1$-$C_3$ alkyl;

$R^{M1}$ is selected from 5-10 membered mono- or bicyclic aryl or heteroaryl comprising one or more heteroatoms selected from the group consisting of N, S and O, which is optionally substituted with $NH_2$, OH, halogen, CN, $C_1$-$C_3$ alkyl, $C_1$-$C_3$ alkoxy;

$R^N$ is selected from the group consisting of H, halogen, $C_1$-$C_6$alkyl, C(O)$C_1$-$C_5$alkyl, $NH_2$, optionally substituted amino, OH, cyano, $C_1$-$C_6$heteroalkyl, $C_3$-$C_{10}$ cycloalkyl, $C_2$-$C_9$heterocycloalkyl, $C_6$-$C_{10}$aryl, $C_2$-$C_9$heteroaryl, $C_2$-$C_6$alkenyl, $C_2$-$C_6$heteroalkenyl and thiol, wherein each heteroalkyl and heteroalkenyl comprises one or more heteroatoms selected from the group consisting of N, S and O, each heterocycloalkyl and heteroaryl comprises one or more heteroatoms selected from the group consisting of N, S and O, and the alkyl, heteroalkyl, cycloalkyl, heterocycloalkyl, aryl, heteroaryl, alkenyl and heteroalkenyl are each optionally substituted with $C_1$-$C_3$ alkyl;

$R^O$ is H, halogen, cyano, $C_1$-$C_6$alkyl, $C_1$-$C_6$heteroalkyl, $C_3$-$C_{10}$cycloalkyl, $C_2$-$C_9$heterocycloalkyl, $C_6$-$C_{10}$aryl, $C_2$-$C_9$heteroaryl, $C_2$-$C_6$alkenyl, $C_2$-$C_6$heteroalkenyl, hydroxy, and thiol, wherein each heteroalkyl and heteroalkenyl comprises one or more heteroatoms selected from the group consisting of N, S and O, each heterocycloalkyl and heteroaryl comprises one or more heteroatoms selected from the group consisting of N, S and O, and the alkyl, heteroalkyl, cycloalkyl, heterocycloalkyl, aryl, heteroaryl, alkenyl and heteroalkenyl are each optionally substituted with $C_1$-$C_3$ alkyl;

alternatively, $R^N$ and $Z^5$ taken together, combine to form a $C_6$-$C_{10}$arene or $C_2$-$C_9$heteroarene, wherein the heteroarene comprises one or more heteroatoms selected from the group consisting of N, S and O, and the arene or heteroarene are each optionally substituted with $C_1$-$C_3$ alkyl; optionally wherein $R^N$ and $R^O$ taken together with the carbon atoms to which they are joined, combine to form a $C_6$-$C_{10}$arene or $C_2$-$C_9$heteroarene, wherein the heteroarene comprises one or more heteroatoms selected from the group consisting of N, S and O, and the arene or heteroarene are each optionally substituted with $C_1$-$C_3$ alkyl;

$R^P$ is selected from the group consisting of H, halogen, $C_1$-$C_6$ alkyl, $C_1$-$C_6$ heteroalkyl comprising one or more heteroatoms selected from the group consisting of N, S and O, $C_3$-$C_{10}$ cycloalkyl and $C_6$-$C_{10}$ aryl, wherein the alkyl, heteroalkyl, cycloalkyl, and aryl are each optionally substituted with $C_1$-$C_3$ alkyl;

$Z^3$ is N or $CR^D$;

$Z^5$ is N or $CR^O$;

$Z^6$ is N or $CR^P$;

Y is absent or is selected from the group consisting of —$CR^HR^I$—, —$SO_2$— and —CO—;

ring 1A is a 5-7 membered heterocycloalkane comprising one or two heteroatoms selected from the list consisting of N, S and O, optionally substituted with $C_1$-$C_3$alkyl; and ring 1D is a $C_6$-$C_{10}$aryl or $C_2$-$C_9$heteroaryl comprising one or more heteroatoms selected from the group consisting of N, S and O, each of which are optionally substituted with $C_1$-$C_3$ alkyl.

Clause 23. The compound of any preceding clause, wherein $R^2$ is a moiety selected from formulae (1d) to (1w)

(1d)

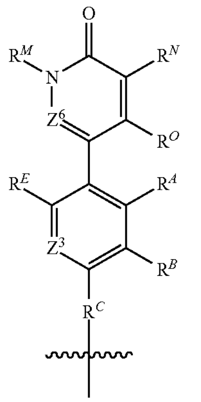

(1e)

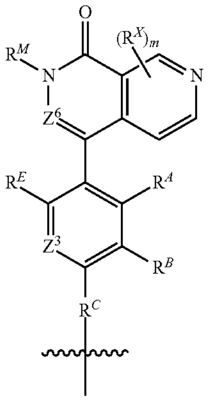

-continued (1f)

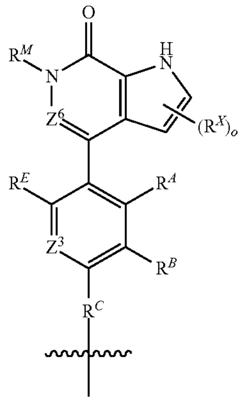

(1g)

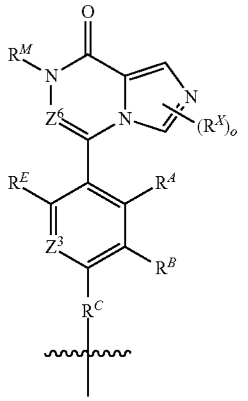

(1h)

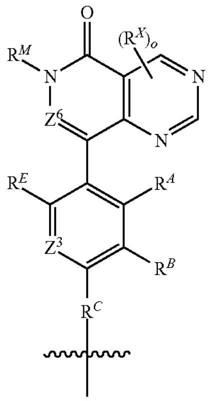

(1j)

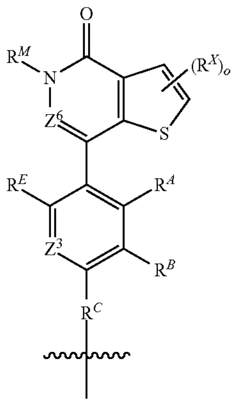

-continued
(1k)
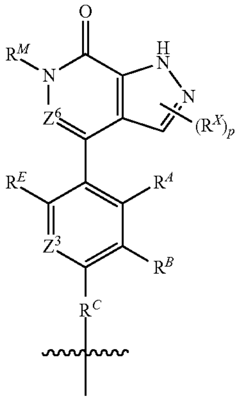
(1m)
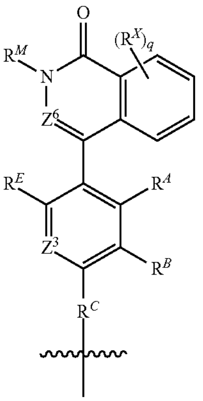
(1n)
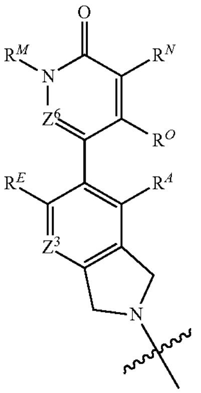
(1p)
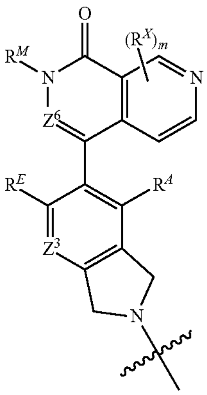
-continued
(1q)
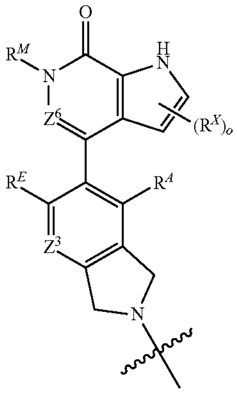
(1r)
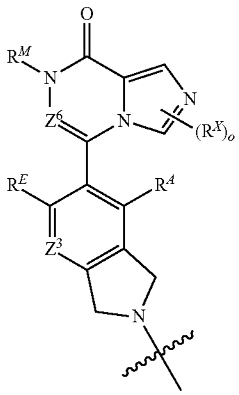
(1s)
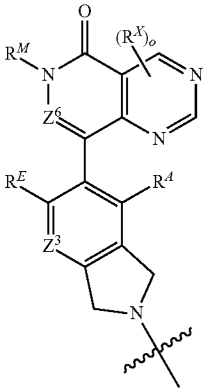
(1t)
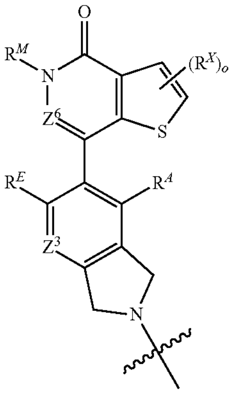

-continued (1u)

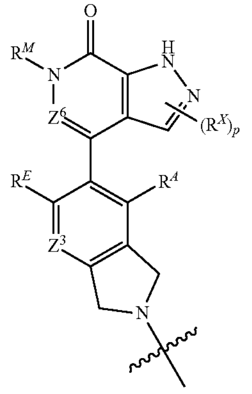

(1v)

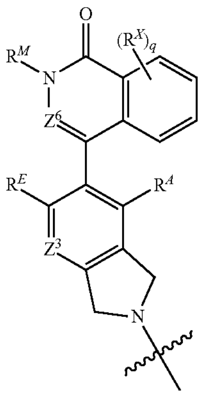

(1w)

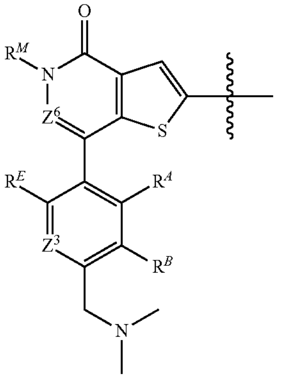

wherein the wavy line intersects the bond between $R^2$ and L;

$R^A$, $R^B$, $R^E$, $R^M$, $Z^3$ and $Z^6$ are as defined in clause 14;

$R^C$ is absent or as defined in clause 14;

$R^N$ is selected from the group consisting of halogen, $C_1$-$C_5$ alkyl, $C_1$-$C_3$ haloalkyl, H, $C(O)C_1$-$C_5$alkyl, $NH_2$, $NHC_1$-$C_3$alkyl and OH;

$R^O$ is H or $C_1$-$C_3$ alkyl;

each $R^X$ is independently selected from the group consisting of halogen, OH, $NH_2$, NH—$C_1$-$C_3$alkyl, $C_1$-$C_5$ alkyl, $C_1$-$C_5$ haloalkyl, $C_1$-$C_5$ alkoxy and $C_1$-$C_4$ haloalkoxy;

m is 0 to 3;

o is 0 to 2;

p is 0 or 1; and q is 0 to 4.

Clause 24. The compound of any preceding clause, wherein $R^2$ is a moiety according to formula (1x)

(1x)

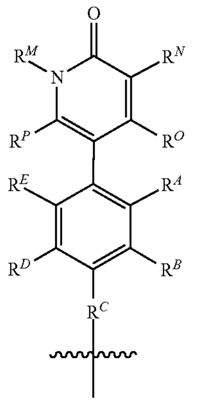

wherein the wavy line intersects the bond between $R^2$ and L;

$R^A$ and $R^E$ are each independently selected from H and $C_1$-$C_3$ alkoxy;

$R^B$ and $R^D$ are each independently selected from $C_1$-$C_3$ alkoxy, H, halogen, $C_1$-$C_3$ alkyl, and $C_1$-$C_3$ haloalkoxy;

$R^C$ is absent, or is Y—$R^{G3}$

Y is selected from the group consisting of —$CR^HR^I$—, and —CO—;

$R^H$ and $R^I$ are each independently selected from H or $C_1$-$C_3$ alkyl; or $R^H$ and $R^I$ taken together form a $C_3$-$C_4$ cycloalkyl;

$R^{G3}$ is selected from the group consisting of $N(R^JR^K)$, $N(C_1$-$C_3$alkyl)(4- to 7-membered monocyclic heterocycloalkylene), or —$N(C_1$-$C_3$alkyl)(7- to 12-membered bicyclic heterocycloalkylene)); —O—; 4- to 7-membered monocyclic heterocycloalkylene; and 7- to 12-membered heterocycloalkylene, wherein each heterocycloalkene comprises one or more heteroatoms selected from the group consisting of N, S and O, and is optionally substituted with $C_1$-$C_3$ alkyl;

$R^J$ is H or $C_{1-3}$alkyl;

$R^K$ is selected from the group consisting of $C_1$-$C_3$ alkyl, $C_2$-$C_3$alkyl-$N(C_1$-$C_3$alkyl$)_2$, $C_2$-$C_3$alkyl-$NHC_1$-$C_3$alkyl, 4- to 7-membered monocyclic heterocycloalkyl, and 7- to 12-membered bicyclic heterocycloalkyl, wherein each monocyclic or bicyclic heterocycloalkyl comprises one or more heteroatoms selected from the group consisting of N, S and O, and is optionally substituted with $C_1$-$C_3$ alkyl;

$R^M$ is $C_1$-$C_3$ alkyl; and $R^N$, $R^O$ and $R^P$ are each independently selected from the group consisting of halogen, $C_1$-$C_3$ alkyl, and $C_1$-$C_3$ haloalkyl.

Clause 25. The compound of any preceding clause, wherein $R^2$ is a moiety of formulae (1y), (1z), (1a') to (1z'), or (1aa)

-continued
(1y)
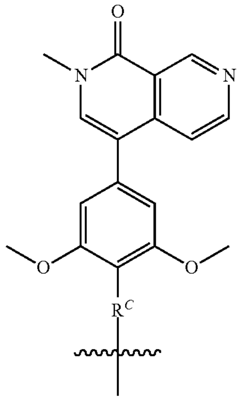
(1c')
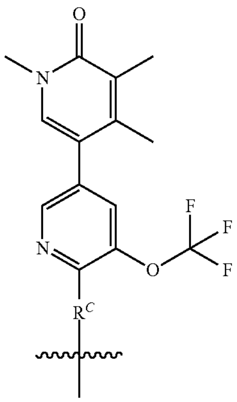
(1z)
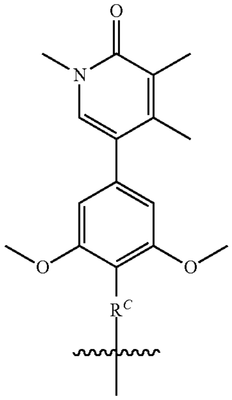
(1d')
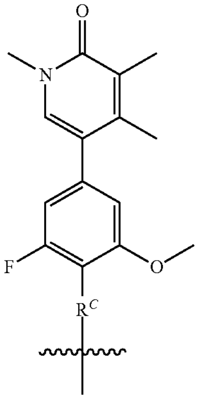
(1a')
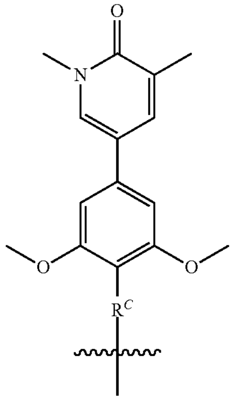
(1e')
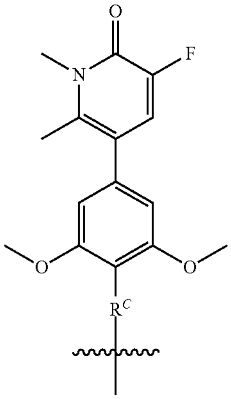
(1b')
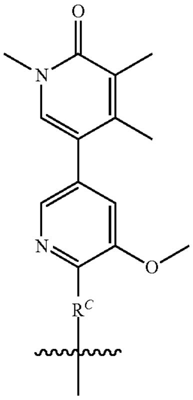
(1f')
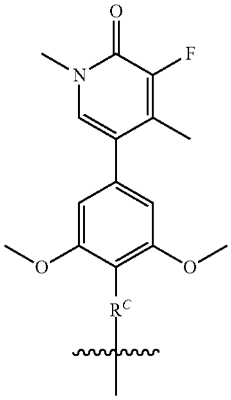

-continued
(1g′)
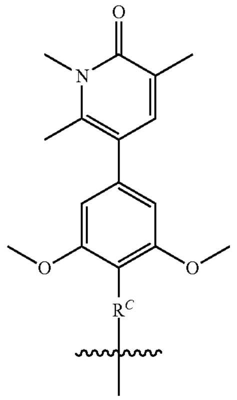
(1h′)
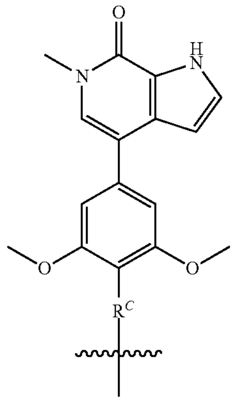
(1j′)
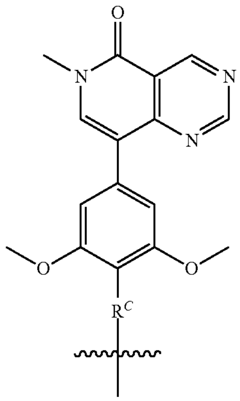
(1k′)
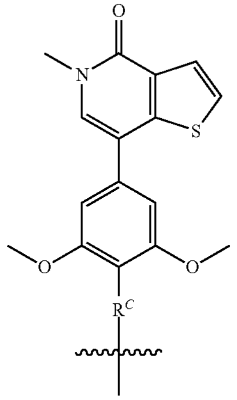
-continued
(1m′)
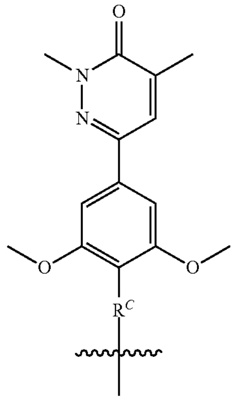
(1n′)
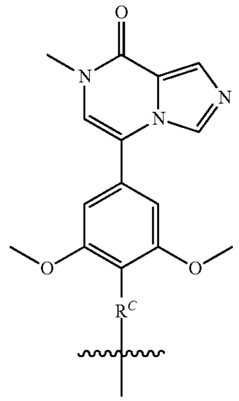
(1p′)
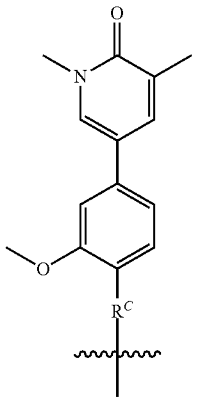
(1q′)
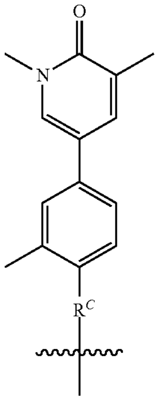

-continued
(1r')
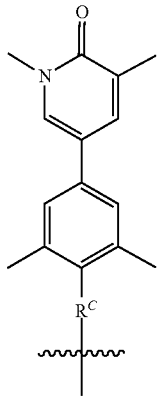
(1s')
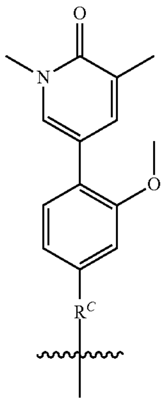
(1t')
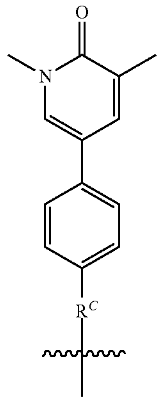
(1u')
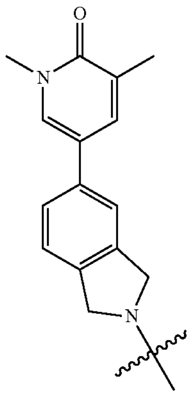
-continued
(1v')
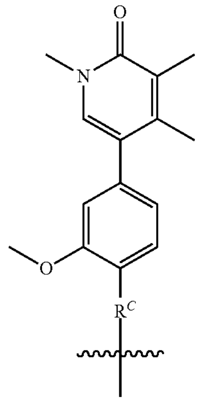
(1w')
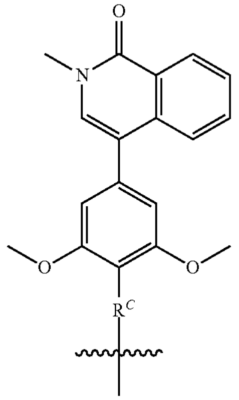
(1x')
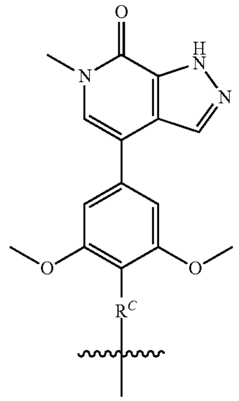
(1y')
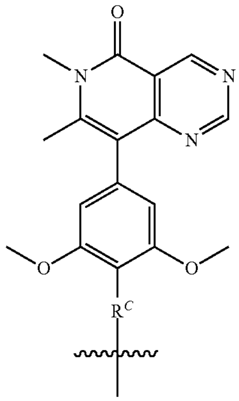

-continued (1z')

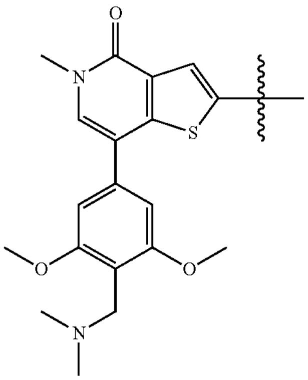

(1aa)

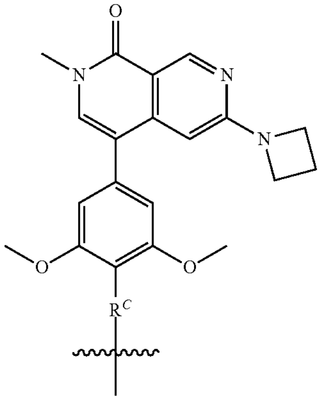

wherein the wavy line intersects the bond between $R^2$ and L;

$R^C$ is absent, or is —Y—$R^{G3}$;

Y is selected from the group consisting of —$CR^HR^I$—, and —CO—;

$R^H$ and $R^I$ are each H; or $R^H$ and $R^I$ taken together form a $C_3$-$C_4$cycloalkyl;

$R^{G3}$ is selected from the group consisting of $N(R^JR^K)$, $N(C_1$-$C_3$alkyl)(4- to 7-membered monocyclic heterocycloalkylene), or $N(C_1$-$C_3$alkyl)(7- to 12-membered bicyclic heterocycloalkylene)); —O—; 4- to 7-membered monocyclic heterocycloalkylene; and 7- to 12-membered bicyclic heterocycloalkylene, wherein each monocyclic or bicyclic heterocycloalkyl comprises one or more heteroatoms selected from the group consisting of N, S and O, and is optionally substituted with $C_1$-$C_3$ alkyl;

$R^J$ is H or $C_1$-$C_3$alkyl;

$R^K$ is selected from the group consisting of $C_1$-$C_3$ alkyl, $C_2$-$C_3$alkyl-$N(C_1$-$C_3$alkyl$)_2$, $C_2$-$C_3$alkyl-$NHC_1$-$C_3$alkyl, 4- to 7-membered monocyclic heterocycloalkyl, and 7- to 12-membered bicyclic heterocycloalkyl, wherein each monocyclic or bicyclic heterocycloalkyl comprises one or more heteroatoms selected from the group consisting of N, S and O, and is optionally substituted with $C_1$-$C_3$alkyl.

Clause 26. The compound of any preceding clause, wherein $R^2$ is a moiety of formulae (1ab) to (1bb):

(1ab)

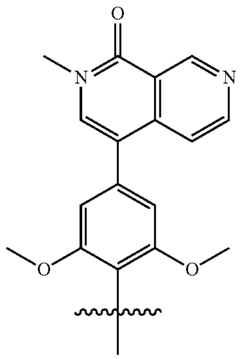

(1ac)

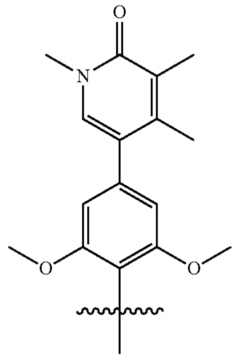

(1ad)

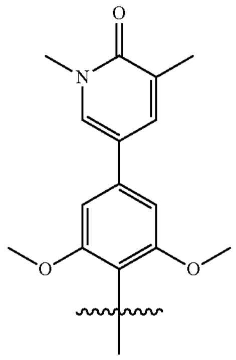

(1ae)

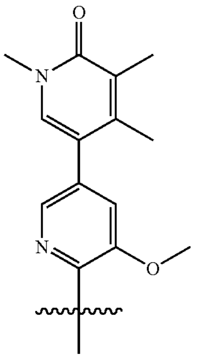

-continued
(1af)
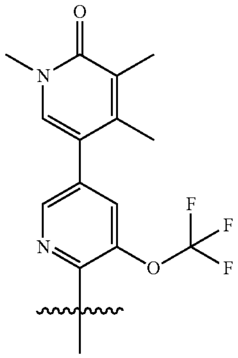
(1ag)
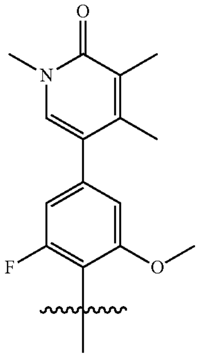
(1ah)
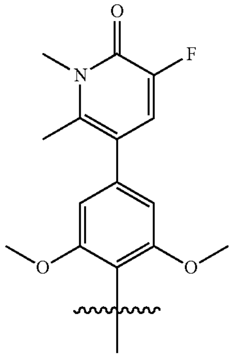
(1aj)
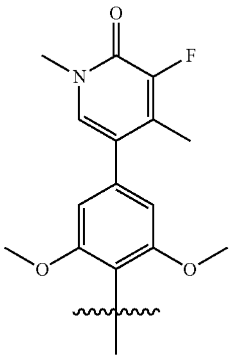
-continued
(1ak)
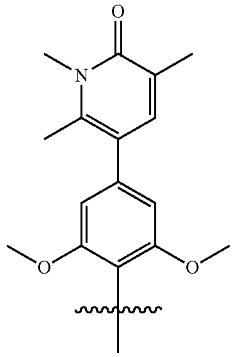
(1am)
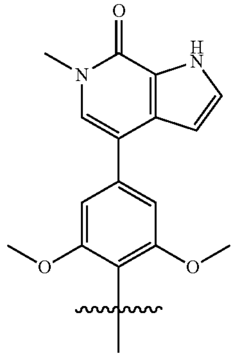
(1an)
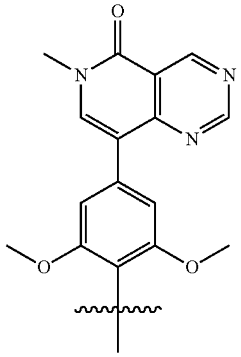
(1ap)
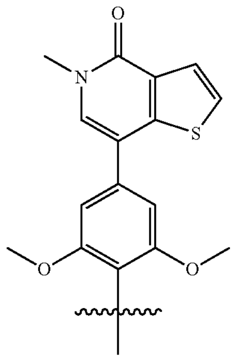

-continued
(1aq)
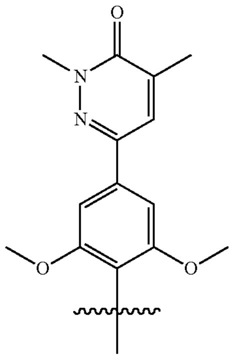
(1ar)
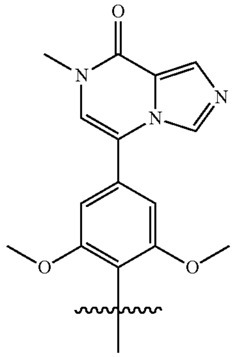
(1as)
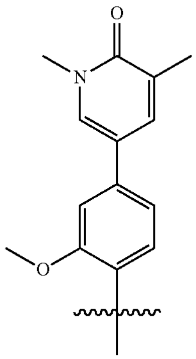
(1at)
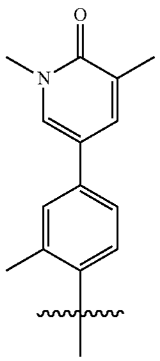
-continued
(1au)
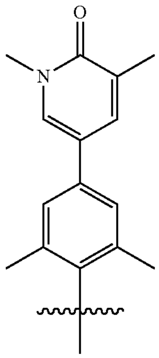
(1av)
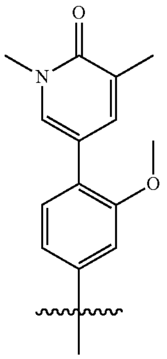
(1aw)
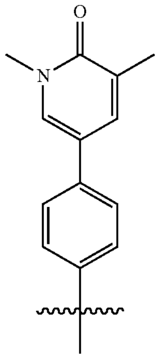
(1ax)
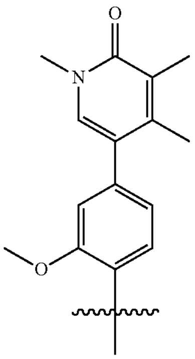

-continued
(1ay)
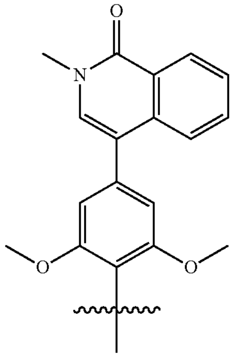
(1az)
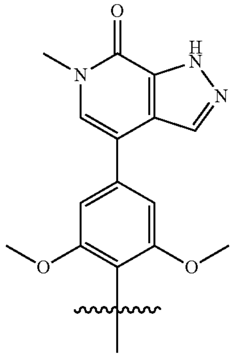
(1ba)
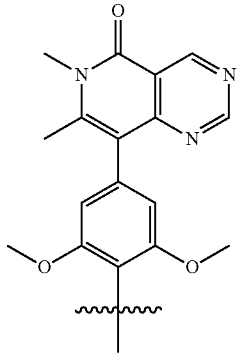
(1bb)
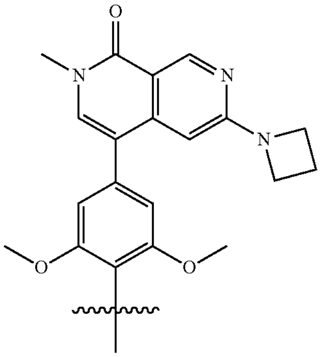
wherein the wavy line intersects the bond between $R^2$ and L.
Clause 27. The compound of any preceding clause, wherein $R^2$ is a moiety of formula (1ac), (1az) or (1bb)
(1ac)
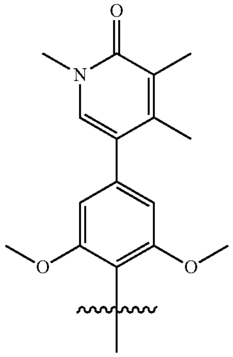
(1az)
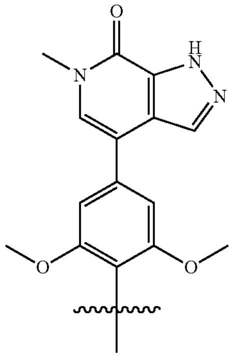
(1bb)
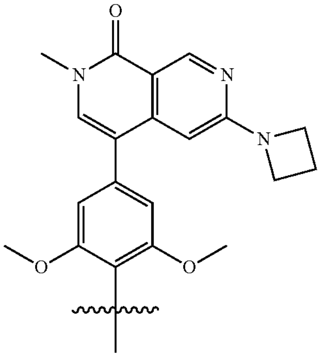
wherein the wavy line intersects the bond between $R^2$ and L.
Clause 28. The compound of any preceding clause, wherein $R^2$ is a moiety of formula (1ac)
(1ac)
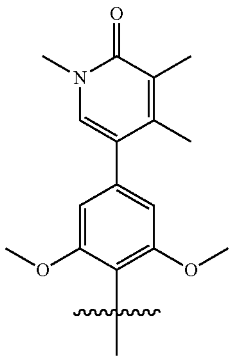

wherein the wavy line intersects the bond between $R^2$ and L.

Clause 29. The compound of any preceding clause, wherein $R^3$ is selected from halogen, OH, $C_1$-$C_4$ alkyl, $C_1$-$C_4$ haloalkyl, $C_1$-$C_4$ alkoxy, and $C_1$-$C_4$ haloalkoxy.

Clause 30. The compound of any preceding clause, wherein $R^3$ is selected from halogen, OH, $C_1$-$C_2$ alkyl, $C_1$-$C_2$ haloalkyl, $C_1$-$C_2$ alkoxy, and $C_1$-$C_2$ haloalkoxy Clause 31. A compound according to any preceding clause, wherein $R^3$ is selected from F, OH, methyl, halomethyl, methoxy, and halomethoxy.

Clause 32. A compound according to any one of clauses 1 to 29, wherein $R^3$ is selected from F, OH, $C_1$-$C_4$ alkyl, $C_1$-$C_4$ fluoroalkyl, $C_1$-$C_4$ difluoroalkyl, $C_1$-$C_4$ trifluoroalkyl, $C_1$-$C_4$ alkoxy, $C_1$-$C_4$ fluoroalkoxy, $C_1$-$C_4$ difluoroalkoxy, and $C_1$-$C_4$ trifluoroalkoxy.

Clause 33. A compound according to any one of clauses 1 to 30 and 32, wherein $R^3$ is selected from F, OH, $C_1$-$C_2$ alkyl, $C_1$-$C_2$ fluoroalkyl, $C_1$-$C_2$ difluoroalkyl, $C_1$-$C_2$ trifluoroalkyl, $C_1$-$C_2$ alkoxy, $C_1$-$C_2$ fluoroalkoxy, $C_1$-$C_2$ difluoroalkoxy, and $C_1$-$C_2$ trifluoroalkoxy.

Clause 34. A compound according to any preceding clause, wherein $R^3$ is selected from F, OH, methyl, fluoromethyl, difluoromethyl, trifluoromethyl, methoxy, fluoromethoxy, difluoromethoxy, and trifluoromethoxy.

Clause 35. A compound according to any preceding clause, wherein $R^3$ is selected from F, OH, and methoxy.

Clause 36. A compound according to any preceding clause, wherein $R^3$ is methoxy.

Clause 37. A compound of formula (II)

(II)

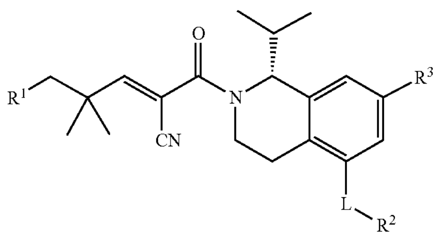

or a pharmaceutically acceptable salt, solvate or derivative thereof, wherein L, $R^1$, $R^2$, and $R^3$ are as defined in any one of clauses 1 to 36, wherein the compound of formula (II) is not (R)-2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or (R)-2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

Clause 38. A compound of formula (III)

(III)

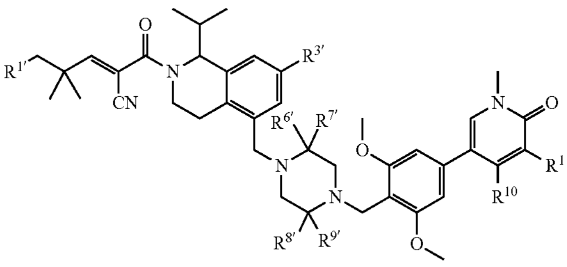

or a pharmaceutically acceptable salt, solvate or derivative thereof, wherein $R^{1'}$ is selected from H, F, $C_1$-$C_4$ alkyl, and methoxy;

$R^{3'}$ is selected from halogen, OH, $C_1$-$C_4$ alkyl, $C_1$-$C_2$ haloalkyl, $C_1$-$C_2$ alkoxy, and $C_1$-$C_2$ haloalkoxy;

$R^{6'}$, $R^{7'}$, $R^{8'}$ and $R^{9'}$ are each H, or $R^{6'}$ and $R^{7'}$ together with the carbon atom to which they are attached form a $C_3$ cycloalkyl, and/or $R^{8'}$ and $R^{9'}$ together with the carbon atom to which they are attached form a $C_3$ cycloalkyl;

$R^{10}$ and $R^{11}$ are independently selected from H and methyl, or $R^{10}$ and $R^{11}$ together with the atoms to which they are attached form a 5- or 6-membered heteroaryl group comprising one or more heteroatoms selected from the group consisting of N, S and O, optionally substituted by a 4- or 5-membered heteroalkyl group comprising one or more heteroatoms selected from the group consisting of N, S and O;

wherein the compound of formula (III) is not 2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or 2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

Clause 39. A compound according to clause 38, wherein $R^{1'}$ is selected from H and F.

Clause 40. A compound according to clause 38 or clause 39, wherein $R^{1'}$ is F.

Clause 41. A compound according to any one of clauses 38 to 40, wherein $R^{3'}$ is selected from F, OH, methyl, halomethyl, methoxy, and halomethoxy.

Clause 42. A compound according to any one of clauses 38 to 40, wherein $R^{3'}$ is selected from F, OH, $C_1$-$C_2$ alkyl, $C_1$-$C_2$ fluoroalkyl, $C_1$-$C_2$ difluoroalkyl, $C_1$-$C_2$ trifluoroalkyl, $C_1$-$C_2$ alkoxy, $C_1$-$C_2$ fluoroalkoxy, $C_1$-$C_2$ difluoroalkoxy, and $C_1$-$C_2$ trifluoroalkoxy.

Clause 43. A compound according to any one of clauses 38 to 42, wherein $R^{3'}$ is selected from F, OH, methyl, fluoromethyl, difluoromethyl, trifluoromethyl, methoxy, fluoromethoxy, difluoromethoxy, and trifluoromethoxy.

Clause 44. A compound according to any one of clauses 38 to 43, wherein $R^{3'}$ is selected from F, OH, and methoxy.

Clause 45. A compound according to any one of clauses 38 to 44, wherein $R^{3'}$ is methoxy.

Clause 46. A compound according to any one of clauses 38 to 45, wherein:

$R^{6'}$ and $R^{7'}$ are each H, and $R^{8'}$ and $R^{9'}$ together with the carbon atom to which they are attached form a cyclopropyl; or $R^{6'}$ and $R^{7'}$ together with the carbon atom to which they are attached form a cyclopropyl, and $R^{8'}$ and $R^{9'}$ are each H; or $R^{6'}$ and $R^{7'}$ together with the carbon atom to which they are attached form a cyclopropyl, and $R^{8'}$ and $R^{9'}$ together with the carbon atom to which they are attached form a cyclopropyl.

Clause 47. A compound according to any one of clauses 38 to 46, wherein:

$R^{6'}$ and $R^{7}$ are each H, and $R^{8'}$ and $R^{9'}$ together with the carbon atom to which they are attached form a cyclopropyl; or $R^{6'}$ and $R^{7'}$ together with the carbon atom to which they are attached form a cyclopropyl, and $R^{8'}$ and $R^{9'}$ are each H.

Clause 48. A compound according to any one of clauses 38 to 47, wherein $R^{6'}$ and $R^{7'}$ together with the carbon atom to which they are attached form a cyclopropyl, and $R^{8'}$ and $R^{9'}$ are each H.

Clause 49. A compound according to any one of clauses 38 to 48, wherein $R^{10}$ and $R^{11}$ are independently selected from H and methyl, or $R^{10}$ and $R^{11}$ together with the atoms to which they are attached form a 5- or 6-membered heteroaryl group comprising one or more N atoms, optionally substituted by a 4- or 5-membered heteroalkyl group comprising one or more N atoms.

Clause 50. A compound according to any one of clauses 38 to 49, wherein $R^{10}$ and $R^{11}$ are each methyl, or $R^{10}$ and $R^{11}$ together with the atoms to which they are attached form a 5- or 6-membered heteroaryl group comprising one or two N atoms, optionally substituted by a 4- or 5-membered heteroalkyl group comprising one N atom.

Clause 51. A compound according to any one of clauses 38 to 50, wherein $R^{10}$ and $R^{11}$ are each methyl, or $R^{10}$ and $R^{11}$ together with the atoms to which they are attached form a 5- or 6-membered heteroaryl group comprising one or two N atoms, optionally substituted by a 4-membered heteroalkyl group comprising one N atom.

Clause 52. A compound according to any one of clauses 38 to 51, wherein $R^{10}$ and $R^{11}$ are each methyl.

Clause 53. A compound of formula (IV)

(IV)

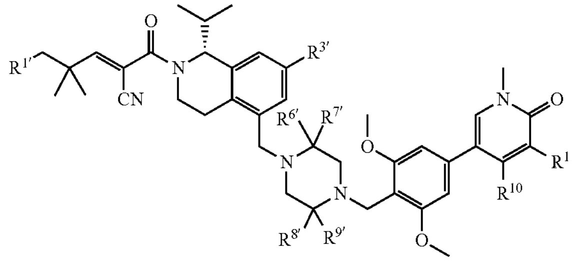

or a pharmaceutically acceptable salt, solvate or derivative thereof, wherein $R^{1'}$, $R^{3'}$, $R^{6'}$, $R^{7'}$, $R^{8'}$, $R^{9'}$, $R^{10}$ and $R^{11}$ are as defined in any one of clauses 38 to 52, wherein the compound of formula (IV) is not (R)-2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or (R)-2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

Clause 54. A compound of formula (V)

(V)

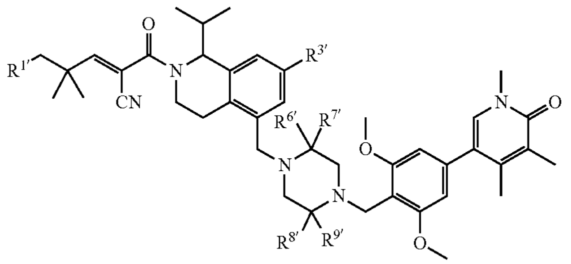

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined in any one of clauses 38 to 52;

wherein the compound of formula (V) is not 2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or 2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

Clause 55. A compound of formula (VI)

(VI)

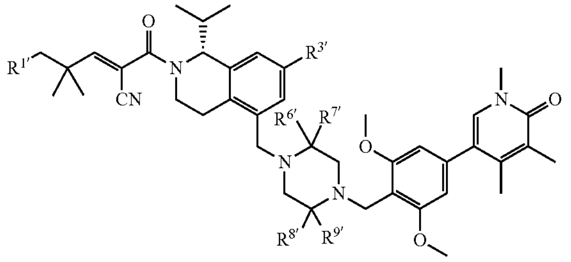

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined in any one of clauses 38 to 52;

wherein the compound of formula (VI) is not (R)-2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile or (R)-2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-7-fluoro-1-isopropyl-1,2,3,4-tetrahydroisoquinoline-2-carbonyl)-4,4-dimethylpent-2-enenitrile.

Clause 56. A compound of formula (VII)

(VII)

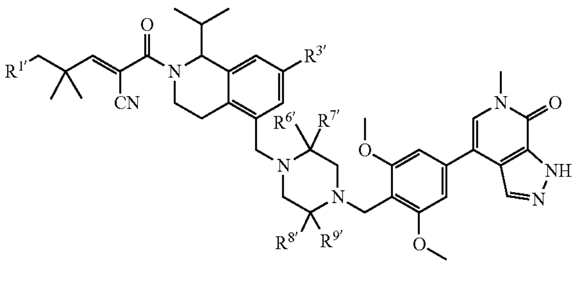

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined in any one of clauses 38 to 52.

Clause 57. A compound of formula (VIII)

(VIII)

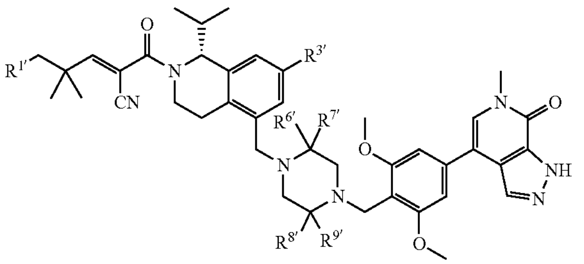

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined in any one of clauses 38 to 52.

Clause 58. A compound of formula (IX)

(IX)

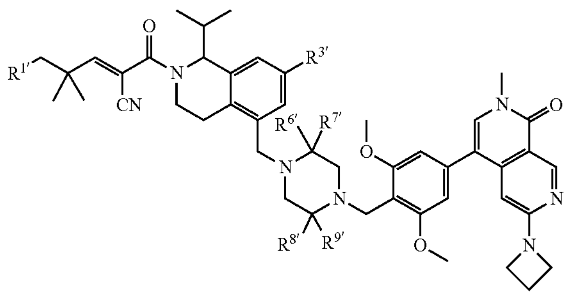

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined in any one of clauses 38 to 52.

Clause 59. A compound of formula (X)

(X)

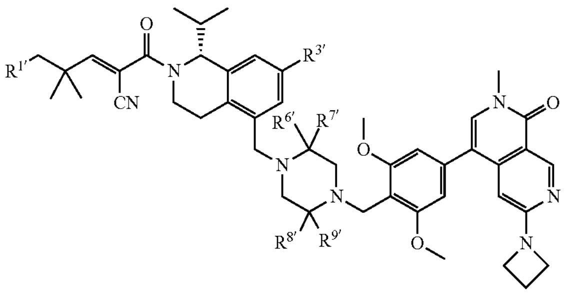

or a pharmaceutically acceptable salt, solvate or derivative thereof, wherein $R^{1'}$, $R^{3'}$, $R^{6'}$, $R^{7'}$, $R^{8'}$ and $R^{9'}$ are as defined in any one of clauses 38 to 52.

Clause 60. The compound according to clause 38, wherein the compound has a structure as shown in Table 1, Table 3 or Table 5 (i.e. the compound is one of compounds 1 to 14 (e.g. one of compounds 1 to 13)).

Clause 61. A pharmaceutical composition comprising a compound of formula (I), (II), (III), (IV), (V), (VI), (VII), (VIII), (IX) or (X) according to any one of clauses 1 to 60, together with a pharmaceutically acceptable carrier, optionally wherein the compound of formula (I), (II), (III), (IV), (V), (VI), (VII), (VIII), (IX) or (X) is present in the composition as a pharmaceutically acceptable salt, solvate or derivative.

Clause 62. A pharmaceutical composition comprising a compound of formula (III), (IV), (V), (VI), (VII), (VIII), (IX), (X) or (XI) according to any one of clauses 38 to 60, together with a pharmaceutically acceptable carrier, optionally wherein the compound of formula (III), (IV), (V), (VI), (VII), (VIII), (IX), (X) or (XI) is present in the composition as a pharmaceutically acceptable salt, solvate or derivative.

Clause 63. A compound according to any one of clauses 1 to 60, or a pharmaceutical composition of clause 61 or clause 62, for use in medicine.

Clause 64. The compound or pharmaceutical composition for use of clause 63, wherein the use comprises the treatment and/or prevention of any disease or condition which is associated with and/or is caused by an abnormal level of BRD9 activity.

Clause 65. The compound or pharmaceutical composition for use of clause 63 or clause 64, for use in the treatment and/or prevention of cancer.

Clause 66. A method of selectively degrading and/or increasing proteolysis of BRD9 in a cell or a subject in need thereof, the method comprising contacting and/or treating the cell with a compound of formula (I), (II), (III), (IV), (V), (VI), (VII), (VIII), (IX), (X) or (XI) as defined in any one of clauses 1 to 60 or the pharmaceutical composition of clause 61 or clause 62.

Clause 67. A method of selectively degrading and/or increasing proteolysis of BRD9 in a cell or a subject in need thereof, the method comprising contacting and/or treating the cell with a compound of formula (III), (IV), (V), (VI), (VII), (VIII), (IX), (X) or (XI) as defined in any one of clauses 38 to 60 or the pharmaceutical composition of clause 62.

Clause 67. A method of making a compound of formula (I), (II), (III), (IV), (V), (VI), (VII), (VIII), (IX), (X) or (XI) as defined in any one of clauses 1 to 60.

Clause 68. A method of making a compound of formula (III), (IV), (V), (VI), (VII), (VIII), (IX), (X) or (XI) as defined in any one of clauses 38 to 60.

Clause 69. A compound library comprising a plurality of compounds according to any one of clauses 1 to 60.

Clause 70. A compound library comprising a plurality of compounds according to any one of clauses 38 to 60.

Clause 71. An intermediate compound in the synthesis of any one of compounds 1 to 14 (for example, a compound of any one of formulae A1, A2, A3, A4, A5, A6, B1, B2, B3, B4, B5, B6, B7, B8, B9, B10, B11, B12, B13, B14, C1, C2, C3, C4, C5, D1, D2, D3, D4, E1, E2, E3, E4, F1, F2, F3, F4, F2-1, F3-1, F4-1, G1, H1, H2, H3, J1, J2, K1, K2, L1, L2, M1, N2, N3, N4, N5, N6, N7, P1, P2, P3, P4, P5, P6, and P7).

Clause 72. A compound of formula H1:

(H1)

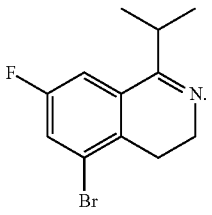

Clause 73. A compound of formula:

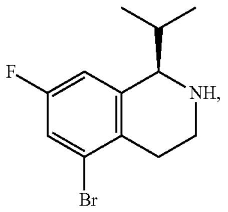

or a salt thereof.

Clause 74. The compound of clause 73, wherein the compound is of formula F2-1:

(F2-1)

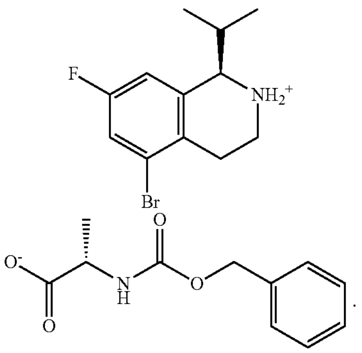

Clause 75. A compound of formula F2:

(F2)

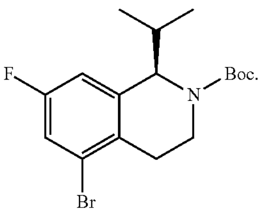

Clause 76. A compound of formula E2:

(E2)

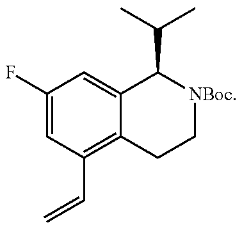

Clause 77. A compound of formula D2:

(D2)

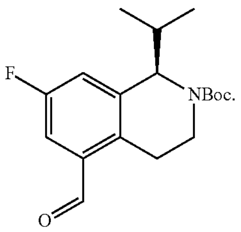

Clause 78. A compound of formula H2:

(H2)

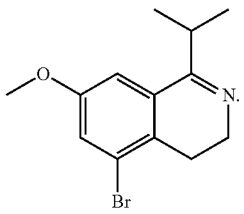

Clause 79. A compound of formula F3:

(F3)

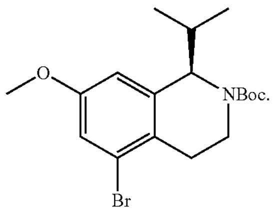

Clause 80. A compound of formula E3:

(E3)

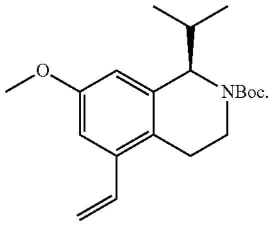

Clause 81. A compound of formula D3:

(D3)

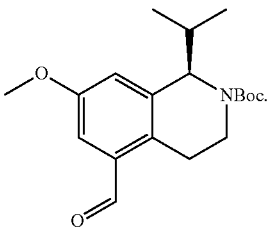

Clause 82. A compound of formula (III):

(III)

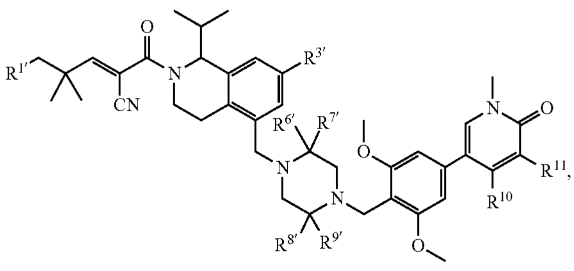

or a pharmaceutically acceptable salt thereof, wherein:

$R^{1'}$ is selected from the group consisting of H, F, $C_1$-$C_4$ alkyl, and methoxy;

$R^{3'}$ is selected from the group consisting of OH, $C_1$-$C_2$ alkoxy, and $C_1$-$C_2$ haloalkoxy;

$R^{6'}$, $R^{7}$, $R^{8'}$ and $R^{9'}$ are each H; or $R^{8'}$ and $R^{9'}$ are each H; and $R^{6'}$ and $R^{7'}$ together with the carbon atom to which they are attached form a $C_3$ cycloalkyl; or $R^{6'}$ and RT are each H; and $R^{8'}$ and $R^{9'}$ together with the carbon atom to which they are attached form a $C_3$ cycloalkyl; and $R^{10}$ and $R^{11}$ are independently selected from the group consisting of H and methyl, or $R^{10}$ and $R^{11}$ together with the atoms to which they are attached form a 5- or 6-membered heteroaryl group comprising one or more heteroatoms selected from the group consisting of N, S, and O, optionally substituted by a 4- or 5-membered heteroalkyl group comprising one or more heteroatoms selected from the group consisting of N, S, and O.

Clause 83. The compound according to Clause 82, or a pharmaceutically acceptable salt thereof, having formula (IV):

(IV)

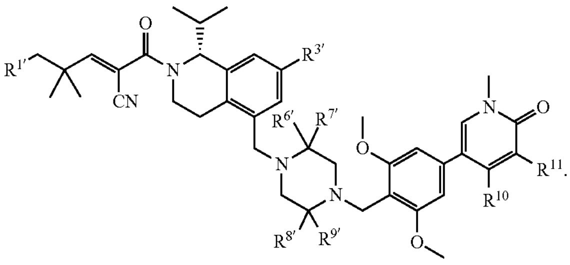

Clause 84. The compound according to Clauses 82 or 83, or a pharmaceutically acceptable salt thereof, wherein $R^{1'}$ is selected from the group consisting of H and F.

Clause 85. The compound according to Clause 84, or a pharmaceutically acceptable salt thereof, wherein $R^{1'}$ is F.

Clause 86. The compound according to any one of Clauses 82-85, or a pharmaceutically acceptable salt thereof, wherein $R^{3'}$ is selected from the group consisting of OH, methoxy, and halomethoxy.

Clause 87. The compound according to Clauses 82-85, or a pharmaceutically acceptable salt thereof, wherein $R^{3'}$ is selected from the group consisting of OH, $C_1$-$C_2$ alkoxy, $C_1$-$C_2$ fluoroalkoxy, $C_1$-$C_2$ difluoroalkoxy, and $C_1$-$C_2$ trifluoroalkoxy.

Clause 88. A compound according to Clause 87, or a pharmaceutically acceptable salt thereof, wherein $R^{3'}$ is selected from the group consisting of OH, methoxy, fluoromethoxy, difluoromethoxy, and trifluoromethoxy.

Clause 89. The compound according to Clause 88, or a pharmaceutically acceptable salt thereof, wherein $R^{3'}$ is selected from the group consisting of OH and methoxy.

Clause 90. The compound according to Clause 89, or a pharmaceutically acceptable salt thereof, wherein $R^{3'}$ is methoxy.

Clause 91. The compound according to any one of Clauses 82-90, or a pharmaceutically acceptable salt thereof, wherein:

(i) $R^{6'}$ and $R^{7'}$ are each H; and $R^{8'}$ and $R^{9'}$ together with the carbon atom to which they are attached form a cyclopropyl; or (ii) $R^{6'}$ and $R^{7'}$ together with the carbon atom to which they are attached form a cyclopropyl; and $R^{8'}$ and $R^{9'}$ are each H.

Clause 92. The compound according to Clause 91, or a pharmaceutically acceptable salt thereof, wherein $R^{6'}$ and $R^{7'}$ together with the carbon atom to which they are attached form a cyclopropyl, and $R^{8'}$ and $R^{9'}$ are each H.

Clause 93. The compound according to any one of Clauses 82-92, or a pharmaceutically acceptable salt thereof, wherein:

$R^{10}$ and $R^{11}$ are independently selected from the group consisting of H and methyl; or $R^{10}$ and $R^{11}$ together with the atoms to which they are attached form a 5- or 6-membered heteroaryl group comprising one or more N atoms, optionally substituted by a 4- or 5-membered heteroalkyl group comprising one or more N atoms.

Clause 94. The compound according to Clauses 82-92, or a pharmaceutically acceptable salt thereof, wherein $R^{10}$ and $R^{11}$ are each methyl.

Clause 95. The compound according to Clause 82, or pharmaceutically acceptable salt thereof, wherein the compound is selected from the group consisting of:

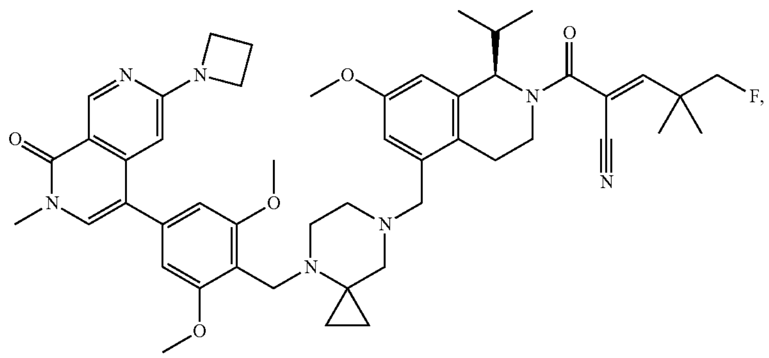
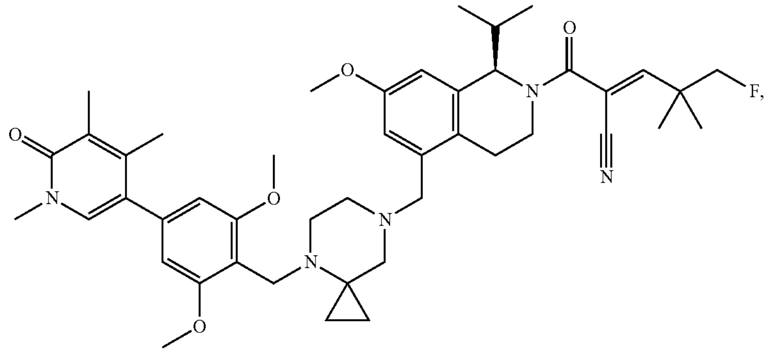
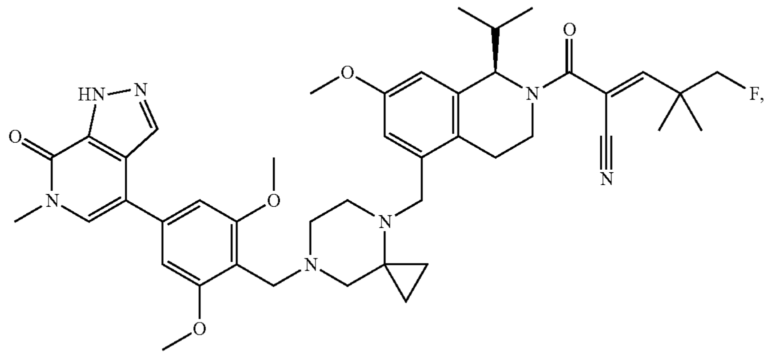
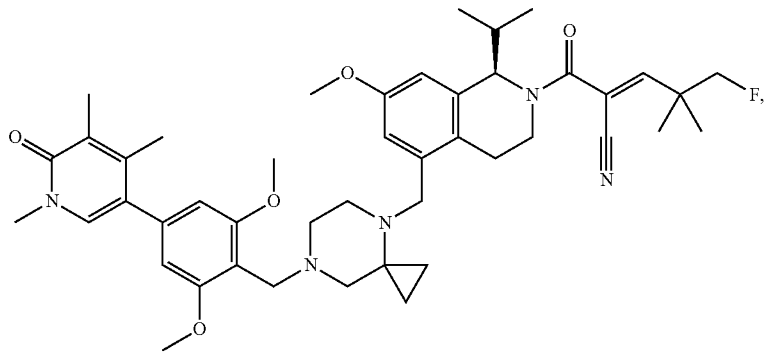

-continued

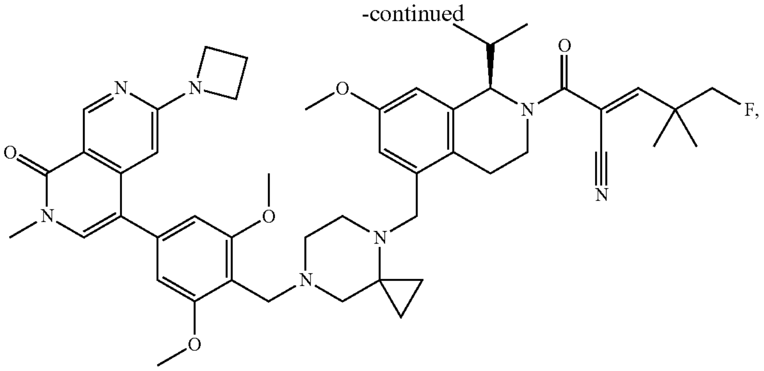

,

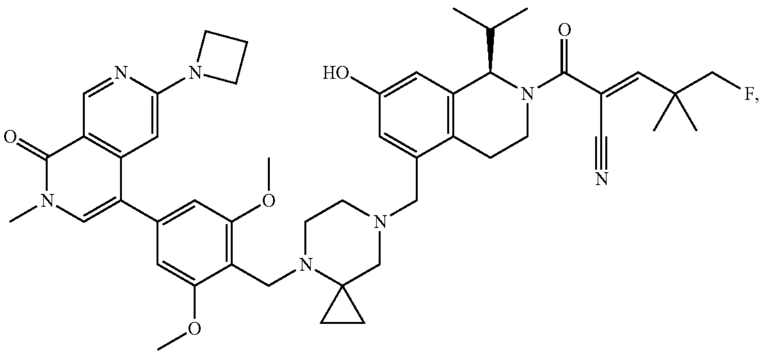

, and

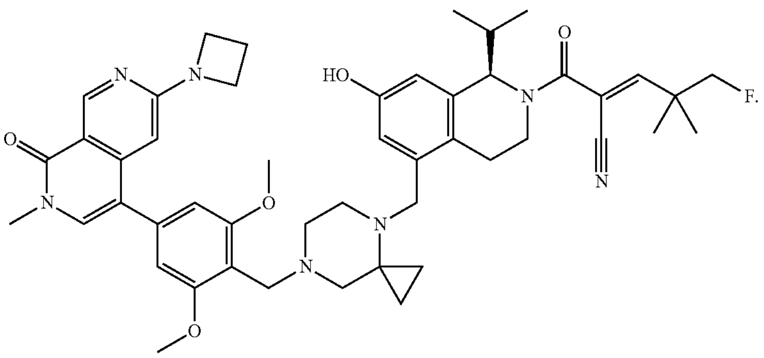

.

Clause 96. The compound of Clause 95, or a pharmaceutically acceptable salt thereof, wherein the compound is:

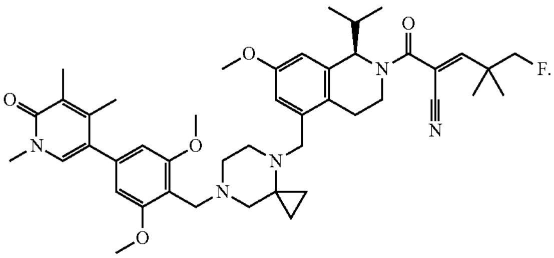 [SMILES: COc1cc(CN2CCN(Cc3c(OC)cc(-c4cn(C)c(=O)c(C)c4C)cc3OC)CC23CC3)c2c(c1)[C@@H](C(C)C)N(C(=O)/C(C#N)=C/C(C)(C)CF)CC2]

.

Clause 97. A pharmaceutical composition comprising the compound of any one of Clauses 82-95, or a pharmaceutically acceptable salt thereof, together with a pharmaceutically acceptable carrier.

Clause 98. A pharmaceutical composition comprising the compound of Clause 96, or a pharmaceutically acceptable salt thereof, together with a pharmaceutically acceptable carrier.

Clause 99. A method of treating cancer in a subject in need thereof, the method comprising administering a therapeutically effective amount of the compound of any one of Clauses 82-95, or a pharmaceutically acceptable salt thereof, to the subject.

Clause 100. A method of treating cancer in a subject in need thereof, the method comprising administering a therapeutically effective amount of the compound of Clause 96, or a pharmaceutically acceptable salt thereof, to the subject.

Clause 101. The method of Clause 100, wherein the cancer is acute myeloid leukaemia, multiple myeloma, chronic lymphocytic leukaemia, acute lymphocytic leukaemia, melanoma, liver cancer, lung cancer, colorectal cancer, colon cancer, brain cancer, thyroid cancer, breast cancer, ovarian cancer, gastric cancer, pancreatic cancer, or prostate cancer.

The present disclosure will now be described in detail with reference to the following non-limiting examples.

| List of Abbreviations: | |
|---|---|
| μL = Microliter | 1,2,3-triazolo[4,5-b]pyridinium 3-oxide hexafluorophosphate |
| μM = Micromolar | HPLC = high performance liquid chromatography |
| NMR = Nuclear Magnetic Resonance | Hz = Hertz |
| ACN = acetonitrile | J = coupling constant (given in Hz unless otherwise indicated) |
| AcOH or HOAc = acetic acid | LCMS = liquid chromatography mass spectrometry |
| BINAP = (2,2'-bis(diphenylphosphino)-1,1'-binaphthyl) | m = multiplet |
| Boc = tert-butoxycarbonyl | M = Molar |
| bs = broad singlet | M + $H^+$ = parent mass spectrum peak plus $H^+$ |
| ° C. = degrees Celsius | mg = Milligram |
| d = doublet | min = minutes |
| δ = chemical shift | mL = Milliliter |
| DCM = Dichloromethane | mM = Millimolar |
| dba = dibenzylideneacetone | mmol = Millimole |
| DIPEA = N,N-Diisopropylethylamine, or Hünig's base | MS = mass spectrum |
| DMF = N,N-dimethylformamide | MsCl = methanesulfonyl chloride |
| DMSO = Dimethylsulfoxide | MTBE = methyl tert-butyl ether |
| dppf = 1,1'-Ferrocenediyl-bis(diphenylphosphine) | nM = nanomolar |
| EtOAc = Ethyl acetate | NMP = N-Methyl-2-pyrrolidone |
| g or G = gram | pTsOH = p-toluenesulfonic acid |
| h or H = Hour(s) | TFA = trifluoroacetic acid |
| HATU = 1-[Bis(dimethylamino)methylene]-1H- | THF = tetrahydrofuran |
| q = quartet | TLC = thin layer chromatography |
| RT or r.t. = room temperature | XPhos = 2-Dicyclohexylphosphino-2',4',6'-triisopropylbiphenyl |
| STAB = sodium triacetoxyborohydride | |
| t = triplet | |
| TBAF = tetra-n-butylammonium fluoride | |

Chemistry—Materials and Methods

All chemicals, unless otherwise stated were commercially available and used without further purification. Solvents were anhydrous and reactions preformed under positive pressure of nitrogen or argon.

Flash column chromatography (FCC) was performed using a Teledyne Isco Combiflash Rf or Rf200i. Prepacked columns RediSep Rf Normal Phase Disposable Columns were used.

NMR data was acquired in Bruker Avance Neo nano bay 400 MHz NMR Spectrometer. Chemical Shifts are reported in ppm relative to dimethyl Sulfoxide (δ 2.50), methanol (δ 3.31), chloroform (δ 7.26) or other solvent as indicated in NMR spectral data. A small amount (1-5 mg) of sample is dissolved in an appropriate deuterated solvent (0.6 mL).

Preparative HPLC was performed on a Gilson Preparative HPLC System with a Waters X-Bridge C18 column (100 mm×19 mm; 5 μm particle size) and a gradient of 5% to 95% acetonitrile in water over 10 min, flow 25 mL/min, with 0.1% formic acid in the aqueous phase.

Liquid Chromatography Mass Spectra (LC-MS) were recorded using positive ion electron spray ionisation ($ESI^+$) on an Agilent InfinityLab Single Quadrupole LC/MSD with a Waters XBridge® C18 3.5 μm column (2.1 mm×50 mm) using $H_2O$+MeCN (5-95%)+0.1% $HCO_2H$ or $H_2O$+MeCN (20-95%)+0.1% $HCO_2H$ as eluent, using a linear gradient over 3 minutes. Alternatively, a Shimadzu LC; Prominence-I series instrument was used, with the following set up:

| HPLC Method A |
|---|
| Column: X-Bridge C8 (150 × 4.6 mm, 5.0 μm) |
| Detection: UV @ 210-400 nm(Max Plot) |
| Sample Diluent: Acetonitrile and Water |
| Mobile Phase A: 10 mM Ammonium Acetate in water |
| Mobile Phase B: Acetonitrile |
| Flow rate: 1.5 mL/Min |
| Runtime: 12.0 Min |
| Elution: Gradient elution |

-continued

| Time in Min | % of Mobile Phase B |
|---|---|
| 0.01 | 10 |
| 8.0 | 100 |
| 10.0 | 100 |
| 10.01 | 10 |
| 12.0 | 10 |

| HPLC Method B | |
|---|---|
| Column: X-select CSH C18 (150 × 4.6 mm, 5.0 μm) | |
| Column Temperature: Ambient | |
| Detection: UV @ 210-400 nm(Max Plot) | |
| Sample Diluent: Acetonitrile and Water | |
| Mobile Phase A: 0.1% Formic acid in water | |
| Mobile Phase B: Acetonitrile | |
| Runtime: 10.0 Min | |
| Flowrate: 2.0 mL/Min | |
| Elution: Gradient elution | |
| **Time in Min** | **% of Mobile Phase B** |
| 0 | 5 |
| 8 | 100 |
| 8.01 | 5 |
| 10 | 5 |

Example 1: Synthesis of Compounds 1 and 2

Compounds 1 and 2 (see Table 1) were made using the following general procedure:

To a solution of the starting material given in Table 7 (1.0 equiv.) and aldehyde given in Table 2 in DMF (10 vol.) was added pyrrolidine (5 equiv.) and the mixture was stirred for 4 h. The volatiles were concentrated in vacuo and purified by reverse phase/Preparative-HPLC to yield the corresponding compound.

TABLE 1

| Compound | Compound structure/name |
|---|---|
| 1 | 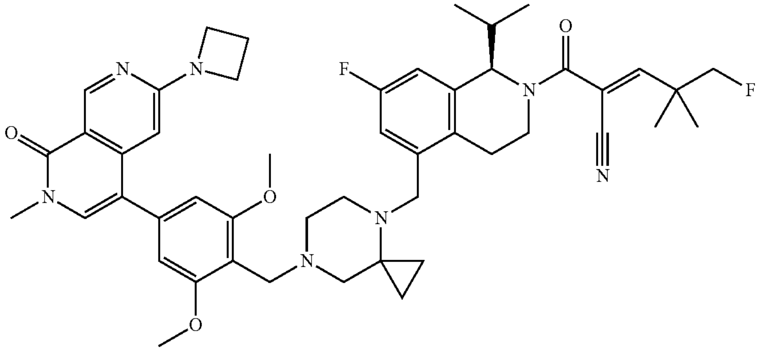 [SMILES: COc1cc(-c2cn(C)c(=O)c3cnc(N4CCC4)cc23)cc(OC)c1CN1CCN(Cc2cc(F)cc3c2CCN(C(=O)/C(C#N)=C/C(C)(C)CF)[C@@H]3C(C)C)C2(CC2)C1] (R,E)-2-(5-((7-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-4-yl)methyl)-7-fluoro-1-isopropyl-1,2,3,4-tetrahydroisoquinoline-2-carbonyl)-5-fluoro-4,4-dimethylpent-2-enenitrile |
| 2 | 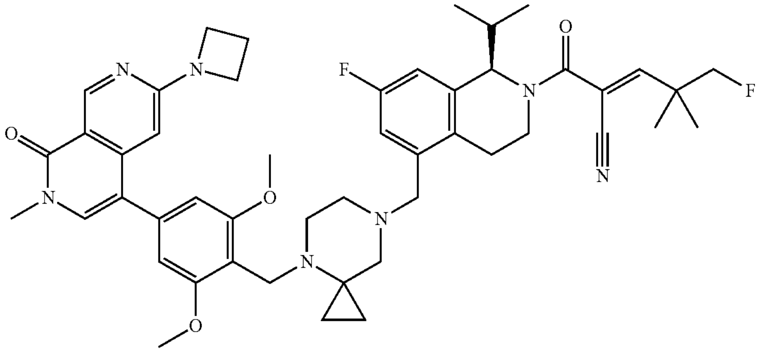 [SMILES: COc1cc(-c2cn(C)c(=O)c3cnc(N4CCC4)cc23)cc(OC)c1CN1CCN(Cc2cc(F)cc3c2CCN(C(=O)/C(C#N)=C/C(C)(C)CF)[C@@H]3C(C)C)CC12CC2] (R,E)-2-(5-((4-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-7-yl)methyl)-7-fluoro-1-isopropyl-1,2,3,4-tetrahydroisoquinoline-2-carbonyl)-5-fluoro-4,4-dimethylpent-2-enenitrile |

TABLE 2

| Compound | Starting material | Aldehyde | LCMS m/z $[M + H]^+$/Yield |
|---|---|---|---|
| 1 | A1 | 3-fluoro-2,2-dimethylpropanal (10 eq) | 834.2/12% |
| 2 | A2 | 3-fluoro-2,2-dimethylpropanal (12 eq) | 834.2/11% |

Example 2: Synthesis of Compounds 3 to 5

Compounds 3 to 5 (see Table 3) were made using the following general procedure:

A solution of starting material given in Table 7 (1.0 equiv.) in DMF (0.1 M) was treated with TMS-Cl (4 eq) and pyrrolidine (6 equiv.). Then, the aldehyde given in Table 4 was added and the reaction mixture was stirred at RT for 4 h. The volatiles were concentrated in vacuo at low temperature (30-35° C.) and purified by Prep-HPLC purification to yield the corresponding compound.

TABLE 3

| Compound | Compound structure/name |
|---|---|
| 3 | 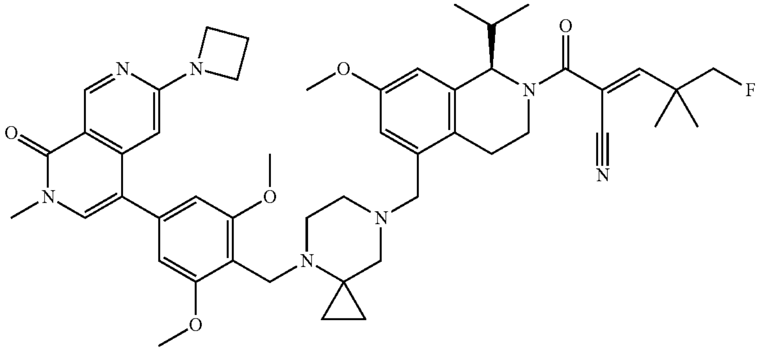 [SMILES: COc1cc(CN2CCN(Cc3c(OC)cc(-c4cn(C)c(=O)c5cnc(N6CCC6)cc45)cc3OC)C3(CC3)C2)c2c(c1)[C@@H](C(C)C)N(C(=O)/C(C#N)=C/C(C)(C)CF)CC2]<br>(R,E)-2-(5-((4-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-7-yl)methyl)-1-isopropyl-7-methoxy-1,2,3,4-tetrahydroisoquinoline-2-carbonyl)-5-fluoro-4,4-dimethylpent-2-enenitrile |
| 4 | 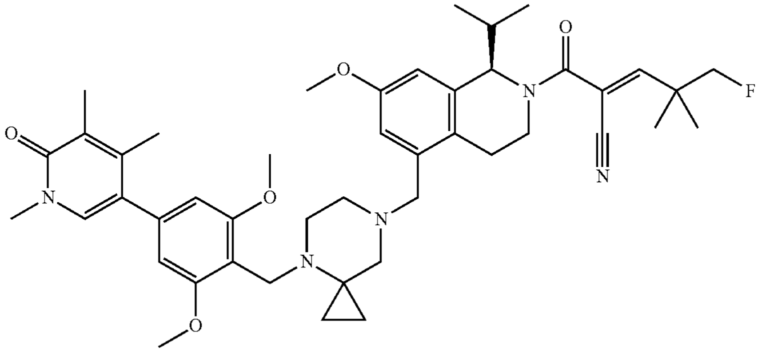 [SMILES: COc1cc(CN2CCN(Cc3c(OC)cc(-c4cn(C)c(=O)c(C)c4C)cc3OC)C3(CC3)C2)c2c(c1)[C@@H](C(C)C)N(C(=O)/C(C#N)=C/C(C)(C)CF)CC2]<br>(R,E)-2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-1-isopropyl-7-methoxy-1,2,3,4-tetrahydroisoquinoline-2-carbonyl)-5-fluoro-4,4-dimethylpent-2-enenitrile |
| 5 | 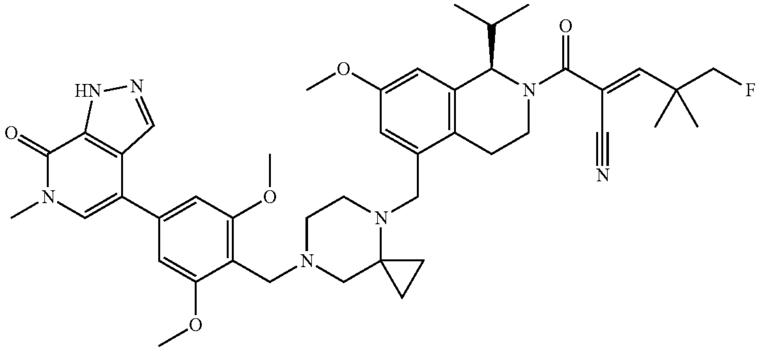 [SMILES: COc1cc(CN2CCN(Cc3c(OC)cc(-c4cn(C)c(=O)c5[nH]ncc45)cc3OC)CC23CC3)c2c(c1)[C@@H](C(C)C)N(C(=O)/C(C#N)=C/C(C)(C)CF)CC2]<br>(R,E)-2-(5-((7-(2,6-dimethoxy-4-(6-methyl-7-oxo-6,7-dihydro-1H-pyrazolo[3,4-c]pyridin-4-yl)benzyl)-4,7-diazaspiro[2.5]octan-4-yl)methyl)-1-isopropyl-7-methoxy-1,2,3,4-tetrahydroisoquinoline-2-carbonyl)-5-fluoro-4,4-dimethylpent-2-enenitrile |

TABLE 4

| Compound | Starting material | Aldehyde | LCMS m/z $[M + H]^+$/Yield |
|---|---|---|---|
| 3 | A4 | 3-fluoro-2,2-dimethylpropanal (10 eq) | 846.4/29% |

TABLE 4-continued

| Compound | Starting material | Aldehyde | LCMS m/z $[M + H]^+$/Yield |
|---|---|---|---|
| 4 | A5 | 3-fluoro-2,2-dimethylpropanal (10 eq) | 768.3/10% |

TABLE 4-continued

| Compound | Starting material | Aldehyde | LCMS m/z [M + H]$^+$/Yield |
|---|---|---|---|
| 5 | A6 | 3-fluoro-2,2-dimethylpropanal (5 eq) | 780.2/3% |

Example 3: Synthesis of (R,E)-2-(5-((4-(2,6-dimethoxy-4-(6-methyl-7-oxo-6,7-dihydro-1H-pyrazolo[3,4-c]pyridin-4-yl)benzyl)-4,7-diazaspiro[2.5]octan-7-yl)methyl)-1-isopropyl-7-methoxy-1,2,3,4-tetrahydroisoquinoline-2-carbonyl)-5-fluoro-4,4-dimethylpent-2-enenitrile (Compound 6)

(6)

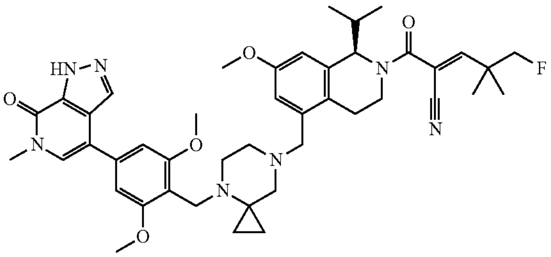

A solution of starting material A3 in DMF (0.1 M) was treated with pyrrolidine (3.0 eq) and TMS-Cl (1.5 eq) and followed by addition of 3-fluoro-2,2-dimethylpropanal (5 eq). The reaction mixture was stirred at 0° C. to RT for 16 h until the reaction was complete. The volatiles were concentrated in vacuo and purified by silica gel column chromatography to yield compound 6 (4%). LCMS m/z=780.2 [M+H]$^+$.

Example 4: Synthesis of Compounds 7 to 14

Compounds 7 to 14 (see Table 5) were made using the following general procedure:

To a stirred solution of the carboxylic acid given in Table 6 (1.0 equiv.) in DMF was added DIPEA (2.5 equiv.) and HATU (1.5 equiv.). The reaction mixture was stirred for 5 min, then the relevant starting compound (1.5 equiv.) was added and the reaction mixture was stirred for 16 h at RT. The reaction was quenched with ice cold water and extracted with EtOAc. The combined organic layers were concentrated in vacuo to afford the crude product. The crude product was purified by silica gel column chromatography/reverse phase preparative HPLC to give the compound.

TABLE 5

| Compound | Compound structure/name |
|---|---|
| 7 | 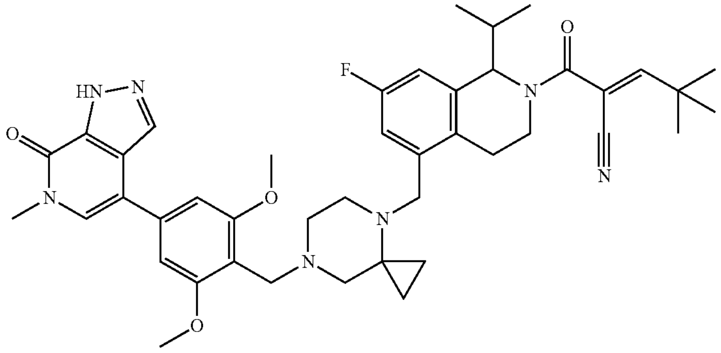 [SMILES: COc1cc(-c2cn(C)c(=O)c3[nH]ncc23)cc(OC)c1CN1CCN(Cc2cc(F)cc3c2CCN(C(=O)/C(C#N)=C/C(C)(C)C)C3C(C)C)C2(CC2)C1] single enantiomer of unknown absolute configuration of (E/Z)-2-(5-((7-(2,6-dimethoxy-4-(6-methyl-7-oxo-6,7-dihydro-1H-pyrazolo[3,4-c]pyridin-4-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile |
| 8 | 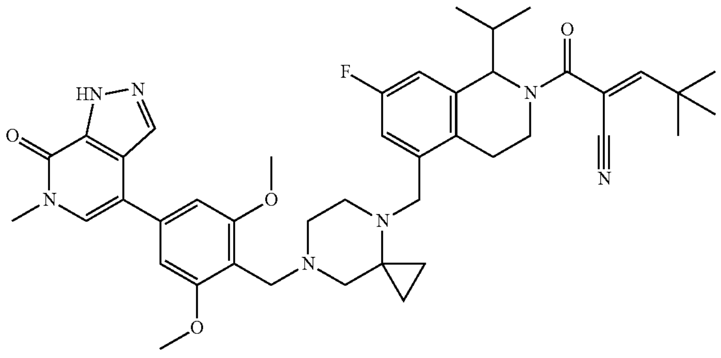 [SMILES: COc1cc(-c2cn(C)c(=O)c3[nH]ncc23)cc(OC)c1CN1CCN(Cc2cc(F)cc3c2CCN(C(=O)/C(C#N)=C/C(C)(C)C)C3C(C)C)C2(CC2)C1] single enantiomer of unknown absolute configuration of (E/Z)-2-(5-((7-(2,6-dimethoxy-4-(6-methyl-7-oxo-6,7-dihydro-1H-pyrazolo[3,4-c]pyridin-4-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile |

TABLE 5-continued

| Compound | Compound structure/name |
|---|---|
| 9 | 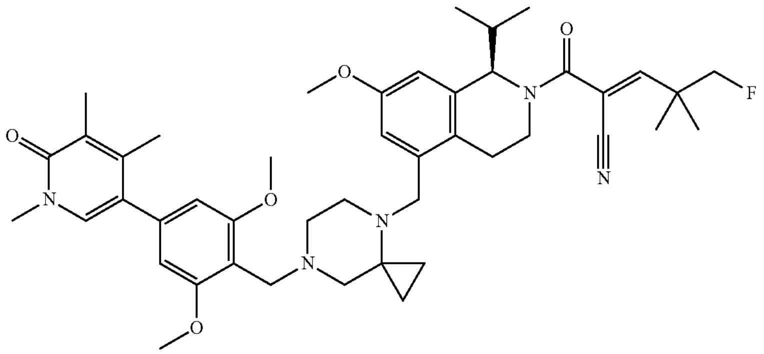 [SMILES: COc1cc(CN2CCN(Cc3c(OC)cc(-c4cn(C)c(=O)c(C)c4C)cc3OC)CC23CC3)c2c(c1)[C@@H](C(C)C)N(C(=O)/C(C#N)=C/C(C)(C)CF)CC2]<br>(R,E/Z)-2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-1-isopropyl-7-methoxy-1,2,3,4-tetrahydroisoquinoline-2-carbonyl)-5-fluoro-4,4-dimethylpent-2-enenitrile |
| 10 | 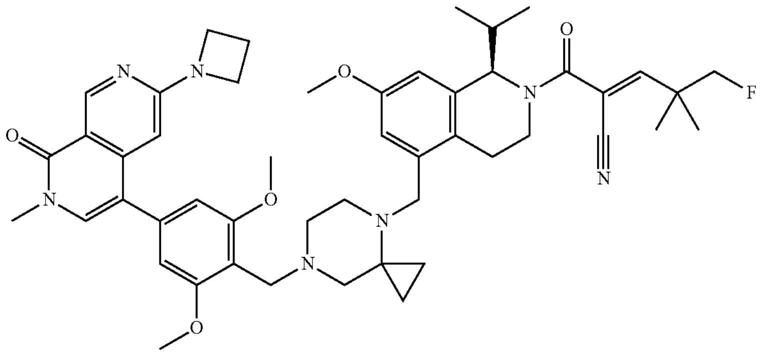 [SMILES: COc1cc(CN2CCN(Cc3c(OC)cc(-c4cn(C)c(=O)c5cnc(N6CCC6)cc45)cc3OC)CC23CC3)c2c(c1)[C@@H](C(C)C)N(C(=O)/C(C#N)=C/C(C)(C)CF)CC2]<br>(R,E/Z)-2-(5-((7-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-4-yl)methyl)-1-isopropyl-7-methoxy-1,2,3,4-tetrahydroisoquinoline-2-carbonyl)-5-fluoro-4,4-dimethylpent-2-enenitrile |
| 11 | 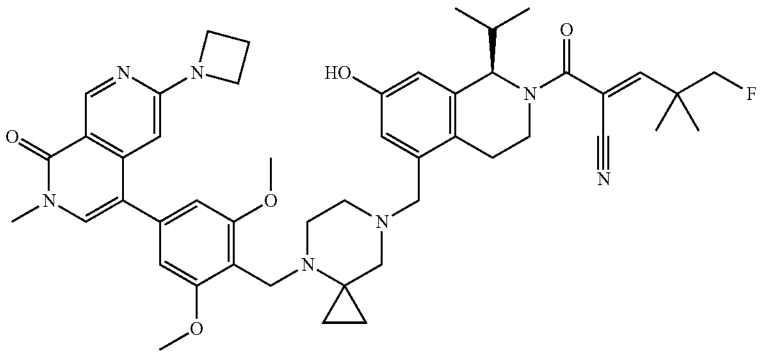 [SMILES: COc1cc(-c2cn(C)c(=O)c3cnc(N4CCC4)cc23)cc(OC)c1CN1CCN(Cc2cc(O)cc3c2CCN(C(=O)/C(C#N)=C/C(C)(C)CF)[C@@H]3C(C)C)CC12CC2]<br>(R,E/Z)-2-(5-((4-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-7-yl)methyl)-7-hydroxy-1-isopropyl-1,2,3,4-tetrahydroisoquinoline-2-carbonyl)-5-fluoro-4,4-dimethylpent-2-enenitrile |

TABLE 5-continued

| Compound | Compound structure/name |
| --- | --- |
| 12 | 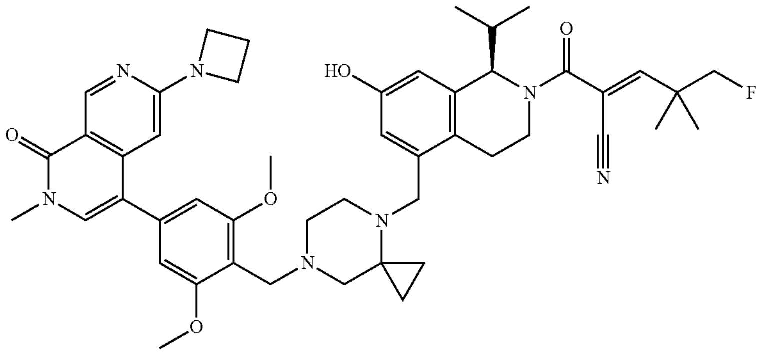 [SMILES: COc1cc(-c2cn(C)c(=O)c3cnc(N4CCC4)cc23)cc(OC)c1CN1CCN(Cc2cc(O)cc3c2CCN(C(=O)/C(C#N)=C/C(C)(C)CF)[C@@H]3C(C)C)C2(CC2)C1]<br>(R,E/Z)-2-(5-((7-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-4-yl)methyl)-7-hydroxy-1-isopropyl-1,2,3,4-tetrahydroisoquinoline-2-carbonyl)-5-fluoro-4,4-dimethylpent-2-enenitrile |
| 13 | 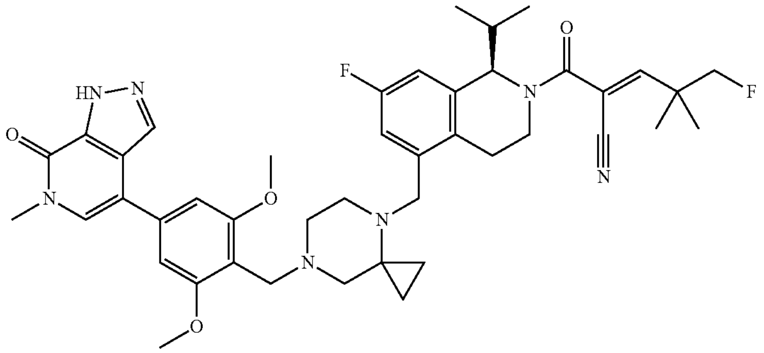 [SMILES: COc1cc(-c2cn(C)c(=O)c3[nH]ncc23)cc(OC)c1CN1CCN(Cc2cc(F)cc3c2CCN(C(=O)/C(C#N)=C/C(C)(C)CF)[C@@H]3C(C)C)C2(CC2)C1]<br>(R,E/Z)-2-(5-((7-(2,6-dimethoxy-4-(6-methyl-7-oxo-6,7-dihydro-1H-pyrazolo[3,4-c]pyridin-4-yl)benzyl)-4,7-diazaspiro[2.5]octan-4-yl)methyl)-7-fluoro-1-isopropyl-1,2,3,4-tetrahydroisoquinoline-2-carbonyl)-5-fluoro-4,4-dimethylpent-2-enenitrile |
| 14 | 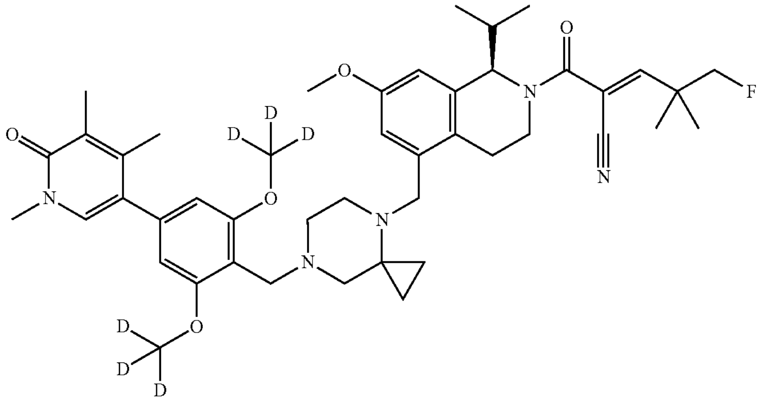 [SMILES: [2H]C([2H])([2H])Oc1cc(-c2cn(C)c(=O)c(C)c2C)cc(OC([2H])([2H])[2H])c1CN1CCN(Cc2cc(OC)cc3c2CCN(C(=O)/C(C#N)=C/C(C)(C)CF)[C@@H]3C(C)C)C2(CC2)C1]<br>(R,E/Z)-2-(5-((7-(2,6-bis(methoxy-$d_3$)-4-(1,4,5-trimethyl-6-oxo-1,6-dihydropyridin-3-yl)benzyl)-4,7-diazaspiro[2.5]octan-4-yl)methyl)-1-isopropyl-7-methoxy-1,2,3,4-tetrahydroisoquinoline-2-carbonyl)-5-fluoro-4,4-dimethylpent-2-enenitrile |

TABLE 6

| Compound | Starting material | Carboxylic acid | LCMS m/z [M + H]$^+$/Yield |
|---|---|---|---|
| 7 | B1 | (E/Z)-2-cyano-4,4-dimethylpent-2-enoic acid | 750.4/40% |
| 8 | B2 | (E/Z)-2-cyano-4,4-dimethylpent-2-enoic acid | 750.4/30% |
| 9 | B3 | (E/Z)-2-cyano-5-fluoro-4,4-dimethylpent-2-enoic acid** | 768.3/49% |
| 10 | B4 | (E/Z)-2-cyano-5-fluoro-4,4-dimethylpent-2-enoic acid | 846.2/10% |
| 11 | B5 | (E/Z)-2-cyano-5-fluoro-4,4-dimethylpent-2-enoic acid | 833.2/34% |
| 12 | B6 | (E/Z)-2-cyano-5-fluoro-4,4-dimethylpent-2-enoic acid | 833.2/69% |
| 13 | B7 | (E/Z)-2-cyano-5-fluoro-4,4-dimethylpent-2-enoic acid | 768.4/23% |

TABLE 6-continued

| Compound | Starting material | Carboxylic acid | LCMS m/z [M + H]$^+$/Yield |
|---|---|---|---|
| 14 | B8 | (E/Z)-2-cyano-5-fluoro-4,4-dimethylpent-2-enoic acid | 774.4/14% |

* (E/Z)-2-cyano-4,4-dimethylpent-2-enoic acid is reported in WO2016210165A1

**(E/Z)-2-cyano-5-fluoro-4,4-dimethylpent-2-enoic acid is reported in WO2024057021A1

Example 5: Synthesis of Compounds A1 to A6

Compounds A1 to A6 (see Table 7) were made using the following general procedure:

To a suspension of the starting material given in Table 8, 9 and 10 (1.0 equiv.) in MeCN (0.05 M) was added $Et_3N$ (3 equiv.) and 3-(3,5-dimethyl-1H-pyrazol-1-yl)-3-oxopropanenitrile (1.1 equiv.). The reaction mixture was heated to 55° C. for 16 h. The volatiles were concentrated in vacuo and purified by flash chromatography to yield the corresponding compound.

TABLE 7

| Compound | Starting material | Compound structure/name | LCMS m/z [M + H]$^+$/ Yield |
|---|---|---|---|
| A1 | B9 | 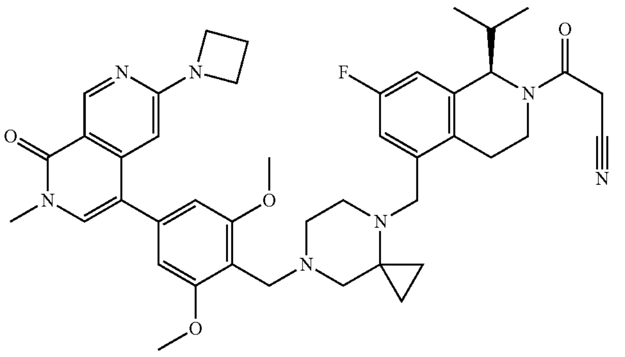 [SMILES: COc1cc(-c2cn(C)c(=O)c3cnc(N4CCC4)cc23)cc(OC)c1CN1CCN(Cc2cc(F)cc3c2CCN(C(=O)CC#N)[C@@H]3C(C)C)C2(CC2)C1] (R)-3-(5-((7-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-4-yl)methyl)-7-fluoro-1-isopropyl-3,4-dihydroisoquinolin-2(1H)-yl)-3-oxopropanenitrile | 748.3/42% |
| A2 | B10 | 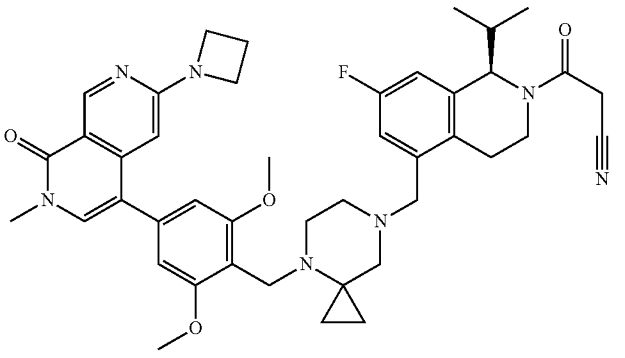 [SMILES: COc1cc(-c2cn(C)c(=O)c3cnc(N4CCC4)cc23)cc(OC)c1CN1CCN(Cc2cc(F)cc3c2CCN(C(=O)CC#N)[C@@H]3C(C)C)CC12CC2] (R)-3-(5-((4-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-7-yl)methyl)-7-fluoro-1-isopropyl-3,4-dihydroisoquinolin-2(1H)-yl)-3-oxopropanenitrile | 748.3/39% |

TABLE 7-continued

| Compound | Starting material | Compound structure/name | LCMS m/z [M + H]+/ Yield |
|---|---|---|---|
| A4 | B11 | 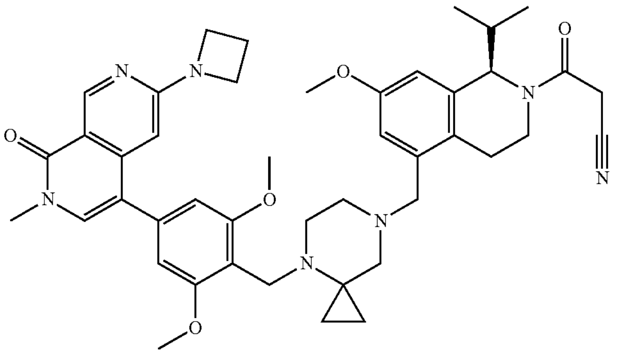 [SMILES: COc1cc(CN2CCN(Cc3c(OC)cc(-c4cn(C)c(=O)c5cnc(N6CCC6)cc45)cc3OC)C3(CC3)C2)c2c(c1)[C@@H](C(C)C)N(C(=O)CC#N)CC2] (R)-3-(5-((4-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-7-yl)methyl)-1-isopropyl-7-methoxy-3,4-dihydroisoquinolin-2(1H)-yl)-3-oxopropanenitrile | 760.6/73% |
| A5 | B12 | 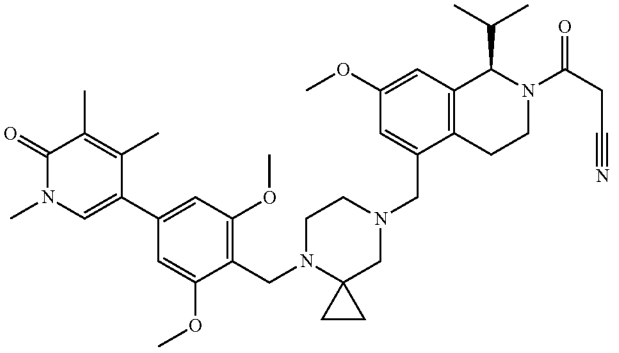 [SMILES: COc1cc(CN2CCN(Cc3c(OC)cc(-c4cn(C)c(=O)c(C)c4C)cc3OC)C3(CC3)C2)c2c(c1)[C@@H](C(C)C)N(C(=O)CC#N)CC2] (R)-3-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-1-isopropyl-7-methoxy-3,4-dihydroisoquinolin-2(1H)-yl)-3-oxopropanenitrile | 682.4/73% |
| A3 | B13 | 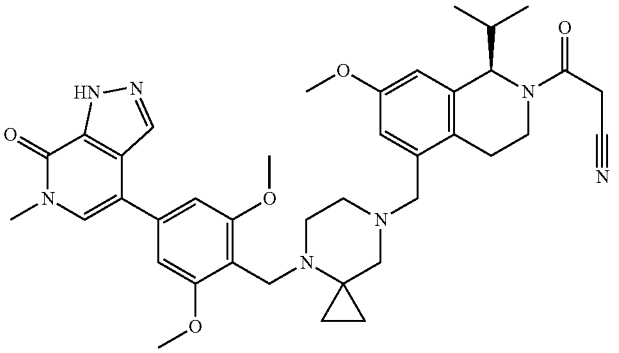 [SMILES: COc1cc(CN2CCN(Cc3c(OC)cc(-c4cn(C)c(=O)c5[nH]ncc45)cc3OC)C3(CC3)C2)c2c(c1)[C@@H](C(C)C)N(C(=O)CC#N)CC2] (R)-3-(5-((4-(2,6-dimethoxy-4-(6-methyl-7-oxo-6,7-dihydro-1H-pyrazolo[3,4-c]pyridin-4-yl)benzyl)-4,7-diazaspiro[2.5]octan-7-yl)methyl)-1-isopropyl-7-methoxy-3,4-dihydroisoquinolin-2(1H)-yl)-3-oxopropanenitrile | 694.2/51% |

TABLE 7-continued

| Compound | Starting material | Compound structure/name | LCMS m/z $[M + H]^+$/ Yield |
|---|---|---|---|
| A6 | B14 | 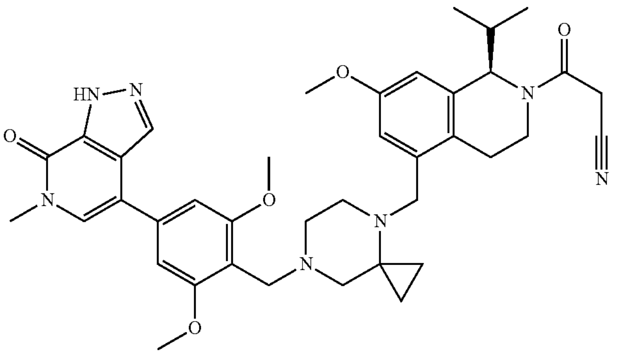 [SMILES: COc1cc(CN2CCN(Cc3c(OC)cc(-c4cn(C)c(=O)c5[nH]ncc45)cc3OC)CC23CC3)c2c(c1)[C@@H](C(C)C)N(C(=O)CC#N)CC2] (R)-3-(5-((7-(2,6-dimethoxy-4-(6-methyl-7-oxo-6,7-dihydro-1H-pyrazolo[3,4-c]pyridin-4-yl)benzyl)-4,7-diazaspiro[2.5]octan-4-yl)methyl)-1-isopropyl-7-methoxy-3,4-dihydroisoquinolin-2(1H)-yl)-3-oxopropanenitrile | 694.2/53% |

Example 6: Synthesis of Compounds B1 to B3, B7, B8 and B12 to B14

Compounds B1 to B3, B7, B8 and B12 to B14 (see Table 8) were made using the following general procedure:

A solution of the starting material given in Table 9 (1.0 equiv.) in DCM or 1,4-dioxane (0.05 M) was treated with HCl (4 M in 1,4-dioxane, 50 equiv.) and the mixture was stirred for 2 h. The volatiles were evaporated in vacuo to yield the compound.

TABLE 8

| Compound | Compound structure/name |
|---|---|
| B1 | 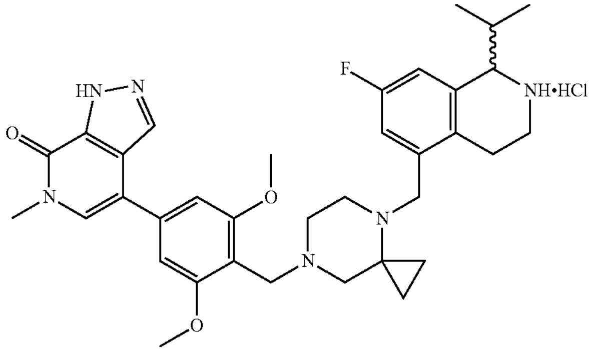 single enantiomer of unknown absolute configuration of 4-(4-((4-((7-fluoro-1-isopropyl-1,2,3,4-tetrahydroisoquinolin-5-yl)methyl)-4,7-diazaspiro[2.5]octan-7-yl)methyl)-3,5-dimethoxyphenyl)-6-methyl-1,6-dihydro-7H-pyrazolo[3,4-c]pyridin-7-one, HCl salt |

TABLE 8-continued

| Compound | Compound structure/name |
| --- | --- |
| B2 | 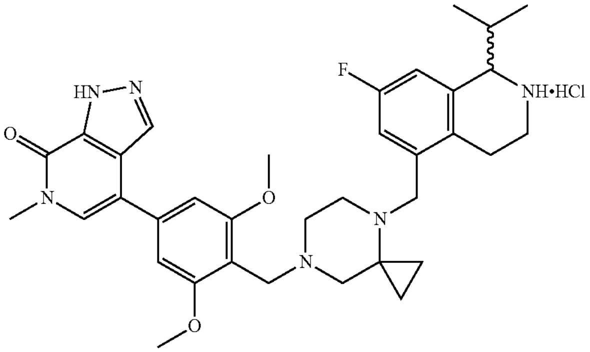<br>single enantiomer of unknown absolute configuration of 4-(4-((4-((7-fluoro-1-isopropyl-1,2,3,4-tetrahydroisoquinolin-5-yl)methyl)-4,7-diazaspiro[2.5]octan-7-yl)methyl)-3,5-dimethoxyphenyl)-6-methyl-1,6-dihydro-7H-pyrazolo[3,4-c]pyridin-7-one, HCl salt |
| B12 | 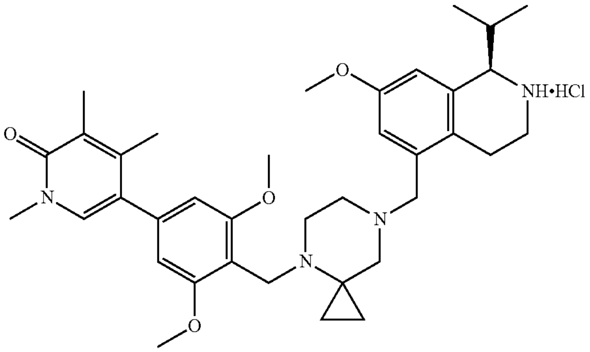<br>(R)-5-(4-((7-((1-isopropyl-7-methoxy-1,2,3,4-tetrahydroisoquinolin-5-yl)methyl)-4,7-diazaspiro[2.5]octan-4-yl)methyl)-3,5-dimethoxyphenyl)-1,3,4-trimethylpyridin-2(1H)-one, HCl salt |
| B3 | 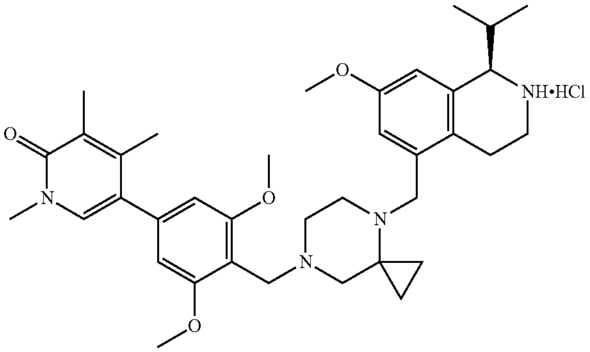<br>(R)-5-(4-((4-((1-isopropyl-7-methoxy-1,2,3,4-tetrahydroisoquinolin-5-yl)methyl)-4,7-diazaspiro[2.5]octan-7-yl)methyl)-3,5-dimethoxyphenyl)-1,3,4-trimethylpyridin-2(1H)-one, HCl salt |

TABLE 8-continued

| Compound | Compound structure/name |
| --- | --- |
| B13 | 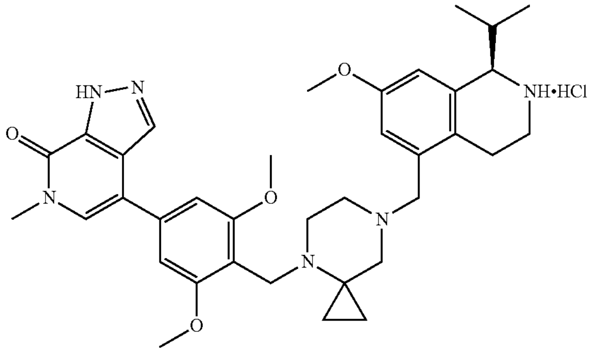<br>(R)-4-(4-((7-((1-isopropyl-7-methoxy-1,2,3,4-tetrahydroisoquinolin-5-yl)methyl)-4,7-diazaspiro[2.5]octan-4-yl)methyl)-3,5-dimethoxyphenyl)-6-methyl-1,6-dihydro-7H-pyrazolo[3,4-c]pyridin-7-one, HCl salt |
| B14 | 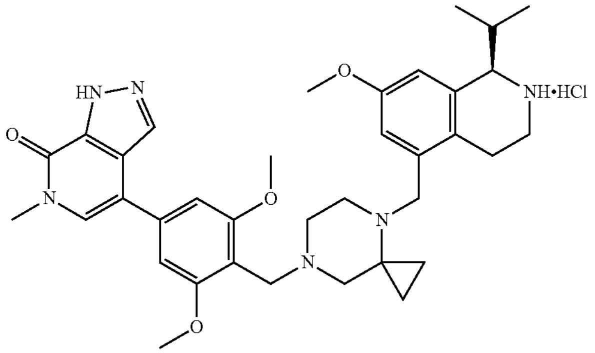<br>(R)-4-(4-((4-((1-isopropyl-7-methoxy-1,2,3,4-tetrahydroisoquinolin-5-yl)methyl)-4,7-diazaspiro[2.5]octan-7-yl)methyl)-3,5-dimethoxyphenyl)-6-methyl-1,6-dihydro-7H-pyrazolo[3,4-c]pyridin-7-one, HCl salt |
| B7 | 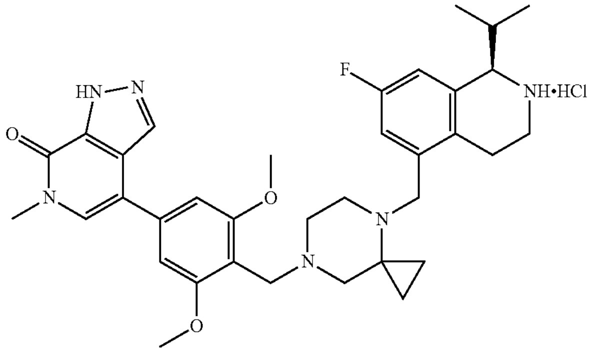<br>(R)-4-(4-((4-((7-fluoro-1-isopropyl-1,2,3,4-tetrahydroisoquinolin-5-yl)methyl)-4,7-diazaspiro[2.5]octan-7-yl)methyl)-3,5-dimethoxyphenyl)-6-methyl-1,6-dihydro-7H-pyrazolo[3,4-c]pyridin-7-one, HCl salt |

TABLE 8-continued

| Compound | Compound structure/name |
| --- | --- |
| B8 | 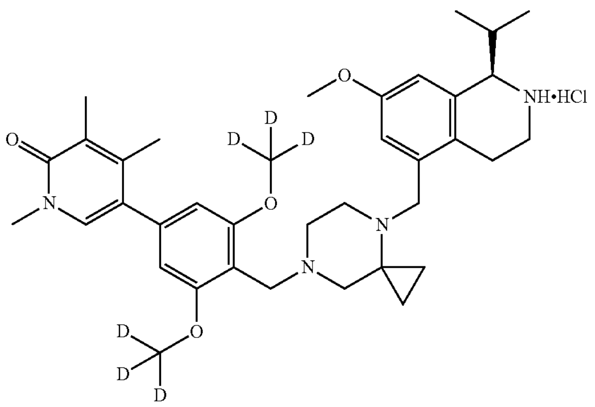<br>(R)-5-(4-((4-((1-isopropyl-7-methoxy-1,2,3,4-tetrahydroisoquinolin-5-yl)methyl)-4,7-diazaspiro[2.5]octan-7-yl)methyl)-3,5-bis(methoxy-d3)phenyl)-1,3,4-trimethylpyridin-2(1H)-one, HCl salt |

TABLE 9

| Compound | Starting material | LCMS m/z [M + H]$^+$/Yield |
| --- | --- | --- |
| B1 | C1 | 615.4/99% |
| B2 | C2 | 615.4/95% |
| B12 | C3 | 615.4/97% |
| B3 | C4 | 615.7/used crude |
| B13 | C5 | 627.6/68% |
| B14 | C6 | 627.3/80% |
| B7 | C7 | 615.1/96% |
| B8 | C8 | 621.4/93% |

Example 7: Synthesis of Compounds B4 to B6 and B9 to Brea

Compounds B4 to B6 and B9 to B11 (see Table 10) were made using the following general procedure:

A solution of Boc protected amine (1.0 equiv.) in DCM (0.05 M) was treated with TFA (11 equiv.) and the mixture was stirred for 2 h. The volatiles were evaporated in vacuo to yield the corresponding amine (TFA salt).

TABLE 10

| Compound | Compound structure/Name |
| --- | --- |
| B9 | 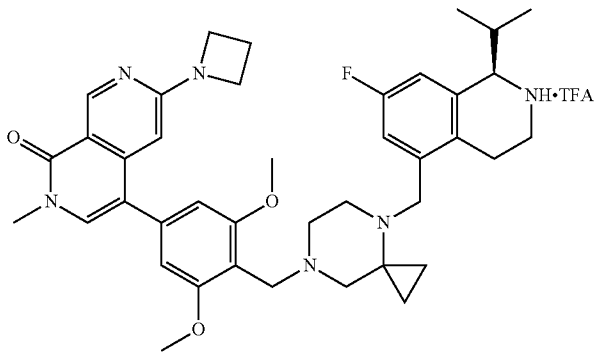<br>(R)-6-(azetidin-1-yl)-4-(4-((4-((7-fluoro-1-isopropyl-1,2,3,4-tetrahydroisoquinolin-5-yl)methyl)-4,7-diazaspiro[2.5]octan-7-yl)methyl)-3,5-dimethoxyphenyl)-2-methyl-2,7-naphthyridin-1(2H)-one, TFA salt |

TABLE 10-continued

| Compound | Compound structure/Name |
| --- | --- |
| B10 | 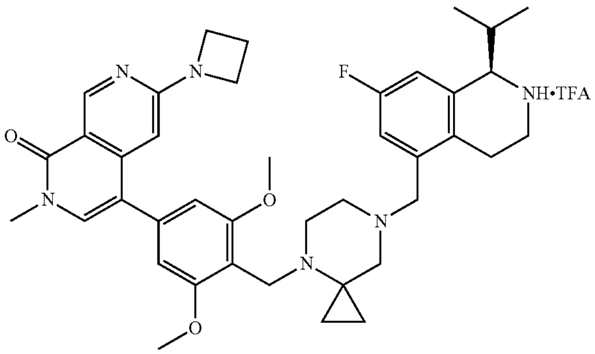 (R)-6-(azetidin-1-yl)-4-(4-((7-((7-fluoro-1-isopropyl-1,2,3,4-tetrahydroisoquinolin-5-yl)methyl)-4,7-diazaspiro[2.5]octan-4-yl)methyl)-3,5-dimethoxyphenyl)-2-methyl-2,7-naphthyridin-1(2H)-one, TFA salt |
| B11 | 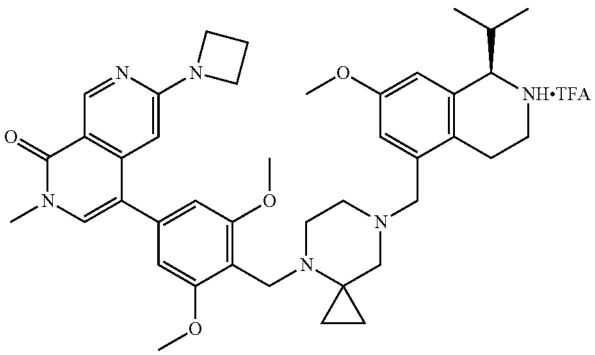 (R)-6-(azetidin-1-yl)-4-(4-((7-((1-isopropyl-7-methoxy-1,2,3,4-tetrahydroisoquinolin-5-yl)methyl)-4,7-diazaspiro[2.5]octan-4-yl)methyl)-3,5-dimethoxyphenyl)-2-methyl-2,7-naphthyridin-1(2H)-one, TFA salt |
| B4 | 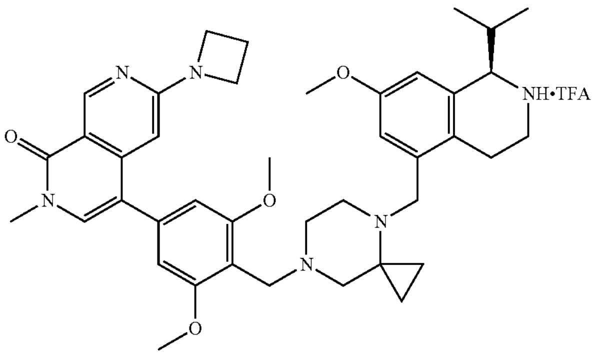 (R)-6-(azetidin-1-yl)-4-(4-((4-((1-isopropyl-7-methoxy-1,2,3,4-tetrahydroisoquinolin-5-yl)methyl)-4,7-diazaspiro[2.5]octan-7-yl)methyl)-3,5-dimethoxyphenyl)-2-methyl-2,7-naphthyridin-1(2H)-one, TFA salt |

TABLE 10-continued

| Compound | Compound structure/Name |
|---|---|
| B5 | 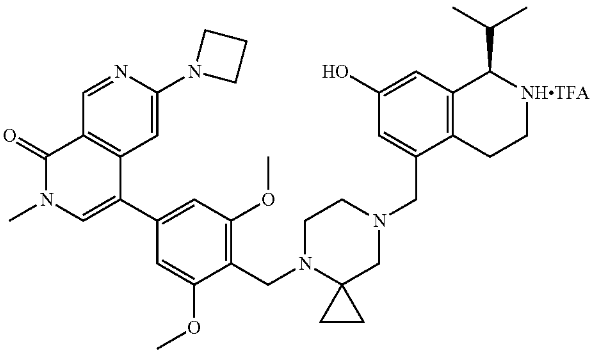 (R)-6-(azetidin-1-yl)-4-(4-((7-((7-hydroxy-1-isopropyl-1,2,3,4-tetrahydroisoquinolin-5-yl)methyl)-4,7-diazaspiro[2.5]octan-4-yl)methyl)-3,5-dimethoxyphenyl)-2-methyl-2,7-naphthyridin-1(2H)-one, TFA salt |
| B6 | 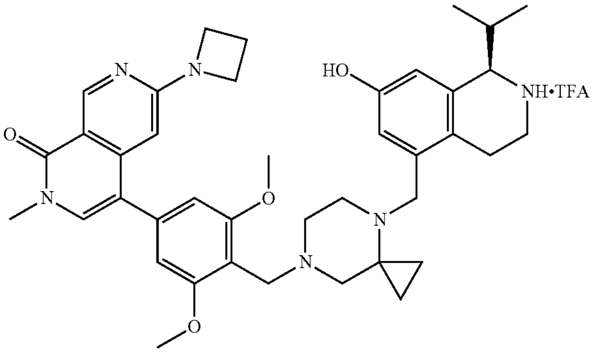 (R)-6-(azetidin-1-yl)-4-(4-((4-((7-hydroxy-1-isopropyl-1,2,3,4-tetrahydroisoquinolin-5-yl)methyl)-4,7-diazaspiro[2.5]octan-7-yl)methyl)-3,5-dimethoxyphenyl)-2-methyl-2,7-naphthyridin-1(2H)-one, TFA salt |

TABLE 11

| Compound | Starting material | LCMS m/z $[M + H]^+$/Yield |
|---|---|---|
| B9 | C9 | 681.4/96% |
| B10 | C10 | 681.3/92% |
| B11 | C11 | 693.6/87% |
| B4 | C12 | 693.7/used crude |
| B5 | C13 | 679.5/98% |
| B6 | C14 | 679.5/81% |

Example 8: Preparation of Compounds C1 and C2

Compounds C1 and C2 (see Table 12) were prepared by separating C15 into enantiomers using the conditions given in Table 12

TABLE 12

| Starting material | SFC separation conditions | Isolated peak 1 | Isolated Peak 2 |
|---|---|---|---|
| C15 | Column: I Cellulose Z-(250*30) mm, 5 μm Mobile Phase: CO2:0.5% isopropylamine in MeOH:MeCN (50:50) Flow rate: 100 mL/min Back pressure: 100 bar Wavelength: 297 nm Cycle time: 8 min | C1 130 mg LCMS m/z = 715.4 $[M + H]^+$ | C2 120 mg LCMS m/z = 715.4 $[M + H]^+$ |

Example 9: Synthesis of Compounds C3 to C15

Compounds C3 to C15 (see Table 13) were made using the following general procedure:

A solution of amine (1 equiv.) and aldehyde (1 equiv.) as given in Table 14 in DCM (0.05 M) was treated with $Et_3N$ (1.5 equiv.). The reaction mixture was stirred for 1 h, then was treated with $NaBH(OAc)_3$ (2.0 equiv.) or MP-$CNBH_3$ (5.0 equiv.). The reaction mixture was stirred at room temperature until the reaction was complete by LCMS. The reaction was quenched by addition of $H_2O$ and extracted with DCM. The combined organic extracts were washed with water, brine, dried over $MgSO_4$ and concentrated in vacuo. Purification by silica gel column chromatography yielded the desired product (III).

TABLE 13

| Compound | Compound name | Compound structure |
|---|---|---|
| C15 | tert-butyl 5-((7-(2,6-dimethoxy-4-(6-methyl-7-oxo-6,7-dihydro-1H-pyrazolo[3,4-c]pyridin-4-yl)benzyl)-4,7-diazaspiro[2.5]octan-4-yl)methyl)-7-fluoro-1-isopropyl-3,4-dihydroisoquinoline-2(1H)-carboxylate | 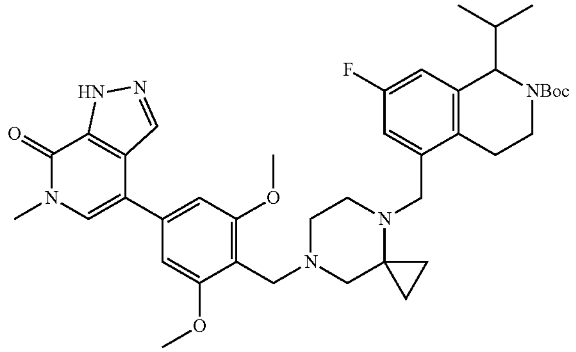 [SMILES: COc1cc(-c2cn(C)c(=O)c3[nH]ncc23)cc(OC)c1CN1CCN(Cc2cc(F)cc3c2CCN(C(=O)OC(C)(C)C)C3C(C)C)C2(CC2)C1] |
| C9 | tert-butyl (R)-5-((7-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-4-yl)methyl)-7-fluoro-1-isopropyl-3,4-dihydroisoquinoline-2(1H)-carboxylate | 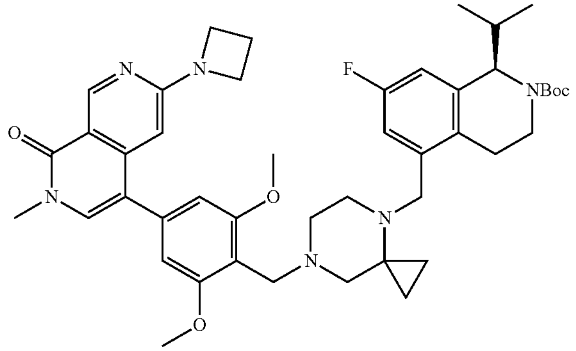 [SMILES: COc1cc(-c2cn(C)c(=O)c3cnc(N4CCC4)cc23)cc(OC)c1CN1CCN(Cc2cc(F)cc3c2CCN(C(=O)OC(C)(C)C)[C@@H]3C(C)C)C2(CC2)C1] |
| C10 | tert-butyl (R)-5-((4-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-7-yl)methyl)-7-fluoro-1-isopropyl-3,4-dihydroisoquinoline-2(1H)-carboxylate | 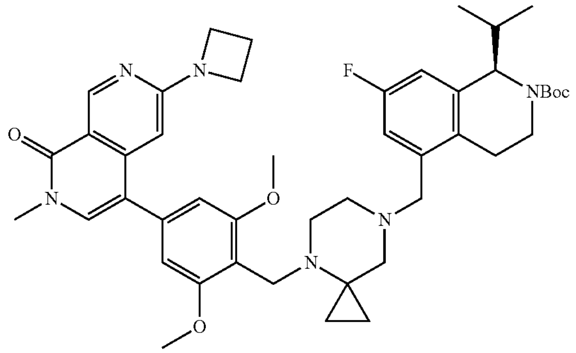 [SMILES: COc1cc(-c2cn(C)c(=O)c3cnc(N4CCC4)cc23)cc(OC)c1CN1CCN(Cc2cc(F)cc3c2CCN(C(=O)OC(C)(C)C)[C@@H]3C(C)C)CC12CC2] |
| C11 | tert-butyl (R)-5-((4-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-7-yl)methyl)-1-isopropyl-7-methoxy-3,4-dihydroisoquinoline-2(1H)-carboxylate | 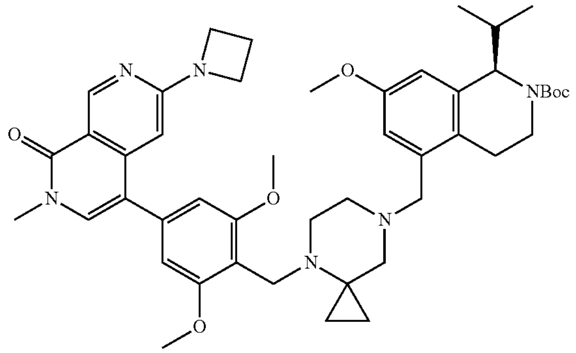 [SMILES: COc1cc(CN2CCN(Cc3c(OC)cc(-c4cn(C)c(=O)c5cnc(N6CCC6)cc45)cc3OC)C3(CC3)C2)c2c(c1)[C@@H](C(C)C)N(C(=O)OC(C)(C)C)CC2] |

TABLE 13-continued

| Compound | Compound name | Compound structure |
|---|---|---|
| C3 | tert-butyl (R)-5-((4-(2,6-dimethoxy-4-(1,4,5-trimethyl-6-oxo-1,6-dihydropyridin-3-yl)benzyl)-4,7-diazaspiro[2.5]octan-7-yl)methyl)-1-isopropyl-7-methoxy-3,4-dihydroisoquinoline-2(1H)-carboxylate | 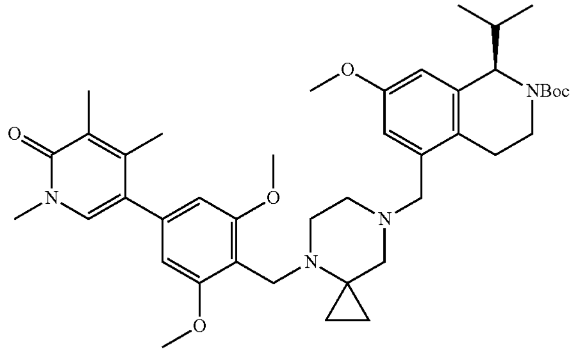 [SMILES: COc1cc(CN2CCN(Cc3c(OC)cc(-c4cn(C)c(=O)c(C)c4C)cc3OC)C3(CC3)C2)c2c(c1)[C@@H](C(C)C)N(C(=O)OC(C)(C)C)CC2] |
| C4 | tert-butyl (R)-5-((7-(2,6-dimethoxy-4-(1,4,5-trimethyl-6-oxo-1,6-dihydropyridin-3-yl)benzyl)-4,7-diazaspiro[2.5]octan-4-yl)methyl)-1-isopropyl-7-methoxy-3,4-dihydroisoquinoline-2(1H)-carboxylate | 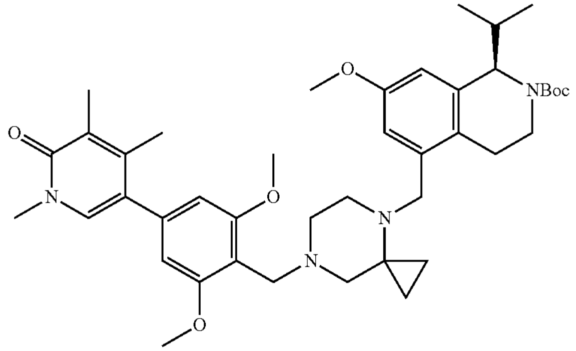 [SMILES: COc1cc(CN2CCN(Cc3c(OC)cc(-c4cn(C)c(=O)c(C)c4C)cc3OC)CC23CC3)c2c(c1)[C@@H](C(C)C)N(C(=O)OC(C)(C)C)CC2] |
| C12 | tert-butyl (R)-5-((7-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-4-yl)methyl)-1-isopropyl-7-methoxy-3,4-dihydroisoquinoline-2(1H)-carboxylate | 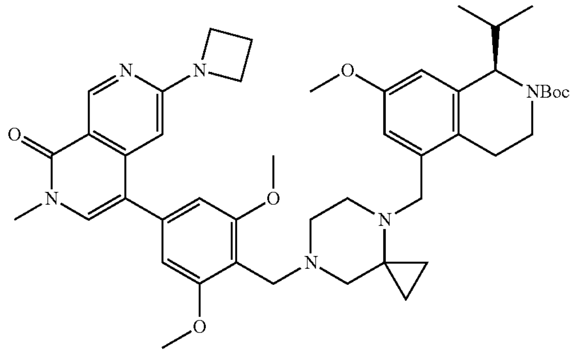 [SMILES: COc1cc(CN2CCN(Cc3c(OC)cc(-c4cn(C)c(=O)c5cnc(N6CCC6)cc45)cc3OC)CC23CC3)c2c(c1)[C@@H](C(C)C)N(C(=O)OC(C)(C)C)CC2] |
| C13 | tert-butyl (R)-5-((4-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-7-yl)methyl)-7-((tert-butoxycarbonyl)oxy)-1-isopropyl-3,4-dihydroisoquinoline-2(1H)-carboxylate | 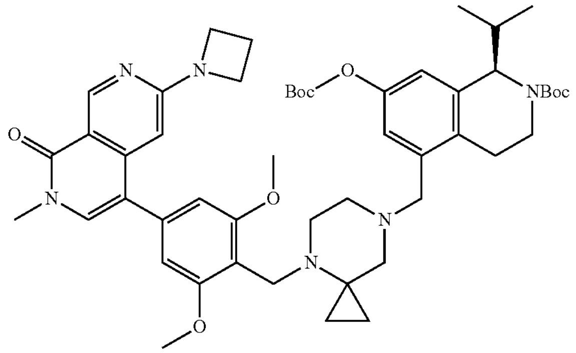 [SMILES: COc1cc(-c2cn(C)c(=O)c3cnc(N4CCC4)cc23)cc(OC)c1CN1CCN(Cc2cc(OC(=O)OC(C)(C)C)cc3c2CCN(C(=O)OC(C)(C)C)[C@@H]3C(C)C)CC12CC2] |

TABLE 13-continued

| Compound | Compound name | Compound structure |
| --- | --- | --- |
| C5 | tert-butyl (R)-5-((4-(2,6-dimethoxy-4-(6-methyl-7-oxo-6,7-dihydro-1H-pyrazolo[3,4-c]pyridin-4-yl)benzyl)-4,7-diazaspiro[2.5]octan-7-yl)methyl)-1-isopropyl-7-methoxy-3,4-dihydroisoquinoline-2(1H)-carboxylate | 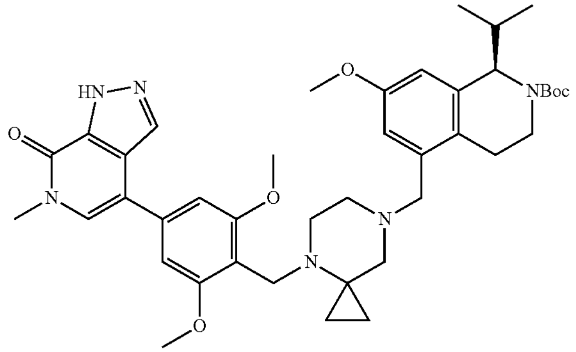 [SMILES: COc1cc(CN2CCN(Cc3c(OC)cc(-c4cn(C)c(=O)c5[nH]ncc45)cc3OC)C3(CC3)C2)c2c(c1)[C@@H](C(C)C)N(C(=O)OC(C)(C)C)CC2] |
| C14 | tert-butyl (R)-5-((7-(4-(6-(azetidin-1-yl)-2-methyl-1-oxo-1,2-dihydro-2,7-naphthyridin-4-yl)-2,6-dimethoxybenzyl)-4,7-diazaspiro[2.5]octan-4-yl)methyl)-7-((tert-butoxycarbonyl)oxy)-1-isopropyl-3,4-dihydroisoquinoline-2(1H)-carboxylate | 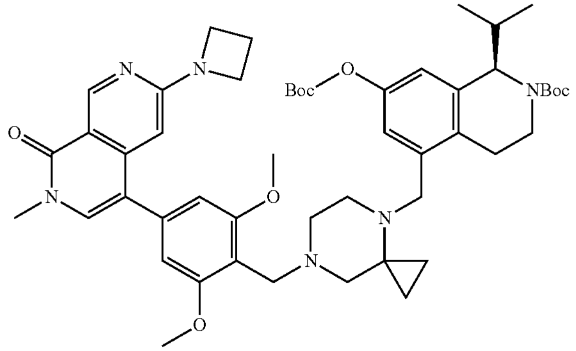 [SMILES: COc1cc(-c2cn(C)c(=O)c3cnc(N4CCC4)cc23)cc(OC)c1CN1CCN(Cc2cc(OC(=O)OC(C)(C)C)cc3c2CCN(C(=O)OC(C)(C)C)[C@@H]3C(C)C)C2(CC2)C1] |
| C6 | tert-butyl (R)-5-((7-(2,6-dimethoxy-4-(6-methyl-7-oxo-6,7-dihydro-1H-pyrazolo[3,4-c]pyridin-4-yl)benzyl)-4,7-diazaspiro[2.5]octan-4-yl)methyl)-1-isopropyl-7-methoxy-3,4-dihydroisoquinoline-2(1H)-carboxylate | 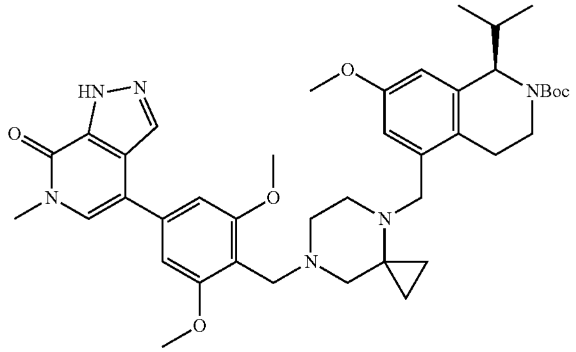 [SMILES: COc1cc(CN2CCN(Cc3c(OC)cc(-c4cn(C)c(=O)c5[nH]ncc45)cc3OC)CC23CC3)c2c(c1)[C@@H](C(C)C)N(C(=O)OC(C)(C)C)CC2] |
| C7 | tert-butyl (R)-5-((7-(2,6-dimethoxy-4-(6-methyl-7-oxo-6,7-dihydro-1H-pyrazolo[3,4-c]pyridin-4-yl)benzyl)-4,7-diazaspiro[2.5]octan-4-yl)methyl)-7-fluoro-1-isopropyl-3,4-dihydroisoquinoline-2(1H)-carboxylate | 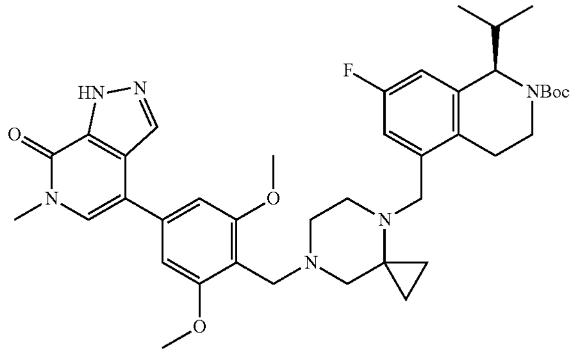 [SMILES: COc1cc(-c2cn(C)c(=O)c3[nH]ncc23)cc(OC)c1CN1CCN(Cc2cc(F)cc3c2CCN(C(=O)OC(C)(C)C)[C@@H]3C(C)C)C2(CC2)C1] |

TABLE 13-continued

| Compound | Compound name | Compound structure |
|---|---|---|
| C8 | tert-butyl (R)-5-((7-(2,6-bis(methoxy-d3)-4-(1,4,5-trimethyl-6-oxo-1,6-dihydropyridin-3-yl)benzyl)-4,7-diazaspiro[2.5]octan-4-yl)methyl)-1-isopropyl-7-methoxy-3,4-dihydroisoquinoline-2(1H)-carboxylate | 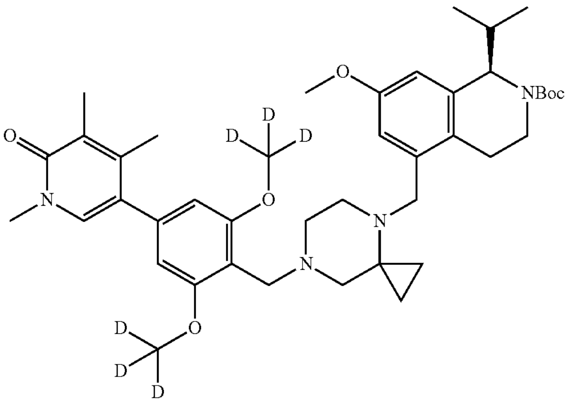 [SMILES: [2H]C([2H])([2H])Oc1cc(-c2cn(C)c(=O)c(C)c2C)cc(OC([2H])([2H])[2H])c1CN1CCN(Cc2cc(OC)cc3c2CCN(C(=O)OC(C)(C)C)[C@@H]3C(C)C)C2(CC2)C1] |

TABLE 14

| Compound | Amine | Aldehyde | LCMS m/z [M + H]$^+$/Yield |
|---|---|---|---|
| C15 | N4 | D1 | 715.4/56% |
| C9 | N6 | D2 | 781.3/72% |
| C10 | N7 | D2 | 781.4/66% |
| C11 | N7 | D3 | 793.4/74% |
| C3 | N2 | D3 | 715.4/55% |
| C4 | N1 | D3 | 715.3/11% |
| C11 | N6 | D3 | 793.3/44% |
| C12 | N7 | D4 | 880.3/22% |
| C5 | N3 | D3 | 728.3/25% |
| C14 | N6 | D4 | 880.3/45% |
| C6 | N4 | D3 | 727.3/38% |
| C7 | N4 | D2 | 715.2/46% |
| C8 | N5 | D3 | 721.4/48% |

Example 10: Synthesis of Compounds D1 to D4

Compounds D1 to D4 (see Table 15) were made using the following general procedure:

To a solution of the starting material given in Table 16 (1 equiv.), sodium periodate (2 equiv.) and N-methyl morpholine (1 equiv.) in 1,4-dioxane:water (2:1) was added osmium tetroxide (4 wt % aqueous solution, 1 equiv.) dropwise at room temperature. The reaction mixture was stirred for 2 h at room temperature before being quenched with cold water and extracted with ethyl acetate. The combined organic layers were washed with brine and dried over anhydrous sodium sulphate, filtered and concentrated in vacuo. The resulting residue was purified by silica gel column chromatography. The appropriate fractions were concentrated in vacuo to give the desired compound.

TABLE 15

| Compound | Compound structure | Compound name |
|---|---|---|
| D1 | 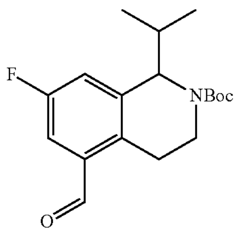 [SMILES: CC(C)C1c2cc(F)cc(C=O)c2CCN1C(=O)OC(C)(C)C] | tert-butyl 7-fluoro-5-formyl-1-isopropyl-3,4-dihydroisoquinoline-2(1H)-carboxylate |
| D2 | 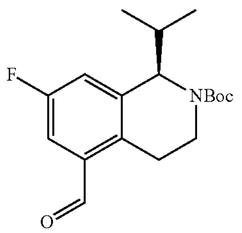 [SMILES: CC(C)[C@@H]1c2cc(F)cc(C=O)c2CCN1C(=O)OC(C)(C)C] | tert-butyl (R)-7-fluoro-5-formyl-1-isopropyl-3,4-dihydroisoquinoline-2(1H)-carboxylate |

TABLE 15-continued

| Compound | Compound structure | Compound name |
|---|---|---|
| D3 | 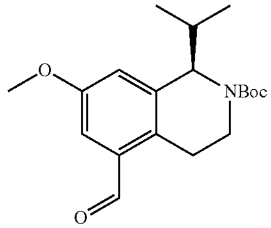 [SMILES: COc1cc(C=O)c2c(c1)[C@@H](C(C)C)N(C(=O)OC(C)(C)C)CC2] | tert-butyl (R)-5-formyl-1-isopropyl-7-methoxy-3,4-dihydroisoquinoline-2(1H)-carboxylate |
| D4 | 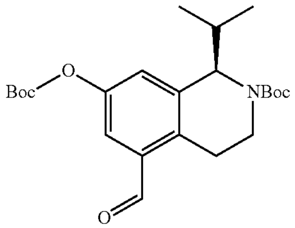 [SMILES: CC(C)[C@@H]1c2cc(OC(=O)OC(C)(C)C)cc(C=O)c2CCN1C(=O)OC(C)(C)C] | tert-butyl (R)-7-((tert-butoxycarbonyl)oxy)-5-formyl-1-isopropyl-3,4-dihydroisoquinoline-2(1H)-carboxylate |

TABLE 16

| Compound | Starting material | Mass isolated, yield | LCMS m/z $[M + H]^+$ |
|---|---|---|---|
| D1 | E1 | 640 mg, 86% | 222.2 $[M\text{-}Boc + H]^+$ |
| D2 | E2 | 1.5 g, 83% | 222.2 $[M\text{-}Boc + H]^+$ |
| D3 | E3 | 79% | 278.2 $[M\text{-}tBu + H]^+$ |
| D4 | E4 | 3 g, 84% | 320.2 $[M + H]^+$ |

Example 11: Synthesis of Compounds E1 to E4

Compounds E1 to E4 (see Table 17) were made using the following general procedure:

To a degassed solution of the starting material given in Table 18 (1 equiv.), potassium trifluoro(vinyl)borate (1 equiv.) and $Cs_2CO_3$ (2 equiv.) in 1,4-dioxane:water (4:1) was added Pd(dppf)$Cl_2$·DCM (0.1 equiv.) at room temperature. The reaction mixture was degassed for 10 mins before being heated at 90° C. for 16 h. The reaction mixture was filtered through celite and the celite was washed with EtOAc. The combined washings were concentrated in vacuo and the resulting residue was purified by silica gel column chromatography. The appropriate fractions were concentrated in vacuo to give the required product.

TABLE 17

| Compound | Compound structure | Compound name |
|---|---|---|
| E1 | 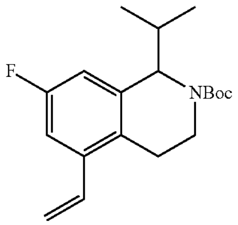 [SMILES: C=Cc1cc(F)cc2c1CCN(C(=O)OC(C)(C)C)C2C(C)C] | tert-butyl 7-fluoro-1-isopropyl-5-vinyl-3,4-dihydroisoquinoline-2(1H)-carboxylate |
| E2 | 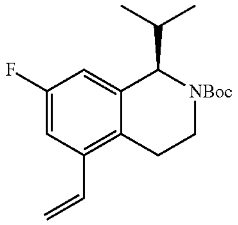 [SMILES: C=Cc1cc(F)cc2c1CCN(C(=O)OC(C)(C)C)[C@@H]2C(C)C] | tert-butyl (R)-7-fluoro-1-isopropyl-5-vinyl-3,4-dihydroisoquinoline-2(1H)-carboxylate |

TABLE 17-continued

| Compound | Compound structure | Compound name |
|---|---|---|
| E3 | 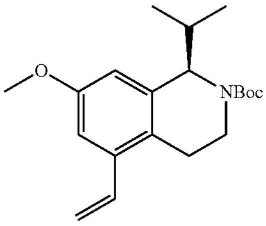 [SMILES: C=Cc1cc(OC)cc2c1CCN(C(=O)OC(C)(C)C)[C@@H]2C(C)C] | tert-butyl (R)-1-isopropyl-7-methoxy-5-vinyl-3,4-dihydroisoquinoline-2(1H)-carboxylate |
| E4 | 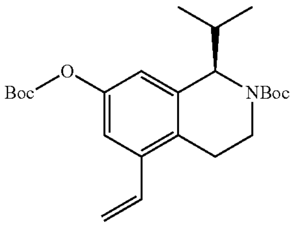 [SMILES: C=Cc1cc(OC(=O)OC(C)(C)C)cc2c1CCN(C(=O)OC(C)(C)C)[C@@H]2C(C)C] | tert-butyl (R)-7-((tert-butoxycarbonyl)oxy)-1-isopropyl-5-vinyl-3,4-dihydroisoquinoline-2(1H)-carboxylate |

TABLE 18

| Compound | Starting material | Mass isolated, yield | LCMS m/z $[M + H]^+$ |
|---|---|---|---|
| E1 | F1 | 730 mg, 84% | 264.2 $[M\text{-}tBu + H]^+$ |
| E2 | F2 | 1.7 g, 96% | 220.2 $[M\text{-}Boc + H]^+$ |
| E3 | F3 | 95% | 232.3 $[M\text{-}Boc + H]^+$ |
| E4 | F4 | 3.5 g, 98% | 318.2 $[M\text{-}Boc + H]^+$ |

Example 12: Synthesis of Compounds F1 to F4

Compounds F1 to F4 (see Table 19) were made using the following general procedure:

To a stirred solution of the starting material given in Table 20 (1 eq) in DCM was added triethylamine (3 eq) and Boc-anhydride (1.5 eq) at 0° C. The reaction mixture was allowed to warm up to RT and was stirred for 12 h. The reaction progress was monitored by TL and LCMS. The reaction mixture was diluted with water and the aqueous phase was extracted with DCM. The combined organic layer was washed with brine, dried over anhydrous sodium sulphate, filtered and concentrated in vacuo. The crude product was purified by flash column chromatography (EtOAc/hexane) to give the product.

TABLE 19

| Compound | Compound structure | Compound name |
|---|---|---|
| F1 | 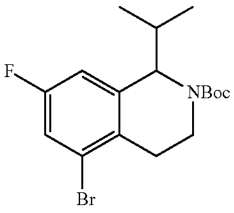 [SMILES: CC(C)C1c2cc(F)cc(Br)c2CCN1C(=O)OC(C)(C)C] | tert-butyl 5-bromo-7-fluoro-1-isopropyl-3,4-dihydroisoquinoline-2(1H)-carboxylate |
| F2 | 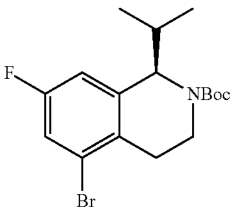 [SMILES: CC(C)[C@@H]1c2cc(F)cc(Br)c2CCN1C(=O)OC(C)(C)C] | tert-butyl (R)-5-bromo-7-fluoro-1-isopropyl-3,4-dihydroisoquinoline-2(1H)-carboxylate |

TABLE 19-continued

| Compound | Compound structure | Compound name |
|---|---|---|
| F3 | 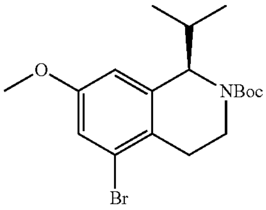 [SMILES: COc1cc(Br)c2c(c1)[C@@H](C(C)C)N(C(=O)OC(C)(C)C)CC2] | tert-butyl (R)-5-bromo-1-isopropyl-7-methoxy-3,4-dihydroisoquinoline-2(1H)-carboxylate |
| F4 | 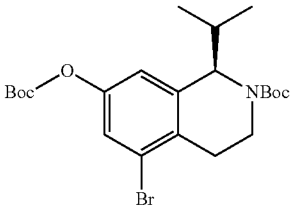 | tert-butyl (R)-5-bromo-7-((tert-butoxycarbonyl)oxy)-1-isopropyl-3,4-dihydroisoquinoline-2(1H)-carboxylate |

TABLE 20

| Compound | Starting material | LCMS m/z |
|---|---|---|
| F1 | G1 | 274.2 [M-Boc + H]$^+$ |
| F2 | H1 | 272.0 [M-Boc + H]$^+$ |
| F3 | H2 | 329.9 [M-tBu + H]$^+$ |
| F4 | H2 | 372.2 [M-Boc + H]$^+$ |

Example 13: Synthesis of Compound F2

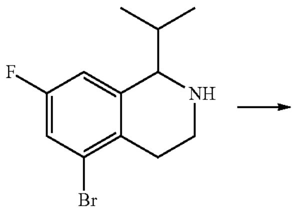

(G1)

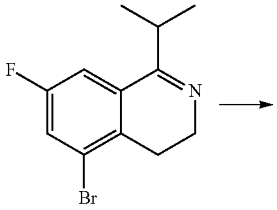

(H1)

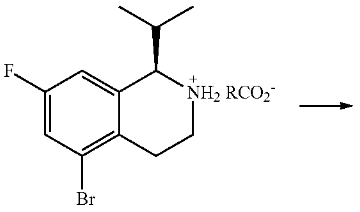

(F2-1)

-continued

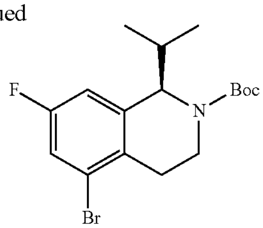

(F2)

Preparation of 5-bromo-7-fluoro-1-isopropyl-3,4-dihydroisoquinoline (H1)

To a stirred solution of G1 (10 g, 36.7 mmol) in DCM (100 mL) was added NBS (6.7 g, 37.5 mmol). The reaction mixture was stirred at RT for 1 h. Then, a solution of 10% NaOH (100 mL) was added to the reaction mixture and stirred at RT for 1 h. The aqueous phase was separated and extracted with DCM. The combined organic layer was dried over anhydrous sodium sulphate, filtered and concentrated in vacuo. The crude material was purified by column chromatography (silica gel, 20-25% EtOAc in hexane), to afford 5-bromo-7-fluoro-1-isopropyl-3,4-dihydroisoquinoline H1 (5.5 g, 20.4 mmol, 55%). LCMS m/z: 272.0 [M+H]$^+$

Preparation of (R)-5-bromo-7-fluoro-1-isopropyl-1,2,3,4-tetrahydroisoquinolin-2-ium, ((benzyloxy)carbonyl)-L-alaninate (F2-1)

To a stirred solution of H1 (20 g, 74.07 mmol) in MeOH (200 mL) was added $Et_3N$ (52.0 mL, 370 mmol). RuCl(p-cymene)[(S,S)-Ts-DPEN] (1.4 g, 2.2 mmol) and formic acid (19.6 mL, 518 mmol) were added at 0° C., then the reaction mixture was allowed to warm to RT and stirred for 12 h. After completion of reaction, the solvent was removed in vacuo. The crude residue was basified with a solution of $NaHCO_3$. The aqueous phase was separated and extracted with 10% MeOH in DCM. The combined organic layer was concentrated to dryness. The crude material was dissolved in $CH_3CN$ (300 mL) and ((benzyloxy)carbonyl)-L-alanine (16.4 g, 73.5 mmol) was added. The reaction mixture was stirred for 4 h at RT, then the reaction mixture was refluxed for 12 h, allowed to cool to RT and stirred for 12 h at RT (thick solid was observed). The resulting solid was filtered and washed with $CH_3CN$ (20 mL), the collected solid was dried under vacuum to afford [(R)-5-bromo-7-fluoro-1-isopropyl-1,2,3,4-tetrahydroisoquinolin-2-ium, ((benzyloxy) carbonyl)-L-alaninate](28 g, 56.5 mmol, 76.3%) which was used in the next step without further purification. LCMS m/z=274.2 $[M+H]^+$.

Preparation of (R)-5-bromo-7-fluoro-1-isopropyl-3,4-dihydroisoquinoline-2(1H)-carboxylate (F2)

To a stirred solution of [(R)-5-bromo-7-fluoro-1-isopropyl-1,2,3,4-tetrahydroisoquinolin-2-ium, ((benzyloxy)carbonyl)-L-alaninate](28 g, 56.5 mmol) in THF (280 mL) and $H_2O$ (280 mL) was added $Na_2CO_3$ (37.4 g, 353 mmol) at RT and the reaction mixture was stirred for 10 min. Boc-anhydride (28.9 g, 132 mmol) was added dropwise at 0° C. and the reaction mixture was allowed to warm to RT and stirred for 12 h. The reaction mixture was quenched with cold water and extracted with DCM (2×200 mL). The combined organic layer was washed with brine and dried over anhydrous sodium sulphate, filtered and concentrated in vacuo. The crude compound was purified by column chromatography (silica gel, 9% EtOAc in hexane) to afford the title compound (20 g, 53.7 mmol, 95%). LCMS m/z=272.0 $[M-Boc+H]^+$ Example 14: Synthesis of Compound F3

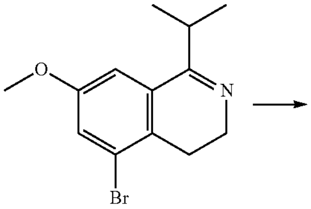

(H2)

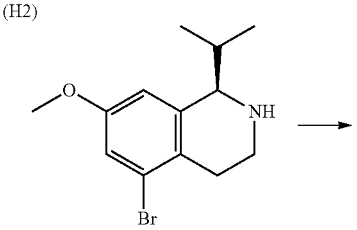

(F3.1)

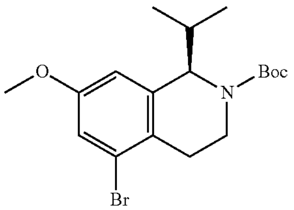

(F3)

Preparation of (R)-5-bromo-1-isopropyl-7-methoxy-1,2,3,4-tetrahydroisoquinoline (F3-1)

To a stirred solution of H2 (5 g, 17.7 mmol) in MeOH (50 mL) was added TEA (9.9 mL, 70.9 mmol), RuCl(p-cymene)[(S,S)-Ts-DPEN](0.225 g, 0.354 mmol) and formic acid (4.0 mL, 106 mmol) at 0° C. The reaction mixture was stirred for 12 h at RT. After completion of the reaction, the solvent was removed. The crude residue was basified with an aq solution of $NaHCO_3$, the aqueous phase was separated and extracted with a solution of 10% MeOH in DCM. The combined organic layer was dried ($Na_2SO_4$) and concentrated under reduced pressure to give the title compound (5 g, 17.6 mmol, 99%) which was used in the next step without further purification. LCMS m/z: 286.2 $[M+H]^+$.

Preparation of tert-butyl (R)-5-bromo-1-isopropyl-7-methoxy-3,4-dihydroisoquinoline-2(1H)-carboxylate (F3)

To a stirred solution of F3-1 (5 g, 17.59 mmol) in THF (50 mL) and $H_2O$ (50 mL) was added $Na_2CO_3$ (4.7 g, 44.0 mmol) and $Boc_2O$ (6.25 mL, 26.4 mmol) at RT. The reaction mixture was stirred for 16 h at RT. After completion of the reaction, the reaction mixture was diluted with water, the aqueous phase was separated and extracted with EtOAc (2×200 mL). The combined organic layer was washed with brine and dried over anhydrous sodium sulphate, filtered and concentrated in vacuo. The crude compound was purified by column chromatography (silica gel, 10% EtOAc in hexane), and further purified by chiral SFC to give the title compound (5.5 g, 14.15 mmol, 80%) as an off-white solid. LCMS m/z: 329.9 $[M-tBu+H]^+$.

Chiral SFC purification method: Column: LUX A3 (250*21) mm, 5 μm—Mobile Phase: $CO_2$: 0.5% Isopropylamine in MeOH—Total Flow: 100 mL/min—Back pressure: 120 bar—Wavelength: 282 nm—Cycle time: 4 min Example 15: Synthesis of Compound F4

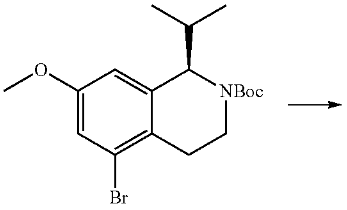

(F3)

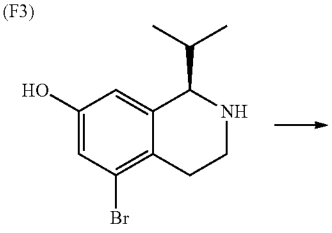

(F4.1)

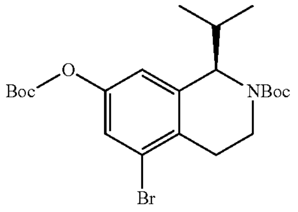 [SMILES: CC(C)[C@@H]1c2cc(OC(=O)OC(C)(C)C)cc(Br)c2CCN1C(=O)OC(C)(C)C]

(F4)

Preparation of (R)-5-bromo-1-isopropyl-1,2,3,4-tetrahydroisoquinolin-7-ol (F4-1)

To a stirred solution of F3 (5 g, 13.0 mmol) in DCM (50 mL) was added $BBr_3$ (1 M in DCM, 26 mL, 26.0 mmol) at 0° C. The resulting reaction mixture was stirred at RT for 16 h. The reaction mixture was quenched with MeOH at 0° C. The solvent was removed in vacuo and the crude product was triturated with pentane twice to afford the title compound (3.5 g, 10.70 mmol, 82%) as a brown solid. LCMS m/z: 272.2 $[M+H]^+$ Preparation of tert-butyl (R)-5-bromo-7-((tert-butoxycarbonyl)oxy)-1-isopropyl-3,4-dihydroisoquinoline-2(1H)-carboxylate (F4)

To a stirred solution of (R)-5-bromo-1-isopropyl-1,2,3,4-tetrahydroisoquinolin-7-ol (3.5 g, 12.95 mmol) in DCM (50 mL) was added TEA (9 mL, 64.8 mmol) followed by Boc-anhydride (8.7 mL, 38.9 mmol) at 0° C. The resulting reaction mixture was stirred at RT for 16 h. Progress of the reaction was monitored by LCMS. The reaction mixture was quenched with cold water and extracted with DCM (2×200 mL). The combined organic layer was dried over sodium sulphate, filtered and concentrated under reduced pressure. The crude product was purified by column chromatography (SiO2/100-200 mesh; ~10% EtOAc/Hexane) to afford the title compound (4 g, 8.41 mmol, 65%) as a colorless gum. LCMS m/z: 372.2 $[M\text{-}Boc+H]^+$ Example 16: Synthesis of Compound G1

To a stirred solution of H3 (1 eq) in THF at 0° C. was added boron trifluoride etherate (1 eq). The reaction mixture was stirred for 15 min, and isopropylmagnesium chloride (2M in THF, 1.5 eq) was added dropwise at 0° C. The reaction mixture was allowed to warm to RT and stirred for 16 h. The progress of the reaction was monitored by TLC. The reaction mixture was quenched with a solution of $NH_4Cl$ and the aqueous phase was extracted with EtOAc. The combined organic layer was dried over anhydrous $Na_2SO_4$, filtered and concentrated under reduced pressure. The crude residue was purified by flash column chromatography (gradient of EtOAc in hexane) to afford G1.

| Compound | Starting material | Compound name | Compound structure | Mass isolated, yield | LCMS m/z $[M + H]^+$ [a] |
|---|---|---|---|---|---|
| G1 | H3 | 5-bromo-7-fluoro-1-isopropyl-1,2,3,4-tetrahydroisoquinoline | 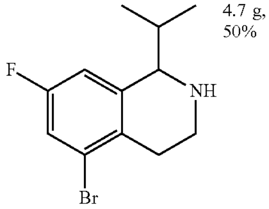 | 4.7 g, 50% | 274.2 |

Example 17: Synthesis of Compound H2

To a stirred solution of J1 (1) (1 eq) in MeOH was added $H_2SO_4$ (6 eq) dropwise at 0° C. The reaction mixture was heated to 85° C. and stirred for 16 h. The reaction was monitored by TLC and LCMS. After completion of the reaction, MeOH was removed under reduced pressure. The crude residue was taken up in water and basified with a solution of aqueous ammonia. The aqueous phase was extracted with DCM. The combined organic layer was dried over $Na_2SO_4$, filtered, and concentrated under reduced pressure to yield the title compound. The crude was used in the next step without further purification.

| Compound | Starting material | Compound name | Compound structure | Mass isolated, yield | LCMS m/z $[M + H]^+$ [a] |
|---|---|---|---|---|---|
| H2 | J1 | 5-bromo-1-isopropyl-7-methoxy-3,4-dihydroisoquinoline | 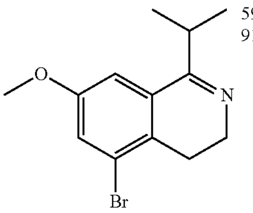 | 590 g, 91% | 282.1 |

Example 18: Synthesis of Compound H3

Crude J2 (1 eq) was dissolved in MeOH. $H_2SO_4$ (9 eq) was added at 0° C. and the reaction mixture was heated to 70° C. for 16 h. The reaction mixture was allowed to cool to RT. The solvent was removed in vacuo. Ice-cold water was slowly added, and pH was adjusted to 8-9 with a solution of 25% aq. $NH_3$ solution. The aqueous layer was extracted with DCM. The organic layer was washed with $H_2O$, dried over anhydrous $Na_2SO_4$, filtered, and concentrated under reduced pressure. The crude product was purified by chromatography (gradient of EtOAc in hexane) to afford the title compound.

| Compound | Starting material | Compound name | Compound structure | Mass isolated, yield | LCMS m/z $[M + H]^+$ [a] |
|---|---|---|---|---|---|
| H3 | J2 | 5-bromo-7-fluoro-3,4-dihydroisoquinoline | 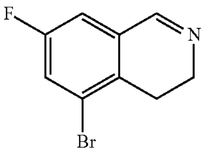 [SMILES: Fc1cc(Br)c2c(c1)C=NCC2] | 3.9 g, 59% | 230.1 $[M + H]^+$ |

Example 19: Synthesis of Compound J1

To a stirred solution of K1 (1 eq) in DCM was added oxalyl chloride (4 eq) dropwise at 0-5° C. The reaction mixture was allowed to warm to RT and stirred for 2 h. The reaction mixture was cooled to −78° C., iron(III) chloride (2 eq) was added in two portions. The reaction mixture was allowed to warm to RT, and stirred for 16 h at RT. The reaction mixture was quenched with ice-cold water and extracted with DCM. The combined organic layer was dried over sodium sulphate, and concentrated under reduced pressure to yield the crude material which was used in the next step without any further purification.

| Compound | Starting material | Compound name | Compound structure | Mass isolated, yield | LCMS m/z $[M + H]^+$ [a] |
|---|---|---|---|---|---|
| J1 | K1 | 7-bromo-10b-isopropyl-9-methoxy-6,10b-dihydro-5H-oxazolo[2,3-a]isoquinoline-2,3-dione | 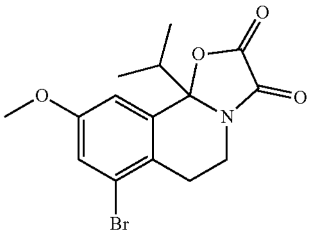 | 340 g, 57% | 282.0 $[M + H]^+$ (a) |

Note:
(a)corresponding imine mass ion was observed from compound fragmentation by LCMS.

Example 20: Synthesis of Compound J2

To a stirred solution of K2 (1 eq) in DCM was added oxalyl chloride (4 eq) dropwise at 0° C. The reaction mixture was allowed to warm to RT and stirred for 2 h. The reaction mixture was cool to −78° C. and iron(III) chloride (2 eq) was added in two portions. The reaction mixture was allowed to warm up to RT and stirred for 16 h. The reaction mixture was filtered through Celite, washed with DCM, and concentrated under reduced pressure to give the crude product which was used in the next step without any further purification.

| Compound | Starting material | Compound name | Compound structure | Mass isolated, yield | LCMS m/z $[M + H]^+$ [a] |
|---|---|---|---|---|---|
| J2 | K2 | 7-bromo-9-fluoro-6,10b-dihydro-5H-oxazolo[2,3-a]isoquinoline-2,3-dione | 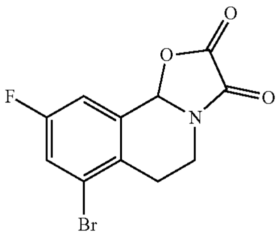 [SMILES: O=C1OC2c3cc(F)cc(Br)c3CCN2C1=O] | 8.5 g, 65% | 230.2 $[M + H]^+$ (a) |

Note:

(a)corresponding imine mass ion was observed from compound fragmentation by LCMS.

Example 21: Synthesis of Compound K1

To a stirred solution of L1 (1 eq) in DCM was added $Et_3N$ (1.5 eq) followed by isobutyryl chloride (1.2 eq) at 0° C. The reaction was warmed to RT and stirred for 16 h. The reaction mixture was cooled to −78° C. and iron(III) chloride (3 eq) was added. The reaction mixture was quenched with cold water and extracted with DCM. The combined organic layers were dried over anhydrous $Na_2SO_4$, filtered and concentrated in vacuo to afford the desired product (II). The resulting crude solid was used without further purification.

| Compound | Starting material | Compound name | Compound structure | LCMS m/z $[M + H]^+$, yield |
|---|---|---|---|---|
| K1 | L1 | N-(2-bromo-4-methoxyphenethyl)isobutyramide | 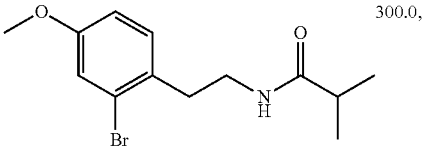 | 300.0, 81% |

Example 22: Synthesis of Compound K2

To a solution of L2 (1 eq) in ethyl formate (1 eq) was added pivalic acid (1 eq) at RT. The reaction mixture was refluxed for 48 h. The reaction progress was monitored by TLC. The reaction was allowed to cool to RT and concentrated under reduced pressure. The crude residue was basified (pH: 8-10) with a solution of sodium bicarbonate and the aqueous phase was extracted with DCM (3×150 mL). The combined organic layer was dried over anhydrous sodium sulphate, filtered and concentrated under reduced pressure. The crude product was purified by flash column chromatography (EtOAc in hexane) to afford the title compound.

| Compound | Starting material | Compound name | Compound structure | LCMS m/z $[M + H]^+$, yield |
|---|---|---|---|---|
| K2 | L2 | N-(2-bromo-4-fluorophenethyl)formamide | 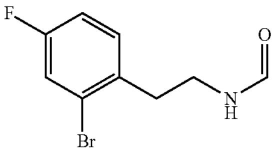 [SMILES: O=CNCCc1ccc(F)cc1Br] | 248.1, 34% |

Example 23: Synthesis of Compounds L1 and L2

Compounds L1 and L2 (see Table 21) were made using the following general procedure:

To a stirred solution of the starting material given in Table 22 (1 eq) in THF at 0° C. was added $BH_3$·THF (1 M in THF, 3 eq). The reaction was allowed to warm to RT, and stirred for 12 h. The reaction mixture was cooled to 0° C. and quenched with MeOH. The reaction was concentrated in vacuo. $H_2O$ was added and the organic phase was extracted with EtOAc. The combined organic fractions were dried over with sodium sulphate, filtered and concentrated to yield the product. The crude material was used in the next step without any further purification

TABLE 21

| Compound | Compound name | Compound structure |
|---|---|---|
| L2 | 2-(2-bromo-4-fluorophenyl) ethan-1-amine | 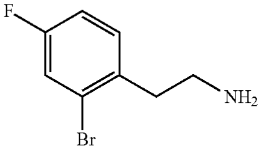 [SMILES: NCCc1ccc(F)cc1Br] |

TABLE 21-continued

| Compound | Compound name | Compound structure |
|---|---|---|
| L1 | 2-(2-bromo-4-methoxyphenyl) ethan-1-amine | 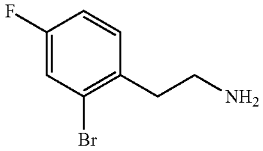 [SMILES: NCCc1ccc(F)cc1Br] |

TABLE 22

| Compound | Starting material | Mass isolated, yield | LCMS m/z $[M + H]^+$ |
|---|---|---|---|
| L2 | 2-(2-bromo-4-fluorophenyl)acetonitrile | 32 g, 64% | 220.2 $[M + H]^+$ |
| L1 | M1 | 12 g, 98% | 230.0 $[M + H]^+$ |

Example 24: Synthesis of Compound M1

To a suspension of tBuOK (2.5 eq) in THF, was added a solution of 1-(isocyanomethylsulfonyl)-4-methyl-benzene (1.5 eq) in THF at −78° C. The reaction mixture was stirred at −78° C. for 30 m and a solution of 2-bromo-4-methoxy-benzaldehyde (1 eq) in THF was added. After stirring for 1 h at −78° C., MeOH (0.3M) was added and the reaction mixture was warmed up to RT, and heated to 60° C. for 2 h. The reaction progress was monitored by TLC. The reaction mixture was allowed to cool to RT, diluted with water, extracted with ethyl acetate and the organic layer was washed with brine. The organic layer was dried over $Na_2SO_4$ and concentrated in vacuo. The resulting crude residue was purified by column chromatography (EtOAc in hexane) to yield the title compound.

| Compound | Compound name | Compound structure | Mass isolated, yield | LCMS m/z $[M - H]^-$ |
|---|---|---|---|---|
| M1 | 2-(2-bromo-4-methoxyphenyl)acetonitrile | 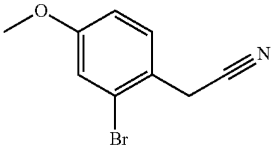 | 12 g, 63% | Used crude |

Example 25: Synthesis of Compounds N1 to N5

Compounds N1 to N5 (see table 23) were made using the following general procedure:

A solution of the starting material given in Table 34 (1.0 equiv.) in DCM or 1,4-dioxane (0.05 M) was treated with HCl (4 M in 1,4-dioxane, 50 equiv.) and the mixture was stirred for 2 h. The volatiles were evaporated in vacuo to yield the product.

TABLE 23

| Compound | Compound name | Compound structure |
|---|---|---|
| N1 | 5-(4-((4,7-diazaspiro[2.5] octan-7-yl)methyl)-3,5-dimethoxyphenyl)-1,3,4-trimethylpyridin-2(1H)-one, HCl salt | 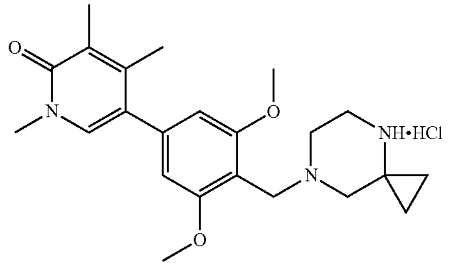 |
| N2 | 5-(4-((4,7-diazaspiro[2.5] octan-4-yl)methyl)-3,5-dimethoxyphenyl)-1,3,4-trimethylpyridin-2(1H)-one, HCl salt | 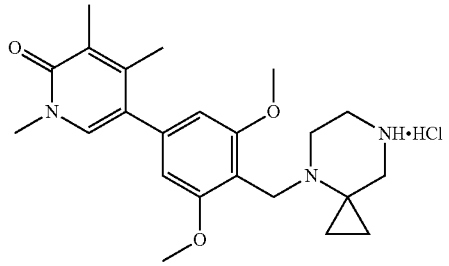 |
| N3 | 4-(4-((4,7-diazaspiro[2.5] octan-4-yl)methyl)-3,5-dimethoxyphenyl)-6-methyl-1,6-dihydro-7H-pyrazolo[ 3,4-c]pyridin-7-one, HCl salt | 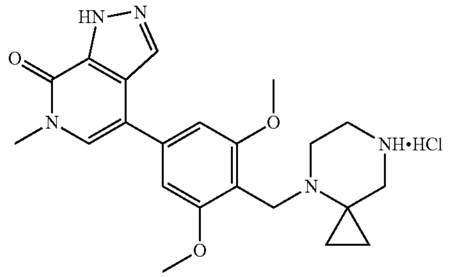 |
| N4 | 4-(4-((4,7-diazaspiro[2.5] octan-7-yl)methyl)-3,5-dimethoxyphenyl)-6-methyl-1,6-dihydro-7H-pyrazolo[ 3,4-c]pyridin-7-one, HCl salt | 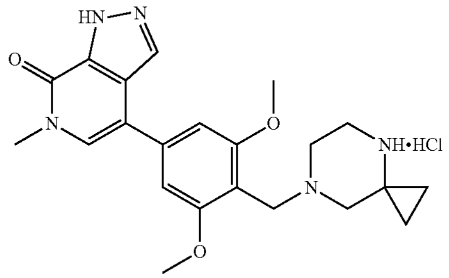 |

TABLE 23-continued

| Compound | Compound name | Compound structure |
|---|---|---|
| N5 | 5-(4-((4,7-diazaspiro[2.5] octan-7-yl)methyl)-3,5-bis(methoxy-d3)phenyl)-1,3,4-trimethylpyridin-2(1H)-one, HCl salt | 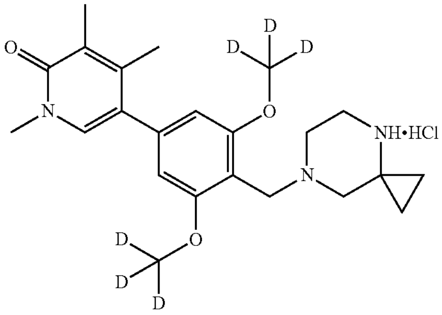 |

TABLE 24

| Compound | Starting material | LCMS m/z $[M+H]^+$/Yield |
|---|---|---|
| N1 | P1 | 398.3/93% |
| N2 | P2 | 398.4/99% |
| N3 | P3 | 410.3/82% |
| N4 | P4 | 410.2/used crude |
| N5 | P5 | 404.2/98% |

Example 26: Synthesis of Compounds N6 and N7

Compounds N6 and N7 (see Table 25) were made using the following general procedure:

A solution of Boc protected amine (1.0 equiv.) as provided in Table 26 in DCM (0.05 M) was treated with TFA (11 equiv.) and the mixture was stirred for 2 h. The volatiles were evaporated in vacuo to yield the corresponding amine (TFA salt).

TABLE 25

| Compound | Compound name | Compound structure |
|---|---|---|
| N6 | 4-(4-((4,7-diazaspiro[2.5]octan-7-yl)methyl)-3,5-dimethoxyphenyl)-6-(azetidin-1-yl)-2-methyl-2,7-naphthyridin-1(2H)-one, TFA salt | 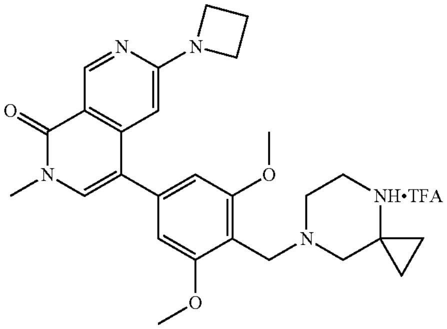 |
| N7 | 4-(4-((4,7-diazaspiro[2.5]octan-4-yl)methyl)-3,5-dimethoxyphenyl)-6-(azetidin-1-yl)-2-methyl-2,7-naphthyridin-1(2H)-one, TFA salt | 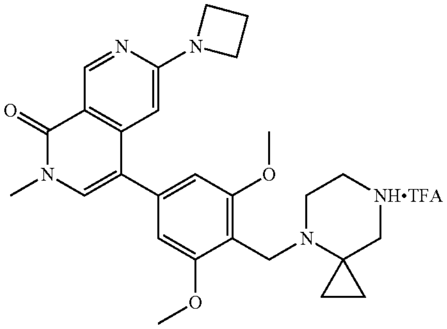 |

TABLE 26

| Compound | Starting material | LCMS m/z $[M + H]^+$/Yield |
|---|---|---|
| N6 | P6 | 476.5/used crude |
| N7 | P7 | 476.2/90% |

Example 27: Synthesis of Compounds P1 to P7

Compounds P1 to P7 (see Table 27) were made using the following general procedure:

A solution of the amine (1 equiv.) and aldehyde (1 equiv.) given in Table 28 in DCM (0.05 M) was treated with $Et_3N$ (1.5 equiv.). The reaction mixture was stirred for 1 h, then was treated with $NaBH(OAc)_3$ (2.0 equiv.) or MP-$NBH_3$ (5.0 equiv.). The reaction mixture was stirred at room temperature until the reaction was complete by LMS. The reaction was quenched by addition of $H_2O$ and extracted with DCM. The combined organic extracts were washed with water, brine, dried over $MgSO_4$ and concentrated in vacuo. Purification by silica gel column chromatography yielded the desired product.

TABLE 27

| Compound | Compound name | Compound structure |
|---|---|---|
| P1 | tert-butyl 7-(2,6-dimethoxy-4-(1,4,5-trimethyl-6-oxo-1,6-dihydropyridin-3-yl)benzyl)-4,7-diazaspiro[2.5]octane-4-carboxylate | 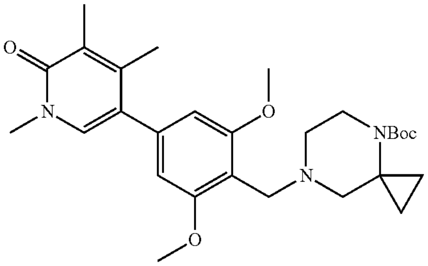 [SMILES: COc1cc(-c2cn(C)c(=O)c(C)c2C)cc(OC)c1CN1CCN(C(=O)OC(C)(C)C)C2(CC2)C1] |
| P2 | tert-butyl 4-(2,6-dimethoxy-4-(1,4,5-trimethyl-6-oxo-1,6-dihydropyridin-3-yl)benzyl)-4,7-diazaspiro[2.5]octane-7-carboxylate | 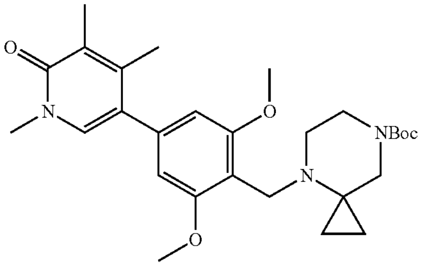 [SMILES: COc1cc(-c2cn(C)c(=O)c(C)c2C)cc(OC)c1CN1CCN(C(=O)OC(C)(C)C)CC12CC2] |
| P3 | tert-butyl 4-(2,6-dimethoxy-4-(6-methyl-7-oxo-6,7-dihydro-1H-pyrazolo[3,4-c]pyridin-4-yl)benzyl)-4,7-diazaspiro[2.5]octane-7-carboxylate | 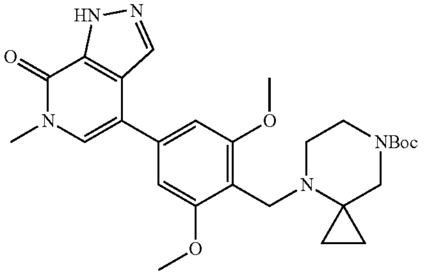 [SMILES: COc1cc(-c2cn(C)c(=O)c3[nH]ncc23)cc(OC)c1CN1CCN(C(=O)OC(C)(C)C)CC12CC2] |
| P4 | tert-butyl 7-(2,6-dimethoxy-4-(6-methyl-7-oxo-6,7-dihydro-1H-pyrazolo[3,4-c]pyridin-4-yl)benzyl)-4,7-diazaspiro[2.5]octane-4-carboxylate | 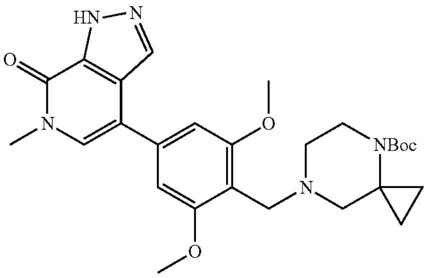 [SMILES: COc1cc(-c2cn(C)c(=O)c3[nH]ncc23)cc(OC)c1CN1CCN(C(=O)OC(C)(C)C)C2(CC2)C1] |

TABLE 27-continued

| Compound | Compound name | Compound structure |
|---|---|---|
| P6 | tert-butyl 7-(4-(6-(azetidin-1-yl)-2-methyl-1-oxo-1,2-dihydro-2,7-naphthyridin-4-yl)-2,6-dimethoxybenzyl)-4,7-diazaspiro[2.5]octane-4-carboxylate | 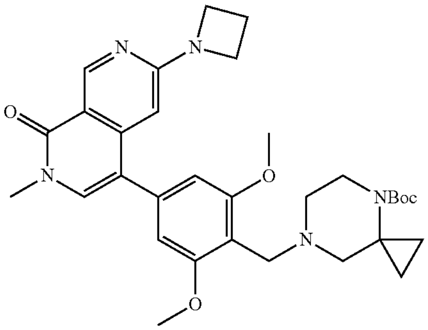 [SMILES: COc1cc(-c2cn(C)c(=O)c3cnc(N4CCC4)cc23)cc(OC)c1CN1CCN(C(=O)OC(C)(C)C)C2(CC2)C1] |
| P7 | tert-butyl 4-(4-(6-(azetidin-1-yl)-2-methyl-1-oxo-1,2-dihydro-2,7-naphthyridin-4-yl)-2,6-dimethoxybenzyl)-4,7-diazaspiro[2.5]octane-7-carboxylate | 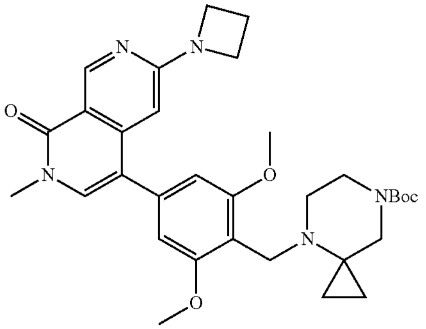 [SMILES: COc1cc(-c2cn(C)c(=O)c3cnc(N4CCC4)cc23)cc(OC)c1CN1CCN(C(=O)OC(C)(C)C)CC12CC2] |
| P5 | tert-butyl 7-(2,6-bis(methoxy-d3)-4-(1,4,5-trimethyl-6-oxo-1,6-dihydropyridin-3-yl)benzyl)-4,7-diazaspiro[2.5]octane-4-carboxylate | 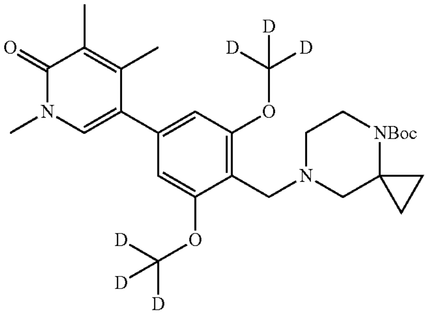 [SMILES: [2H]C([2H])([2H])Oc1cc(-c2cn(C)c(=O)c(C)c2C)cc(OC([2H])([2H])[2H])c1CN1CCN(C(=O)OC(C)(C)C)C2(CC2)C1] |

TABLE 28

| Compound | Starting aldehyde* | Starting amine** | LCMS m/z [M + H]+/Yield |
|---|---|---|---|
| P1 | 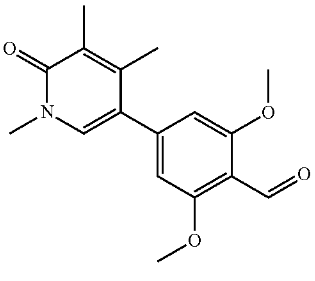 [SMILES: COc1cc(-c2cn(C)c(=O)c(C)c2C)cc(OC)c1C=O] | 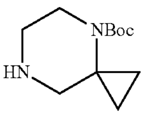 [SMILES: CC(C)(C)OC(=O)N1CCNCC12CC2] | 498.3/95% |

TABLE 28-continued
| Compound | Starting aldehyde* | Starting amine** | LCMS m/z $[M + H]^+$/Yield |
|---|---|---|---|
| P2 | 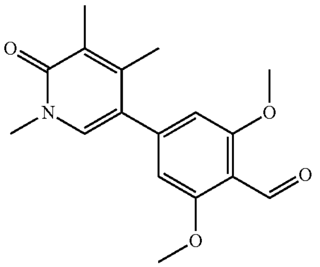 [SMILES: COc1cc(-c2cn(C)c(=O)c(C)c2C)cc(OC)c1C=O] | 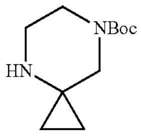 | 498.4/94% |
| P3 | 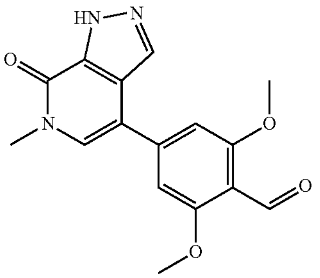 [SMILES: COc1cc(-c2cn(C)c(=O)c3[nH]ncc23)cc(OC)c1C=O] | 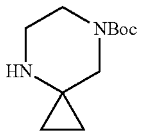 | 510.2/56% |
| P4 | 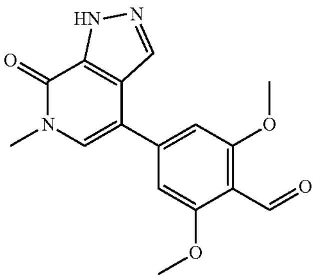 [SMILES: COc1cc(-c2cn(C)c(=O)c3[nH]ncc23)cc(OC)c1C=O] | 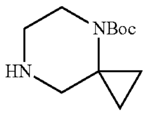 [SMILES: CC(C)(C)OC(=O)N1CCNCC12CC2] | 510.3/94% |
| P6 | 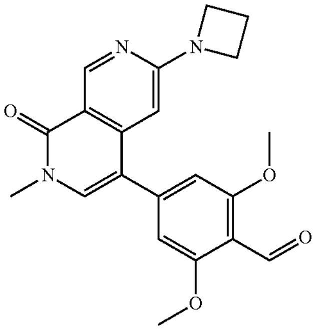 [SMILES: COc1cc(-c2cn(C)c(=O)c3cnc(N4CCC4)cc23)cc(OC)c1C=O] | 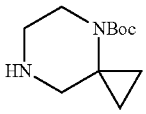 [SMILES: CC(C)(C)OC(=O)N1CCNCC12CC2] | 576.2/74% |
| P7 | 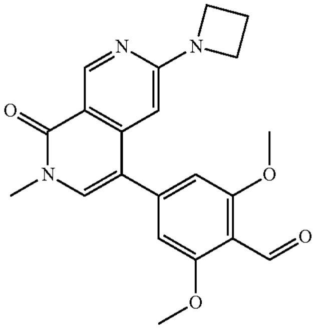 [SMILES: COc1cc(-c2cn(C)c(=O)c3cnc(N4CCC4)cc23)cc(OC)c1C=O] | 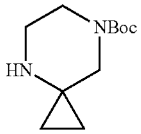 | 576.2/64% |

TABLE 28-continued

| Compound | Starting aldehyde* | Starting amine** | LCMS m/z [M + H]$^+$/Yield |
| --- | --- | --- | --- |
| P5 | 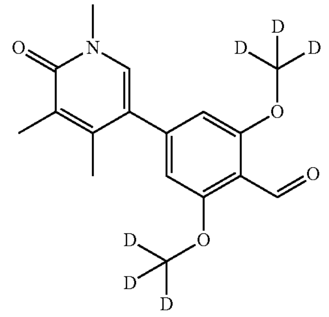 [SMILES: [2H]C([2H])([2H])Oc1cc(-c2cn(C)c(=O)c(C)c2C)cc(OC([2H])([2H])[2H])c1C=O] | 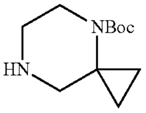 [SMILES: CC(C)(C)OC(=O)N1CCNCC12CC2] | 504.2/98% |

*Synthesised according to WO2021178920, except for the aldehyde used to synthesise P5 (see Example 28)
**Commercially available

Example 28: Synthesis of 2,6-bis(methoxy-da)-4-(1,4,5-trimethyl-6-oxo-1,6-dihydropyridin-3-yl)benzaldehyde

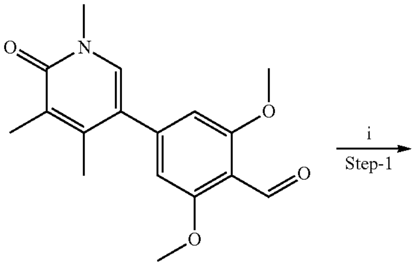

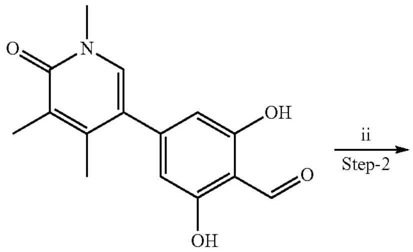

-continued

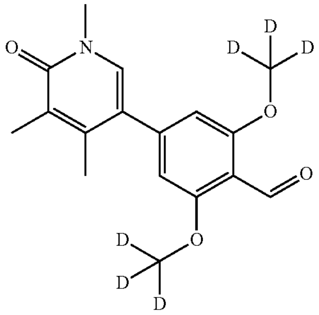

Step 1: Preparation of 2,6-dihydroxy-4-(1,4,5-trimethyl-6-oxo-1,6-dihydropyridin-3-yl)benzaldehyde To a stirred solution of 2,6-dimethoxy-4-(1,4,5-trimethyl-6-oxo-1,6-dihydropyridin-3-yl)benzaldehyde (20 g, 66.4 mmol) in DCM (250 mL) at 0° C. was added $BBr_3$ (199 mL, 199 mmol), the reaction was stirred at RT for 32 h. The reaction was monitored by LCMS and TLC. The reaction mixture was quenched with ice water (1 L) and stirred for 45 mins. The solid precipitate was filtered and dried to high vacuum for 16 h to obtain the title compound (15 g, 72%) which was used in the next step without further purification. LCMS m/z=274.2 $[M+H]^+$

Step 2: Preparation of 2,6-bis(methoxy-$d_3$)-4-(1,4,5-trimethyl-6-oxo-1,6-dihydropyridin-3-yl)benzaldehyde To a stirred solution of 2,6-dihydroxy-4-(1,4,5-trimethyl-6-oxo-1,6-dihydropyridin-3-yl)benzaldehyde (10 g, 36.6 mmol) in DMF (100 mL) was added $K_2CO_3$ (20.23 g, 146 mmol) and CD31 (5.45 mL, 110 mmol) under N2 at 0° C. The reaction mixture was stirred for 2 h at RT. The reaction mixture was quenched with ice cold water (500 mL). The precipitate was filtered and dried under vacuum to obtain the title compound (7.2 g, 62%) which was used in the next step without further purification. LCMS m/z=308.4 $[M+H]^+$

Example 29: Synthesis of (E)-5-(4-((4-((2-(4,4-dimethylpent-2-enoyl)-1-methyl-1,2,3,4-tetrahydroisoquinolin-5-yl)methyl)-4,7-diazaspiro[2.5]octan-7-yl)methyl)-3,5-dimethoxyphenyl)-1,3,4-trimethylpyridin-2(1H)-one (DE1)

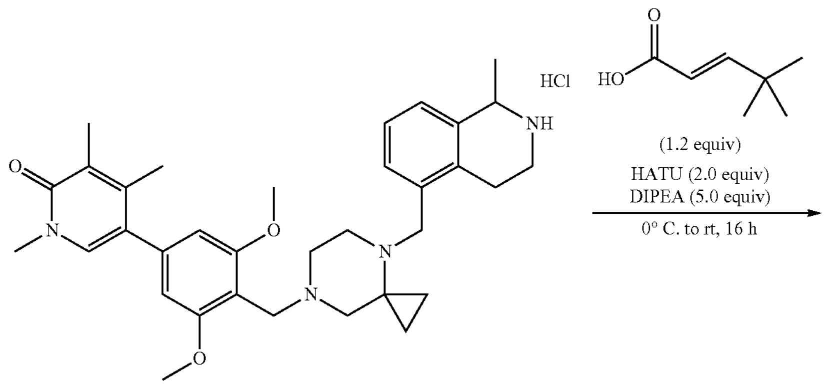

g

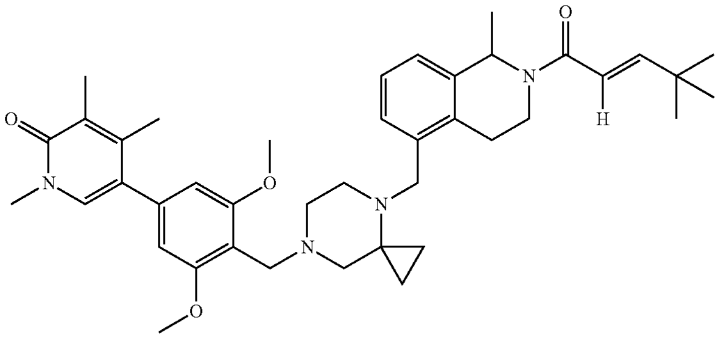

BL1

To a stirred solution of 5-(3,5-dimethoxy-4-((4-((1-methyl-1,2,3,4-tetrahydroisoquinolin-5-yl)methyl)-4,7-diazaspiro[2.5]octan-7-yl)methyl)phenyl)-1,3,4-trimethylpyridin-2(1H)-one hydrochloride (g) (1.0 equiv) in DMF at 0° C. was added DIPEA (5.0 equiv) followed by (E)-4,4-dimethylpent-2-enoic acid (1.2 equiv) (see below for confirmation of stereochemistry) and HATU (2.0 equiv). The resultant mixture was stirred for 15 min before being allowed to warm to ambient temperature and then stir for 16 h. Then mixture was quenched with iced water and the resultant solid was collected by vacuum filtration and then purified by reverse-phase column chromatography (eluent=0.1% aqueous $NH_4OAc$ in MeCN) to give (E)-5-(4-((4-((2-(4,4-dimethylpent-2-enoyl)-1-methyl-1,2,3,4-tetrahydroisoquinolin-5-yl)methyl)-4,7-diazaspiro[2.5]octan-7-yl)methyl)-3,5-dimethoxyphenyl)-1,3,4-trimethylpyridin-2(1H)-one (DE1).

LCMS: m/z=667.3 ($[M+H]^+$), $t_R$=2.38 min (Method A). $^1H$ NMR (400 MHz, DMSO-$d_6$): δ 7.52 (s, 1H), 7.19-7.07 (m, 3H), 6.75 (dd, J=15.4, 8.8 Hz, 1H), 6.59 (s, 2H), 6.36 (d, J=15.4 Hz, 1H), 5.54-5.46 and 5.30-5.23 (m, 1H), 4.54-4.45 and 4.17-4.08 (m, 1H), 3.82 (s, 6H), 3.92-3.65 (br m, 3H), 3.47 (s, 3H), 3.08-2.59 (m, 6H), 2.07 (s, 3H), 2.06 (s, 3H), 1.49-1.47 and 1.38-1.37 (m, 3H), 1.08 (s, 9H), 1.16-1.02 (m, 1H), 0.86 (s, 3H), 0.72-0.31 (br m, 4H).

Example 30: (R,E)-5-(4-((4-((2-(5-fluoro-4,4-dimethylpent-2-enoyl)-1-isopropyl-7-methoxy-1,2,3,4-tetrahydroisoquinolin-5-yl)methyl)-4,7-diazaspiro[2.5]octan-7-yl)methyl)-3,5-dimethoxyphenyl)-1,3,4-trimethylpyridin-2(1H)-one

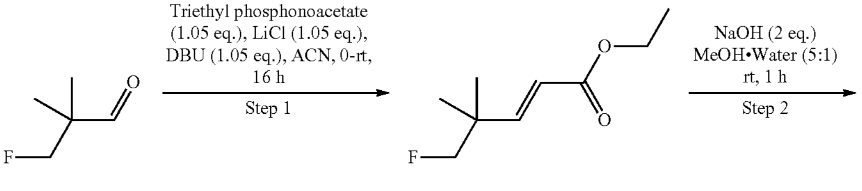

-continued

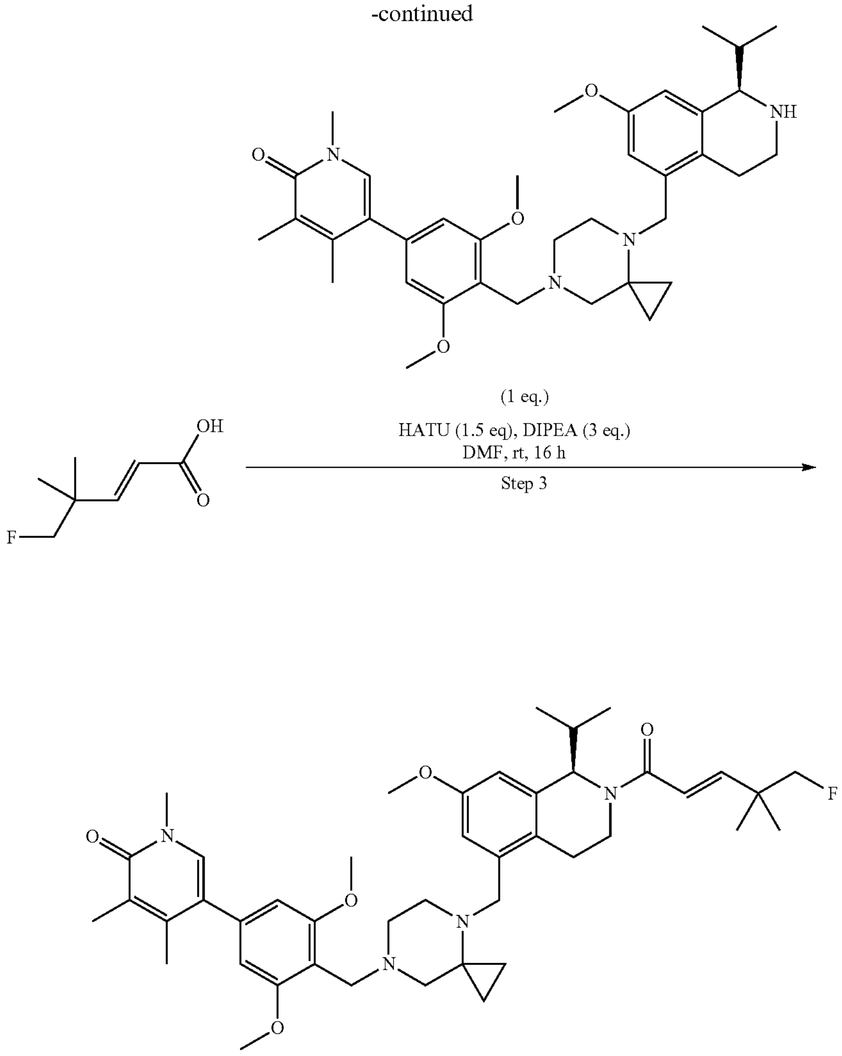

Step 1: ethyl (E/Z)-5-fluoro-4,4-dimethylpent-2-enoate

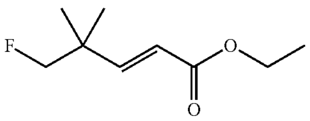

To a stirred solution of 3-fluoro-2,2-dimethylpropanal (500 mg, 4.80 mmol, 1 eq) in MeCN (20 ml) was added triethyl phosphonoacetate (1.000 ml, 5.04 mmol, 1.05 eq) and lithium chloride (214 mg, 5.04 mmol, 1.05 eq) at 0° C. Then added DBU (0.760 ml, 5.04 mmol, 1.05 eq) at 0° C. and allowed to stir for 16 h at RT. After completion, the reaction mixture was diluted with water and extracted with EtOAc. The organic layers were dried over $Na_2SO_4$ and concentrated in vacuo. The resulting residue was purified by silica column chromatography (gradient=10% EtOAc in pet-ether) to afforded ethyl (E)-5-fluoro-4,4-dimethylpent-2-enoate (500 mg, 2.81 mmol, 58.6% yield) as colourless liquid. MS (ESI): m/z: 175.3 $[M+H]^+$ Step 2: (E/Z)-5-fluoro-4,4-dimethylpent-2-enoic acid

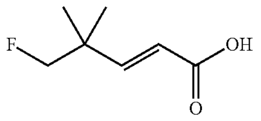

To a stirred solution of ethyl (E)-5-fluoro-4,4-dimethyl-pent-2-enoate (390 mg, 2.239 mmol, 1 eq) in MeOH (10 ml) and water (2 ml) was added NaOH (179 mg, 4.48 mmol, 2 eq) at RT. The resulting mixture was stirred for 1 h at RT before being concentrated in vacuo. The resulting residue was dissolved in water and the pH was adjusted 3-4 with 2M HCl before being extracted with DCM. The combined organic layers were dried over $Na_2SO_4$ and concentrated in vacuo to afforded (E/Z)-5-fluoro-4,4-dimethylpent-2-enoic acid (300 mg, 2.032 mmol, 91% yield) as off white solid. MS (ESI): m/z: 145.2 $[M-1]^+$ Step 3: (R,E)-5-(4-((4-((2-(5-fluoro-4,4-dimethylpent-2-enoyl)-1-isopropyl-7-methoxy-1,2,3,4-tetrahydroisoquinolin-5-yl)methyl)-4,7-diazaspiro[2.5]octan-7-yl)methyl)-3,5-dimethoxyphenyl)-1,3,4-trimethylpyridin-2(1H)-one

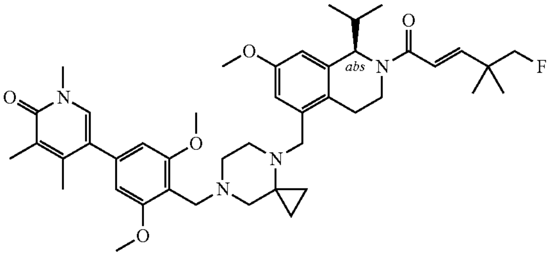 [SMILES: COc1cc(CN2CCN(Cc3c(OC)cc(-c4cn(C)c(=O)c(C)c4C)cc3OC)CC23CC3)c2c(c1)[C@@H](C(C)C)N(C(=O)/C=C/C(C)(C)CF)CC2]

To a stirred solution of (E/Z)-5-fluoro-4,4-dimethylpent-2-enoic acid (150 mg, 1.026 mmol) in DMF (5 ml) was added (R)-5-(4-((4-((1-isopropyl-7-methoxy-1,2,3,4-tetrahydroisoquinolin-5-yl)methyl)-4,7-diazaspiro[2.5]octan-7-yl)methyl)-3,5-dimethoxyphenyl)-1,3,4-trimethylpyridin-2(1H)-one (631 mg, 1.026 mmol) and HATU (585 mg, 1.539 mmol) followed by DIPEA (0.538 ml, 3.08 mmol) at RT. The resulting mixture was stirred for 16 h at RT before being concentrated in vacuo and purified by prep HPLC. The product containing fractions were lyophilised and the resulting solid was treated with $NaHCO_3$ solution and extract with 10% MeOH in DCM. The organic layers were dried over $Na_2SO_4$, concentrated in vacuo and lyophilised to afford (R,E)-5-(4-((4-((2-(5-fluoro-4,4-dimethylpent-2-enoyl)-1-isopropyl-7-methoxy-1,2,3,4-tetrahydroisoquinolin-5-yl)methyl)-4,7-diazaspiro[2.5]octan-7-yl)methyl)-3,5-dimethoxyphenyl)-1,3,4-trimethylpyridin-2(1H)-one (60 mg, 0.080 mmol, 7.8% yield) as off white solid. MS (ESI): retention time=1.96 min, m/z: 743.4 $[M+H]^+$ 1H-NMR (400 MHz, DMSO-d6): δ 7.52 (s, 1H), 6.46-6.74 (m, 6H), 5.15-5.17 (m, 1H), 4.19-4.31 (m, 2H), 3.62-3.78 (m, 13H), 3.46-3.50 (m, 5H), 3.19-3.30 (m, 1H), 2.72-2.79 (m, 2H), 2.61 (s, 2H), 2.33-2.50 (m, 3H), 2.06 (s, 7H), 1.08 (t, J=−1.60 Hz, 6H), 0.86-0.94 (m, 6H), 0.56 (s, 2H), 0.34 (s, 2H).

Example 31: (R)-2-(5-((7-(2,5-dimethoxy-4-(1,4,5-trimethyl-6-oxo-1,6-dihydropyridin-3-yl)benzyl)-4,7-diazaspiro[2.5]octan-4-yl)methyl)-1-isopropyl-7-methoxy-1,2,3,4-tetrahydroisoquinoline-2-carbonyl)-5-fluoro-4,4-dimethylpent-2-enenitrile Scheme

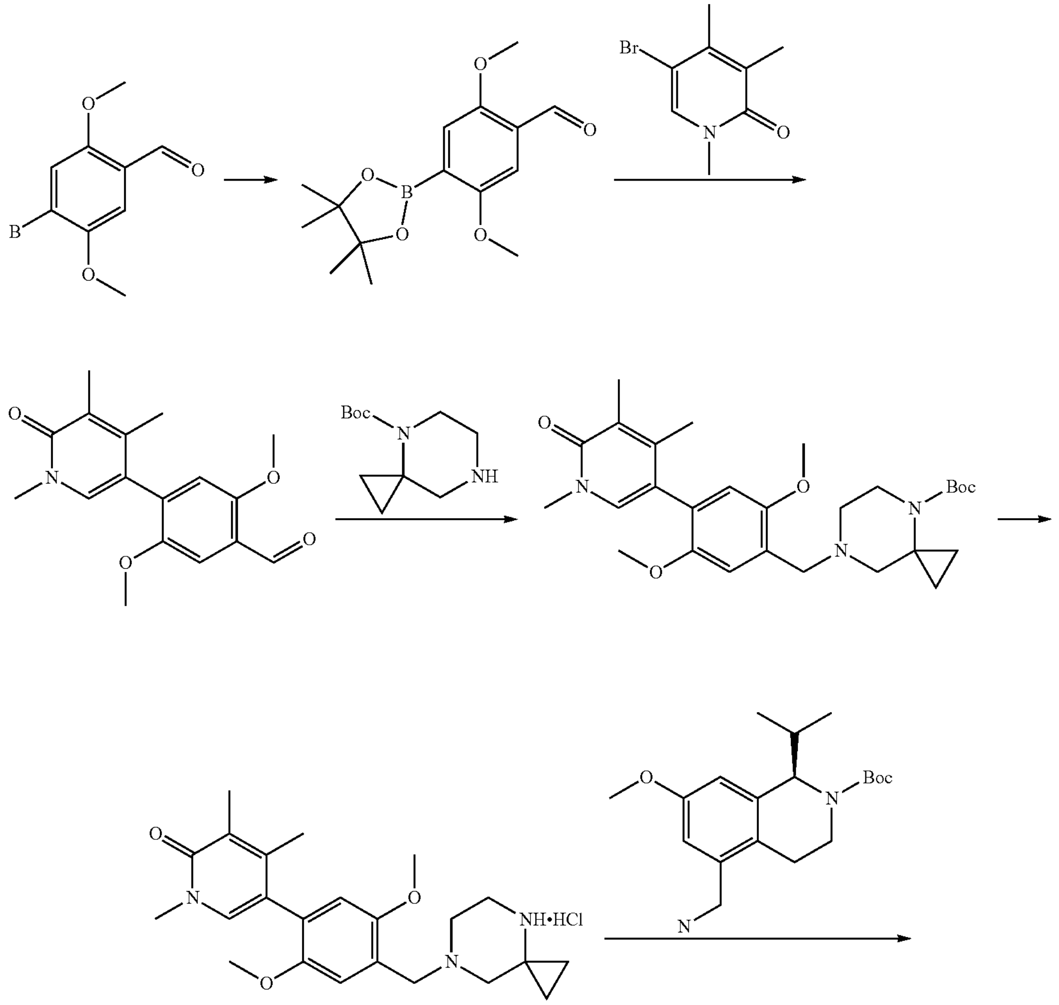

-continued

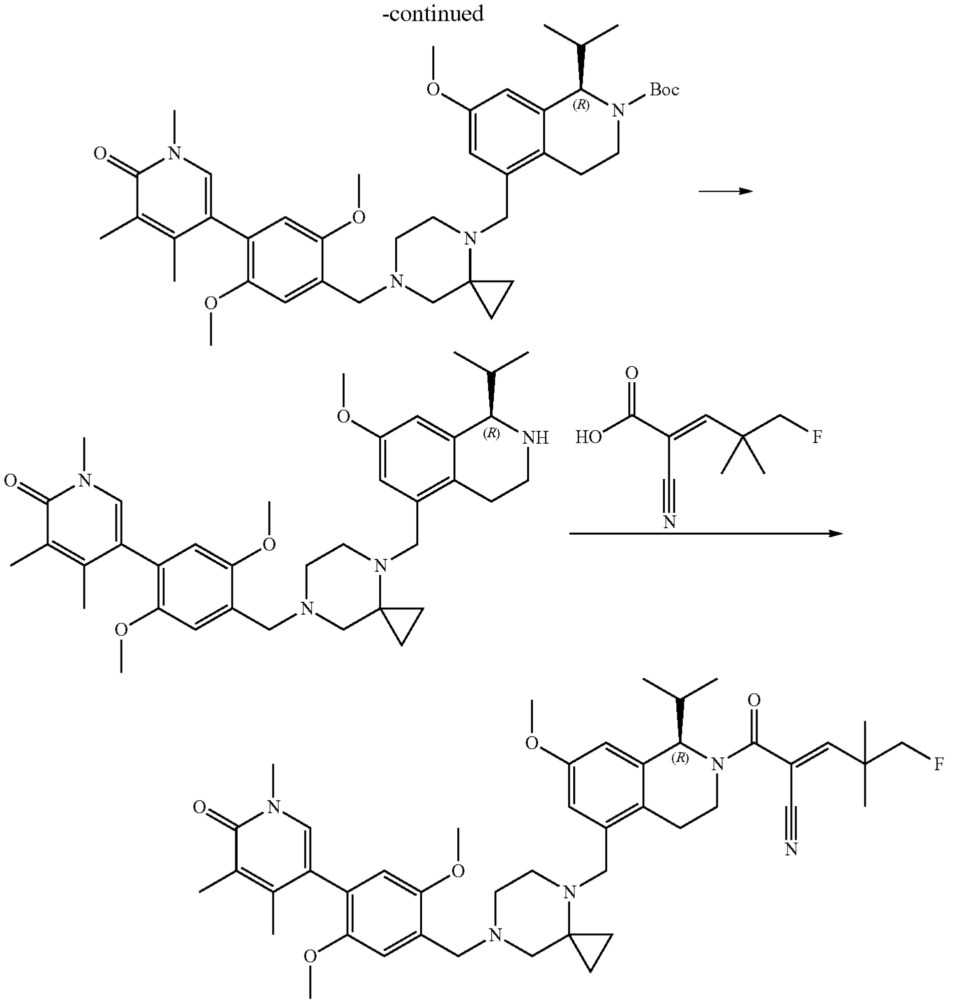

2,5-dimethoxy-4-(4,4,5,5-tetramethyl-1,3,2-dioxaborolan-2-yl)benzaldehyde

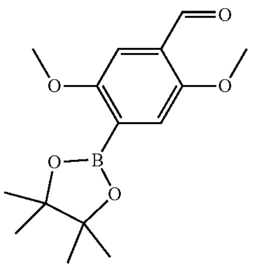

To the stirred solution of 4-bromo-2,5-dimethoxybenzaldehyde (2.5 g, 10.20 mmol) in 1,4-dioxane (25 mL) was added 4,4,4',4',5,5,5',5'-octamethyl-2,2'-bi(1,3,2-dioxaborolane) (3.37 g, 13.26 mmol) followed by potassium acetate (2.50 g, 25.5 mmol). The reaction mixture was degassed with nitrogen for 15 min then $PdCl_2$(dppf)DCM (0.416 g, 0.510 mmol) was added at RT. The reaction mixture was stirred at 85° C. for 6 h before being cooled to RT. The reaction mixture was diluted with EtOAc (200 mL) and was washed with water (50 mL), brine (50 mL) and the organic layer was dried over anhydrous $Na_2SO_4$ and concentrated in vacuo to afford crude 2,5-dimethoxy-4-(4,4,5,5-tetramethyl-1,3,2-dioxaborolan-2-yl)benzaldehyde (3.0 g, 3.59 mmol, 35.2% yield). The crude was used in the next step without further purification. LCMS m/z=292.2 $[M+H]^+$.

2,5-dimethoxy-4-(1,4,5-trimethyl-6-oxo-1,6-dihydropyridin-3-yl) benzaldehyde

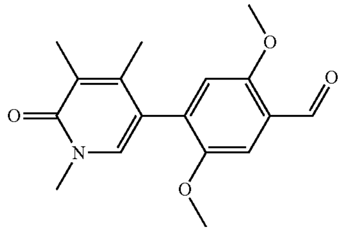 [SMILES: COc1cc(-c2cn(C)c(=O)c(C)c2C)c(OC)cc1C=O]

To a stirred solution of 5-bromo-1,3,4-trimethylpyridin-2(1H)-one (3.5 g, 16.20 mmol)) in 1,4-dioxane (32 mL) and water (8 mL) was added 2,5-dimethoxy-4-(4,4,5,5-tetramethyl-1,3,2-dioxaborolan-2-yl)benzaldehyde (5.68 g, 19.44 mmol), $K_3PO_4$ (10.3 g, 48.6 mmol) and the reaction mixture was purged with N2 for 10 minutes. $PdCl_2$(dppf) (0.59 g, 0.810 mmol) was added at 25° C. and the reaction was stirred at 80° C. for 12 h. The reaction mixture was cooled to RT and was then diluted with EtOAc (200 mL). The organic phase was washed with water (50 mL), brine (50 mL), dried over anhydrous $Na_2SO_4$ and was concentrated in vacuo. The resulting residue was purified by silica gel column chromatography (gradient=0-100% EtOAc in hexane). The appropriate fractions were combined and concentrated in vacuo to afford 2,5-dimethoxy-4-(1,4,5-trimethyl-6-oxo-1,6-dihydropyridin-3-yl)benzaldehyde (2.2 g, 6.06 mmol, 37% yield). LCMS m/z=302.2 $[M+H]^+$.

tert-butyl 7-(2,5-dimethoxy-4-(1,4,5-trimethyl-6-oxo-1,6-dihydropyridin-3-yl)benzyl)-4,7-diazaspiro [2.5]octane-4-carboxylate

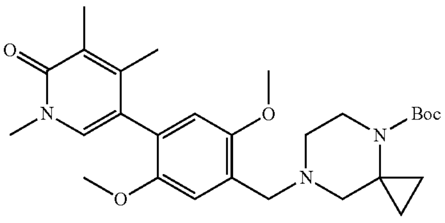 [SMILES: COc1cc(-c2cn(C)c(=O)c(C)c2C)c(OC)cc1CN1CCN(C(=O)OC(C)(C)C)C2(CC2)C1]

To a stirred solution of 2,5-dimethoxy-4-(1,4,5-trimethyl-6-oxo-1,6-dihydropyridin-3-yl)benzaldehyde (2.2 g, 7.30 mmol) in 1,2-dichloroethane (15 mL) and methanol (5 mL) was added triethylamine (1.02 mL, 7.30 mmol), tert-butyl 4,7-diazaspiro[2.5]octane-4-carboxylate (1.40 g, 6.57 mmol) and acetic acid (1.25 mL, 21.9 mmol) under N2 atmosphere. The reaction mixture was stirred at RT for 2 h then $MPCNBH_3$ (2 g) was added and the reaction mixture was kept at 70° C. for 3 h. After completion of the reaction, reaction mixture was cooled to RT before being diluted with 10% MeOH in DCM (100 mL). The reaction mixture was washed with water (20 mL), brine (15 mL), saturated aqueous $NaHCO_3$ (15 mL) solution, and the organic phase was dried over anhydrous $Na_2SO_4$ before being concentrated in vacuo. The resulting residue was purified by silica gel column chromatography (gradient=0-10% MeOH in DCM) to afford tert-butyl 7-(2,5-dimethoxy-4-(1,4,5-trimethyl-6-oxo-1,6-dihydropyridin-3-yl)benzyl)-4,7-diazaspiro [2.5]octane-4-carboxylate (3.4 g, 5.12 mmol, 70% yield). LCMS m/z=498.2 $[M+H]^+$.

5-(4-((4,7-diazaspiro[2.5]octan-7-yl)methyl)-2,5-dimethoxyphenyl)-1,3,4-trimethylpyridin-2(1H)-one hydrochloride

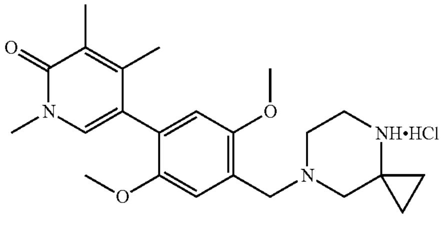

To a stirred solution of tert-butyl 7-(2,5-dimethoxy-4-(1,4,5-trimethyl-6-oxo-1,6-dihydropyridin-3-yl)benzyl)-4,7-diazaspiro[2.5]octane-4-carboxylate (5 g, 10.05 mmol) in DCM (50 mL) was added HCl in 1,4-dioxane (4N, 20 mL) at 0° C. under $N_2$ atmosphere. The reaction mixture was stirred at 25° C. for 6 h then was concentrated in vacuo. The resulting residue was triturated with n-pentane, then MTBE, and the resulting solid was dried under vacuum to afford 5-(4-((4,7-diazaspiro[2.5]octan-7-yl)methyl)-2,5-dimethoxyphenyl)-1,3,4-trimethylpyridin-2(1H)-one hydrochloride (5 g, 8.64 mmol, 75% yield). LCMS m/z=398.2 $[M+H]^+$.

tert-butyl (R)-5-((7-(2,5-dimethoxy-4-(1,4,5-trimethyl-6-oxo-1,6-dihydropyridin-3-yl)benzyl)-4,7-diazaspiro[2.5]octan-4-yl)methyl)-1-isopropyl-7-methoxy-3,4-dihydroisoquinoline-2(1H)-carboxylate

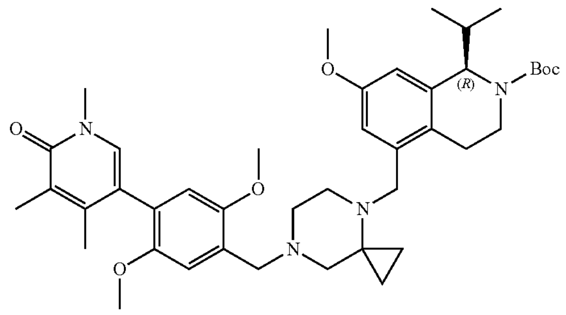

To a stirred solution of 5-(4-((4,7-diazaspiro[2.5]octan-7-yl)methyl)-2,5-dimethoxyphenyl)-1,3,4-trimethylpyridin-2(1H)-one hydrochloride (4 g, 9.22 mmol) in 1,2-dichloroethane (30 mL) and methanol (10 mL) was added triethylamine (1.29 ml, 9.22 mmol), tert-butyl (R)-5-formyl-1-isopropyl-7-methoxy-3,4-dihydroisoquinoline-2(1H)-carboxylate (3.07 g, 9.22 mmol) and acetic acid (1.58 mL, 27.7 mmol) under N2 atmosphere. The reaction mixture was stirred at RT for 2 h then $MPCNBH_3$ (4 g, 9.22 mmol) was added. The reaction mixture was heated to 70° C. for 3 h then was cooled to RT. Reaction mixture was diluted with 10% MeOH in DCM (300 mL) and the organic phase was washed with water (120 mL), brine (50 mL), saturated aqueous $NaHCO_3$ (50 mL) then was dried over anhydrous $Na_2SO_4$ and was concentrated in vacuo. The resulting residue was purified by silica gel column chromatography (gradient=0-10% MeOH in DCM) to afford tert-butyl (R)-5-((7-(2,5-dimethoxy-4-(1,4,5-trimethyl-6-oxo-1,6-dihydropyridin-3-yl)benzyl)-4,7-diazaspiro[2.5]octan-4-yl)methyl)-1-isopropyl-7-methoxy-3,4-dihydroisoquinoline-2(1H)-carboxylate (1.6 g, 2.148 mmol, 23% yield). LCMS m/z=715.4 $[M+H]^+$.

(R)-5-(4-((4-((1-isopropyl-7-methoxy-1,2,3,4-tetrahydroisoquinolin-5-yl)methyl)-4,7-diazaspiro[2.5]octan-7-yl)methyl)-2,5-dimethoxyphenyl)-1,3,4-trimethylpyridin-2(1H)-one hydrochloride

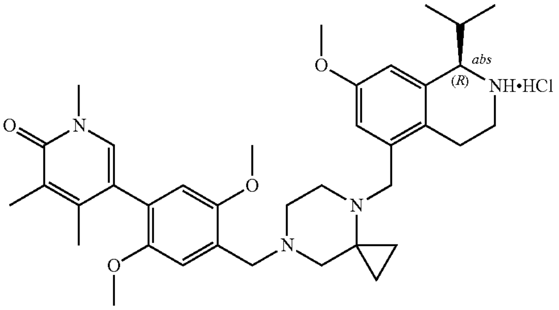

To a stirred solution of tert-butyl (R)-5-((7-(2,5-dimethoxy-4-(1,4,5-trimethyl-6-oxo-1,6-dihydropyridin-3-yl)benzyl)-4,7-diazaspiro[2.5]octan-4-yl)methyl)-1-isopropyl-7-methoxy-3,4-dihydroisoquinoline-2(1H)-carboxylate (1.6 g, 1.97 mmol) in DCM (20 mL) was added HCl in 1,4-dioxane (4N, 4.92 mL, 19.7 mmol) at 0° C. under N2 atmosphere. The reaction mixture was stirred at RT for 6 h before being concentrated in vacuo. The resulting residue was triturated with n-pentane, MTBE, then dried under vacuum to afford (R)-5-(4-((4-((1-isopropyl-7-methoxy-1,2,3,4-tetrahydroisoquinolin-5-yl)methyl)-4,7-diazaspiro[2.5]octan-7-yl)methyl)-2,5-dimethoxyphenyl)-1,3,4-trimethylpyridin-2(1H)-one hydrochloride (1.2 g, 1.71 mmol, 87% yield). LCMS m/z=615.4 $[M+H]^+$.

(R,E)-2-(5-((7-(2,5-dimethoxy-4-(1,4,5-trimethyl-6-oxo-1,6-dihydropyridin-3-yl)benzyl)-4,7-diazaspiro[2.5]octan-4-yl)methyl)-1-isopropyl-7-methoxy-1,2,3,4-tetrahydroisoquinoline-2-carbonyl)-5-fluoro-4,4-dimethylpent-2-enenitrile

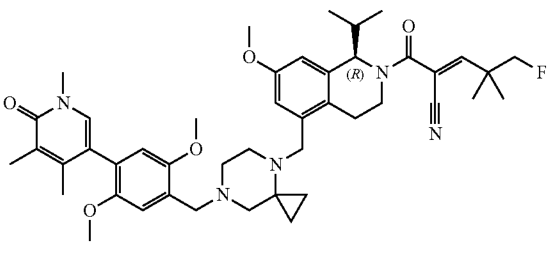

To a stirred solution of (R)-5-(4-((4-((1-isopropyl-7-methoxy-1,2,3,4-tetrahydroisoquinolin-5-yl)methyl)-4,7-diazaspiro[2.5]octan-7-yl)methyl)-2,5-dimethoxyphenyl)-1,3,4-trimethylpyridin-2(1H)-one hydrochloride (0.9 g, 1.38 mmol), (E/Z)-2-cyano-5-fluoro-4,4-dimethylpent-2-enoic acid (0.36 g, 2.073 mmol) in DMF (0.1 mL) was added DIPEA (1.21 mL, 6.91 mmol) followed by HATU (1.05 g, 2.76 mmol) at 0° C. under N2 atmosphere. The reaction mixture warmed to 25° C. before being stirred for 6 h. The reaction mixture was diluted with 10% MeOH in DCM (50 mL) then the organic phase was washed with water (12 mL), brine (10 mL), saturated aqueous $NaHCO_3$ (10 mL), dried over anhydrous $Na_2SO_4$ and was concentrated in vacuo. The resulting residue was purified by reverse phase prep-HPLC to afford (R)-2-(5-((7-(2,5-dimethoxy-4-(1,4,5-trimethyl-6-oxo-1,6-dihydropyridin-3-yl)benzyl)-4,7-diazaspiro[2.5]octan-4-yl)methyl)-1-isopropyl-7-methoxy-1,2,3,4-tetrahydroisoquinoline-2-carbonyl)-5-fluoro-4,4-dimethylpent-2-enenitrile (215 mg, 0.05 mmol, 4% yield). LCMS m/z=768.4 $[M+H]^+$, rt=2.32 min HPLC: RT—13.051 (98.95%) 210-400 nm HPLC Method: Column: ACE_Excel3_SuperC18 (4.6×150 mm, 3 μm) Mobile phase A 10 mm Ammonium Acetate in $H_2O$ Mobile phase B: Acetonitrile Flowrate: 1.2 mL/min Example 32: Degradation of BRD9

A suspension of MV4-11 cells (ATCC CRL-9591) was prepared in phenol red-free assay media (IMDM Thermo Scientific 21056023+10% FBS ATCC 302025) and cells were seeded at 20,000 cells per well (45 μL) in sterile black poly-d-lysine coated 384 well plates (Greiner 781948). Compounds were prepared at 1000× final concentration in DMSO, diluted 1:100 in assay media, and 5 μL compound was added to each well of the cell plate. Cells were incubated for 24 hours at 37° C. with 5% $CO_2$. All the following incubations for immunofluorescence staining were at room temperature. 15 μL of 16% PFA was added to each well (3.7% final concentration) and the cells were fixed for 15 min then washed twice with DPBS. Cells were permeabilised with 0.1% Triton X-100 for 10 min, Triton X-100 was removed, then blocked with 1% BSA in DPBS for 1 hour. Cells were stained with 25 μL anti-BRD9 E4Q3F antibody (CST 48306) diluted 1:25600 in 1% BSA in DPBS for 2-3 hours. Wells were washed twice with DPBS then incubated with 25 μL of 1% BSA containing a 1:1000 dilution of Anti-rabbit Alexa Fluor™ 647 secondary antibody (Thermo Scientific A21244) and 1 μg/mL Hoechst nuclear counter stain (Abcam ab228551) for 1 hour. Wells were washed twice with DPBS prior to imaging on a Perkin Elmer Operetta CLS with 10× air lens. Images were processed using Harmony High-Content Imaging and Analysis Software (Perkin Elmer) and the mean contrast ratio of Alexa Fluor™ 647 in central nuclei was used to quantify BRD9 protein levels. Data was further analysed using Dotmatics software and % BRD9 remaining was calculated by normalisation to average data from high and low control wells (cells treated with DMSO or 100 nM CFT-8634 respectively).

Example 33: Degradation of BRD4

A suspension of MV4-11 cells (ATCC CRL-9591) was prepared in phenol red-free assay media (IMDM Thermo Scientific 21056023+10% FBS ATCC 302025) and cells were seeded at 20,000 cells per well (45 μL) in sterile black poly-d-lysine coated 384 well plates (Greiner 781948 or Revvity 6057500). Compounds were prepared at 1000× final concentration in DMSO, diluted 1:100 in assay media, and 5 μL compound was added to each well of the cell plate. Cells were incubated for 24 hours at 37° C. with 5% $CO_2$. All the following incubations for immunofluorescence staining were at room temperature unless otherwise stated. 15 μL of 16% PFA was added to each well (3.7% final concentration) and the cells were fixed for 15 min then washed twice with DPBS. Cells were permeabilised with 0.5% Triton X-100 for 10 min, Triton X-100 was removed, then blocked with 1% BSA and 0.5% Triton X-100 in DPBS for 1 hour. Cells were stained with 25 μL anti-BRD4 BL-149-2H5 antibody (Bethyl Labs A700-004) diluted 1:2000 in 1% BSA and 0.5% Triton X-100 in DPBS overnight at 4° C. Block buffer alone was added to a subset of DMSO-treated wells as a control. Wells were washed twice with DPBS then incubated with 25 μL of 1% BSA and 0.5% Triton X-100 block solution containing a 1:1000 dilution of Anti-rabbit Alexa Fluor™ 488 secondary antibody (Thermo Scientific A11008) and 1 μg/mL Hoechst nuclear counter stain (Abcam ab228551) for 1 hour. Wells were washed twice with DPBS prior to imaging on a Perkin Elmer Operetta CLS with 10× air lens. Images were processed using Harmony High-Content Imaging and Analysis Software (Perkin Elmer) and the mean contrast ratio of Alexa Fluor™ 488 in central nuclei was used to quantify BRD4 protein levels. Data was further analysed using Dotmatics software and % BRD4 remaining was calculated by normalisation to average data from high and low control wells (DMSO-treated cells stained with antibody or excluding primary antibody respectively).

BRD9/BRD4 Degradation Results

The degradation of BRD9/BRD9 was detected according to the procedure outlined above for a number of exemplary compounds of the disclosure. The results are shown in Table 29. In particular, the table shows the BRD9 degradation efficiency of 1 μM of indicated example compound at 6 h of treatment and the BRD4 degradation efficiency of 1 μM of indicated example compound at 24 h of treatment. Although the absolute stereochemistry of compound numbers 7 and 8 was not tested, according to the BRD9 degradation data (see Table 29), it is our understanding that compound 7 is (R,E/Z)-2-(5-((7-(2,6-dimethoxy-4-(6-methyl-7-oxo-6,7-dihydro-1H-pyrazolo[3,4-c]pyridin-4-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile, and compound 8 is (S,E/Z)-2-(5-((7-(2,6-dimethoxy-4-(6-methyl-7-oxo-6,7-dihydro-1H-pyrazolo[3,4-c]pyridin-4-yl)benzyl)-4,7-diazaspiro[2.5]octan-4-yl)methyl)-7-fluoro-1-isopropyl-1,2,3,4-tetrahydroisoquinoline-2-carbonyl)-4,4-dimethylpent-2-enenitrile.

TABLE 29

| | BRD9 | | BRD4 | |
|---|---|---|---|---|
| Compound number | $DC_{50}$ (nM) | $D_{max}$ (%) | $DC_{50}$ (nM) | $D_{max}$ (%) |
| 1 | 0.0388 | 97.4 | 2579 | 80.55 |
| 2 | 3.7 | 84.99 | N/A | 4.53 |
| 3 | 0.5309 | 91.89 | N/A | 24.66 |
| 4 | 0.8292 | 95.38 | N/A | 40.54 |
| 5 | 0.0091 | 93.42 | 1148 | 86.75 |
| 6 | 0.1858 | 91.08 | 845.8 | 77.15 |
| 7 | 0.1008 | 87.43 | 1090 | 66 |
| 8 | 27.25 | 52.29 | n.t. | n.t. |
| 9 | 0.0237 | 95.64 | N/A | 9.276 |
| 10 | 0.014 | 96.14 | N/A | 31.44 |
| 11 | 0.4589 | 89.25 | N/A | 16.8 |
| 12 | 0.024 | 92.07 | N/A | 41.11 |
| 13 | 0.0866 | 94.19 | N/A | 42.98 |
| 14 | 0.0388 | 87.17 | N/A | 29.05 |
| Comparative example 1 | 0.8869 | 92.1 | N/A | 0 |
| Comparative example 2 | 0.0779 | 95.26 | 523.5 | 78.79 |
| Comparative example 3 | 1.279 | 91.87 | N/A | 0 |

N/A = degradation of 50% was not achieved and so a $DC_{50}$ value could not be calculated; n.t. = not tested.

Comparative example 1=(R,E)-2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-1-isopropyl-1,2,3,4-tetrahydroisoquinoline-2-carbonyl)-5-fluoro-4,4-dimethylpent-2-enenitrile (i.e. compound C103 found in WO2024057021A1)

Comparative example 2=(R,E)-2-(5-((7-(2,6-dimethoxy-4-(1,4,5-trimethyl-6-oxo-1,6-dihydropyridin-3-yl)benzyl)-4,7-diazaspiro[2.5]octan-4-yl)methyl)-1-isopropyl-1,2,3,4-tetrahydroisoquinoline-2-carbonyl)-5-fluoro-4,4-dimethylpent-2-enenitrile (i.e. compound C77 found in WO2024057021A1)

Comparative example 3=(E/Z)-2-(5-((4-(2,6-dimethoxy-4-(1,4,5-trimethyl-6-oxo-1,6-dihydropyridin-3-yl)benzyl)-4,7-diazaspiro[2.5]octan-7-yl)methyl)-1-isopropyl-1,2,3,4-tetrahydroisoquinoline-2-carbonyl)-4,4-dimethylpent-2-enenitrile (i.e. compound $C_{81}$ found in WO2024057021A1)

Example 34: Metabolic Stability in Cryopreserved Hepatocytes (Human, Rat, Dog, Mouse)

Cryopreserved hepatocytes (human, Preci; rat, BioIVT; Dog Beagle, BioIVT; mouse, BioIVT) were thawed in a single step, as follows.

1. INVITROGRO™ HT medium (BioIVT) was pre-warmed to 37° C.
2. 2.49 mL of INVITROGRO™ HT medium was transferred to a sterile 50 mL conical tube.
3. Hepatocyte vial was thawed in a water bath at 37° C., and the vial contents were emptied into the conical tube containing prewarmed INVITROGRO™ HT medium.
4. The tube was centrifuged at 50 g force (483 rpm) for 5 min.
5. The supernatant was carefully removed, and the pellet resuspended into incubation media
6. Cell viability was determined using a trypan blue assay, and cell count was measured using Hemocytometer.

Master stock solution (10 mM) of test compounds or assay controls were prepared in 100% DMSO. Intermediate working stock solutions (1 mM) of test compounds were prepared by diluting 10 μL (test compounds) of 10 mM master stock solution with 90 μL of DMSO. Final working stock solution (2 μM) was prepared by diluting 2 μL of intermediate working stock with 998 μL of incubation media. In the case of assay controls, intermediate working stock solutions (3 mM) of assay controls were prepared by diluting 30 μL of 10 mM master stock solution with 70 μL of DMSO. Final working stock solution (6 μM) was prepared by diluting 2 μL of intermediate working stock with 998 μL of incubation media.

40 g/mL stock of Tolbutamide was prepared in DMSO. 12.5 μL of 40 mg/mL (stock) was added in one litre of acetonitrile to a final Concentration of 500 ng/mL. 10 mg/mL stock of Telmisartan was prepared in DMSO. 25 μL of 10 mg/mL (stock) was added in one litre of acetonitrile to a final Concentration of 250 ng/mL.

Assay Procedure

Working stock (200 μL of 2 μM & 6 μM) solution of test compounds and assay controls were added to equal volume (200 μL) of cell suspension ($2*10^6$ cells/mL) (48 well plates (Cat-677180, Make-Griener bio-one) were used in this assay). Final test compound and assay control concentration was 1 μM & 3 μM and final cell density was $1*10^6$ cells/mL (Viability at 0 min-87.22% and at 120 min-79.59%) in the assay. Resulting mixture was incubated at 37° C. for 120 min with constant shaking at 250 rpm on a shaker (Heidolph Vibramax). At each time point (0, 5, 10, 15, 30, 60, 90, 120 min), 50 μL of cell suspension was removed and precipitated with 200 μL of acetonitrile containing internal standard (Tolbutamide, 500 ng/mL, Telmisartan, 250 ng/mL). Samples were mixed well and centrifuged for 10 min at 4000 rpm. After centrifugation, supernatant was separated and analyzed by LC-MS/MS.

| | |
|---|---|
| QC Compounds | Umbelliferone (MW = 162.14)<br>Quinidine (MW = 324.42)<br>Propranolol (MW = 259.34)<br>Verapamil (MW = 454.60) |
| Replicates | n = 2 |
| Final DMSO concentration | 0.10% |
| Assay readout | $Cl_{int}$ in vitro (mL/min/kg body weight), $t_{1/2}$ (min) |

Calculations $$\%\ PCR = (\text{Peak area ratio at each time point, } tn)/(\text{Peak area ratio at } t0 \text{ min})^{*}100$$

$$\text{Half life (min)} = 0.693/Kel$$

$$\text{Intrinsic clearance, } CL_{int}(\mu L/\text{min}/106 \text{ cells}) = [Kel/\text{Cell density}]^{*}1000$$

$$\text{Hepatic intrinsic clearance, } CLh_{int}(\text{mL/min/kg body weight}) = [Kel/\text{Cell density}]^{*}\text{Hepatocellularity value}^{*}\text{Liver weight (g/kg } bwt)$$

$$\text{Hepatic blood clearance, } CL_{hb}(\text{well stirred})(\text{mL/min/kg body weight}) = (CL_{int}{}^{*}\text{hepatic blood flow})/(CL_{int} + \text{hepatic blood flow})$$

Scaling Factors

| Species | Hepatocellularity value (*$10^6$ cells/g liver) | Liver weight (g/kg body weight) | Hepatic blood flow (mL/min/kg body weight) |
|---|---|---|---|
| Human | 120 | 26 | 21 |
| Rat | 120 | 40 | 55 |
| Dog | 240 | 32 | 31 |
| Mouse | 120 | 88 | 90 |

Acceptance

| Species | Umbelliferone | Quinidine | Propranolol |
|---|---|---|---|
| Human | 47.75-192.07 | 0.66-9.84 | 5.0-15.0 |
| Rat | 27-350 | 39-189 | — |
| Dog | 27.15-205.92 | 0.7-6.06 | — |
| Mouse | >154 | 43.47-187 | — |

Bioanalytic Details

| LC-Conditions | |
|---|---|
| Column | Kinetex ®C18 100Å 5 μm 50 × 2.1 mm |
| Mobile Phase A) | 5 mM Ammonium formate in Ultra pure water type 1 with 0.1% formic acid |
| Mobile Phase B) | Acetonitrile with 0.1% formic acid in water |
| Flow Rate (mL/min) | 0.800 mL/min |
| Autosampler Temperature | 8° C. |
| Column Oven Temperature | 40° C. |

-continued

| LC-Conditions | |
|---|---|
| Rinsing Solvent | Methanol:Acetonitrile: Ultra pure water type 1:IPA (1:1:1:1) |

Hepatic Intrinsic Clearance

Hepatic intrinsic clearance was detected according to the procedure outlined above for a number of exemplary compounds of the disclosure. The results are shown in Table 30.

TABLE 30

| | Hepatic intrinsic clearance (mL/min/kg body weight) | | | |
|---|---|---|---|---|
| Compound number | Mouse | Human | Rat | Dog |
| 1 | n.t. | 28.734 | n.t. | n.t. |
| 2 | n.t. | 21.611 | n.t. | n.t. |
| 3 | 39.963 | 13.698 | 25.201 | 54.867 |
| 4 | n.t. | 22.659 | n.t. | n.t. |
| 5 | n.t. | 20.595 | 25.457 | 31.133 |
| 6 | 25.048 | 16.369 | 16.341 | 28.467 |
| 7 | n.t. | 18.6 | n.t. | n.t. |
| 8 | n.t. | n.t. | n.t. | n.t. |
| 9 | 90.168 | 26.108 | 25.905 | 65.979 |
| 10 | n.t. | 25.537 | 10.914 | 33.17 |
| 11 | n.t. | 22.945 | 18.1 | 72.036 |
| 12 | n.t. | 19.651 | n.t. | 29.735 |
| 13 | n.t. | 16.847 | n.t. | n.t. |
| 14 | n.t. | n.t. | n.t. | n.t. |
| Comparative example 1 | n.t. | 33.05026481 | n.t. | n.t. |
| Comparative example 2 | n.t. | 51.369 | n.t. | n.t. |
| Comparative example 3 | n.t. | 40.865 | n.t. | n.t. |

n.t. = not tested.

Example 35: Mechanism of Degradation

A suspension of MOLM-13 cells (AddexBio C0003003) or MV4-11 cells (ATCC CRL-9591) was prepared in phenol red-free assay media (RPMI 1640 Thermo Scientific 12027599+20% FBS ATCC 302025 and IMDM Thermo Scientific 21056023+10% FBS ATCC 302025 respectively) and cells were seeded at 20,000 cells per well (40 μL).

Cells seeded in sterile black poly-d-lysine coated 384 well plates (Perkin Elmer 6057500). Inhibitor compounds were prepared at 11× final concentration in DMSO and 5 μL of DMSO and inhibitor added in alternative rows (final concentration of 4 uM MLN4294/10 uM Bortezomib/10 uM POI Ligand).

Plates incubated for 1 hour at 37° C. with 5% $CO_2$. Compounds were prepared at 1000× final concentration in DMSO, diluted 1:100 in assay media, and 5 μL compound was added to each well of the cell plate. Each compound treated in DMSO and inhibitor rows. Cells were incubated for 4 hours at 37° C. with 5% $CO_2$. All the following incubations for immunofluorescence staining were at room temperature. 15 μL of 16% PFA was added to each well (3.7% final concentration) and the cells were fixed for 15 min then washed twice with DPBS. Cells were permeabilised with 0.1% Triton X-100 for 10 min, Triton X-100 was removed, then blocked with 1% BSA in DPBS for 1 hour. Cells were stained with 25 μL anti-BRD9 E4Q3F antibody (CST 48306) diluted 1:25600 in 1% BSA in DPBS for 2-3 hours. Wells were washed twice with DPBS then incubated with 25 μL of 1% BSA containing a 1:1000 dilution of Anti-rabbit Alexa Fluor™ 647 secondary antibody (Thermo Scientific A21244) and 1 μg/mL Hoechst nuclear counter stain (Abcam ab228551) for 1 hour. Wells were washed twice with DPBS prior to imaging on a Perkin Elmer Operetta CLS with 10× air lens. Images were processed using Harmony High-Content Imaging and Analysis Software (Perkin Elmer) and the mean contrast ratio of Alexa Fluor™ 647 in central nuclei was used to quantify BRD9 protein levels.

Data was further analysed using Dotmatics software and % BRD9 remaining was calculated by normalisation to average data of appropriate co-treatment wells from high and low control wells (cells treated with DMSO or cells treated with DMSO with no primary antibody added respectively).

Results

Figure 2:
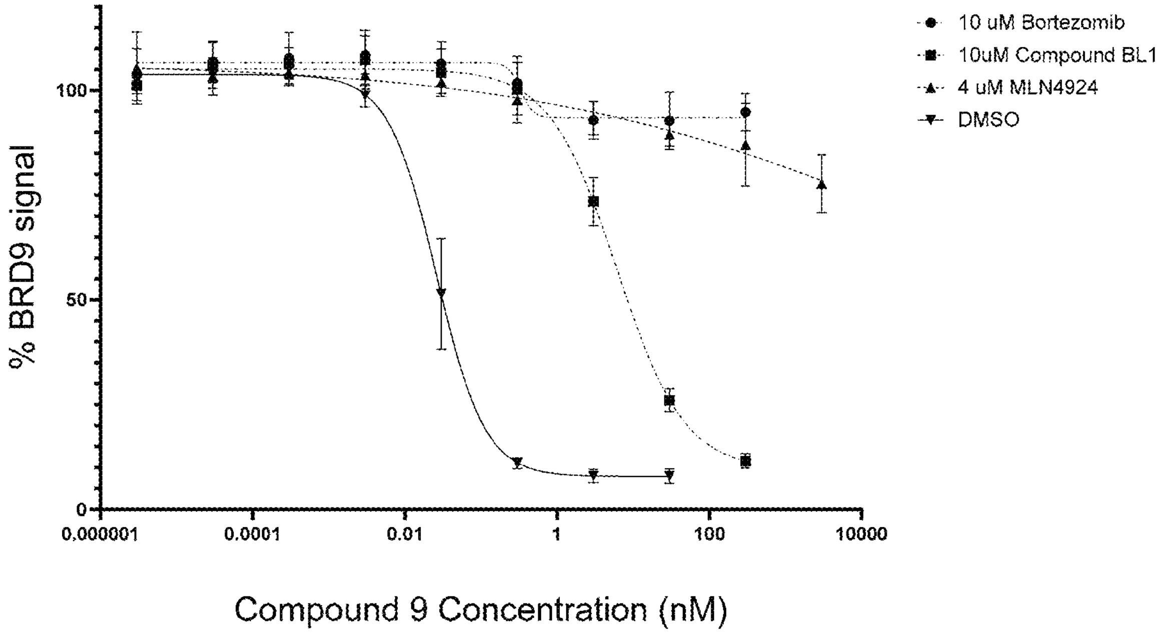
FIG. 2 is a line graph showing that dose dependent degradation of BRD9 at 4 hrs in MOLM-13 cells induced by compound 9 can be out-competed using the BRD9 binding ligand BL1, and prevented by pre-treating with the Neddylation inhibitor MLN4924 or Bortezomib.

Dose dependent degradation of BRD9 in MOLM-13 or MV4-11 cells can be out-competed using the BRD9 binding ligand BL1 (5-(3,5-dimethoxy-4-((4-methyl-4,7-diazaspiro[2.5]octan-7-yl)methyl)phenyl)-1,3,4-trimethylpyridin-2(1H)-one), confirming the binding site of the degrader. compound 9 (see Table 5) degradation was prevented by pre-treating with the Neddylation inhibitor MLN4924 or Bortezomib confirming a proteasome dependent mechanism (see FIGS. 1 and 2).

Example 36: Determination of the Dependency of BRD9 Degradation on the Presence of CN A suspension of MV4-11 cells (ATCC CRL-9591) was prepared in phenol red-free assay media (IMDM Thermo Scientific 21056023+10% FBS ATCC 302025) and cells were seeded at 20,000 cells per well (45 μL) for time points: 24 hours. Cells seeded in sterile black poly-d-lysine coated 384 well plates (Perkin Elmer 6057500). Compounds were prepared at 1000× final concentration in DMSO, diluted 1:100 in assay media, and 5 μL compound was added to each well of the cell plate. Cells were incubated for 0.5, 1, 2, 4, 6, 24 & 48 hours at 37° C. with 5% $CO_2$. All the following incubations for immunofluorescence staining were at room temperature. 15 μL of 16% PFA was added to each well (3.7% final concentration) and the cells were fixed for 15 min then washed twice with DPBS. Cells were permeabilised with 0.1% Triton X-100 for 10 min, Triton X-100 was removed, then blocked with 1% BSA in DPBS for 1 hour. Cells were stained with 25 μL anti-BRD9 E4Q3F antibody (CST 48306) diluted 1:25600 in 1% BSA in DPBS for 2-3 hours. Wells were washed twice with DPBS then incubated with 25 μL of 1% BSA containing a 1:1000 dilution of Anti-rabbit Alexa Fluor™ 647 secondary antibody (Thermo Scientific A21244) and 1 μg/mL Hoechst nuclear counter stain (Abcam ab228551) for 1 hour. Wells were washed twice with DPBS prior to imaging on a Perkin Elmer Operetta CLS with 10× air lens. Images were processed using Harmony High-Content Imaging and Analysis Software (Perkin Elmer) and the mean contrast ratio of Alexa Fluor™ 647 in central nuclei was used to quantify BRD9 protein levels. Data was further analysed using Dotmatics software and % BRD9 remaining was calculated by normalisation to average data from high and low control wells (cells treated with DMSO or cells treated with DMSO with no primary antibody added respectively).

Results

Figure 3:
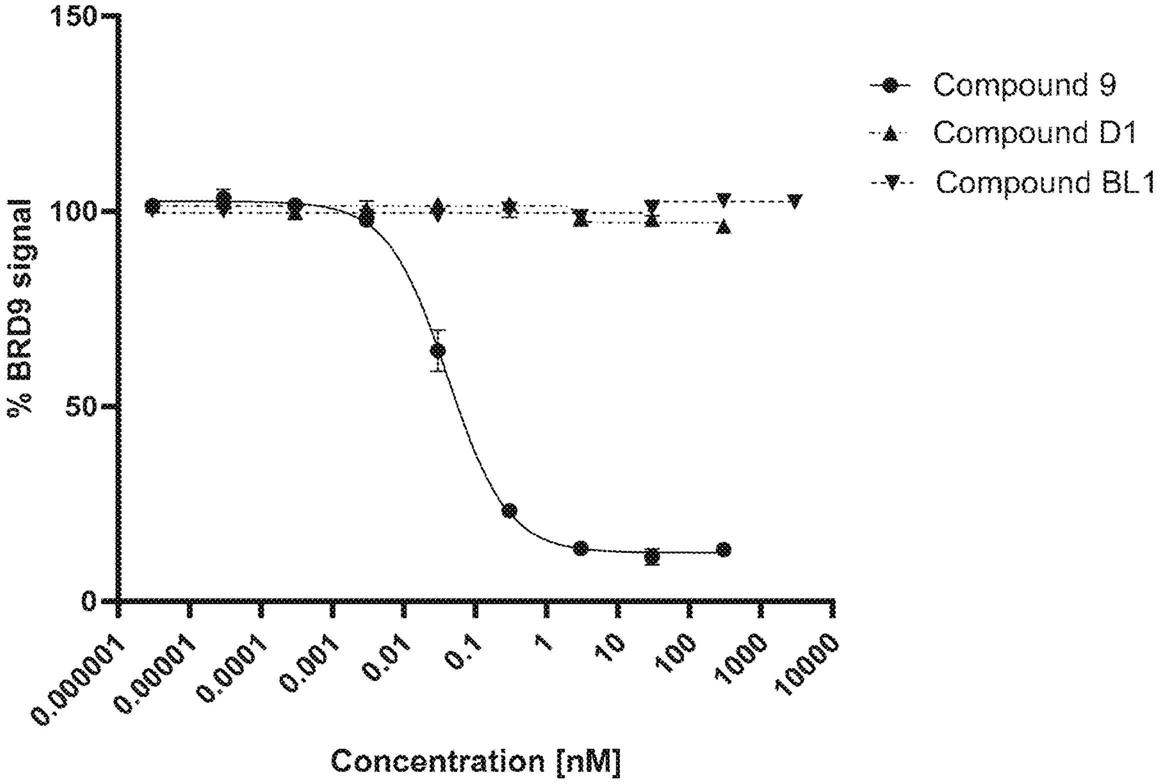
FIG. 3 is a line graph showing that dose dependent degradation of BRD9 at 6 hrs in MV4-11 cells by compound 9 is driven uniquely by the cyanoacrylamide moiety. Compound DE1 ((E)-5-(4-((4-((2-(4,4-dimethylpent-2-enoyl)-1-methyl-1,2,3,4-tetrahydroisoquinolin-5-yl)methyl)-4,7-diazaspiro[2.5]octan-7-yl)methyl)-3,5-dimethoxyphenyl)-1,3,4-trimethylpyridin-2(1H)-one), a des-Cyano molecule, and compound BL1, a BRD9 ligand, show no activity.

Dose dependent degradation of BRD9 at 6 hrs in MV4-11 cells by compounds of formula (III) is driven uniquely by the cyanoacrylamide moiety; a molecule designed without the covalent cyano group did not drive degradation of BRD9 (see FIG. 3).

Example 37: Determination of the Dependency of BRD9 Degradation on DCAF16

A suspension of NCI-H358 Parental or NCI-H358 DCAF16 KO (Promega) was prepared in phenol red-free assay media (RPMI 1640 Thermo Scientific 12027599+10% FBS ATCC 302025 and cells were seeded at 20,000 cells per well (40 μL).

Cells seeded in sterile PhenoPlate 384-well, black, optically clear flat-bottom (Revvity 6057302).

Plates incubated for 1 hour at 37° C. with 5% $CO_2$. Compounds were prepared at 1000× final concentration in DMSO, diluted 1:100 in assay media, and 5 μL compound was added to each well of the cell plate. Each compound treated in DMSO and inhibitor rows. Cells were incubated for 4 hours at 37° C. with 5% $CO_2$. All the following incubations for immunofluorescence staining were at room temperature. 15 μL of 16% PFA was added to each well (3.7% final concentration) and the cells were fixed for 15 min then washed twice with DPBS.

Cells were permeabilised with 0.1% Triton X-100 for 10 min, Triton X-100 was removed, then blocked with 1% BSA in DPBS for 1 hour. Cells were stained with 25 μL anti-BRD9 E4Q3F antibody (CST 48306) diluted 1:25600 in 1% BSA in DPBS for 2-3 hours. Wells were washed twice with DPBS then incubated with 25 μL of 1% BSA containing a 1:1000 dilution of Anti-rabbit Alexa Fluor™ 647 secondary antibody (Thermo Scientific A21244) and 1 μg/mL Hoechst nuclear counter stain (Abcam ab228551) for 1 hour. Wells were washed twice with DPBS prior to imaging on a Perkin Elmer Operetta CLS with 10× air lens. Images were processed using Harmony High-Content Imaging and Analysis Software (Perkin Elmer) and the mean contrast ratio of Alexa Fluor™ 647 in central nuclei was used to quantify BRD9 protein levels.

Data was further analysed using Dotmatics software and % BRD9 remaining was calculated by normalisation to average data of appropriate co-treatment wells from high and low control wells (cells treated with DMSO or cells treated with DMSO with no primary antibody added respectively).

Results

Figure 4:
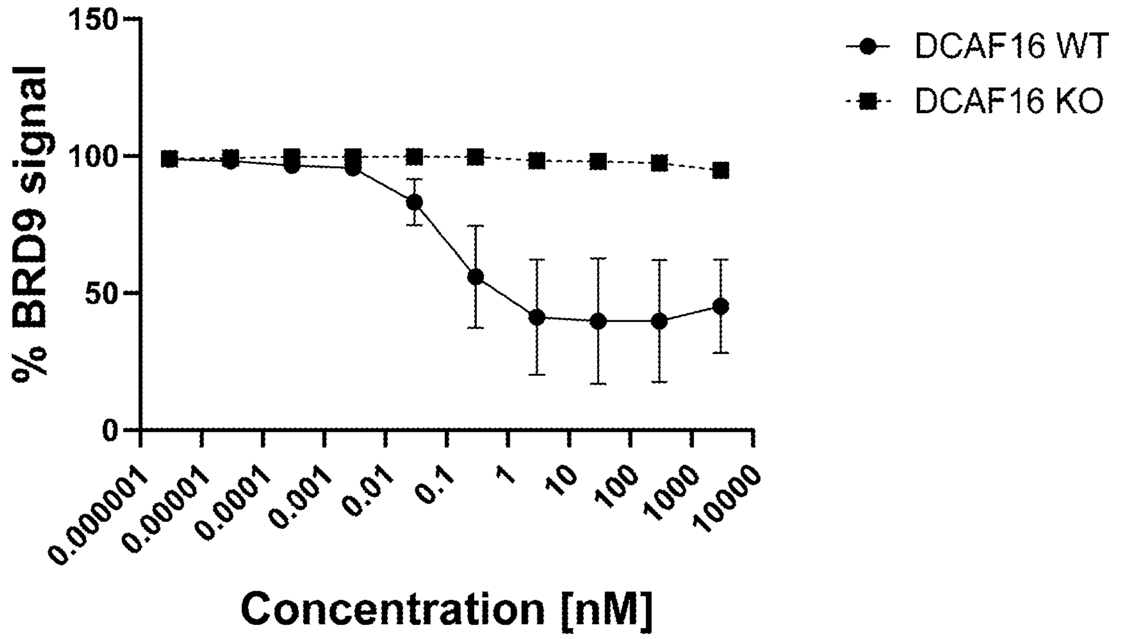
FIG. 4 is a line graph showing shows that BRD9 degradation induced by compound 9 (see Table 5) is dependent on the expression of DCAF16.

Removal of DCAF16 via CRISPR in the H-358 cell line resulted in loss of BRD9 degradation, highlighting the dependency of the cyanoacylamide moiety of the compounds of formula (III) on the E3 ligase DCAF16 (see FIG. 4).

Example 38: Selectivity of Compounds of Formula (III)

Proteomics Method

TMT LC-MS Global Proteomics Sample Preparation

MV4; 11 cells were seeded at 8×10^5 for 6 h and 24 h time points and $6.2\times10^5$ cells for 48 h. After seeding, cells were immediately treated with 100 μM of indicated compounds in triplicate. At indicated time points, cells were washed twice with PBS, pelleted, and resuspended in 100 μL of lysis buffer (50 mM Tris pH 7.6, 150 mM NaCl, 2% SDS, 10% glycerol, protease inhibitors (Pierce A32961), 1 mM PMSF, 250 U benzonase (Thermo Fisher, 88701) and sonicated for 1 minute at 100% power with a probe sonicator. Cell debris was removed by centrifugation at 21,000×g for 10 min.

FASP-Based Tryptic Digestion

246 μg of each sample was used for FASP as follows: Dithiothreitol was added to a final concentration of 83.3 mM, incubated at 99° C. for 5 mins, then cooled to room temperature. VIVACON 500 filter units, 30,000 MWCO (Sartorius Stedim, Biotech GmbH, 37079 Goettingen, Germany) were washed with 8 M urea in 100 mM Tris/HCl pH 8.5, centrifuged at 14,000×g, 20° C. for 15 mins. Samples were loaded in 50 μL aliquots plus 200 μL 8 M urea, centrifuged at 14,000×g, 20° C. for 15 mins. The filter units were washed with 8 M urea, centrifuged at 14,000×g, 20° C. for 15 mins. 100 μL 50 mM Iodoacetamide in 8 M urea was added to the filter units and incubated for 30 mins in the dark. Filter units were centrifuged at 14,000×g, 20° C. for 10 mins, then washed with 100 μL 8 M urea, centrifuged at 14,000×g, 20° C. for 15 mins. This wash step was repeated two times, for a total of three washes. Filters were further washed with 100 μL 50 mM Triethylammonium Bicarbonate Buffer pH 8.5 (TEAB, (Thermo Fisher Scientific)), centrifuged at 14,000×g, 20° C. for 10 mins. This wash step was repeated two times, for a total of three washes. Filter units were transferred to new tubes and 1.25% (w/w) trypsin (Pierce MS grade, Thermo Fisher Scientific, Loughborough, LE11 5RG, UK) in 60 μL 50 mM TEAB was added. The Filter units were sealed with Parafilm and digestion performed overnight at 37° C. with shaking. Following overnight digestion, the filter units were centrifuged at 14,000×g, 20° C. for 20 min. and the flow through containing the peptides was retained. The filter units were washed with 40 μL 50 mM TEAB, centrifuged at 14,000×g, 20° C. for 10 mins and then 50 μL 0.5M NaCl, centrifuged at 14,000×g, 20° C. for 20 mins and these washes were added to the flow through. Peptide samples were desalted and cleaned up using Sep-Pak cartridges according to the manufacturer's instructions (Waters, Milford, Massachusetts, USA). Eluate from the Sep-Pak cartridge was evaporated to dryness and resuspended in 100 μl 50 mM TEAB and 10 μl used for a peptide assay. All chemicals from Merck Life Science UK Limited, Dorset, SP8 4XT unless otherwise stated.

For global proteomics, samples were combined to a total of 100 μg each TMT plex and desalted using a SepPak cartridge according to the manufacturer's instructions (Waters, Milford, Massachusetts, USA). Eluate from the SepPak cartridge was evaporated to dryness and resuspended in buffer A (20 mM ammonium hydroxide, pH 10) prior to fractionation by high pH reversed-phase chromatography using an Ultimate 3000 liquid chromatography system (Thermo Fisher Scientific). In brief, the sample was loaded onto an XBridge BEH C18 Column (130 Å, 3.5 μm, 2.1 mm×150 mm, Waters, UK) in buffer A, and peptides were eluted with an increasing gradient of buffer B (20 mM Ammonium Hydroxide in acetonitrile, pH 10) from 0-95% over 60 minutes. The resulting fractions (20 in total) were evaporated to dryness and resuspended in 1% formic acid prior to analysis by nano-LC MSMS using an Orbitrap Fusion Lumos mass spectrometer (Thermo Scientific).

TMT LS-MS Proteomics Data Analysis

Raw data files were converted to mzML format using msconvert proteowizard (version 3.0.22167). Database searches were performed using MSFragger (version 4.0)[2] within FragPipe (version 21.1). A precursor mass tolerance of 20 ppm and fragment mass tolerance of 0.6 Da was used. Two missed cleavages were allowed with a minimum peptide length of six and maximum length of fifty. Searches were performed against the reference human proteome from Uniprot (release 2023_05) including only reviewed accessions. Carbamidomethylation of cysteine (+57.02146 Da) and TMTpro labelling of Lysine (+304.20715 Da) were set as fixed modifications. Oxidation of methionine (+15.9949 Da), N-terminal acetylation (+42.0106 Da), and N-terminal TMTpro labelling (+304.20715 Da) were set as variable modifications. False-discovery rate filtering was set to 1% at the PSM, peptide, and protein level. Each channel intensity was normalized to the median intensity of all channels to account for protein loading differences and log 2 transformation was applied. For global proteomics, internal reference scaling normalisation[3] was performed to correct for batch effect between plexes and proteins with less than two unique peptides were excluded. Statistical analysis was performed with the moderated t-statistics implemented in the limma package (v 3.56.2) within the R framework[4]. A single linear model was constructed to test degrader vs equal concentration of negative control compound. P-values were adjusted using the Benjamini & Hochberg method to account for multiple comparisons[1]. Proteins were considered significantly altered if they met the criteria of an adjusted p-value <0.01 and an absolute $\log_2$ fold-change >1.

Results

Figure 5A:
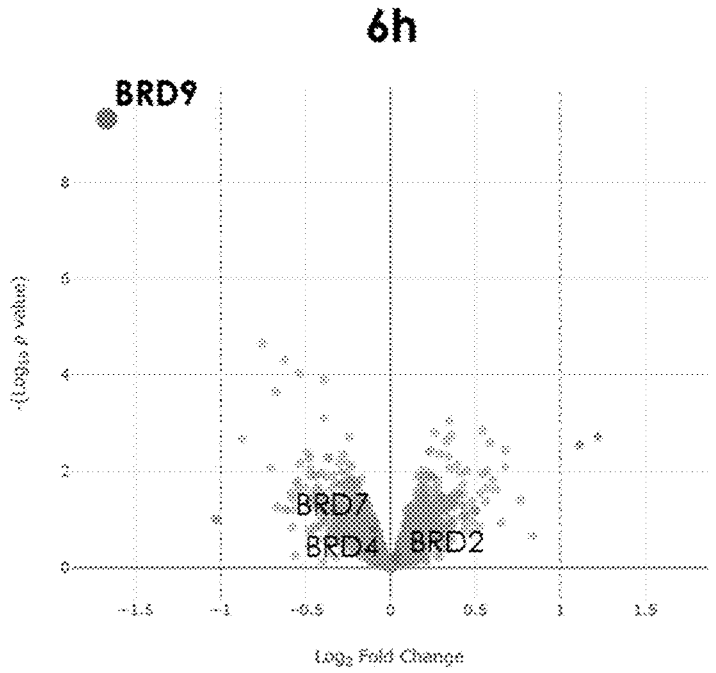
FIG. 5*a* is a volcano plot showing that TMT Proteomics shows significant degradation of BRD9 at 6 hrs in the MV4-11 cell line with minimal down or up-regulated proteins observed including bromodomain containing proteins. Contrast shown compares compound 9 (see Table 5) and the negative control compound 5-[4-[[4-[[(1R)-2-[(E)-5-fluoro-4,4-dimethyl-pent-2-enoyl]-1-isopropyl-7-methoxy-3,4-dihydro-1H-isoquinolin-5-yl]methyl]-4,7-diazaspiro[2.5]octan-7-yl]methyl]-3,5-dimethoxy-phenyl]-1,3,4-trimethyl-pyridin-2-one.
Figure 5B:
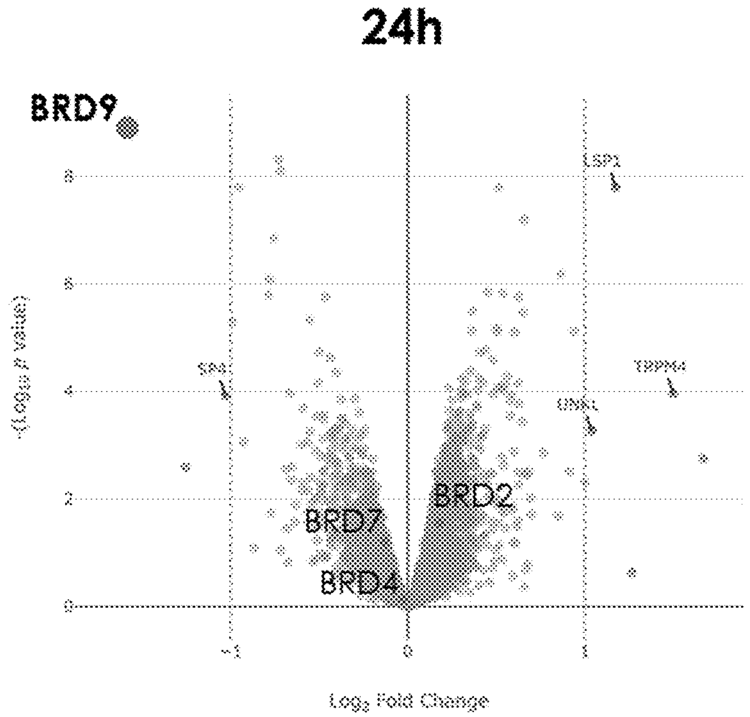
FIG. 5*b* is a volcano plot showing that TMT Proteomics shows significant degradation of BRD9 at 24 hrs in the MV4-11 cell line with minimal down or up-regulated proteins observed including bromodomain containing proteins. Contrast shown compares compound 9 (see Table 5) and the negative control compound 5-[4-[[4-[[(1R)-2-[(E)-5-fluoro-4,4-dimethyl-pent-2-enoyl]-1-isopropyl-7-methoxy-3,4-dihydro-1H-isoquinolin-5-yl]methyl]-4,7-diazaspiro[2.5]octan-7-yl]methyl]-3,5-dimethoxy-phenyl]-1,3,4-trimethyl-pyridin-2-one.
Figure 5C:
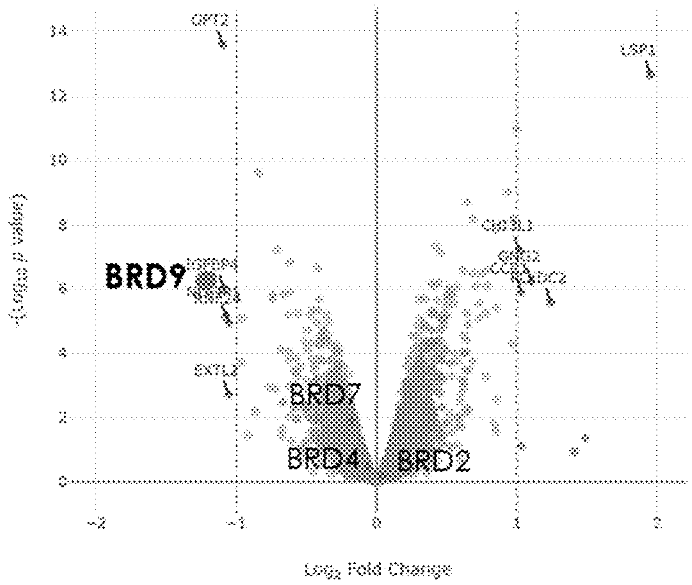
FIG. 5*c* is a volcano plot showing that TMT Proteomics shows significant degradation of BRD9 at 48 hrs in the MV4-11 cell line with minimal down or up-regulated proteins observed including bromodomain containing proteins. Contrast shown compares compound 9 (see Table 5) and the negative control compound 5-[4-[[4-[[(1R)-2-[(E)-5-fluoro-4,4-dimethyl-pent-2-enoyl]-1-isopropyl-7-methoxy-3,4-dihydro-1H-isoquinolin-5-yl]methyl]-4,7-diazaspiro[2.5]octan-7-yl]methyl]-3,5-dimethoxy-phenyl]-1,3,4-trimethyl-pyridin-2-one.

Compound 9 (see Table 5) is a selective degrader of BRD9 at 6, 24 and 48 hours in the MV4-11 cells, with limited off-target protein degradation observed and significantly no degradation of other bromodomain containing proteins observed, as demonstrated in FIGS. 5*a* to 5*c*.

In FIG. 5*a*, TMT Proteomics shows significant degradation of BRD9 at 6 hrs in the MV4-11 cell line with minimal down or up-regulated proteins observed including bromodomain containing proteins. Contrast shown compares compound 9 (see Table 5) and the negative control compound 5-[4-[[4-[[(1R)-2-[(E)-5-fluoro-4,4-dimethyl-pent-2-enoyl]-1-isopropyl-7-methoxy-3,4-dihydro-1H-isoquinolin-5-yl]methyl]-4,7-diazaspiro[2.5]octan-7-yl]methyl]-3,5-dimethoxy-phenyl]-1,3,4-trimethyl-pyridin-2-one.

In FIG. 5*b*, TMT Proteomics shows significant degradation of BRD9 at 24 hrs in the MV4-11 cell line with minimal down or up-regulated proteins observed including bromodomain containing proteins. Contrast shown compares compound 9 (see Table 5) and the negative control compound 5-[4-[[4-[[(1R)-2-[(E)-5-fluoro-4,4-dimethyl-pent-2-enoyl]-1-isopropyl-7-methoxy-3,4-dihydro-1H-isoquinolin-5-yl]methyl]-4,7-diazaspiro[2.5]octan-7-yl]methyl]-3,5-dimethoxy-phenyl]-1,3,4-trimethyl-pyridin-2-one.

In FIG. 5*c*, TMT Proteomics shows significant degradation of BRD9 at 48 hrs in the MV4-11 cell line with minimal down or up-regulated proteins observed including bromodomain containing proteins. Contrast shown compares compound 9 (see Table 5) and the negative control compound 5-[4-[[4-[[(1R)-2-[(E)-5-fluoro-4,4-dimethyl-pent-2-enoyl]-1-isopropyl-7-methoxy-3,4-dihydro-1H-isoquinolin-5-yl]methyl]-4,7-diazaspiro[2.5]octan-7-yl]methyl]-3,5-dimethoxy-phenyl]-1,3,4-trimethyl-pyridin-2-one.

Example 39: In Vivo Efficacy Study with the Luciferase Tagged MV4-11 Disseminated Model Cell Culture The MV4-11-luc tumour cells were maintained in vitro in RPMI 1640 medium supplemented with 10% fetal bovine serum and 1% Antibiotic-Antimycotic at 37° C. in an atmosphere of 5% $CO_2$ in air. The tumour cells were routinely sub-cultured twice weekly. The cells growing in an exponential growth phase were harvested and counted for tumour inoculation.

Tumour Inoculation

Each mouse was inoculated via tail vein with $2\times10^6$ MV4-11-luc cells in 0.2 mL of PBS for tumour development. Animals were randomized when the average bioluminescence reached $4.76\times10^6$ photons/second on day 6 after cell inoculation. The test article administration and the animal numbers in each group are shown in Table 31 below:

TABLE 31

| Treatment group | Dose (mg/kg) | $N^a$(designated) | Route/ Schedule$^b$ |
|---|---|---|---|
| Vehicle | — | 5 | PO/BID *14 days |
| Compound 9 | 50 | 5 | PO/BID *14 days |
| Compound 9 | 30 | 5 | PO/BID *14 days |
| Compound 9 | 10 | 5 | PO/BID *14 days |
| Compound 9 | 3 | 5 | PO/BID *14 days |
| Compound 9 | 1 | 5 | PO/BID *14 days |
| Compound 9 | 100 | 5 | PO/QD *14 days |
| Compound 9 | 30 | 5 | PO/QD *14 days |
| Compound 9 | 10 | 5 | PO/QD *14 days |
| Compound 9 | 3 | 5 | PO/QD *14 days |

Testing Article Formulation Preparation

The methods of preparation for the formulations of Venetoclax and Compound 9 are given in Table 32.

TABLE 32

| Test article | Conc. (mg/mL) | Formulation |
|---|---|---|
| Venetoclax | 7.5 | Dissolve 255.10 mg Venetoclax in 1.696 mL Propylene Glycol, sonicate until completely dissolved, then add 0.170 mL Tween 80 and 10.178 mL PEG400 and 21.884 mL water, mix well one by one to get a homogeneous suspension. |
| Compound 9 | 10 | Dissolve 325.50 mg Compound 9 in 6.380 mL PEG400, sonicate until completely dissolved, then add 3.190 mL Solutol and 22.329 mL water, mix well one by one to get a clear solution. |
| | 5 | Dissolve 326.54 mg Compound 9 in 12.800 mL PEG400, sonicate until completely dissolved, then add 6.400 mL Solutol and 44.801 mL water, mix well one by one to get a clear solution. |
| | 3 | Dissolve 196.55 mg Compound 9 in 12.841 mL PEG400, sonicate until completely dissolved, then add 6.421 mL Solutol and 44.944 mL water, mix well one by one to get a clear solution. |

Bioluminescence Measurements and Endpoints

The surgically inoculated mice were weighed and intraperitoneally administered luciferin at a dose of 150 mg/kg. After 15 minutes of the luciferin administration, the animals were pre-anaesthetized with the mixture gas of oxygen and isoflurane. When the animals were in a complete anaesthetic state, the mice were moved into the imaging chamber for bioluminescence measurements with an IVIS (Lumina III) imaging system.

The major endpoint was to see if the tumour growth could be delayed, decreased, or prevented entirely, as well as the survival time of the animals. The body weight was measured daily, and the bioluminescence signals were measured weekly. The bioluminescence signals were then used for calculations of T/C value. The T/C value (in percent) is an indication of antitumour effectiveness; T and C are the mean bioluminescence of the treated and control groups, respectively, on a given day. For individual mice with >20% body weight loss or who showed moribund, they were considered as reaching the endpoint and were euthanized.

TGI was calculated for each group using the following formula:

$$TGI(\%) = \left[1 - (T_i - T_0)/(V_i - V_0)\right] \times 100$$

where $T_i$ is the average tumour bioluminescence of a treatment group on a given day, $T_0$ is the average tumour bioluminescence of the treatment group on the day of randomization start, $V_i$ is the average tumour bioluminescence of the vehicle control group on the same day with $T_i$, and $V_0$ is the average tumour bioluminescence of the vehicle control group on the day of randomization start.

8 mice in each group were euthanized for the collection of bone marrow on day 7, 14 and 21, respectively.

Sample Collection

Plasma, bone marrow and whole blood were collected at pre-determined time points as shown in experimental design.

Bone marrow: bone marrow was collected at PG-D7, PG-D14, PG-D21 2 h after dosing from all groups, N=8 for every group per collection. The samples were kept at −4 degrees before FACS analysis (human CD11b, c-Myc, Bcl-2, CD86 and BRD9) and Giemsa staining.

Results: 14 Day Dose Finding Study

Figure 6A:
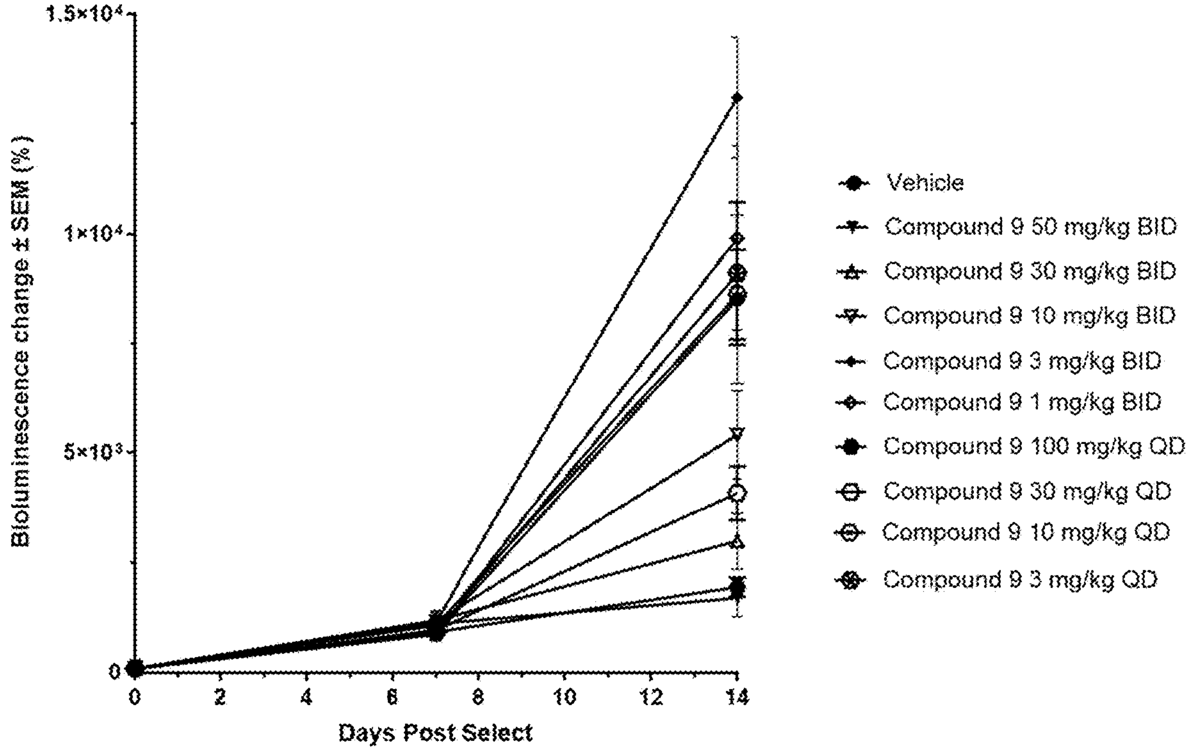
FIG. 6*a* is a line graph showing the 14-day change in tumour bioluminescence (±SEM) in mice inoculated with luciferase tagged MV4-11 and treated Compound 9 or a vehicle control.
Figure 6B:
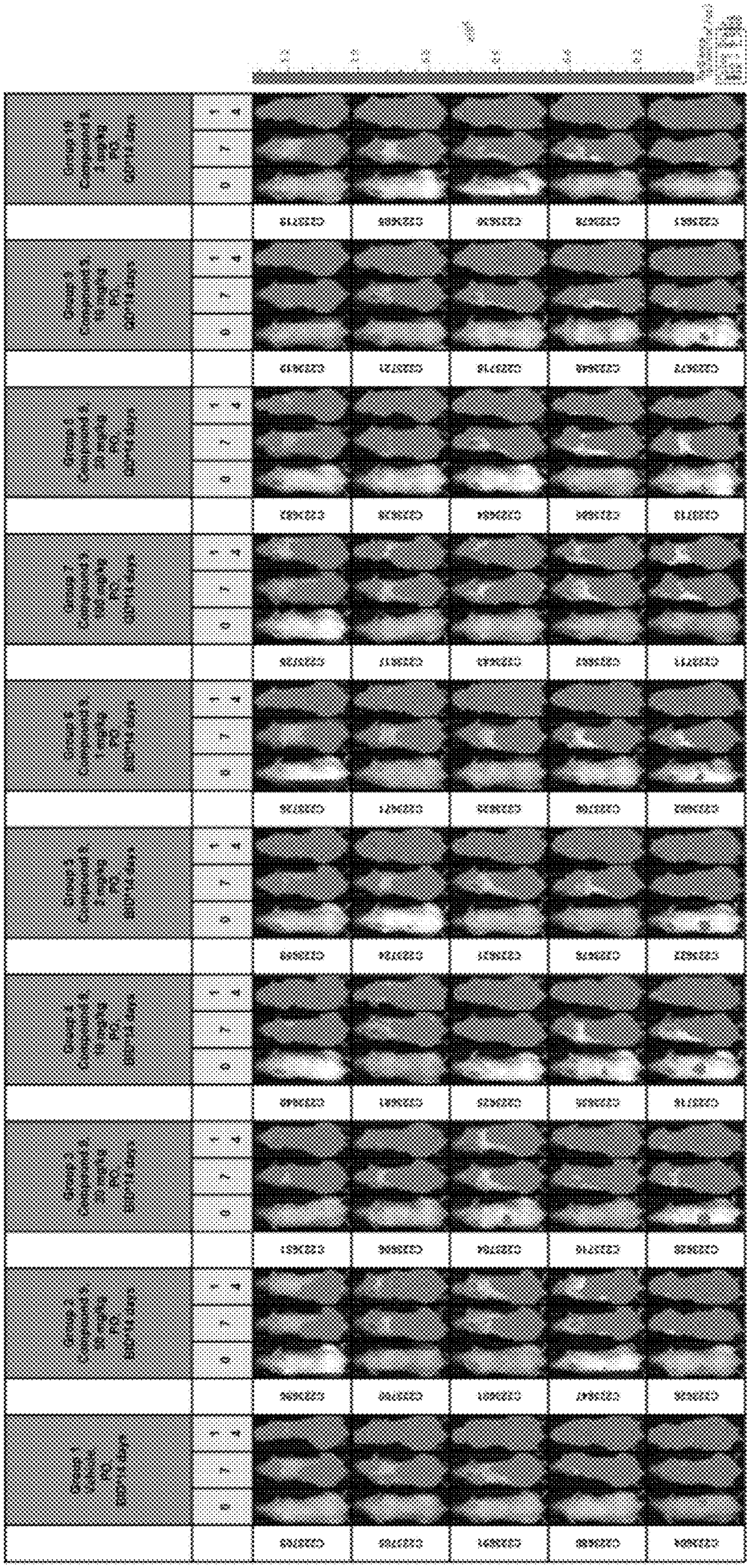
FIG. 6*b* is a series of bioluminescence images of mice inoculated with luciferase tagged MV4-11 and treated with Compound 9 or vehicle control. Images are taken at 0, 7 and 14 days post-study initiation.
Figure 7:
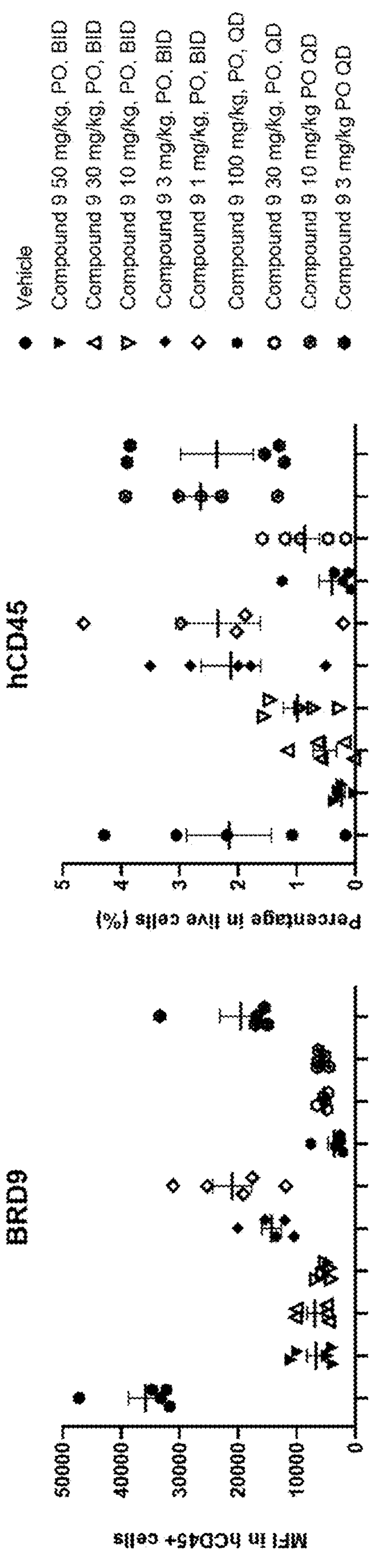
FIG. 7 is a scatter plot showing hCD45 levels in the bone marrow 14 days post-treatment, in animals implanted with luciferase-expressing MV4-11 cells and treated with Compound 9, Venetoclax or vehicle control.

As can be seen from FIG. 6*a* and FIG. 6*b*, Compound 9 dose dependently decreases the expansion of luciferase expressing MV4-11 cells during a 14-day study. Further, FIG. 7 demonstrates that Compound 9 induces dose-dependent degradation of BRD9, which is associated with decreased hCD45 levels in the bone marrow 14 days post-treatment in animals implanted with luciferase-expressing MV4-11 cells.

Summary

Compound 9 showed a dose dependent suppression of disease burden when dosed either on a BID or QD schedule.

Efficacy was clearly observed at the 10 mg/kg, 30 mg/kg and 50 mg/kg BID and 30 mg/kg and 100 mg/kg QD schedule. The disease control was confirmed with a dose dependent decrease in hCD45 and BRD9 expression.

Results: 21 Day Efficacy Study

Figure 8A:
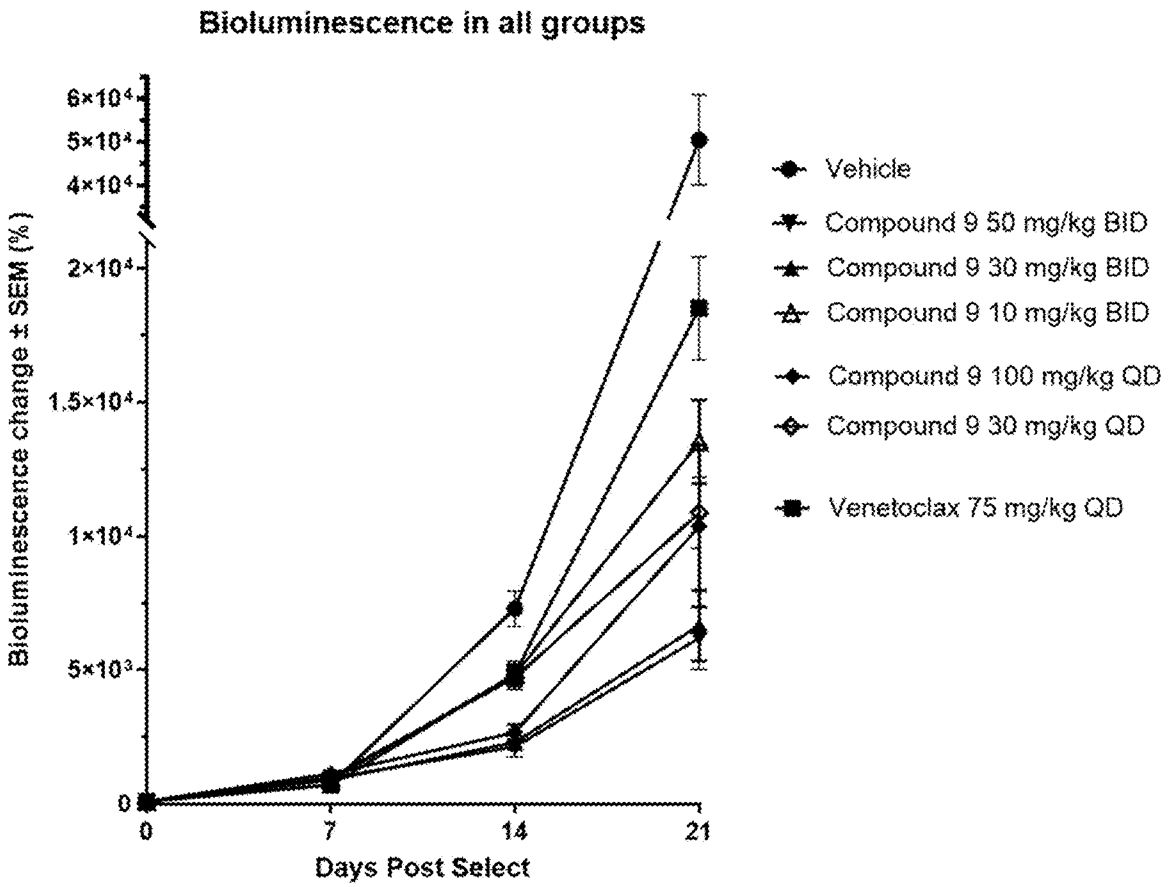
FIG. 8*a* is a line graph showing a plot showing the 21-day change in tumour bioluminescence (±SEM) in mice inoculated with luciferase tagged MV4-11 and treated Compound 9 or a vehicle control.
Figure 8B:
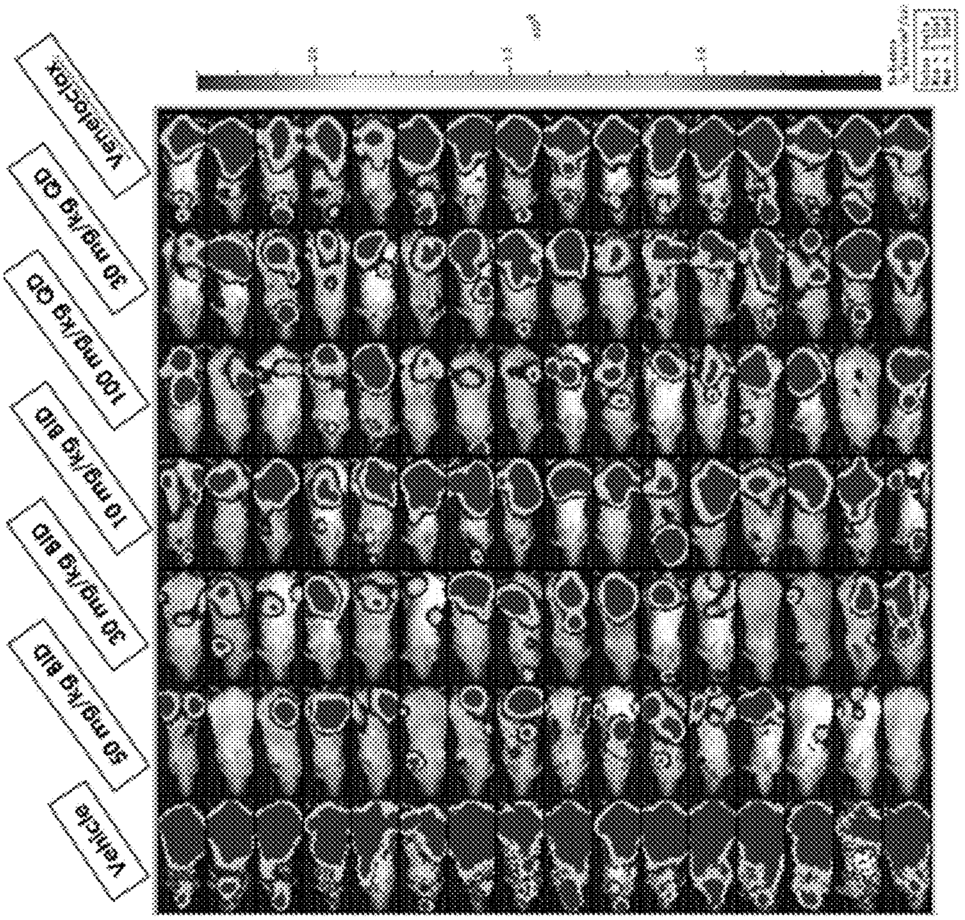
FIG. 8*b* is a series of bioluminescence images of mice inoculated with luciferase tagged MV4-11 cells and treated with Compound 9, Venetoclax or vehicle control. Images are taken at 21 days post-treatment initiation.

Table 33 provides the tumour bioluminescence of the treatment control group, and the Venetoclax- and Compound 9-treated groups. It can be seen that Compound 9 dose dependently decreases the expansion of luciferase expressing MV4-11 cells during a 21-day study and shows superior efficacy compared to the standard of care agent Venetoclax. The results are further illustrated in FIG. 8.

TABLE 33

| Group | Treatment | Bioluminescence ($\times 10^6$ photons/second) [a] | T/C [b] (%) | TGI [b] (%) | p value [c] |
|---|---|---|---|---|---|
| 1 | Vehicle, PO BID | 2451.1 ± 419.9 | — | — | — |
| 2 | Compound 9, 50 mg/kg, PO BID | 325.3 ± 66.0 | 13.3 | 86.9 | $p < 0.0001$ |
| 3 | Compound 9, 30 mg/kg, PO BID | 282.4 ± 45.9 | 11.5 | 88.7 | $p < 0.0001$ |
| 4 | Compound 9, 10 mg/kg, PO BID | 610.4 ± 64.3 | 24.9 | 75.2 | $p < 0.0001$ |
| 5 | Compound 9, 100 mg/kg, PO QD | 488.8 ± 147.0 | 19.9 | 80.2 | $p < 0.0001$ |
| 6 | Compound 9, 30 mg/kg, PO QD | 550.6 ± 76.0 | 22.5 | 77.7 | $p < 0.0001$ |
| 7 | Venetoclax, 75 mg/kg, PO QD | 873.2 ± 104.9 | 35.6 | 64.5 | $p < 0.0001$ |

[a] Mean ± SEM.

[b] T/C (%) = T/C × 100, TGI (%) = $[1-(T_i - T_0)/(V_i - V_0)] \times 100$.

[c] A one-way ANOVA was performed to compare tumour bioluminescence among treatment groups and vehicle group.

Pharmacodynamic Measurements

PD mice (N=5) received identical handling and care as the efficacy arm of the study. Mice were treated for a total of 20 days. On Day 20 of treatment, mice were euthanized, and cardiac blood, spleen, and bone marrow were collected. Spleen weights were also measured and recorded. The collected blood and bone marrow were used for flow cytometry analysis as below.

Flow Cytometry Analysis:

For day 20 PD (bone marrow) and day 35 Efficacy (blood) samples, the absolute tumour burden was measured as a percentage of hCD45+ cells relative to total bone marrow or PBMC cell population. Six additional targets (hCD14, hCD11 b, hCD34, hCD117, hCD86, hBRD9) were also profiled in flow cytometry samples.

Pharmacodynamic Datasets

Figure 9:
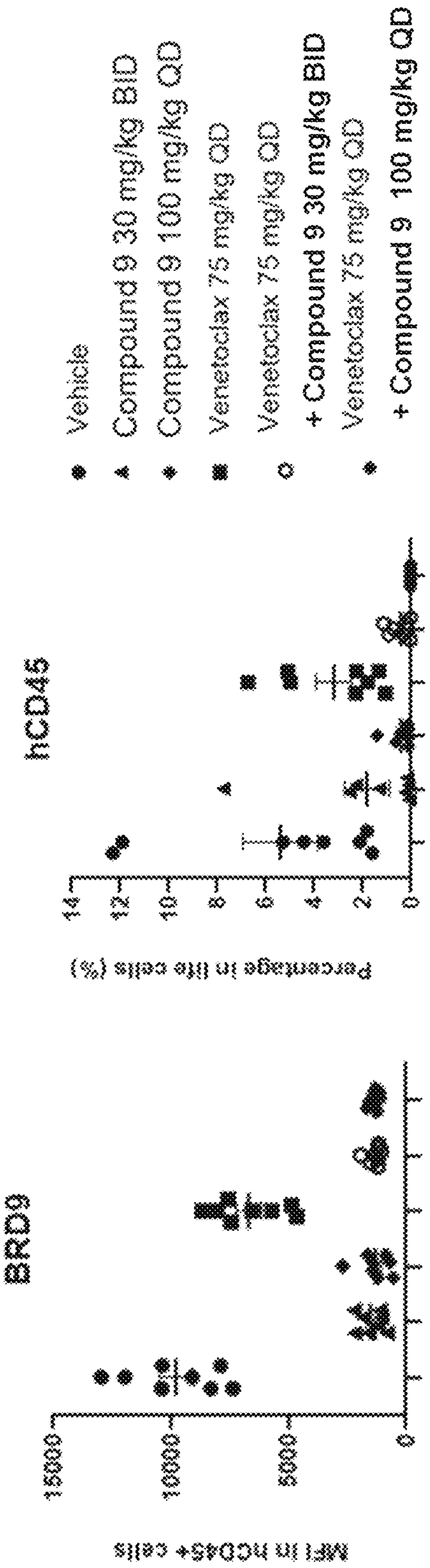
FIG. 9 is a scatter plot showing hCD45 levels in the bone marrow 21 days post-treatment, in animals implanted with luciferase-expressing MV4-11 cells and treated with Compound 9, Venetoclax or vehicle control.

FIG. 9 shows that Compound 9 induces dose-dependent degradation of BRD9, which is associated with decreased hCD45 levels in the bone marrow 21 days post-treatment in animals implanted with luciferase-expressing MV4-11 cells.

Summary

Compound 9 demonstrated potent, dose-dependent inhibition of disease burden when administered as monotherapy, either BID or QD. This effect correlated with BRD9 degradation and reduced hCD45 levels in the bone marrow.

Example 40: Survival Study with the DFAM 68555 AML PDX Disseminated Model

Efficacy

Fifty-eight female NSG mice were each intravenously implanted with $5\times10^5$ DFAM-68555-V4 cells via the tail vein. Two days post implantation, mice were randomized by bodyweight into treatment groups, mice were weighed biweekly.

Mice were treated for a total of 40 days. Cheek bleeds were performed on day 35 for flow cytometry analysis of tumour burden. Mice were monitored for survival based on morbidity criteria and on study day 49, it was decided that any further takedowns would include an endpoint collection of cheek bleed blood and bone marrow for flow cytometry analysis.

Following our institutional IACUC protocol, any animals showing signs of morbidity including body weight loss of >20%, laboured breathing, persistent recumbency, any condition interfering with eating or drinks (e.g., difficulty with ambulation), distended abdomens due to enlarged organs or ascites, emaciation, and/or hind-limb paralysis were euthanized.

Results

Day 20 Disease Monitoring in Bone Marrow

Table 34 provides the 20-day bone marrow hCD45 levels of animals treated with either Vehicle, Venetoclax (100 mg/kg) or Compound 9 (50 mg/kg BID or 100 mg/kg QD). Significant differences from levels of human CD45 in the control animals were assessed by one way ANOVA and Tukeys multiple comparison.

TABLE 34

| Groups | Mean % hCD45 | *p value vs Vehicle | *p value vs Venetoclax | *p value vs COMPOUND 9 BID dosing |
|---|---|---|---|---|
| Vehicle | 23.10 | | | |
| Venetoclax | 18.17 | 0.62 (ns) | | |
| Compound 9 50 mg/kg BID | 0.27 | 0.0002 | 0.0021 | |
| Compound 9 100 mg/kg QD | 1.76 | 0.0004 | 0.0044 | 0.98 (ns) |

*$P < 0.05$ is considered significant; NS, not significant.

*Statistical analysis performed using Ordinary one-way ANOVA and Tukey's multiple comparisons test Day 35 Disease Monitoring in Peripheral Blood Table 35 provides the 35-day blood hCD45 levels of animals treated with either Vehicle, Venetoclax (100 mg/kg) or Compound 9 (50 mg/kg BID or 100 mgkg QD). Blood samples were taken from all animals on day 35 and levels of human CD45 measured by flow cytometry. Significant differences from levels of human CD45 in the control animals were assessed by one way ANOVA and Tukeys multiple comparison.

TABLE 35

| Groups | Mean % hCD45 | *p value vs Vehicle | *p value vs Venetoclax | *p value vs Compound 9 BID dosing |
|---|---|---|---|---|
| Vehicle | 75.61 | | | |
| Venetoclax | 42.54 | <0.0001 | | |
| Compound 9 50 mg/kg BID | 0.15 | <0.0001 | <0.0001 | |
| Compound 9 100 mg/kg QD | 0.39 | <0.0001 | <0.0001 | >0.999 (ns) |

*P < 0.05 is considered significant; NS, not significant.

Figure 10:
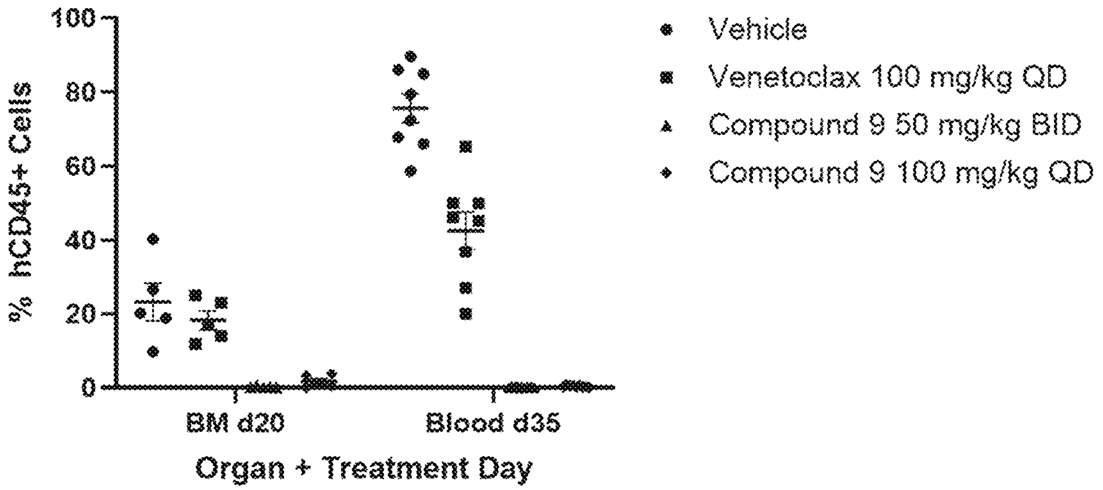
FIG. 10 is a scatter plot showing changes in human CD45 levels in mice implanted with the DFAM 68555 model at Day 20 in bone marrow and day 35 in peripheral blood.

*Statistical analysis performed using Ordinary one-way ANOVA and Tukey's multiple comparisons test The changes in human CD45 levels in mice implanted with the DFAM 68555 model at Day 20 in bone marrow and day 35 in peripheral blood are summarised in FIG. 10.

Survival Data

Table 36 provides a survival analysis of DFAM68555 model with animals treated with either Vehicle, Venetoclax (100 mg/kg) or Compound 9 (50 mg/kg BID or 100 mgkg QD). Significant differences in survival compared to vehicle treated animals was assessed by Log-rank (Mantel-Cox) test.

TABLE 36

| Groups | Median days survival | *p value vs Vehicle | *p value vs Venetoclax | *p value vs Compound 9 BID dosing |
|---|---|---|---|---|
| Vehicle | 36.0 | | | |
| Venetoclax | 37.0 | 0.096 (ns) | | |
| Compound 9 50 mg/kg BID | 61.0 | <0.0001 | <0.0001 | |
| Compound 9 100 mg/kg QD | 54.0 | <0.0001 | <0.0001 | 0.011 |

*P < 0.05 is considered significant; NS, not significant.

Figure 11:
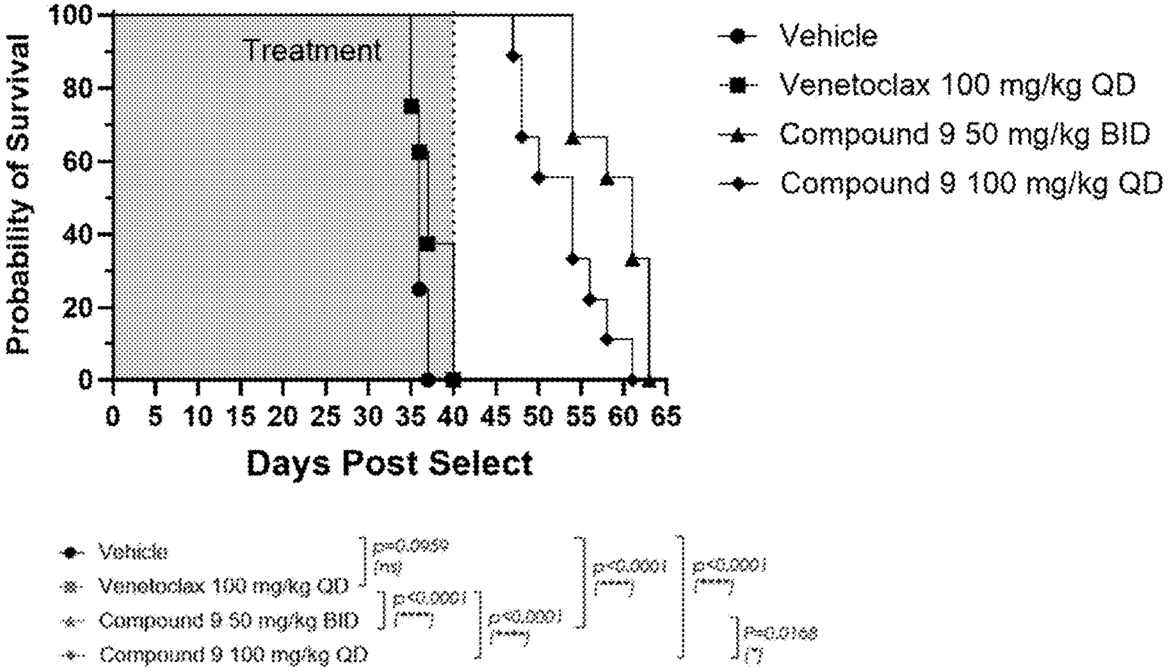
FIG. 11 is a Kaplan-Meier plot demonstrating the survival rates for mice inoculated with DFAM-68555-V4 cells and treated with Compound 9, Venetoclax or vehicle control.
Figure 12A:
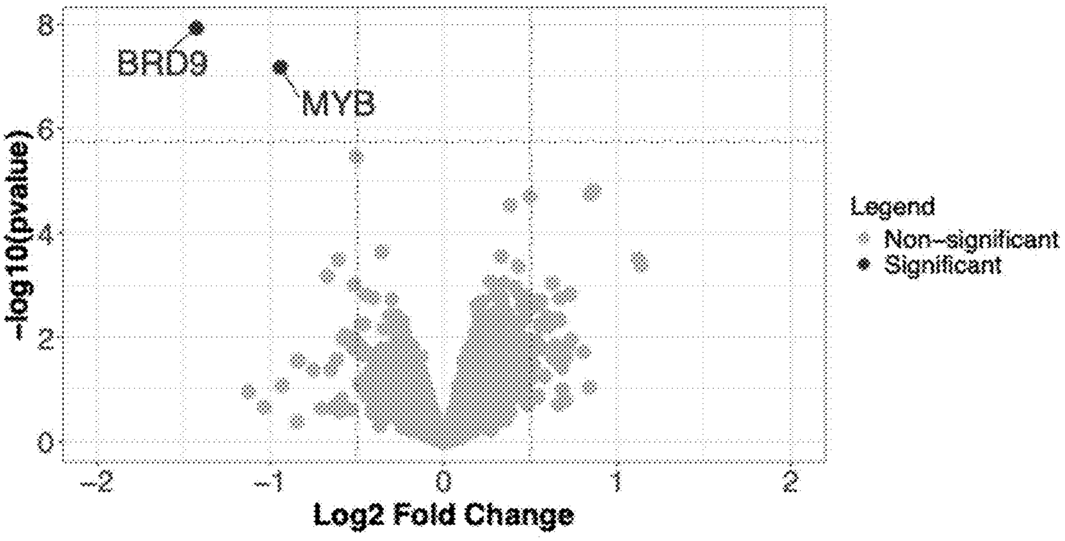
FIG. 12*a* is a volcano plot comparing the differentially expressed proteins for Compound 9 in comparison to DMSO at 6 hours treatment ordered by log 2 fold change.
Figure 12B:
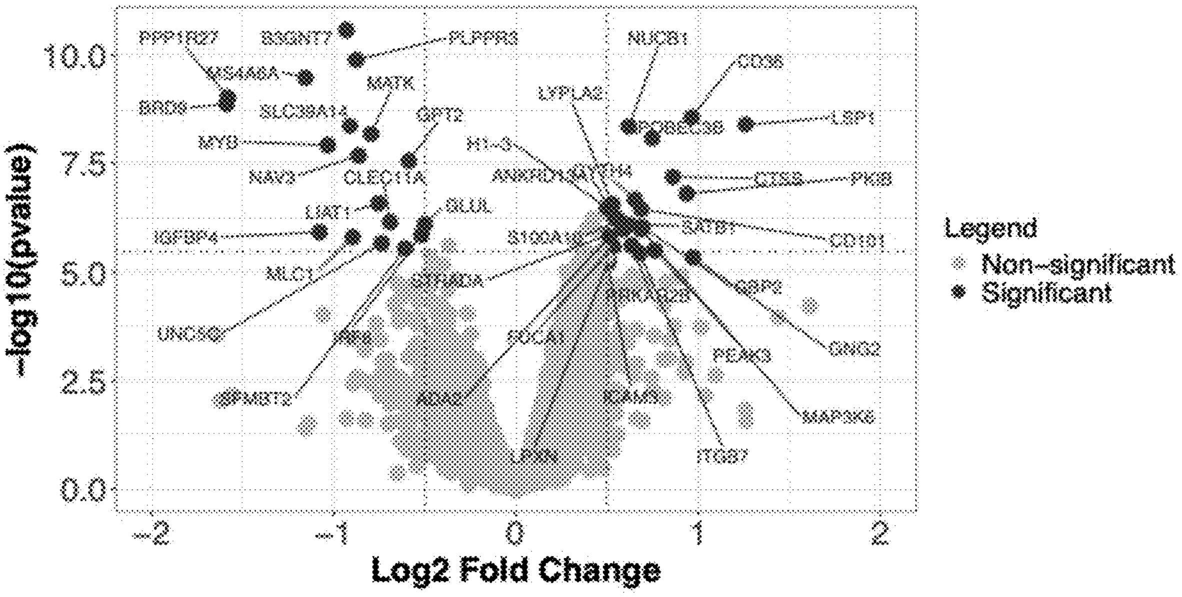
FIG. 12*b* is a volcano plot comparing the differentially expressed proteins for Compound 9 in comparison to DMSO at 24 hours treatment ordered by log 2 fold change.

*Statistical analysis performed using the Log-rank (Mantle-Cox) test for survival FIG. 11 presents a Kaplan-Meier survival plot comparing the survival outcomes of vehicle-treated animals with those receiving the standard of care, Venetoclax, and Compound 9 administered at 50 mg/kg twice daily (BID) and 100 mg/kg once daily (QD).

Summary

Compound 9 induced significant monotherapy survival benefit in the DFAM68555 model compared to the standard of care Venetoclax (100 mg/kg), and vehicle treated animals. A 25-day survival benefit was observed compared to Vehicle animals when compound 9 was administered BID at 50 mg/kg. The survival benefit for either dosing schedule of Compound 9 was significantly better than responses observed with the standard of care Venetoclax.

Example 41: TMT LC-MS Global Proteomics Sample Preparation

Methods

MV4; 11 cells were seeded at 8×10→5 for 6 h. After seeding, cells were immediately treated with 100 nM of indicated compounds in triplicate. At indicated time points, cells were washed twice with PBS, pelleted, and resuspended in 100 μL of lysis buffer (50 mM Tris pH 7.6, 150 mM NaCl, 2% SDS, 10% glycerol, protease inhibitors (Pierce A32961), 1 mM PMSF, 250 U benzonase (Thermo Fisher, 88701) and sonicated for 1 minute at 100% power with a probe sonicator. Cell debris was removed by centrifugation at 21,000×g for 10 min.

TMT Labelling, High pH Reversed-Phase Chromatography

Approximately 60 μg of each sample was labelled with Tandem Mass Tag (TMTpro) 18-plex reagents according to the manufacturer's protocol (Thermo Fisher Scientific, Loughborough, LE11 5RG, UK).

TMT LS-MS Proteomics Data Analysis

Raw data files were converted to mzML format using msconvert proteowizard (version 3.0.22167). Database searches were performed using MSFragger (version 4.0) within FragPipe (version 21.1). A precursor mass tolerance of 20 ppm and fragment mass tolerance of 0.6 Da was used. Two missed cleavages were allowed with a minimum peptide length of six and maximum length of fifty. Searches were performed against the reference human proteome from Uniprot (release 2023_05) including only reviewed accessions. Carbamidomethylation of cysteine (+57.02146 Da) and TMTpro labelling of Lysine (+304.20715 Da) were set as fixed modifications. Oxidation of methionine (+15.9949 Da), N-terminal acetylation (+42.0106 Da), and N-terminal TMTpro labelling (+304.20715 Da) were set as variable modifications. False-discovery rate filtering was set to 1% at the PSM, peptide, and protein level. Each channel intensity was normalized to the median intensity of all channels to account for protein loading differences and log 2 transformation was applied. In addition, internal reference scaling normalisation was performed to correct for batch effect between plexes and proteins with less than two unique peptides were excluded. Statistical analysis was performed with the moderated t-statistics implemented in the limma package (v 3.56.2) within the R framework. P-values were adjusted using the Benjamini & Hochberg method to account for multiple comparisons. To identify proteins degraded as a result of compound treatment and to assess downstream changes caused by this degradation, proteins meeting the following criteria were considered significant: an adjusted p-value <0.001 and an absolute log 2 fold-change >0.5. Significant proteins with log 2 fold change <−0.5 were considered downregulated by the compound while significant proteins with log 2 fold change >0.5 were considered up-regulated.

Results

FIG. **12*a*** shows a volcano plot comparing the differentially expressed proteins for Compound 9 in comparison to DMSO at 6 hours treatment ordered by log 2 fold change. The proteins downregulated by Compound 9 were BRD9 and MYB. No proteins were upregulated proteins.

FIG. **12*b*** shows a volcano plot comparing the differentially expressed proteins for Compound 9 in comparison to DMSO at 24 hours treatment ordered by log 2 fold change. The proteins downregulated by Compound 9 were BRD9, PPP1 R27, MS4A6A, IGFBP4, MYB, B3GNT7, SLC39A14, MLC1, PLPPR3, NAV3, MATK, LIAT1, UNC5C, CLEC11A, SFMBT2, GPT2, IRF8, and GLUL. The proteins upregulated by Compound 9 were LSP1, GNG2, CD36, PKIB, CTSS, PEAK3, APOBEC3B, GBP2, MAP3K6, CD101, ITGB7, CYTH4, PRKAR2B, SATB1, NUCB1, STRADA, S100A10, ANKRD13A, FUCA1, LYPLA2, ADA2, LPXN, ICAM3, and H1-3.

Example 42: Cryo-EM Determination of Compound 9: BRD9:DDA1:DCAF16:DDB1 Ternary Protein Complex Protein Expression and Purification BRD9 Bromo Domain Expression and Purification ($His_6$-TEV)-hBRD9 bomodomain (134-250) was expressed in *Escherichia coli* BL21 (DE3) cells, grown in Luria Broth (LB) medium plus 0.2% glucose, overnight at 18° C. Cells were harvested by centrifugation for 10 min at 900 g, and lysed by resuspending in Buffer A in presence of 20 mM Imidazole and Protease Inhibitor tablets (SIGMAFAST™ Protease Inhibitor Cocktail Tablets, EDTA-Free Cat #S8830). Lysates were homogenized using an Ultraturrax (IKA) cell disruptor. Insoluble proteins were removed by centrifugation at 50,000 g, and cleared lysate was passed over nickel resin (Ni-NTA Superflow Qiagen Cat no. 30410) in batch mode. Resin was washed with Buffer A+45 mM imidazole and target complex was eluted with Buffer A+300 mM Imidazole. For $His_6$-tag cleavage, samples were incubated with TEV protease at 4° C. overnight and proteolyzed complex was captured via reverse NiNTA in Buffer A. For final purification, samples were loaded onto a size exclusion Superdex 75 prep grade column pre-equilibrated with Buffer C (25 mM Hepes pH 7.5, 200 mM NaCl, 10% glycerol, 1 mM TCEP). Fractions were collected and analysed by SDS-PAGE. Highest purity fractions (>95% purity) were concentrated, aliquoted and frozen at −80° C.

DDA1:DCAF16:DDB1 Expression and Purification hDDA1 (1-102) and ($His_6$-TEV)-hDCAF16 (1-216)+hDDB1ΔB(1-1140)-A396-705 were co-expressed in *Spodoptera frugiperda* (Sf9) baculovirus cells for 64 hrs at 26° C., after which cells were pelleted for 10 min at 900 g. The cell pellet was resuspended in Buffer A (50 mM Tris-HCl pH 8.0, 300 mM NaCl, 10% Glycerol, 2 mM TCEP) in the presence of 20 mM Imidazole and Protease Inhibitor tablets (SIGMAFAST™ Protease Inhibitor Cocktail Tablets, EDTA-Free Cat #S8830). Total lysate was cleared via centrifugation at 50000 g for 30 min at 4° C. and passed over nickel resin (Ni-NTA Superflow Qiagen Cat no. 30410) in batch mode. Resin was washed with Buffer A+20 mM Imidazole and target complex was eluted with Buffer A+600 mM Imidazole. $His_6$ cleavable tag was cleaved off over night by TEV protease, dialysed in Buffer A plus 20 mM Imidazole. The proteolyzed complex was captured via reverse NiNTA in Buffer A plus 20 mM Imidazole. Prior to loading on an MonoQ ion exchange column (Cytiva), buffer was adjusted to 50 mM NaCl. Complex was eluted from the Mono Q column via gradient to Buffer B (25 mM Tris-HCl pH 8.2, 1 M NaCl, 10% Glycerol, 1 mM TCEP) and further purified via final size exclusion using a size exclusion Superdex 200 prep grade column (Cytiva) in Buffer C (25 mM Tris-HCl pH 8.0, 300 mM NaCl, 10% Glycerol, 1 mM TCEP). Fractions were collected and analysed by SDS-PAGE. Highest purity fractions (>95% purity) were concentrated, aliquoted and frozen at −80° C.

Complex Preparation

Ternary complex was formed by incubating DDA1:DCAF16:DDB1 complex and BRD9 bromodomain, in a molar ratio of 1:2.5 with a 7.5 molar excess of Compound 9. Intact ternary complex was obtained from analytical Size Exclusion Chromatography Superdex 200 prep grade column (Cytiva) in Buffer C (25 mM Tris-HCl pH 8.0, 300 mM NaCl, 10% Glycerol, 1 mM TCEP). Complex containing fractions were pooled and concentrated to 7.2 mg/ml for Cryo-EM grid preparation.

Grid Preparation, Data Collection and Processing

Cryo-EM grids were prepared using a Vitrobot MarkIV (ThermoFisher). Briefly, 4 µl of protein sample at 7.2 mg/ml were applied to twice glow-discharged (Pelco easiGlow) UltrAuFoil R1.2/1.3 grids. Grids were blotted using a Vitrobot Mark IV (ThermoFisher) with the chamber equilibrated at 95% humidity and 4° C. and frozen by plunging into a liquid ethane-propane mixture. Grids were screened using a Glacios cryo-transmission electron microscope (ThermoFisher) operated at 200 kV. All cryo-EM data were acquired on a Titan Krios G2 transmission electron microscope (Thermo Fisher) operated at 300 keV, located at the SciLife lab in Stockholm, Sweden. All cryo-EM data were recorded using the EPU software (Thermo Fisher). 15,372 micrographs were collected with a nominal stage tilt of 40° with ~10% of micrographs untilted. All image processing was performed in cryoSPARC v4.7. Data were motion corrected, the contrast transfer function (CTF) of the motion corrected micrographs was estimated, and particles were picked using the blob picker and Topaz. Particles were re-extracted unbinned, subjected to NU-refinement, global CTF refinement, NU-refinement, reference-based motion correction and NU-refinement. The final map was generated by local refinement with a mask on the bromodomain, DCAF16 and the proximal beta-propeller of DDB1 for the final 2.7 Å reconstruction.

Figure 13:
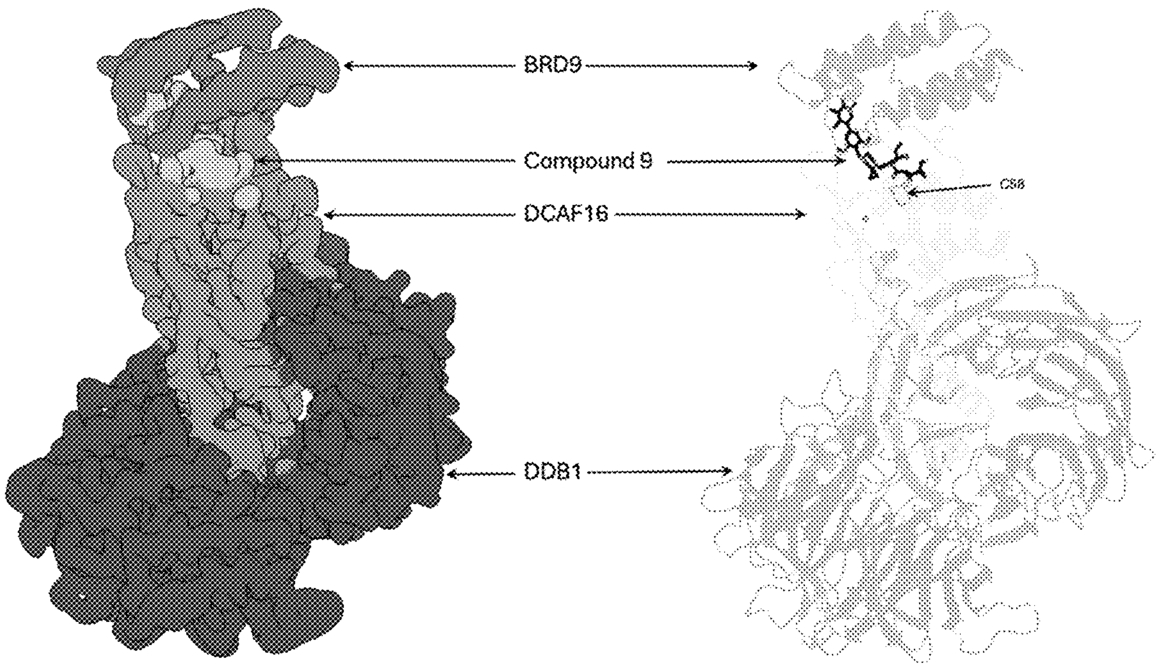
FIG. 13 is an image the CryoEM density and atomic structure of the ternary complex of DDB1:DCAF16:BRD9.

FIG. 13 shows the CryoEM density and atomic structure. The left panel shows CryoEM density map for the ternary complex of DDB1:DCAF16:BRD9 induced by Compound 9. The right panel shows the refined atomic level structure of the ternary complex built into the CryoEM density, mediated by Compound 9 covalently bound to Cys58 on DCAF16.

Figure 14:
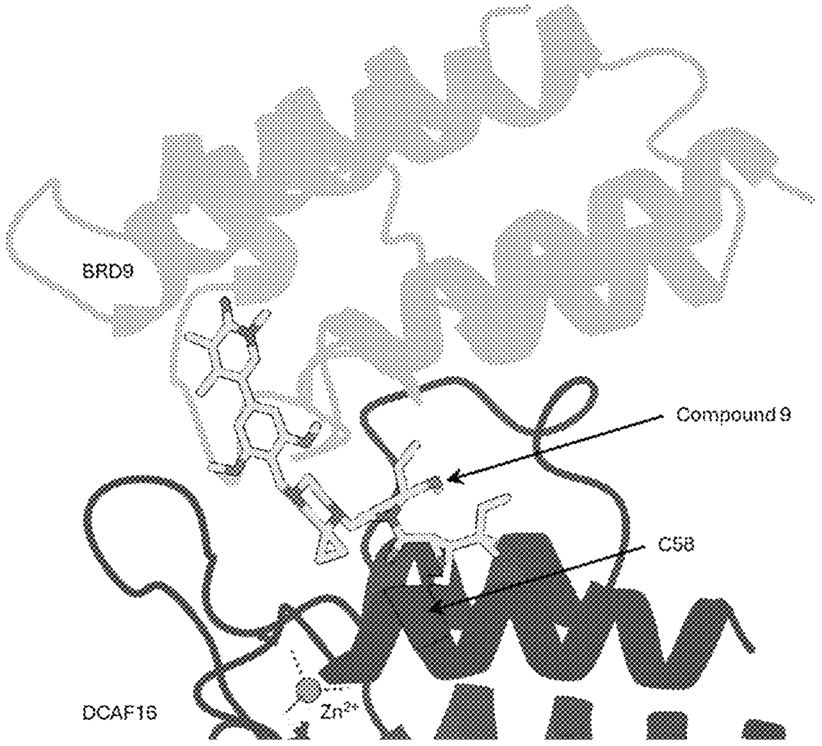
FIG. 14 is an image showing the atomic level structure of the binding between Compound 9, BRD9, and DCAF16.

FIG. 14 shows the refined atomic level structure of the binding between Compound 9, BRD9, and DCAF16 in more detail. BRD9 seems to adopt a tilted orientation such that its N- and C-terminus are aligned with those of DCAF16 in the ternary complex mediated by Compound 9, covalently linked to Cys58 on DCAF16.

The invention claimed is:
1. A compound, or a pharmaceutically acceptable salt thereof, wherein the compound is:
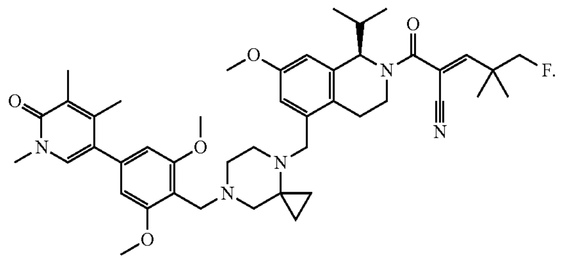 [SMILES: COc1cc(CN2CCN(Cc3c(OC)cc(-c4cn(C)c(=O)c(C)c4C)cc3OC)CC23CC3)c2c(c1)[C@@H](C(C)C)N(C(=O)/C(C#N)=C/C(C)(C)CF)CC2]
2. A pharmaceutical composition comprising the compound of claim 1, or a pharmaceutically acceptable salt thereof, together with a pharmaceutically acceptable carrier.
* * * * *